(12) United States Patent
Marliere et al.

(10) Patent No.: US 10,036,003 B2
(45) Date of Patent: *Jul. 31, 2018

(54) ALKENOL DEHYDRATASE VARIANTS OF LINALOOL DEHYDRATASE-ISOMERASE

(71) Applicants: Global Bioenerigies, Evry (FR); Scientist of Fortune S.A., Luxembourg (LU)

(72) Inventors: Philippe Marliere, Tournai (BE); Marc Delcourt, Paris (FR); Sabine Mazaleyrat, Bois le Roi (FR)

(73) Assignees: Global Bioenergies, Evry (FR); Scientist of Fortune, S.A., Luxembourg (LU)

( * ) Notice: Subject to any disclaimer, the term of this patent is extended or adjusted under 35 U.S.C. 154(b) by 72 days.

This patent is subject to a terminal disclaimer.

(21) Appl. No.: 14/891,665

(22) PCT Filed: May 16, 2014

(86) PCT No.: PCT/EP2014/060085
§ 371 (c)(1),
(2) Date: Dec. 21, 2015

(87) PCT Pub. No.: WO2014/184345
PCT Pub. Date: Nov. 20, 2014

(65) Prior Publication Data
US 2016/0186161 A1 Jun. 30, 2016

(30) Foreign Application Priority Data
May 17, 2013 (EP) .................................... 13168380
Dec. 9, 2013 (EP) .................................... 13196247

(51) Int. Cl.
*C12N 9/88* (2006.01)
*C12P 5/00* (2006.01)

(52) U.S. Cl.
CPC .................. *C12N 9/88* (2013.01); *C12P 5/00* (2013.01); *C12Y 402/01027* (2013.01); *C12Y 402/01127* (2013.01)

(58) Field of Classification Search
CPC ....... C12P 5/07; C12P 5/26; C12Y 402/01127
See application file for complete search history.

(56) References Cited

U.S. PATENT DOCUMENTS

| 8,703,455 B2 * | 4/2014 | Marliere ................. C12P 5/007 435/167 |
| 8,895,278 B2 * | 11/2014 | Marliere ................. C12P 5/007 435/167 |
| 8,975,050 B2 * | 3/2015 | Marliere ................. C12P 5/007 435/167 |

FOREIGN PATENT DOCUMENTS

| WO | 2012018624 A2 | 2/2012 |
| WO | 2013028519 A1 | 2/2013 |
| WO | WO 2013/057194 | 4/2013 |
| WO | WO 2014/033129 | 3/2014 |

OTHER PUBLICATIONS

International Search Report received in PCT/EP2014/060085 dated Oct. 21, 2014.
Written Opinion received in PCT/EP2014/060085 dated Oct. 21, 2014.
Brodkorb D et al., "Linalool dehydratase-isomerase, a bifunctional enzyme in the anaerobic degradation of monoterpenes", Journal of Biological Chemistry (2010) 285(40): 30436-30442.
Ludeke F et al., "Physiology of deletion mutants in the anaerobic [beta]-myrcene degradation pathway in Castellaniella defrag", BMC Microbiology, (2012) 12(1): 192 (abstract, figures 2, 3; tables 1, 2).
Reich H et al., "Conversion of allyl alcohols to 1,3-dienes by sequential sulfenate sulfoxide [2,3]-sigmatropic rearrangement and syn-elimination", Journal of the American Chemical Society (1982) vol. 104, No. 25, pp. 7051-7059 (abstract; figure 1).
Vavilov D et al., "Synthesis of isoprene from 1,3-dioxolane and isobutylene", Russian Journal of Applied Chemistry (2010) 83(9): 1598-1601 (abstract).
Database Uniprot [online], XP002703976 (Nov. 30, 2010).
International Preliminary Report and Written Opinion from PCT/EP2014/060085 dated Nov. 17, 2015.
Japanese Office Action dated May 22, 2018 and received in corresponding Japanese Application 2016-513384 along with English Translation.

* cited by examiner

*Primary Examiner* — Karen Cochrane Carlson
(74) *Attorney, Agent, or Firm* — Michele M Wales; Inhouse Patent Counsel, LLC

(57) ABSTRACT

Described are alkenol dehydratase variants having improved activity in catalyzing the conversion of a compound corresponding to the general formula $C_nH_{2n}O$ into $C_nH_{2n-2}$ +$H_2O$ with $3<n<7$. In particular, described are alkenol dehydratase variants having, e.g., an improved activity in converting but-2-en-1-ol (crotyl alcohol) into 1,3 butadiene and/or an improved activity in converting but-3-en-2-ol into 1,3 butadiene and/or an improved activity in converting 3-methylbut-2-en-1-ol (prenol) or 3-methylbut-3-en-2-ol (isoprenol) into isoprene and/or an improved activity in converting 2,3-dimethyl-but-2-en-1-ol into dimethyl-butadiene.

26 Claims, 26 Drawing Sheets

SEQ ID NO:2

Figure 1A:
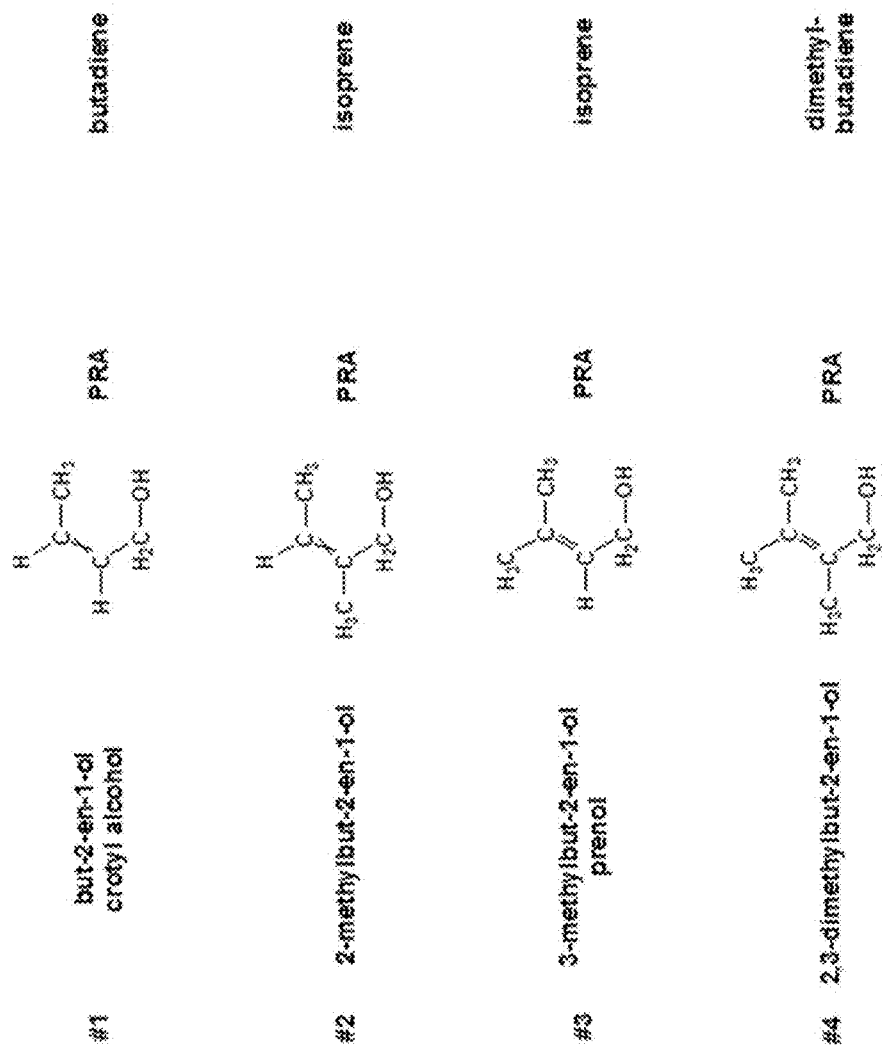

Nucleotide sequence coding for crotyl alcohol dehydratase (codon-optimised for expression in E.coli):

<u>ATGCACCATCATCATCATCAC</u>*ATG*CGTTTTACCCTGAAAACCACCGCAATTGTGAGCGCAGCAG
CACTGCTGGCAGG
TTTTGGTCCTCCGCCTCGTGCAGCAGAACTGCCTCCGGGTCGTCTGGCAACCACCGAAGATTATT
TTGCACAGCAGGCAA
AACAGGCAGTTACACCGGATGTTATGGCACAGCTGGCATATATGAACTATATTGATTTTATCAGCC
CGTTTTATAGCCGT
GGCTGTAGCTTTGAAGCATGGGAACTGAAACATACACCGCAGCGTGTTATCAAATATAGCATTGC
CTTTTATGCCTATGG
TCTGGCAAGCGTTGCACTGATTGATCCGAAACTGCGTGCACTGGCAGGTCATGATCTGGATATTG
CAGTTAGCAAAATGA
AATGCAAACGTGTTTGGGGTGATTGGGAAGAAGATGGTTTTGGCACCGATCCGATTGAAAAAGAA
AACATTATGTATAAA
GGCCATCTGAATCTGATGTATGGTCTGTATCAGCTGGTTACCGGTAGCCGTCGTTATGAAGCAGA
ACATGCACATCTGAC
CCGTATTATTCATGATGAAATTGCAGCAAATCCGTTTGCCGGTATTGTTTGTGAACCGGATAACTA
TTTTGTGCAGTGTA
ATAGCGTTGCCTATCTGAGCCTGTGGGTTTATGATCGTCTGCATGGCACCGATTATCGTGCAGCA
ACCCGTGCATGGCTG
GATTTTATTCAGAAAGATCTGATTGATCCTGAACGCGGTGCCTTTTATCTGAGCTATCATCCGGAA
AGTGGTGCAGTTAA
ACCGTGGATTAGCGCATATACCACCGCATGGACCCTGGCAATGGTTCATGGTATGGACCCTGCA
TTTAGCGAACGTTATT
ATCCGCGTTTTAAACAGACCTTTGTGGAAGTGTATGATGAAGGTCGTAAAGCACGTGTTCGTGAA
ACCGCAGGCACCGAT
GATGCAGATGGTGGTGTTGGTCTGGCCAGCGCATTTACCCTGCTGCTGGCACGTGAAATGGGTG
ATCAGCAACTGTTCGA
TCAGCTGCTGAATCATCTGGAACCTCCGGCAAAACCGAGCATTGTTAGCGCCAGCCTGCGTTATG
AACATCCGGGTAGCC
TGCTGTTTGATGAACTGCTGTTTCTGGCAAAAGTTCATGCCGGTTTTGGTGCCCTGCTGCGTATG
CCTCCTCCGGCAGCA
AAACTGGCAGGTAAGTAATAA

SEQ ID N°3

<u>MHHHHHH</u>*M(1)*RFTLKTTAIVSAAALLAGFGPPPRAAELPPGRLATTEDYFAQQAKQAVTPDVMAQLA
YMNYIDFISPFYSRGCSFEAWELKHTPQRVIKYSIAFYAYGLASVALIDPKLRALAGHDLDIAVSKMKCK
RVWGDWEEDGFGTDPIEKENIMYKGHLNLMYGLYQLVTGSRRYEAEHAHLTRIIHDEIAANPFAGIVC
EPDNYFVQCNSVAYLSLWVYDRLHGTDYRAATRAWLDFIQKDLIDPERGAFYLSYHPESGAVKPWIS
AYTTAWTLAMVHGMDPAFSERYYPRFKQTFVEVYDEGRKARVRETAGTDDADGGVGLASAFTLLLA
REMGDQQLFDQLLNHLEPPAKPSIVSASLRYEHPGSLLFDELLFLAKVHAGFGALLRMPPPAAKLAGK
(397)*

Figure 16

SEQ ID NO: 4
Nucleotide sequence for variant V195F-G132A:

<u>ATGCATCATCATCATCATCAC</u>*ATCACAAGTTTGTACAAAAAAGCAGGCTGTTTT*ACCCTGA
AAACCACCGCAATTGTGAGCGCAGCAGCACTGCTGGCAGGTTTTGGTCCTCCGCCTCGT
GCAGCAGAACTGCCTCCGGGTCGTCTGGCAACCACCGAAGATTATTTTGCACAGCAGGC
AAAACAGGCAGTTACACCGGATGTTATGGCACAGCTGGCATATATGAACTATATTGATTTT
ATCAGCCCGTTTTATAGCCGTGGCTGTAGCTTTGAAGCATGGGAACTGAAACATACACCG
CAGCGTGTTATCAAATATAGCATTGCCTTTTATGCCTATGGTCTGGCAAGCGTTGCACTG
ATTGATCCGAAACTGCGTGCACTGGCAGGTCATGATCTGGATATTGCAGTTAGCAAAATG
AAATGCAAACGTGTTTGGGCGGATTGGGAAGAAGATGGTTTTGGCACCGATCCGATTGA
AAAAGAAAACATTATGTATAAAGGCCATCTGAATCTGATGTATGGTCTGTATCAGCTGGTT
ACCGGTAGCCGTCGTTATGAAGCAGAACATGCACATCTGACCCGTATTATTCATGATGAA
ATTGCAGCAAATCCGTTTGCCGGTATTTTTTGTGAACCGGATAACTATTTTGTGCAGTGTA
ATAGCGTTGCCTATCTGAGCCTGTGGGTTTATGATCGTCTGCATGGCACCGATTATCGTG
CAGCAACCCGTGCATGGCTGGATTTTATTCAGAAAGATCTGATTGATCCTGAACGCGGTG
CCTTTTATCTGAGCTATCATCCGGAAAGTGGTGCAGTTAAACCGTGGATTAGCGCATATA
CCACCGCATGGACCCTGGCAATGGTTCATGGTATGGACCCTGCATTAGCGAACGTTATT
ATCCGCGTTTTAAACAGACCTTTGTGGAAGTGTATGATGAAGGTCGTAAAGCACGTGTTC
GTGAAACCGCAGGCACCGATGATGCAGATGGTGGTGTTGGTCTGGCCAGCGCATTTACC
CTGCTGCTGGCACGTGAAATGGGTGATCAGCAACTGTTCGATCAGCTGCTGAATCATCTG
GAACCTCCGGCAAAACCGAGCATTGTTAGCGCCAGCCTGCGTTATGAACATCCGGGTAG
CCTGCTGTTTGATGAACTGCTGTTTCTGGCAAAAGTTCATGCCGGTTTTGGTGCCCTGCT
GCGTATGCCTCCTCCGGCAGCAAAACTGGCAGGTAAGTAATAA

SEQ ID NO: 5
Amino acid sequence for variant V195F-G132A:

<u>MHHHHHH</u>*ITSLYKKAGCF(3)*TLKTTAIVSAAALLAGFGPPPRAAELPPGRLATTEDYFAQQAK
QAVTPDVMAQLAYMNYIDFISPFYSRGCSFEAWELKHTPQRVIKYSIAFYAYGLASVALIDPKL
RALAGHDLDIAVSKMKCKRVWADWEEDGFGTDPIEKENIMYKGHLNLMYGLYQLVTGSRRY
EAEHAHLTRIIHDEIAANPFAGIFCEPDNYFVQCNSVAYLSLWVYDRLHGTDYRAATRAWLDFI
QKDLIDPERGAFYLSYHPESGAVKPWISAYTTAWTLAMVHGMDPAFSERYYPRFKQTFVEVY
DEGRKARVRETAGTDDADGGVGLASAFTLLLAREMGDQQLFDQLLNHLEPPAKPSIVSASLR
YEHPGSLLFDELLFLAKVHAGFGALLRMPPPAAKLAGK(397)*

Figure 23

SEQ ID NO: 6
Nucleotide sequence for variant V195F:

ATGCATCATCATCATCATCACATCACAAGTTTGTACAAAAAAGCAGGCTGTTTTACCCTGA
AAACCACCGCAATTGTGAGCGCAGCAGCACTGCTGGCAGGTTTTGGTCCTCCGCCTCGT
GCAGCAGAACTGCCTCCGGGTCGTCTGGCAACCACCGAAGATTATTTTGCACAGCAGGC
AAAACAGGCAGTTACACCGGATGTTATGGCACAGCTGGCATATATGAACTATATTGATTTT
ATCAGCCCGTTTTATAGCCGTGGCTGTAGCTTTGAAGCATGGGAACTGAAACATACACCG
CAGCGTGTTATCAAATATAGCATTGCCTTTTATGCCTATGGTCTGGCAAGCGTTGCACTG
ATTGATCCGAAACTGCGTGCACTGGCAGGTCATGATCTGGATATTGCAGTTAGCAAAATG
AAATGCAAACGTGTTTGGGGTGATTGGGAAGAAGATGGTTTTGGCACCGATCCGATTGAA
AAAGAAAACATTATGTATAAAGGCCATCTGAATCTGATGTATGGTCTGTATCAGCTGGTTA
CCGGTAGCCGTCGTTATGAAGCAGAACATGCACATCTGACCCGTATTATTCATGATGAAA
TTGCAGCAAATCCGTTTGCCGGTATTTTTTGTGAACCGGATAACTATTTTGTGCAGTGTAA
TAGCGTTGCCTATCTGAGCCTGTGGGTTTATGATCGTCTGCATGGCACCGATTATCGTGC
AGCAACCCGTGCATGGCTGGATTTTATTCAGAAAGATCTGATTGATCCTGAACGCGGTGC
CTTTTATCTGAGCTATCATCCGGAAAGTGGTGCAGTTAAACCGTGGATTAGCGCATATAC
CACCGCATGGACCCTGGCAATGGTTCATGGTATGGACCCTGCATTTAGCGAACGTTATTA
TCCGCGTTTTAAACAGACCTTTGTGGAAGTGTATGATGAAGGTCGTAAAGCACGTGTTCG
TGAAACCGCAGGCACCGATGATGCAGATGGTGGTGTTGGTCTGGCCAGCGCATTTACCC
TGCTGCTGGCACGTGAAATGGGTGATCAGCAACTGTTCGATCAGCTGCTGAATCATCTG
GAACCTCCGGCAAAACCGAGCATTGTTAGCGCCAGCCTGCGTTATGAACATCCGGGTAG
CCTGCTGTTTGATGAACTGCTGTTTCTGGCAAAAGTTCATGCCGGTTTTGGTGCCCTGCT
GCGTATGCCTCCTCCGGCAGCAAAACTGGCAGGTAAGTAATAA

SEQ ID NO: 7
Amino acid sequence for variant V195F:

MHHHHHHITSLYKKAGCF(3)TLKTTAIVSAAALLAGFGPPPRAAELPPGRLATTEDYFAQQAK
QAVTPDVMAQLAYMNYIDFISPFYSRGCSFEAWELKHTPQRVIKYSIAFYAYGLASVALIDPKL
RALAGHDLDIAVSKMKCKRVWGDWEEDGFGTDPIEKENIMYKGHLNLMYGLYQLVTGSRRY
EAEHAHLTRIIHDEIAANPFAGIFCEPDNYFVQCNSVAYLSLWVYDRLHGTDYRAATRAWLDFI
QKDLIDPERGAFYLSYHPESGAVKPWISAYTTAWTLAMVHGMDPAFSERYYPRFKQTFVEVY
DEGRKARVRETAGTDDADGGVGLASAFTLLLAREMGDQQLFDQLLNHLEPPAKPSIVSASLR
YEHPGSLLFDELLFLAKVHAGFGALLRMPPPAAKLAGK(397)*

Figure 24

SEQ ID NO: 8

Nucleotide sequence for wild type enzyme encoded by peT300NT/DEST:

<u>ATGCATCATCATCATCATCAC</u>*ATCACAAGTTTGTACAAAAAAGCAGGCTGTTTT*ACCCTGA
AAACCACCGCAATTGTGAGCGCAGCAGCACTGCTGGCAGGTTTTGGTCCTCCGCCTCGT
GCAGCAGAACTGCCTCCGGGTCGTCTGGCAACCACCGAAGATTATTTTGCACAGCAGGC
AAAACAGGCAGTTACACCGGATGTTATGGCACAGCTGGCATATATGAACTATATTGATTTT
ATCAGCCCGTTTTATAGCCGTGGCTGTAGCTTTGAAGCATGGGAACTGAAACATACACCG
CAGCGTGTTATCAAATATAGCATTGCCTTTTATGCCTATGGTCTGGCAAGCGTTGCACTG
ATTGATCCGAAACTGCGTGCACTGGCAGGTCATGATCTGGATATTGCAGTTAGCAAAATG
AAATGCAAACGTGTTTGGGGTGATTGGGAAGAAGATGGTTTTGGCACCGATCCGATTGAA
AAAGAAAACATTATGTATAAAGGCCATCTGAATCTGATGTATGGTCTGTATCAGCTGGTTA
CCGGTAGCCGTCGTTATGAAGCAGAACATGCACATCTGACCCGTATTATTCATGATGAAA
TTGCAGCAAATCCGTTTGCCGGTATTGTTTGTGAACCGGATAACTATTTTGTGCAGTGTAA
TAGCGTTGCCTATCTGAGCCTGTGGGTTTATGATCGTCTGCATGGCACCGATTATCGTGC
AGCAACCCGTGCATGGCTGGATTTTATTCAGAAAGATCTGATTGATCCTGAACGCGGTGC
CTTTTATCTGAGCTATCATCCGGAAAGTGGTGCAGTTAAACCGTGGATTAGCGCATATAC
CACCGCATGGACCCTGGCAATGGTTCATGGTATGGACCCTGCATTTAGCGAACGTTATTA
TCCGCGTTTTAAACAGACCTTTGTGGAAGTGTATGATGAAGGTCGTAAAGCACGTGTTCG
TGAAACCGCAGGCACCGATGATGCAGATGGTGGTGTTGGTCTGGCCAGCGCATTTACCC
TGCTGCTGGCACGTGAAATGGGTGATCAGCAACTGTTCGATCAGCTGCTGAATCATCTG
GAACCTCCGGCAAAACCGAGCATTGTTAGCGCCAGCCTGCGTTATGAACATCCGGGTAG
CCTGCTGTTTGATGAACTGCTGTTTCTGGCAAAAGTTCATGCCGGTTTTGGTGCCCTGCT
GCGTATGCCTCCTCCGGCAGCAAAACTGGCAGGTAAGTAATAA

SEQ ID NO: 9

Amino acid sequence for wild type enzyme encoded by peT300NT/DEST:

<u>MHHHHHH</u>*ITSLYKKAGCF(3)*TLKTTAIVSAAALLAGFGPPPRAAELPPGRLATTEDYFAQQAK
QAVTPDVMAQLAYMNYIDFISPFYSRGCSFEAWELKHTPQRVIKYSIAFYAYGLASVALIDPKL
RALAGHDLDIAVSKMKCKRVWGDWEEDGFGTDPIEKENIMYKGHLNLMYGLYQLVTGSRRY
EAEHAHLTRIIHDEIAANPFAGIVCEPDNYFVQCNSVAYLSLWVYDRLHGTDYRAATRAWLDFI
QKDLIDPERGAFYLSYHPESGAVKPWISAYTTAWTLAMVHGMDPAFSERYYPRFKQTFVEVY
DEGRKARVRETAGTDDADGGVGLASAFTLLLAREMGDQQLFDQLLNHLEPPAKPSIVSASLR
YEHPGSLLFDELLFLAKVHAGFGALLRMPPPAAKLAGK(397)*

Figure 25

ALKENOL DEHYDRATASE VARIANTS OF LINALOOL DEHYDRATASE-ISOMERASE

This Application is a 371 National Phase filing of EP 2014060085 filed May 16, 2014, which claims foreign priority of EP13168380.7, filed May 17, 2013 and EP 13196247.4, filed Dec. 9, 2013, which are all incorporated by reference in their entirety.

The subject matter disclosed in this application was as part of a joint research agreement between Scientist of Fortune, S.A. and Global Bioenergies S.A. dated Jul. 8, 2011.

The present invention relates to alkenol dehydratase variants having improved activity in catalyzing the conversion of a compound corresponding to the general formula $C_nH_{2n}O$ into $C_nH_{2n-2}+H_2O$ with $3<n<7$. In particular, the present invention relates to alkenol dehydratase variants having, e.g., an improved activity in converting but-2-en-1-ol (crotyl alcohol) into 1,3 butadiene and/or an improved activity in converting but-3-en-2-ol into 1,3 butadiene and/or an improved activity in converting 3-methylbut-2-en-1-ol (prenol) or 3-methylbut-3-en-2-ol (isoprenol) into isoprene and/or an improved activity in converting 2,3-dimethyl-but-2-en-1-ol into dimethyl-butadiene.

Butadiene (1,3 butadiene) is a conjugated diene with the formula $C_4H_6$. It is an important industrial chemical used as a monomer in the production of synthetic rubber. There exist different possibilities to produce butadiene. Butadiene is, for example, produced as a by-product of the steam cracking process used to produce ethylene and other olefins. In this process butadiene occurs in the C4 stream and is normally isolated from other by-products by extraction into a polar aprotic solvent, such as acetonitrile, from which it is then stripped. Butadiene can also be produced by the catalytic dehydrogenation of normal butane or it can be produced from ethanol. In the latter case, two different processes are in use. In a single-step process, ethanol is converted to butadiene, hydrogen and water at 400-450° C. over a metal oxide catalyst (Kirshenbaum, I. (1978), Butadiene. In M. Grayson (Ed.), *Encyclopedia of Chemical Technology*, 3rd ed., vol. 4, pp. 313-337. New York: John Wiley & Sons). In a two-step process, ethanol is oxidized to acetaldehyde which reacts with additional ethanol over a tantalum-promoted porous silica catalyst at 325-350° C. to yield butadiene (Kirshenbaum, I. (1978), loc cit.). Butadiene can also be produced by catalytic dehydrogenation of normal butenes.

For the past two decades, genetic engineering technologies have made possible the modification of the metabolism of microorganisms, and hence their use to produce key substances which they would otherwise produce at a low yield. By enhancing naturally occurring metabolic pathways, these technologies open up new ways to bio-produce numerous compounds of industrial relevance. Several industrial compounds such as amino-acids for animal feed, biodegradable plastics or textile fibres are now routinely produced using genetically modified organisms. There are however no bio-processes using microorganisms in place for the large scale production of the major petrochemically derived molecules, in particular butadiene, since no microorganisms are known as natural producers of butadiene even in small quantities. Given the large amounts of rubber produced worldwide and the increasing environmental concerns and the limited resources for producing butadiene using chemical processes, there is a need to provide alternative, environmentally-friendly and sustainable processes for the production of butadiene. The same holds true for the production of other conjugated dienes, such as isoprene or dimethylbutadiene.

Recent work has shown that it is possible to generate butadiene through an enzymatic process by converting crotyl alcohol and but-3-en-2-ol into 1,3 butadiene utilizing a dehydratase, in particular a linalool dehydratase-isomerase. The same enzyme can also be used to convert other compounds corresponding to the general formula $C_nH_{2n}O$ into $C_nH_{2n-2}+H_2O$, with $3<n<7$ (FIG. 1).

However, the turnover rate of the enzymes occurring in nature is not yet suitable for industrial applications and hence, there is a need for improvements, i.e., to increase the activity of such enzymes, in particular as regards to a further increase in efficiency of the above processes so as to make them more suitable for industrial purposes.

The present invention addresses this need by providing the embodiments as defined in the claims.

Thus, the present invention provides an alkenol dehydratase variant which is characterized in that it is capable of converting at least one alkenol compound corresponding to the general formula $C_nH_{2n}O$ into a conjugated diene $C_nH_{2n-2}$ with an improved activity over the activity of the alkenol dehydratase from which it is derived.

In particular, the present invention provides a corresponding alkenol dehydratase variant of wherein,
(i) the compound corresponding to the general formula $C_nH_{2n}O$ is crotyl alcohol, but-3-en-2-ol or but-3-en-1-ol and the compound corresponding to the general formula $C_nH_{2n-2}$ is 1,3 butadiene; or
(ii) the compound corresponding to the general formula $C_nH_{2n}O$ is prenol, isoprenol, 2-methyl-but-3-en-1-ol, 2-methyl-but-2-en-1-ol, 3-methyl-but-3-en-2-ol or 2-methyl-but-3-en-2-ol and the compound corresponding to the general formula $C_nH_{2n-2}$ is isoprene; or
(iii) the compound corresponding to the general formula $C_nH_{2n}O$ is 2,3-dimethyl-but-2-en-1-ol, 2,3-dimethyl-but-3-en-2-ol or 2,3-dimethyl-but-3-en-1-ol and the compound corresponding to the general formula $C_nH_{2n-2}$ is dimethylbutadiene.

Thus, compounds to be converted can in particular be crotyl alcohol, but-3-en-2-ol or but-3-en-1-ol (leading to 1,3 butadiene) or prenol, isoprenol, 2-methyl-but-3-en-1-ol, 2-methyl-but-2-en-1-ol, 3-methyl-but-3-en-2-ol or 2-methyl-but-3-en-2-ol (leading to isoprene) or 2,3-dimethyl-but-2-en-1-ol, 2,3-dimethyl-but-3-en-2-ol or 2,3-dimethyl-but-3-en-1-ol (leading to dimethylbutadiene). An improved enzyme variant or an enzyme variant capable of catalyzing a reaction with increased activity is defined as an enzyme variant which differs from the wildtype enzyme and which catalyzes the respective conversion of an alkenol as defined above into a conjugated diene so that the specific activity of the enzyme variant is higher than the specific activity of the wildtype enzyme for at least one given concentration of an alkenol substrate (preferably any alkenol concentration higher than 0 M and up to 1 M). A specific activity is defined as the number of moles of substrate converted to moles of product by unit of time by mole of enzyme. $K_{cat}$ (turnover number) is the specific activity at saturating concentration of substrate.

In particular, in accordance with this first aspect, the present invention provides enzymes which are capable of converting crotyl alcohol into 1,3 butadiene with a turnover rate of at least $0.033 \times 10^{-3}$ s$^{-1}$ of crotyl alcohol into 1,3 butadiene. Such enzymes can be provided by effecting mutations at specific positions in an alkenol dehydratase and the variants obtained by effecting such mutations show an improved activity in catalyzing the conversion of crotyl alcohol into 1,3 butadiene. In a preferred embodiment, the enzyme is capable of converting crotyl alcohol into 1,3 butadiene with a turnover rate of at least $0.05 \times 10^{-3}$ s$^{-1}$, at least $0.1 \times 10^{-3}$ s$^{-1}$, at least $0.15 \times 10^{-3}$ s$^{-1}$, or at least $0.2 \times 10^{-3}$ s$^{-1}$, more preferably of at least $0.5 \times 10^{-3}$ s$^{-1}$ and even more preferably of at least $1.0 \times 10^{-3}$ s$^{-1}$ of crotyl alcohol into 1,3 butadiene. In a particularly preferred embodiment the enzyme has a turnover rate of at least $2 \times 10^{-3}$ s$^{-1}$ of crotyl alcohol into 1,3 butadiene and in a particularly preferred embodiment of at least $4 \times 10^{-3}$ s$^{-1}$. In a most preferred embodiment, the enzyme has a turnover rate of at least $10 \times 10^{-3}$ s$^{-1}$ or at least 1 s$^{-1}$, or at least 10 s$^{-1}$ and even more preferably of at least 100 s$^{-1}$ of crotyl alcohol into 1,3 butadiene. The corresponding wild-type enzyme has a turnover rate of about $0.03 \times 10^{-3}$ s$^{-1}$ of crotyl alcohol into 1,3 butadiene.

In another embodiment, the present invention provides enzymes which are capable of converting crotyl alcohol into 1,3 butadiene with a turnover rate (i.e., a $K_{cat}$-value) which is at least 1.5 times as high compared to the turnover rate of the corresponding wild type enzyme having the amino acid sequence as shown in SEQ ID NO:1. In a preferred embodiment, the enzymes which are capable of converting crotyl alcohol into 1,3 butadiene have a turnover rate (i.e., a $K_{cat}$-value) which is at least 2 times, at least 3 times, at least 5 times or even at least 10 times as high compared to the turnover rate of the corresponding wild type enzyme having the amino acid sequence as shown in SEQ ID NO:1. In even more preferred embodiments, the turnover rate is at least 100 times or even at least 500 times as high compared to that of the corresponding wild type enzyme having the amino acid sequence as shown in SEQ ID NO:1.

The turnover rate of an enzyme capable of converting crotyl alcohol into 1,3 butadiene may be determined by methods known to the person skilled in the art. In one embodiment, this turnover rate is determined as described in the Examples appended hereto. In a particular embodiment this turnover rate can be measured by incubating the enzyme, preferably a cell lysate containing the overexpressed recombinant protein, in vitro. Alternatively, a purified enzyme can be used. More specifically, the enzyme whose turnover rate is to be assessed may be determined as outlined in the following: Michaelis-Menten $k_{cat}$ and $K_m$ steady state kinetics constants for the reaction of conversion of crotyl alcohol into 1,3 butadiene may be determined using the following protocol: The alkenol dehydratase variant is sub-cloned into the commercial Novagen peT-25b+ or pET DEST bacterial expression vector and transformed into BL21(DE3) competent cells and plated out on LB agar plates supplemented with the appropriate antibiotic. Isolated transformants are used to inoculate auto-induction medium (Studier F. W, Protein Expr. Purif. 41 (2005), 207-234) and the culture is incubated overnight at 30° C. in a shaker incubator. The cell pellets containing the overexpressed recombinant enzyme are stored overnight at −80° C. before being resuspended in a lysis buffer (50 mM Tris-Cl pH7.5, 4 mM DTT, 25 mM MgCl$_2$, 25 mM KCl) supplemented with Merck Novagen Lysonase (100 µl of Lysonase in 15 ml of lysis buffer for a cell pellet produced from 1 litre culture). The cell suspension is incubated for 10 minutes at room temperature followed by 20 minutes on ice. Cell lysates are clarified by centrifugation and the supernatant is concentrated 2-fold using a filtration concentrator. The amount of the enzyme variant present in the concentrated soluble fraction is estimated on SDS-PAGE gel against a BSA calibration curve using gel densitometry. Enzymatic reactions are set up in 2 ml glass vials with 450 µl of the cell lysate supernatant, a range of 0 to 100 mM trans-crotyl alcohol, 4 mM DTT, 25 mM MgCl2, 25 mM KCl, 4 mM glutathion and 50 mM Tris-Cl pH7.5. The vials are sealed and incubated for 1 to 6 hours at 37° C. The enzymatic reactions are stopped by incubating them for 5 minutes at 80° C. and the 1,3 butadiene produced is quantified by gas chromatography as described in Example 7. In order to quantify the absolute amount of 1,3 butadiene produced by the reaction, the gas chromatograph is calibrated using a range of concentrations of pure butadiene (1 to 10,000 ppm). The calibration table is linear in this range of butadiene concentrations. The production rates of butadiene (mole of butadiene/mole enzyme/sec) are plotted as a function of the concentration of trans crotyl alcohol and the curve is fitted using the Michaelis Menten equation ($V=(V_{max}*(\text{substrate}))/(K_m+(\text{substrate}))$) to extract the $k_{cat}$ (s$^{-1}$) and the $K_m$ values (mM).

Moreover, in accordance with the first aspect the present invention also provides enzymes which are capable of converting but-3-en-2-ol into 1,3 butadiene with a turnover rate of at least $1.1 \times 10^{-4}$ s$^{-1}$ of but-3-en-2-ol into 1,3 butadiene. Such enzymes can be provided by effecting mutations at specific positions in an alkenol dehydratase and the variants obtained by effecting such mutations show an improved activity in catalyzing the conversion of but-3-en-2-ol into 1,3 butadiene. In a preferred embodiment, the enzyme is capable of converting but-3-en-2-ol into 1,3 butadiene with a turnover rate of at least $5 \times 10^{-4}$ s$^{-1}$, more preferably of at least $1 \times 10^{-3}$ s$^{-1}$ or $5 \times 10^{-3}$ s$^{-1}$, particularly preferred of at least $10.0 \times 10^{-3}$ s$^{-1}$ of but-3-en-2-ol into 1,3 butadiene. In a most preferred embodiment, the enzyme has a turnover rate of at least $13 \times 10^{-3}$ s$^{-1}$ of but-3-en-2-ol into 1,3 butadiene or even more preferred, of at least $20 \times 10^{-3}$ s$^{-1}$ or at least 1 s$^{-1}$, or at least 10 s$^{-1}$ and even more preferably of at least 100 s$^{-1}$. The corresponding wild-type enzyme has a turnover rate of about $1.0 \times 10^{-4}$ s$^{-1}$ of but-3-en-2-ol into 1,3 butadiene.

In another embodiment, the present invention provides enzymes which are capable of converting but-3-en-2-ol into 1,3 butadiene with a turnover rate (i.e., a $K_{cat}$-value) which is at least 1.5 times as high compared to the turnover rate of the corresponding wild type enzyme having the amino acid sequence as shown in SEQ ID NO:1. In a preferred embodiment, the enzymes which are capable of converting but-3-en-2-ol into 1,3 butadiene have a turnover rate (i.e., a $K_{cat}$-value) which is at least 2 times, at least 3 times, at least 5 times or even at least 10 times as high compared to the turnover rate of the corresponding wild type enzyme having the amino acid sequence as shown in SEQ ID NO:1. In even more preferred embodiments, the turnover rate is at least 100 times or even at least 500 times as high compared to that of the corresponding wild type enzyme having the amino acid sequence as shown in SEQ ID NO:1.

The turnover rate of an enzyme capable of converting but-3-en-2-ol into 1,3 butadiene may be determined by methods known to the person skilled in the art. In one embodiment, this turnover rate is determined as described in the Examples appended hereto. In a particular embodiment this turnover rate can be measured by incubating the enzyme, preferably a cell lysate containing the overexpressed recombinant protein, in vitro. Alternatively, a purified enzyme can be used. More specifically, the enzyme whose turnover rate is to be assessed may be determined as outlined in the following: Michaelis-Menten $k_{cat}$(s$^{-1}$) and $K_m$ values (mM) steady state kinetics constants for the reaction of conversion of but-3-en-2-ol into 1,3 butadiene may be determined using the following protocol: The alkenol dehydratase variant is sub-cloned into the commercial Novagen peT-25b+ bacterial expression vector and transformed into BL21(DE3) competent cells and plated out on LB agar plates supplemented with the appropriate antibiotic. Isolated transformants are used to inoculate autoinduction medium (Studier F. W, Protein Expr. Purif. 41 (2005), 207-234) and the culture is incubated overnight at 30° C. in a shaker incubator. Cell pellets containing the overexpressed recombinant enzyme are stored overnight at −80° C. before being resuspended in a lysis buffer (50 mM Tris-Cl pH7.5, 4 mM DTT, 25 mM $MgCl_2$, 25 mM KCl) supplemented with Merck Novagen Lysonase (100 µl of Lysonase in 15 ml of lysis buffer for a cell pellet produced from 1 litre culture). The cell suspension is incubated for 10 minutes at room temperature followed by 20 minutes on ice. Cell lysates are clarified by centrifugation and the supernatant is concentrated 2-fold using a centrifugal concentrator. The amount of the enzyme variant present in the concentrated soluble fraction is estimated on SDS-PAGE gel against a BSA calibration curve using gel densitometry. Enzymatic reactions are set up in 2 ml glass vials with 450 µl of the cell lysate supernatant, a range of 0 to 100 mM but-3-en-2-ol, 4 mM DTT, 25 mM MgCl2, 25 mM KCl, 4 mM glutathion and 50 mM Tris-Cl pH7.5. The vials are sealed and incubated for 1 to 6 hours at 37° C. The enzymatic reactions are stopped by incubating for 5 minutes at 80° C. and the 1,3 butadiene produced is quantified by gas chromatography as described above The production rates of butadiene (mole of butadiene/mole enzyme/sec) are plotted as a function of the concentration of but-3-en-2-ol and the curve is fitted using Michaelis Menten equation ($V=(V_{max}*(\text{substrate}))/(K_m+(\text{substrate}))$) to extract the kcat ($s^{-1}$) and the Km values (mM).

Moreover, in accordance with the first aspect the present invention also provides enzymes which are capable of converting prenol into isoprene with a turnover rate of at least $3.3\times10^{-4}$ $s^{-1}$, preferably of at least $5\times10^{-4}$ $s^{-1}$, more preferably of at least $1\times10^{-3}$ $s^{-1}$, of at least $1\times10^{-2}$ $s^{-1}$ or of at least $1\times10^{-1}$ $s^{-1}$, and even more preferably of at least $5\times10^{-1}$ $s^{-1}$ or of at least $9\times10^{-1}$ $s^{-1}$ or at least 1 $s^{-1}$, or at least 10 $s^{-1}$ and even more preferably of at least 100 $s^{-1}$ of prenol into isoprene. The corresponding wild-type enzyme has a turnover rate of about $3.0\times10^{-4}$ $s^{-1}$ of prenol into isoprene.

In another embodiment, the present invention provides enzymes which are capable of converting prenol into isoprene with a turnover rate (i.e., a $K_{cat}$-value) which is at least 1.5 times as high compared to the turnover rate of the corresponding wild type enzyme having the amino acid sequence as shown in SEQ ID NO:1. In a more preferred embodiment, the enzymes which are capable of converting prenol into isoprene have a turnover rate (i.e., a $K_{cat}$-value) which is at least 2 times, at least 3 times, at least 5 times or even at least 10 times as high compared to the turnover rate of the corresponding wild type enzyme having the amino acid sequence as shown in SEQ ID NO:1. In even more preferred embodiments, the turnover rate is at least 100 times or even at least 500 times as high compared to that of the corresponding wild type enzyme having the amino acid sequence as shown in SEQ ID NO:1.

Such enzymes can be provided by effecting mutations at specific positions in an alkenol dehydratase and the variants obtained by effecting such mutations show an improved activity in catalyzing the conversion of prenol into isoprene. The turnover rate of an enzyme capable of converting prenol into isoprene may be determined by methods known to the person skilled in the art. In one embodiment, this turnover rate is determined as described in the Examples appended hereto. In a particular embodiment this turnover rate can be measured by incubating the enzyme, preferably a cell lysate containing the overexpressed recombinant protein, in vitro. Alternatively, a purified enzyme can be used. More specifically, the enzyme whose turnover rate is to be assessed may be determined as outlined in the following: Michaelis-Menten $k_{cat}$ and $K_m$ steady state kinetic constants for the reaction of conversion of prenol into isoprene may be determined using the following protocol: The alkenol dehydratase variant to be tested is sub-cloned into the commercial pET300/NT-DEST expression vector (Life technologies), transformed into BL21(DE3) competent cells and plated out on LB agar plates supplemented with the appropriate antibiotic. Isolated transformants are used to inoculate auto-induction medium (Studier F. W, Protein Expr. Purif. 41 (2005), 207-234) and the cultures are incubated overnight at 30° C. in a shaker incubator. Cell pellets obtained from a 200 ml culture and containing the overexpressed recombinant enzyme are stored overnight at −80° C. before being resuspended in 3 ml of lysis buffer (50 mM Tris-Cl pH7.5, 4 mM DTT, 25 mM $MgCl_2$, 25 mM KCl, 20 mM glutathion) supplemented with 10 µl Merck Novagen Lysonase. The cell suspension is incubated for 10 minutes at room temperature followed by 20 minutes on ice. Cell lysates are clarified by centrifugation (10 000 rpm for 20 minutes) and the supernatant is concentrated 3-fold using a filtration concentrator (Millipore Amicon) to a final volume of 1 ml. 500 µl enzymatic reactions are set up in 2 ml glass vials with 200 µl of the concentrated cell lysate supernatant (variant), with 200 µl of the concentrated cell lysate supernatant (cell transformed with empty vector) and a range of 20, 40, 80, 120 mM prenol concentrations (Sigma Aldrich). The vials are sealed and incubated for 20, 40, 60, 90, 120 and 180 min at 37° C. The amount of enzyme variants is quantified on SDS-PAGE gel against a BSA calibration curve. The enzymatic reactions are stopped by incubation for 5 minutes at 80° C. and the isoprene produced is quantified by gas chromatography. For the GC headspace analysis, 100 µl of the headspace gas is injected in a Bruker GC450 system equipped with a Restek RT-Alumina column (30 m×0.32 mm) and a Flame ionization detection system (FID). The GC analysis method used to detect isoprene is characterised by a constant oven temperature at 180° C., injector port temperature at 200° C. with a split ratio of 1:10 and the FID detector temperature at 250° C. Nitrogen is used as a carrier gas (constant flow of 1.5 ml/min) and a mixture of air (air flow 300 ml/min), nitrogen (25 ml/min flow) and hydrogen (flow of 30 ml/min) is used to supply the FID detection system. Using these parameters, isoprene has a retention time of 5.75 min. The production rates of isoprene (mole of isoprene/mole enzyme/sec) are plotted as a function of the concentration of prenol and the curve is fitted using the Michaelis Menten equation ($V=(V_{max}*(\text{substrate}))/(K_m+(\text{substrate}))$) to extract the $k_{cat}$ ($s^{-1}$) and the $K_m$ values (mM).

Moreover, in accordance with the first aspect the present invention also provides enzymes which are capable of converting isoprenol into isoprene with a turnover rate of at least $3.3\times10^{-5}$ $s^{-1}$, preferably of at least $5\times10^{-5}$ $s^{-1}$, even more preferably of at least $1\times10^{-4}$ $s^{-1}$ and particularly preferred of at least $3\times10^{-4}$ $s^{-1}$ or at least 1 $s^{-1}$, or at least 10 $s^{-1}$ and even more preferably of at least 100 $s^{-1}$ of isoprenol into isoprene. The corresponding wild-type enzyme has a turnover rate of about $3.0\times10^{-5}$ $s^{-1}$ of isoprenol into isoprene.

In another embodiment, the present invention provides enzymes which are capable of converting isoprenol into isoprene with a turnover rate (i.e., a $K_{cat}$-value) which is at least 1.5 times as high compared to the turnover rate of the corresponding wild type enzyme having the amino acid sequence as shown in SEQ ID NO:1. In a more preferred embodiment, the enzymes which are capable of converting isoprenol into isoprene have a turnover rate (i.e., a $K_{cat}$-value) which is at least 2 times, at least 3 times, at least 5 times or even at least 10 times as high compared to the turnover rate of the corresponding wild type enzyme having the amino acid sequence as shown in SEQ ID NO:1. In even more preferred embodiments, the turnover rate is at least 100 times or even at least 500 times as high compared to that of the corresponding wild type enzyme having the amino acid sequence as shown in SEQ ID NO:1.

Such enzymes can be provided by effecting mutations at specific positions in an alkenol dehydratase and the variants obtained by effecting such mutations show an improved activity in catalyzing the conversion of isoprenol into isoprene. The turnover rate of an enzyme capable of converting isoprenol into isoprene may be determined by methods known to the person skilled in the art. In one embodiment, this turnover rate is determined as described in the Examples appended hereto. In a particular embodiment this turnover rate can be measured by incubating the enzyme, preferably a cell lysate containing the overexpressed recombinant protein, in vitro. Alternatively, a purified enzyme can be used. More specifically, the enzyme whose turnover rate is to be assessed may be determined as already outlined for the determination of the Michaelis-Menten $k_{cat}$ and $K_m$ steady state kinetic constants for the reaction of conversion of prenol into isoprene above, with the exception that isoprenol is used as the substrate instead of prenol.

By providing such enzymes, the present invention allows to dramatically increase the production efficiency of conjugated dienes corresponding to the general formula $C_nH_{2n-2}$, with 3<n<7, such as butadiene, isoprene or dimethyl-butadiene from crotyl alcohol, 3-methyl-but-2-en-1-ol (prenol) or isoprenol or from 2,3-dimethyl-but-2-en-1-ol, respectively.

The term "alkenol dehydratase" refers to an enzyme which can dehydrate an alkenol, preferably, it is an enzyme which can dehydrate at least one compound corresponding to the general formula $C_nH_{2n}O$, with 3<n<7, and wherein the product of the reaction is $C_nH_{2n-2}+H_2O$. This activity can be measured in assays as described herein further below and in the appended Examples. In one preferred embodiment the alkenol dehydratase is a crotyl alcohol dehydratase or a but-3-en-2-ol dehydratase. The term "crotyl alcohol dehydratase" in the context of the present invention refers to an enzyme which is capable converting crotyl alcohol and/or but-3-en-2-ol into 1,3 butadiene. The term "but-3-en-2-ol dehydratase" in the context of the present invention refers to an enzyme which is capable converting but-3-en-2-ol into 1,3 butadiene. These activities can be measured by assays as described further below and in particular in the Example section. It could be shown that enzymes classified as linalool dehydratase-isomerase (EC 4.2.1.127) are suitable alkenol dehydratases and are able to catalyze the conversion of various compounds corresponding to the general formula $C_nH_{2n}O$, with 3<n<7, into $C_nH_{2n-2}+H_2O$, such as, e.g., the conversion of crotyl alcohol or but-3-en-2-ol into 1,3 butadiene or other of other compounds as described herein. A linalool dehydratase-isomerase is an enzyme which has the ability to convert geraniol to linalool via an isomerisation and the ability to convert linalool to myrcene via a dehydration reaction. Thus, in a preferred embodiment the term "alkenol dehydratase" when used in the context of the present invention refers to a linalool dehydratase-isomerase. In another preferred embodiment, the term "alkenol dehydratase" refers to an enzyme which is derived from a linalool dehydratase-isomerase and which has the ability to convert crotyl alcohol or but-3-en-2-ol into 1,3 butadiene. The enzyme designated linalool dehydratase-isomerase has been identified in *Castellaniella defragrans* (formerly *Alcaligenes defragrans*) strain 65Phen (Brodkorb et al., J. Biol. Chem. 285 (2010), 30436-30442). Linalool dehydratase-isomerase is a bifunctional enzyme which is involved in the anaerobic degradation of monoterpenes. The native enzyme has been found to have a molecular mass of 160 kDa and is assumed to be a homotetramer of 40 kDa subunits. The enzyme catalyzes in vitro two reactions in both directions depending on the thermodynamic driving forces. On the one hand, the enzyme catalyzes the isomerisation of the primary allylalcohol geraniol into its stereoisomer linalool which bears a tertiary allyl alcohol motif. On the other hand, the enzyme catalyzes the water secession (dehydration) from the tertiary alcohol linalool to the corresponding acyclic monoterpene beta-myrcene, a molecule bearing a conjugated diene motif. In *Castellaniella defragrans* the protein is expressed as a precursor protein with a signal peptide for a periplasmatic location which is cleaved after transport through the membrane. The enzyme is classified as EC 4.2.1.127. A linalool dehydratase-isomerase has the capacity to catalyze the following reaction under anaerobic conditions:

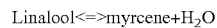
Linalool<=>myrcene+$H_2O$

This activity can, e.g., be measured with an assay as described in Brodkorb et al. (loc. cit.). In such an assay, vials are prewarmed at 35° C., anoxic protein solution is transferred into the vials and DTT is added to 2 mM. The reaction mixtures are sealed with a butyl septum and the headspace is flushed with $CO_2/N_2$ (10/90 (v/v)). The reaction is started by adding a distinct concentration of linalool and incubated at 35° C. The conversion of linalool into myrcene is assessed by investigating the production of myrcene, e.g. by gas chromatography.

In a preferred embodiment, a linalool dehydratase-isomerase also has the capacity to catalyze the isomerisation of geraniol into linalool under anaerobic conditions:

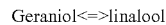
Geraniol<=>linalool

This activity can, e.g., be measured with an assay as described in Brodkorb et al. (loc. cit.). In such an assay, vials are prewarmed at 35° C., anoxic protein solution is transferred into the vials and DTT is added to 2 mM. The reaction mixtures are sealed with a butyl septum and the headspace is flushed with $CO_2/N_2$ (10/90 (v/v)). The reaction is started by adding a distinct concentration of geraniol and incubated at 35° C. The conversion of geraniol into linalool is assessed by investigating the production of myrcene, i.e. the product of the second reaction catalyzed by the enzyme, e.g. by gas chromatography.

Geraniol, linalool and myrcene are acyclic $C_{10}$-terpenoids produced by plants, belonging to the class of allylalcohols and hydrocarbons, respectively. Lüddecke and Harder (Z. Naturforsch. 66c (2011), 409-412) reported on a high substrate specificity of linalool dehydratase-isomerase.

As mentioned above, it had been found that linalool dehydratase-isomerase can act on crotyl alcohol and/or of but-3-en-2-ol converting it into 1,3 butadiene. The present invention provides now improved variants of enzymes which are capable of converting crotyl alcohol and/or but-3-en-2-ol into 1,3 butadiene. The inventors used as a model enzyme the linalool dehydratase-isomerase of *Castellaniella defragrans* shown in SEQ ID NO: 1 and could show that it is possible to provide variants of this enzyme which show increased activity with respect to the conversion of crotyl alcohol and/or but-3-en-2-ol into 1,3 butadiene.

In one preferred embodiment the variants of the present invention are characterized by the feature that they are derived from an alkenol dehydratase, more preferably a linalool dehydratase-isomerase, having the amino acid sequence shown in SEQ ID NO:1 or a highly related sequence (at least 60% identical) and in which mutations are effected at one or more of the indicated positions and by the feature that they show the ability to convert crotyl alcohol and but-3-en-2-ol into 1,3 butadiene or to catalyze both reactions and that they can do this with an improved activity. In a preferred embodiment the variant according to the present invention is derived from a sequence which shows at least 80% sequence identity to SEQ ID NO:1 and in which one or more substitutions and/or deletions and/or insertions at the positions indicated herein below have been effected.

However, the teaching of the present invention is not restricted to the linalool dehydratase-isomerase enzyme of *Castellaniella defragrans* shown in SEQ ID NO: 1 which had been used as a model enzyme but can be extended to alkenol dehydratases from other organisms, in particular to other linalool dehydratase-isomerases, or to enzymes which are structurally related to SEQ ID NO:1 such as, e.g., truncated variants of the enzyme. Thus, the present invention also relates to variants of alkenol dehydratases, in particular to other linalool dehydratase-isomerases, which are structurally related to the *Castellaniella defragrans* sequence (SEQ ID NO: 1) and which show one or more substitutions and/or deletions and/or insertions at positions corresponding to any of the positions as indicated hereinbelow. The term "structurally related" refers to alkenol dehydratases, in particular to linalool dehydratase-isomerases, which show a sequence identity of at least n % to the sequence shown in SEQ ID NO: 1 with n being an integer between 60 and 100, preferably 60, 65, 70, 75, 80, 85, 90, 91, 92, 93, 94, 95, 96, 97, 98 or 99. In a preferred embodiment the structurally related alkenol dehydratases is of prokaryotic origin, even more preferably it stems from a bacterium, most preferably of a bacterium of the genus *Castellaniella*.

Thus, in one embodiment the variant of an alkenol dehydratase, in particular of a linalool dehydratase-isomerase, according to the present invention has or preferably is derived from a sequence which is at least n % identical to SEQ ID NO:1 with n being an integer between 60 and 100, preferably 60, 65, 70, 75, 80, 85, 90, 91, 92, 93, 94, 95, 96, 97, 98 or 99, and it has (a) substitution(s) and/or (a) deletion and/or (an) insertion(s) at a position as indicated below. When the sequences which are compared do not have the same length, the degree of identity either refers to the percentage of amino acid residues in the shorter sequence which are identical to amino acid residues in the longer sequence or to the percentage of amino acid residues in the longer sequence which are identical to amino acid residues in the shorter sequence. Preferably, it refers to the percentage of amino acid residues in the shorter sequence which are identical to amino acid residues in the longer sequence. The degree of sequence identity can be determined according to methods well known in the art using preferably suitable computer algorithms such as CLUSTAL.

When using the Clustal analysis method to determine whether a particular sequence is, for instance, at least 60% identical to a reference sequence default settings may be used or the settings are preferably as follows: Matrix: blosum 30; Open gap penalty: 10.0; Extend gap penalty: 0.05; Delay divergent: 40; Gap separation distance: 8 for comparisons of amino acid sequences. For nucleotide sequence comparisons, the Extend gap penalty is preferably set to 5.0.

In a preferred embodiment ClustalW2 is used for the comparison of amino acid sequences. In the case of pairwise comparisons/alignments, the following settings are preferably chosen: Protein weight matrix: BLOSUM 62; gap open: 10; gap extension: 0.1. In the case of multiple comparisons/alignments, the following settings are preferably chosen: Protein weight matrix: BLOSUM 62; gap open: 10; gap extension: 0.2; gap distance: 5; no end gap.

Preferably, the degree of identity is calculated over the complete length of the sequence.

Amino acid residues located at a position corresponding to a position as indicated herein-below in the amino acid sequence shown in SEQ ID NO:1 can be identified by the skilled person by methods known in the art. For example, such amino acid residues can be identified by aligning the sequence in question with the sequence shown in SEQ ID NO:1 and by identifying the positions which correspond to the above indicated positions of SEQ ID NO:1. The alignment can be done with means and methods known to the skilled person, e.g. by using a known computer algorithm such as the Lipman-Pearson method (Science 227 (1985), 1435) or the CLUSTAL algorithm. It is preferred that in such an alignment maximum homology is assigned to conserved amino acid residues present in the amino acid sequences.

In a preferred embodiment ClustalW2 is used for the comparison of amino acid sequences. In the case of pairwise comparisons/alignments, the following settings are preferably chosen: Protein weight matrix: BLOSUM 62; gap open: 10; gap extension: 0.1. In the case of multiple comparisons/alignments, the following settings are preferably chosen: Protein weight matrix: BLOSUM 62; gap open: 10; gap extension: 0.2; gap distance: 5; no end gap.

When the amino acid sequences of alkenol dehydratases are aligned by means of such a method, regardless of insertions or deletions that occur in the amino acid sequences, the positions of the corresponding amino acid residues can be determined in each of the alkenol dehydratases.

In the context of the present invention, "substituted with another amino acid residue" means that the respective amino acid residues at the indicated position can be substituted with any other possible amino acid residues, e.g. naturally occurring amino acids or non-naturally occurring amino acids (Brustad and Arnold, Curr. Opin. Chem. Biol. 15 (2011), 201-210), preferably with an amino acid residues selected from the group consisting of alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine and valine. Preferred substitutions for certain positions are indicated further below. Moreover, the term "substituted" or "substitution" also means that the respective amino acid residue at the indicated position is modified.

Such modifications include naturally occurring modifications and non-naturally occurring modifications. Naturally occurring modifications include but are not limited to eukaryotic post-translational modification, such as attachment of functional groups (e.g. acetate, phosphate, hydroxyl, lipids (myristoylation of glycine residues) and carbohydrates (e.g. glycosylation of arginine, asparagines etc.). Naturally occurring modifications also encompass the change in the chemical structure by citrullination, carbamylation and disulphide bond formation between cysteine residues; attachment of co-factors (FMN or FAD that can be covalently attached) or the attachment of peptides (e.g. ubiquitination or sumoylation).

Non-naturally occurring modifications include, e.g., in vitro modifications such as biotinylation of lysine residue or the inclusion of non-canonical amino acids (see Liu and Schultz, Annu. Rev. Biochem. 79 (2010), 413-44 and Wang et al., Chem. Bio. 2009 Mar. 27; 16 (3), 323-336; doi: 101016/jchembiol.2009.03.001).

In the context of the present invention, "deleted" or "deletion" means that the amino acid at the corresponding position is deleted.

In the context of the present invention, "inserted" or "insertion" means that at the respective position one or two, preferably one amino acid residue is inserted, preferably in front of the indicated position.

The present invention also relates to the use of the alkenol dehydratase as described herein-above or of a host cell comprising such a alkenol dehydratase for the conversion of crotyl alcohol into 1,3 butadiene.

A. Variants with an Improved Activity to Convert Crotyl Alcohol into 1,3 Butadiene In a second aspect, the present invention relates to a variant of an alkenol dehydratase showing an improved activity in converting an alkenol as defined above, preferably crotyl alcohol into 1,3 butadiene, over the corresponding alkenol dehydratase from which it is derived, wherein the alkenol dehydratase variant is characterized in that it shows one or more substitutions, deletions and/or insertions in comparison to the corresponding sequence from which it is derived and wherein these substitutions, deletions and/or insertions occur at one or more of the positions corresponding to positions 195, 116, 80, 106, 119, 357, 75, 132, 73, 199, 123, 68, 126, 159, 227, 367, 234, 192, 157, 169, 181, 156, 122, 84, 318, 389, 115, 76, 390, 255, 247, 50, 251, 158, 324, 281, 285, 98, 95, 186, 248, 72, 175, 245, 173, 310, 140, 18, 20, 170, 269, 382, 39, 77, 144, 168, 386, 12, 151, 230, 194, 207, 114, 108, 210, 70, 364 and 10 in the amino acid sequence shown in SEQ ID NO:1.

In a preferred embodiment, the variant according to the invention is characterized in that it contains at least two deletions, substitutions and/or insertions wherein the deletion/insertion/substitution is at position 173 in the amino acid sequence shown in SEQ ID NO:1 or at a position corresponding to this position and another deletion/insertion/substitution is at position 181 in the amino acid sequence shown in SEQ ID NO:1 or at a position corresponding to this position. Preferably, such a variant further has one or more substitutions, deletions and/or insertions in comparison to the corresponding sequence from which it is derived and wherein these substitutions, deletions and/or insertions occur at one or more of the positions corresponding to positions 195, 116, 80, 106, 119, 357, 75, 132, 73, 199, 123, 68, 126, 159, 227, 367, 234, 192, 157, 169, 156, 122, 84, 318, 389, 115, 76, 390, 255, 247, 50, 251, 158, 324, 281, 285, 98, 95, 186, 248, 72, 175, 245, 310, 140, 18, 20, 170, 269, 382, 39, 77, 144, 168, 386, 12, 151, 230, 194, 207, 114, 108, 210, 70, 364 and 10 in the amino acid sequence shown in SEQ ID NO:1.

In a preferred embodiment, the variant according to the invention is characterized in that it contains at least two deletions, substitutions and/or insertions wherein the deletion/insertion/substitution is at position 132 in the amino acid sequence shown in SEQ ID NO:1 or at a position corresponding to this position and another deletion/insertion/substitution is at position 195 in the amino acid sequence shown in SEQ ID NO:1 or at a position corresponding to this position. Preferably, such a variant further has one or more substitutions, deletions and/or insertions in comparison to the corresponding sequence from which it is derived and wherein these substitutions, deletions and/or insertions occur at one or more of the positions corresponding to positions 116, 80, 106, 119, 357, 75, 73, 199, 123, 68, 126, 159, 227, 367, 234, 192, 157, 169, 181, 156, 122, 84, 318, 389, 115, 76, 390, 255, 247, 50, 251, 158, 324, 281, 285, 98, 95, 186, 248, 72, 175, 245, 173, 310, 140, 18, 20, 170, 269, 382, 39, 77, 144, 168, 386, 12, 151, 230, 194, 207, 114, 108, 210, 70, 364 and 10 in the amino acid sequence shown in SEQ ID NO:1.

In a preferred embodiment, the variant according to the invention is characterized in that it contains at least two deletions, substitutions and/or insertions wherein the deletion/insertion/substitution is at position 324 in the amino acid sequence shown in SEQ ID NO:1 or at a position corresponding to this position and another deletion/insertion/substitution is at position 195 in the amino acid sequence shown in SEQ ID NO:1 or at a position corresponding to this position. Preferably, such a variant further has one or more substitutions, deletions and/or insertions in comparison to the corresponding sequence from which it is derived and wherein these substitutions, deletions and/or insertions occur at one or more of the positions corresponding to positions 132, 116, 80, 106, 119, 357, 75, 73, 199, 123, 68, 126, 159, 227, 367, 234, 192, 157, 169, 181, 156, 122, 84, 318, 389, 115, 76, 390, 255, 247, 50, 251, 158, 281, 285, 98, 95, 186, 248, 72, 175, 245, 173, 310, 140, 18, 20, 170, 269, 382, 39, 77, 144, 168, 386, 12, 151, 230, 194, 207, 114, 108, 210, 70, 364 and 10 in the amino acid sequence shown in SEQ ID NO:1.

In a preferred embodiment, the variant according to the invention is characterized in that it contains at least two deletions, substitutions and/or insertions wherein the deletion/insertion/substitution is at position 119 in the amino acid sequence shown in SEQ ID NO:1 or at a position corresponding to this position and another deletion/insertion/substitution is at position 195 in the amino acid sequence shown in SEQ ID NO:1 or at a position corresponding to this position. Preferably, such a variant further has one or more substitutions, deletions and/or insertions in comparison to the corresponding sequence from which it is derived and wherein these substitutions, deletions and/or insertions occur at one or more of the positions corresponding to positions 324, 132, 116, 80, 106, 357, 75, 73, 199, 123, 68, 126, 159, 227, 367, 234, 192, 157, 169, 181, 156, 122, 84, 318, 389, 115, 76, 390, 255, 247, 50, 251, 158, 281, 285, 98, 95, 186, 248, 72, 175, 245, 173, 310, 140, 18, 20, 170, 269, 382, 39, 77, 144, 168, 386, 12, 151, 230, 194, 207, 114, 108, 210, 70, 364 and 10 in the amino acid sequence shown in SEQ ID NO:1.

In a preferred embodiment, the variant according to the invention is characterized in that it contains at least two deletions, substitutions and/or insertions wherein the deletion/insertion/substitution is at position 199 in the amino acid sequence shown in SEQ ID NO:1 or at a position corresponding to this position and another deletion/insertion/substitution is at position 195 in the amino acid sequence shown in SEQ ID NO:1 or at a position corresponding to this position. Preferably, such a variant further has one or more substitutions, deletions and/or insertions in comparison to the corresponding sequence from which it is derived and wherein these substitutions, deletions and/or insertions occur at one or more of the positions corresponding to positions 119, 324, 132, 116, 80, 106, 357, 75, 73, 123, 68, 126, 159, 227, 367, 234, 192, 157, 169, 181, 156, 122, 84, 318, 389, 115, 76, 390, 255, 247, 50, 251, 158, 281, 285, 98, 95, 186, 248, 72, 175, 245, 173, 310, 140, 18, 20, 170, 269, 382, 39, 77, 144, 168, 386, 12, 151, 230, 194, 207, 114, 108, 210, 70 364 and 10 in the amino acid sequence shown in SEQ ID NO:1.

In a preferred embodiment, the variant according to the invention is characterized in that it contains at least two deletions, substitutions and/or insertions wherein the deletion/insertion/substitution is at position 132 in the amino acid sequence shown in SEQ ID NO:1 or at a position corresponding to this position and another deletion/insertion/substitution is at position 310 in the amino acid sequence shown in SEQ ID NO:1 or at a position corresponding to this position. Preferably, such a variant further has one or more substitutions, deletions and/or insertions in comparison to the corresponding sequence from which it is derived and wherein these substitutions, deletions and/or insertions occur at one or more of the positions corresponding to positions 199, 195, 119, 324, 116, 80, 106, 357, 75, 73, 123, 68, 126, 159, 227, 367, 234, 192, 157, 169, 181, 156, 122, 84, 318, 389, 115, 76, 390, 255, 247, 50, 251, 158, 281, 285, 98, 95, 186, 248, 72, 175, 245, 173, 140, 18, 20, 170, 269, 382, 39, 77, 144, 168, 386, 12, 151, 230, 194, 207, 114, 108, 210, 70, 364 and 10 in the amino acid sequence shown in SEQ ID NO:1.

In a preferred embodiment, the variant according to the invention is characterized in that it contains at least two deletions, substitutions and/or insertions wherein the deletion/insertion/substitution is at position 132 in the amino acid sequence shown in SEQ ID NO:1 or at a position corresponding to this position and another deletion/insertion/substitution is at position 140 in the amino acid sequence shown in SEQ ID NO:1 or at a position corresponding to this position. Preferably, such a variant further has one or more substitutions, deletions and/or insertions in comparison to the corresponding sequence from which it is derived and wherein these substitutions, deletions and/or insertions occur at one or more of the positions corresponding to positions 199, 195, 119, 324, 116, 80, 106, 357, 75, 73, 123, 68, 126, 159, 227, 367, 234, 192, 157, 169, 181, 156, 122, 84, 318, 389, 115, 76, 390, 255, 247, 50, 251, 158, 281, 285, 98, 95, 186, 248, 72, 175, 245, 173, 310, 140, 18, 20, 170, 269, 382, 39, 77, 144, 168, 386, 12, 151, 230, 194, 207, 114, 108, 210, 70, 364 and 10 in the amino acid sequence shown in SEQ ID NO:1.

In even more preferred embodiments, the variant according to the invention showing an improved activity in converting crotyl alcohol into 1,3 butadiene is characterized in that it has multiple mutations. As it is exemplified in the examples further below, variants have been found bearing multiple mutations which exhibit an increase in the reaction rate of the conversion of crotyl alcohol into 1,3 butadiene. These variants bearing multiple mutations are summarized in the following:

Accordingly, in a very preferred embodiment, the variant according to the invention is characterized in that it comprises deletions, substitutions and/or insertions wherein the deletions/insertions/substitutions are at positions 195, 18, 20, 73, 132, 170, 181, 199, 269 and 367 in the amino acid sequence shown in SEQ ID NO:1 or at positions corresponding to these positions. Preferably, such a variant has the following substitutions in the amino acid sequence shown in SEQ ID NO:1 or at positions corresponding to these position:
V195FA18IF20LG73SG132MR170KI181LD199NW269AL367F.

In another preferred embodiment, the variant according to the invention is characterized in that it comprises deletions, substitutions and/or insertions wherein the deletions/insertions/substitutions are at positions 195, 73, 170, 181 and 324 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FG73SR170KI181LF324S.

In another preferred embodiment, the variant according to the invention is characterized in that it comprises deletions, substitutions and/or insertions wherein the deletions/insertions/substitutions are at positions 195, 367 and 382 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FL367FG382D.

In another preferred embodiment, the variant according to the invention is characterized in that it comprises deletions, substitutions and/or insertions wherein the deletions/insertions/substitutions are at positions 195, 18, 73, 170, 199, 324 and 367 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FA18IG73SR170KD199NF324SL367F.

In another preferred embodiment, the variant according to the invention is characterized in that it comprises deletions, substitutions and/or insertions wherein the deletions/insertions/substitutions are at positions 195, 18, 20, 39, 132, 170, 181, 324 and 367 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FA18IF20LD39AG132VR170KI181LF324SL367F.

In another preferred embodiment, the variant according to the invention is characterized in that it comprises deletions, substitutions and/or insertions wherein the deletions/insertions/substitutions are at positions 195, 132, 73 and 77 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FG132AG73SE77I.

In another preferred embodiment, the variant according to the invention is characterized in that it comprises deletions, substitutions and/or insertions wherein the deletions/insertions/substitutions are at positions 195, 73, 181, 324 and 367 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FG73SI181LF324SL367F.

In another preferred embodiment, the variant according to the invention is characterized in that it comprises deletions, substitutions and/or insertions wherein the deletions/insertions/substitutions are at positions 195, 18, 20, 39, 73, 144, 170, 181, 199, 324 and 367 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FA18VF20LD39AG73SI144TR170KI181LD199NF324SL367F.

In another preferred embodiment, the variant according to the invention is characterized in that it comprises deletions, substitutions and/or insertions wherein the deletions/insertions/substitutions are at positions 195, 18, 73, 123, 132, 170, 181, 199 and 269 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FA18VG73SS123EG132SR170KI181LD199NW269A.

In another preferred embodiment, the variant according to the invention is characterized in that it comprises deletions, substitutions and/or insertions wherein the deletions/insertions/substitutions are at positions 195, 18, 39, 170, 181, 199, 324, and 367 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FA18VD39AR170KI181LD199NF324SL367F.

In another preferred embodiment, the variant according to the invention is characterized in that it comprises deletions, substitutions and/or insertions wherein the deletions/insertions/substitutions are at positions 195, 73, 132, 170, 181 and 269 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FG73SG132QR170KI181SW269A.

In another preferred embodiment, the variant according to the invention is characterized in that it comprises deletions, substitutions and/or insertions wherein the deletions/insertions/substitutions are at positions 195, 18, 20, 39, 132, 170, 181 and 269 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FA18VF20LD39AG132KR170KI181LW269A.

In another preferred embodiment, the variant according to the invention is characterized in that it comprises deletions, substitutions and/or insertions wherein the deletions/insertions/substitutions are at positions 195, 18, 132 and 269 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FA18VG132MW269A.

In another preferred embodiment, the variant according to the invention is characterized in that it comprises deletions, substitutions and/or insertions wherein the deletions/insertions/substitutions are at positions 195, 132, 170, 173, 181 and 324 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FG132VR170KA173RI181LF324S.

In another preferred embodiment, the variant according to the invention is characterized in that it comprises deletions, substitutions and/or insertions wherein the deletions/insertions/substitutions are at positions 195, 132, 73, and 77 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FG132AG73SE77L.

In another preferred embodiment, the variant according to the invention is characterized in that it comprises deletions, substitutions and/or insertions wherein the deletions/insertions/substitutions are at positions 195, 18, 73, 170, 173, and 389 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FA18VG73SR170KA173RP389L.

In another preferred embodiment, the variant according to the invention is characterized in that it comprises deletions, substitutions and/or insertions wherein the deletions/insertions/substitutions are at positions 195, 168, 170, 324, and 367 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FS168NR170KF324SL367F.

In another preferred embodiment, the variant according to the invention is characterized in that it comprises deletions, substitutions and/or insertions wherein the deletions/insertions/substitutions are at positions 195, 39, 73, 77, 132, 170, 199, 367, and 382 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FD39AG73SE77IG132QR170KD199NL367FG382D.

In another preferred embodiment, the variant according to the invention is characterized in that it comprises deletions, substitutions and/or insertions wherein the deletions/insertions/substitutions are at positions 195, 18, 73, 77, and 386 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FA18VG73SE77IR386S.

In another preferred embodiment, the variant according to the invention is characterized in that it comprises deletions, substitutions and/or insertions wherein the deletions/insertions/substitutions are at positions 195, 39, 73, 170, 181, 199, and 324 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FD39AG73SR170KI181LD199NF324S.

In another preferred embodiment, the variant according to the invention is characterized in that it comprises deletions, substitutions and/or insertions wherein the deletions/insertions/substitutions are at positions 195 and 324 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FF324S.

In another preferred embodiment, the variant according to the invention is characterized in that it comprises deletions, substitutions and/or insertions wherein the deletions/insertions/substitutions are at positions 132, 195, 73, and 77 in the amino acid sequence shown in SEQ ID NO:1 or at positions corresponding to these positions. Preferably, such a variant has the following substitutions in the amino acid sequence shown in SEQ ID NO:1 or at positions corresponding to these positions: G132AV195FG73S-E77L.

In another preferred embodiment, the variant according to the invention is characterized in that it comprises deletions, substitutions and/or insertions wherein the deletions/insertions/substitutions are at positions 195, 132, and 324 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FG132VF324S.

In another preferred embodiment, the variant according to the invention is characterized in that it comprises deletions, substitutions and/or insertions wherein the deletions/insertions/substitutions are at positions 195, 199, and 324 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FD199NF324S.

In another preferred embodiment, the variant according to the invention is characterized in that it comprises deletions, substitutions and/or insertions wherein the deletions/insertions/substitutions are at positions 195, 170, 173, and 324 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FR170KA173RF324S.

In another preferred embodiment, the variant according to the invention is characterized in that it comprises deletions, substitutions and/or insertions wherein the deletions/insertions/substitutions are at positions 195, 132, 181, and 324 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FG132MI181LF324S.

In another preferred embodiment, the variant according to the invention is characterized in that it comprises deletions, substitutions and/or insertions wherein the deletions/insertions/substitutions are at positions 195, 132, and 324 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FG132QF324S.

In another preferred embodiment, the variant according to the invention is characterized in that it comprises deletions, substitutions and/or insertions wherein the deletions/insertions/substitutions are at positions 195, 132, and 324 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FG132MF324S.

In another preferred embodiment, the variant according to the invention is characterized in that it comprises deletions, substitutions and/or insertions wherein the deletions/insertions/substitutions are at positions 195, 132, and 324 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FG132LF324S.

In another preferred embodiment, the variant according to the invention is characterized in that it comprises deletions, substitutions and/or insertions wherein the deletions/insertions/substitutions are at positions 195, 119, 123, and 367 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FD119GS123EL367F.

In another preferred embodiment, the variant according to the invention is characterized in that it comprises deletions, substitutions and/or insertions wherein the deletions/insertions/substitutions are at positions 195 and 12 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FS12L.

In another preferred embodiment, the variant according to the invention is characterized in that it comprises deletions, substitutions and/or insertions wherein the deletions/insertions/substitutions are at positions 195, 132, and 199 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FG132AD199N.

In another preferred embodiment, the variant according to the invention is characterized in that it comprises deletions, substitutions and/or insertions wherein the deletions/insertions/substitutions are at positions 195, 119, and 123 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FD119GS123E.

In another preferred embodiment, the variant according to the invention is characterized in that it comprises deletions, substitutions and/or insertions wherein the deletions/insertions/substitutions are at positions 195, 119, and 132 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FD119GG132A.

In another preferred embodiment, the variant according to the invention is characterized in that it comprises deletions, substitutions and/or insertions wherein the deletions/insertions/substitutions are at positions 132, 195, and 170 in the amino acid sequence shown in SEQ ID NO:1 or at positions corresponding to these positions. Preferably, such a variant has the following substitutions in the amino acid sequence shown in SEQ ID NO:1 or at positions corresponding to these positions: G132AV195FR170K.

In another preferred embodiment, the variant according to the invention is characterized in that it comprises deletions, substitutions and/or insertions wherein the deletions/insertions/substitutions are at positions 195, 132, and 324 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FG132RF324S.

In another preferred embodiment, the variant according to the invention is characterized in that it comprises deletions, substitutions and/or insertions wherein the deletions/insertions/substitutions are at positions 195, 132, and 199 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FG132TD199N.

In another preferred embodiment, the variant according to the invention is characterized in that it comprises deletions, substitutions and/or insertions wherein the deletions/insertions/substitutions are at positions 195, 132, 199, and 324 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FG132AD199NF324S.

In another preferred embodiment, the variant according to the invention is characterized in that it comprises deletions, substitutions and/or insertions wherein the deletions/insertions/substitutions are at positions 195, 132, and 173 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FG132AA173R.

In another preferred embodiment, the variant according to the invention is characterized in that it comprises deletions, substitutions and/or insertions wherein the deletions/insertions/substitutions are at positions 195, 132, and 170 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FG132AR170K.

In another preferred embodiment, the variant according to the invention is characterized in that it comprises deletions, substitutions and/or insertions wherein the deletions/insertions/substitutions are at positions 195, 132, 199, and 324 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FG132ED199NF324S.

In another preferred embodiment, the variant according to the invention is characterized in that it comprises deletions, substitutions and/or insertions wherein the deletions/insertions/substitutions are at positions 132, 195, and 20 in the amino acid sequence shown in SEQ ID NO:1 or at positions corresponding to these positions. Preferably, such a variant has the following substitutions in the amino acid sequence shown in SEQ ID NO:1 or at positions corresponding to these positions: G132AV195FF20L.

In another preferred embodiment, the variant according to the invention is characterized in that it comprises deletions, substitutions and/or insertions wherein the deletions/insertions/substitutions are at positions 195, 132, and 269 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FG132AW269A.

In another preferred embodiment, the variant according to the invention is characterized in that it comprises deletions, substitutions and/or insertions wherein the deletions/insertions/substitutions are at positions 195, 132, and 199 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FG132SD199N.

In another preferred embodiment, the variant according to the invention is characterized in that it comprises deletions, substitutions and/or insertions wherein the deletions/insertions/substitutions are at positions 195, 132, and 199 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FG132ND199N.

In another preferred embodiment, the variant according to the invention is characterized in that it comprises deletions, substitutions and/or insertions wherein the deletions/insertions/substitutions are at positions 195, 132, 199, and 324 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FG132QD199NF324S.

In another preferred embodiment, the variant according to the invention is characterized in that it comprises deletions, substitutions and/or insertions wherein the deletions/insertions/substitutions are at positions 132, 195, and 269 in the amino acid sequence shown in SEQ ID NO:1 or at positions corresponding to these positions. Preferably, such a variant has the following substitutions in the amino acid sequence shown in SEQ ID NO:1 or at positions corresponding to these positions: G132AV195FW269A.

In another preferred embodiment, the variant according to the invention is characterized in that it comprises deletions, substitutions and/or insertions wherein the deletions/insertions/substitutions are at positions 195, 132, and 199 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FG132KD199N.

In another preferred embodiment, the variant according to the invention is characterized in that it comprises deletions, substitutions and/or insertions wherein the deletions/insertions/substitutions are at positions 132, 195, and 39 in the amino acid sequence shown in SEQ ID NO:1 or at positions corresponding to these positions. Preferably, such a variant has the following substitutions in the amino acid sequence shown in SEQ ID NO:1 or at positions corresponding to these positions: G132AV195FD39A.

In another preferred embodiment, the variant according to the invention is characterized in that it comprises deletions, substitutions and/or insertions wherein the deletions/insertions/substitutions are at positions 132, 195, and 18 in the amino acid sequence shown in SEQ ID NO:1 or at positions corresponding to these positions. Preferably, such a variant has the following substitutions in the amino acid sequence shown in SEQ ID NO:1 or at positions corresponding to these positions: G132AV195FA18I.

In another preferred embodiment, the variant according to the invention is characterized in that it comprises deletions, substitutions and/or insertions wherein the deletions/insertions/substitutions are at positions 132, 195, and 119 in the amino acid sequence shown in SEQ ID NO:1 or at positions corresponding to these positions. Preferably, such a variant has the following substitutions in the amino acid sequence shown in SEQ ID NO:1 or at positions corresponding to these positions: G132AV195FD119G.

In another preferred embodiment, the variant according to the invention is characterized in that it comprises deletions, substitutions and/or insertions wherein the deletions/insertions/substitutions are at positions 132, 195, and 173 in the amino acid sequence shown in SEQ ID NO:1 or at positions corresponding to these positions. Preferably, such a variant has the following substitutions in the amino acid sequence shown in SEQ ID NO:1 or at positions corresponding to these positions: G132AV195FA173R.

In another preferred embodiment, the variant according to the invention is characterized in that it comprises deletions, substitutions and/or insertions wherein the deletions/insertions/substitutions are at positions 195, 132, 181, and 199 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FG132QI181SD199N.

In another preferred embodiment, the variant according to the invention is characterized in that it comprises deletions, substitutions and/or insertions wherein the deletions/insertions/substitutions are at positions 195, 132, 199, and 324 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FG132RD199NF324S.

In another preferred embodiment, the variant according to the invention is characterized in that it comprises deletions, substitutions and/or insertions wherein the deletions/insertions/substitutions are at positions 195, 132, 181, and 199 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FG132KI181LD199N.

In another preferred embodiment, the variant according to the invention is characterized in that it comprises deletions, substitutions and/or insertions wherein the deletions/insertions/substitutions are at positions 132 and 324 in the amino acid sequence shown in SEQ ID NO:1 or at positions corresponding to these positions. Preferably, such a variant has the following substitutions in the amino acid sequence shown in SEQ ID NO:1 or at positions corresponding to these positions: G132RF324S.

In another preferred embodiment, the variant according to the invention is characterized in that it comprises deletions, substitutions and/or insertions wherein the deletions/insertions/substitutions are at positions 195, 119, and 132 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FD119GG132K.

In another preferred embodiment, the variant according to the invention is characterized in that it comprises deletions, substitutions and/or insertions wherein the deletions/insertions/substitutions are at positions 195, 132, and 20 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FG132AF20L.

In another preferred embodiment, the variant according to the invention is characterized in that it comprises deletions, substitutions and/or insertions wherein the deletions/insertions/substitutions are at positions 195, 119, and 122 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195 FD119GV122L.

In another preferred embodiment, the variant according to the invention is characterized in that it comprises deletions, substitutions and/or insertions wherein the deletions/insertions/substitutions are at positions 195, 132, 199, and 324 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FG132TD199NF324S.

In another preferred embodiment, the variant according to the invention is characterized in that it comprises deletions, substitutions and/or insertions wherein the deletions/insertions/substitutions are at positions 195, 119, 123, and 324 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FD119GS123EF324S.

In another preferred embodiment, the variant according to the invention is characterized in that it comprises deletions, substitutions and/or insertions wherein the deletions/insertions/substitutions are at positions 195, 119, and 151 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FD119GY151M.

In another preferred embodiment, the variant according to the invention is characterized in that it comprises deletions, substitutions and/or insertions wherein the deletions/insertions/substitutions are at positions 195 and 230 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FA230Q.

In another preferred embodiment, the variant according to the invention is characterized in that it comprises deletions, substitutions and/or insertions wherein the deletions/insertions/substitutions are at positions 132, 195, and 18 in the amino acid sequence shown in SEQ ID NO:1 or at positions corresponding to these positions. Preferably, such a variant has the following substitutions in the amino acid sequence shown in SEQ ID NO:1 or at positions corresponding to these positions: G132AV195FA18V.

In another preferred embodiment, the variant according to the invention is characterized in that it comprises deletions, substitutions and/or insertions wherein the deletions/insertions/substitutions are at positions 195, 132, and 18 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FG132AA18I.

In another preferred embodiment, the variant according to the invention is characterized in that it comprises deletions, substitutions and/or insertions wherein the deletions/insertions/substitutions are at positions 195, 122, and 132 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FV122LG132Q.

In another preferred embodiment, the variant according to the invention is characterized in that it comprises deletions, substitutions and/or insertions wherein the deletions/insertions/substitutions are at positions 195, 132, and 324 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FG132KF324S.

In another preferred embodiment, the variant according to the invention is characterized in that it comprises deletions, substitutions and/or insertions wherein the deletions/insertions/substitutions are at positions 195, 119, and 251 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FD119GY251M.

In another preferred embodiment, the variant according to the invention is characterized in that it comprises deletions, substitutions and/or insertions wherein the deletions/insertions/substitutions are at positions 195, 132, and 18 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FG132AA18V.

In another preferred embodiment, the variant according to the invention is characterized in that it comprises deletions, substitutions and/or insertions wherein the deletions/insertions/substitutions are at positions 195, 132, 199, and 324 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FG132VD199NF324S.

In another preferred embodiment, the variant according to the invention is characterized in that it comprises deletions, substitutions and/or insertions wherein the deletions/insertions/substitutions are at positions 195, 132, and 199 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FG132LD199N.

In another preferred embodiment, the variant according to the invention is characterized in that it comprises deletions, substitutions and/or insertions wherein the deletions/insertions/substitutions are at positions 195, 132, 199, and 324 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FG132MD199NF324S.

In another preferred embodiment, the variant according to the invention is characterized in that it comprises deletions, substitutions and/or insertions wherein the deletions/insertions/substitutions are at positions 195, 126, 132, and 199 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FK126AG132AD199N.

In another preferred embodiment, the variant according to the invention is characterized in that it comprises deletions, substitutions and/or insertions wherein the deletions/insertions/substitutions are at positions 195, 119, and 132 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FD119GG132T.

In another preferred embodiment, the variant according to the invention is characterized in that it comprises deletions, substitutions and/or insertions wherein the deletions/insertions/substitutions are at positions 195, 132, and 39 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FG132AD39A.

In another preferred embodiment, the variant according to the invention is characterized in that it comprises deletions, substitutions and/or insertions wherein the deletions/insertions/substitutions are at positions 195, 132, and 119 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FG132AD119G.

In another preferred embodiment, the variant according to the invention is characterized in that it comprises deletions, substitutions and/or insertions wherein the deletions/insertions/substitutions are at positions 132, 194, and 207 in the amino acid sequence shown in SEQ ID NO:1 or at positions corresponding to these positions. Preferably, such a variant has the following substitutions in the amino acid sequence shown in SEQ ID NO:1 or at positions corresponding to these positions: G132AI194RS207A.

In another preferred embodiment, the variant according to the invention is characterized in that it comprises deletions, substitutions and/or insertions wherein the deletions/insertions/substitutions are at positions 195, 132, and 285 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FG132AY285L.

In another preferred embodiment, the variant according to the invention is characterized in that it comprises deletions, substitutions and/or insertions wherein the deletions/insertions/substitutions are at positions 195, 132, and 199 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FG132RD199N.

In another preferred embodiment, the variant according to the invention is characterized in that it comprises deletions, substitutions and/or insertions wherein the deletions/insertions/substitutions are at positions 195, 132, and 389 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FG132KP389S.

In another preferred embodiment, the variant according to the invention is characterized in that it comprises deletions, substitutions and/or insertions wherein the deletions/insertions/substitutions are at positions 195, 132, and 318 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FG132QV318A.

In another preferred embodiment, the variant according to the invention is characterized in that it comprises deletions, substitutions and/or insertions wherein the deletions/insertions/substitutions are at positions 195, 132, and 159 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FG132QY159M.

In another preferred embodiment, the variant according to the invention is characterized in that it comprises deletions, substitutions and/or insertions wherein the deletions/insertions/substitutions are at positions 195, 132, and 199 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FG132ND199N.

In another preferred embodiment, the variant according to the invention is characterized in that it comprises deletions, substitutions and/or insertions wherein the deletions/insertions/substitutions are at positions 195, 119, and 123 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FD119GS123Q.

In another preferred embodiment, the variant according to the invention is characterized in that it comprises deletions, substitutions and/or insertions wherein the deletions/insertions/substitutions are at positions 195, 132, and 199 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FG132QD199N.

In another preferred embodiment, the variant according to the invention is characterized in that it comprises deletions, substitutions and/or insertions wherein the deletions/insertions/substitutions are at positions 195, 132, 114, and 122 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FG132AA114SV122I.

In another preferred embodiment, the variant according to the invention is characterized in that it comprises deletions, substitutions and/or insertions wherein the deletions/insertions/substitutions are at positions 195, 199, and 367 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FD199NL367F.

In another preferred embodiment, the variant according to the invention is characterized in that it comprises deletions, substitutions and/or insertions wherein the deletions/insertions/substitutions are at positions 195, 119, and 132 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FD119GG132S.

In another preferred embodiment, the variant according to the invention is characterized in that it comprises deletions, substitutions and/or insertions wherein the deletions/insertions/substitutions are at positions 195, 132, and 367 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FG132KL367F.

In another preferred embodiment, the variant according to the invention is characterized in that it comprises deletions, substitutions and/or insertions wherein the deletions/insertions/substitutions are at positions 195, 119, and 123 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FD119GS123H.

In another preferred embodiment, the variant according to the invention is characterized in that it comprises deletions, substitutions and/or insertions wherein the deletions/insertions/substitutions are at positions 195, 132, 169, and 199 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FG132KR169ND199N.

In another preferred embodiment, the variant according to the invention is characterized in that it comprises deletions, substitutions and/or insertions wherein the deletions/insertions/substitutions are at positions 195, 132, and 199 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FG132DD199N.

In another preferred embodiment, the variant according to the invention is characterized in that it comprises deletions, substitutions and/or insertions wherein the deletions/insertions/substitutions are at positions 195, 132, 199, and 119 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FG132TD199N/D119G.

In another preferred embodiment, the variant according to the invention is characterized in that it comprises deletions, substitutions and/or insertions wherein the deletions/insertions/substitutions are at positions 195, 122, and 132 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FV122IG132L.

In another preferred embodiment, the variant according to the invention is characterized in that it comprises deletions, substitutions and/or insertions wherein the deletions/insertions/substitutions are at positions 195, 199, and 318 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FD199NV318A.

In another preferred embodiment, the variant according to the invention is characterized in that it comprises deletions, substitutions and/or insertions wherein the deletions/insertions/substitutions are at positions 195, 119, and 132 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FD119GG132N.

In another preferred embodiment, the variant according to the invention is characterized in that it comprises deletions, substitutions and/or insertions wherein the deletions/insertions/substitutions are at positions 195, 119, 123, and 367 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FD119GS123EL367F.

In another preferred embodiment, the variant according to the invention is characterized in that it comprises deletions, substitutions and/or insertions wherein the deletions/insertions/substitutions are at positions 195, 132, and 119 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FG132KD119G.

In another preferred embodiment, the variant according to the invention is characterized in that it comprises deletions, substitutions and/or insertions wherein the deletions/insertions/substitutions are at positions 195, 119, and 324 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FLD119GGF324S.

In another preferred embodiment, the variant according to the invention is characterized in that it comprises deletions, substitutions and/or insertions wherein the deletions/insertions/substitutions are at positions 195, 106, 119, 123, and 132 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FI106ND119GS123EG132M.

In another preferred embodiment, the variant according to the invention is characterized in that it comprises deletions, substitutions and/or insertions wherein the deletions/insertions/substitutions are at positions 195, 132, and 199 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FG132HD199N.

In another preferred embodiment, the variant according to the invention is characterized in that it comprises deletions, substitutions and/or insertions wherein the deletions/insertions/substitutions are at positions 195, 132, and 181 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FG132QI181L.

In another preferred embodiment, the variant according to the invention is characterized in that it comprises deletions, substitutions and/or insertions wherein the deletions/insertions/substitutions are at positions 195, 158, and 324 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FM158IF324S.

In another preferred embodiment, the variant according to the invention is characterized in that it comprises deletions, substitutions and/or insertions wherein the deletions/insertions/substitutions are at positions 195, 123, and 324 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FS123TF324S.

In another preferred embodiment, the variant according to the invention is characterized in that it comprises deletions, substitutions and/or insertions wherein the deletions/insertions/substitutions are at positions 195, 122, and 132 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FV122LG132V.

In another preferred embodiment, the variant according to the invention is characterized in that it comprises deletions, substitutions and/or insertions wherein the deletions/insertions/substitutions are at positions 195, 199, and 251 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FD199N/Y251L.

In another preferred embodiment, the variant according to the invention is characterized in that it comprises deletions, substitutions and/or insertions wherein the deletions/insertions/substitutions are at positions 195, 119, and 123 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FD119GS123R.

In another preferred embodiment, the variant according to the invention is characterized in that it comprises deletions, substitutions and/or insertions wherein the deletions/insertions/substitutions are at positions 195, 119, and 123 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FD119GS123D.

In another preferred embodiment, the variant according to the invention is characterized in that it comprises deletions, substitutions and/or insertions wherein the deletions/insertions/substitutions are at positions 132, and 195 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FG132T In another preferred embodiment, the variant according to the invention is characterized in that it comprises deletions, substitutions and/or insertions wherein the deletions/insertions/substitutions are at positions 195, 132, and 227 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FG132VA227I.

In another preferred embodiment, the variant according to the invention is characterized in that it comprises deletions, substitutions and/or insertions wherein the deletions/insertions/substitutions are at positions 195, 119, 132, and 251 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FD119GG132KY251M.

In another preferred embodiment, the variant according to the invention is characterized in that it comprises deletions, substitutions and/or insertions wherein the deletions/insertions/substitutions are at positions 195, 132, 158, and 199 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FG132KM158ID199N.

In another preferred embodiment, the variant according to the invention is characterized in that it comprises deletions, substitutions and/or insertions wherein the deletions/insertions/substitutions are at positions 195, 123, and 199 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FS123ED199N.

In another preferred embodiment, the variant according to the invention is characterized in that it comprises deletions, substitutions and/or insertions wherein the deletions/insertions/substitutions are at positions 195, 132, 169, and 199 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FG132KR169TD199N.

In another preferred embodiment, the variant according to the invention is characterized in that it comprises deletions, substitutions and/or insertions wherein the deletions/insertions/substitutions are at positions 195, 119, 132, and 251 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FD119GG132EY251M.

In another preferred embodiment, the variant according to the invention is characterized in that it comprises deletions, substitutions and/or insertions wherein the deletions/insertions/substitutions are at positions 195, 119, 132, and 251 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FD119GG132AY251M.

In another preferred embodiment, the variant according to the invention is characterized in that it comprises deletions, substitutions and/or insertions wherein the deletions/insertions/substitutions are at positions 195, 115, and 119 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FG115AD119G.

In another preferred embodiment, the variant according to the invention is characterized in that it comprises deletions, substitutions and/or insertions wherein the deletions/insertions/substitutions are at positions 195, 123, and 132 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FS123RG132K.

In another preferred embodiment, the variant according to the invention is characterized in that it comprises deletions, substitutions and/or insertions wherein the deletions/insertions/substitutions are at positions 195, 119, and 123 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FD119GS123K.

In another preferred embodiment, the variant according to the invention is characterized in that it comprises deletions, substitutions and/or insertions wherein the deletions/insertions/substitutions are at positions 195, 119, and 367 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FD119GL367F.

In another preferred embodiment, the variant according to the invention is characterized in that it comprises deletions, substitutions and/or insertions wherein the deletions/insertions/substitutions are at positions 195, 106, 119, and 123 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FI106ND119GS123E.

In another preferred embodiment, the variant according to the invention is characterized in that it comprises deletions, substitutions and/or insertions wherein the deletions/insertions/substitutions are at positions 195, 106, 119, 123, and 132 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FI106ND119GS123EG132Q.

In another preferred embodiment, the variant according to the invention is characterized in that it comprises deletions, substitutions and/or insertions wherein the deletions/insertions/substitutions are at positions 195, 132, and 169 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FG132TR169T.

In another preferred embodiment, the variant according to the invention is characterized in that it comprises deletions, substitutions and/or insertions wherein the deletions/insertions/substitutions are at positions 195, 132, and 199 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FG132KD199N.

In another preferred embodiment, the variant according to the invention is characterized in that it comprises deletions, substitutions and/or insertions wherein the deletions/insertions/substitutions are at positions 195, 132, and 119 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FG132AD119L.

In another preferred embodiment, the variant according to the invention is characterized in that it comprises deletions, substitutions and/or insertions wherein the deletions/insertions/substitutions are at positions 195, 132, and 140 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FG132T.

In another preferred embodiment, the variant according to the invention is characterized in that it comprises deletions, substitutions and/or insertions wherein the deletions/insertions/substitutions are at positions 195, 132, and 357 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FG132TS357N.

In another preferred embodiment, the variant according to the invention is characterized in that it comprises deletions, substitutions and/or insertions wherein the deletions/insertions/substitutions are at positions 195, 119, 132, and 251 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FD119GG132SY251M.

In another preferred embodiment, the variant according to the invention is characterized in that it comprises deletions, substitutions and/or insertions wherein the deletions/insertions/substitutions are at positions 195, 123, and 132 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FS123QG132S.

In another preferred embodiment, the variant according to the invention is characterized in that it comprises deletions, substitutions and/or insertions wherein the deletions/insertions/substitutions are at positions 195, 76, and 199 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FF76LD199N.

In another preferred embodiment, the variant according to the invention is characterized in that it comprises deletions, substitutions and/or insertions wherein the deletions/insertions/substitutions are at positions 195, 106, 119, and 123 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FI106ND119GS123E.

In another preferred embodiment, the variant according to the invention is characterized in that it comprises deletions, substitutions and/or insertions wherein the deletions/insertions/substitutions are at positions 195 and 175 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FH175N.

In another preferred embodiment, the variant according to the invention is characterized in that it comprises deletions, substitutions and/or insertions wherein the deletions/insertions/substitutions are at positions 195, 84, and 132 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FT84IG132R.

In another preferred embodiment, the variant according to the invention is characterized in that it comprises deletions, substitutions and/or insertions wherein the deletions/insertions/substitutions are at positions 195, 169, and 199 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FG132AD119G.

In another preferred embodiment, the variant according to the invention is characterized in that it comprises deletions, substitutions and/or insertions wherein the deletions/insertions/substitutions are at positions 195, 132, and 207 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FG132AS207C.

In another preferred embodiment, the variant according to the invention is characterized in that it comprises deletions, substitutions and/or insertions wherein the deletions/insertions/substitutions are at positions 195, and 84 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FT84I.

In another preferred embodiment, the variant according to the invention is characterized in that it comprises deletions, substitutions and/or insertions wherein the deletions/insertions/substitutions are at positions 195 and 227 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FA227S.

In another preferred embodiment, the variant according to the invention is characterized in that it comprises deletions, substitutions and/or insertions wherein the deletions/insertions/substitutions are at positions 195 and 75 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FS75N.

In another preferred embodiment, the variant according to the invention is characterized in that it comprises deletions, substitutions and/or insertions wherein the deletions/insertions/substitutions are at positions 195 and 77 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FE77L.

In another preferred embodiment, the variant according to the invention is characterized in that it comprises deletions, substitutions and/or insertions wherein the deletions/insertions/substitutions are at positions 195 and 76 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FF76L.

In another preferred embodiment, the variant according to the invention is characterized in that it comprises deletions, substitutions and/or insertions wherein the deletions/insertions/substitutions are at positions 195, 132, and 108 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FG132AP108I.

In another preferred embodiment, the variant according to the invention is characterized in that it comprises deletions, substitutions and/or insertions wherein the deletions/insertions/substitutions are at positions 195, 132, and 210 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FG132AY210L.

In another preferred embodiment, the variant according to the invention is characterized in that it comprises deletions, substitutions and/or insertions wherein the deletions/insertions/substitutions are at positions 195, 132, and 70 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FG132AY70A.

In another preferred embodiment, the variant according to the invention is characterized in that it comprises deletions, substitutions and/or insertions wherein the deletions/insertions/substitutions are at positions 195, 18, 20, 70, 73, 132, 170, 181, 199, 324, 364, and 367 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FA18IF20LY70FG73SG132MR170KI181LD199NF324SG364SL367F.

In another preferred embodiment, the variant according to the invention is characterized in that it comprises deletions, substitutions and/or insertions wherein the deletions/insertions/substitutions are at positions 195, 18, 20, 73, 132, 170, 181, 199, 324, and 367 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FA18IF20LG73SG132MR170KI181LD199NF324SL367F.

In another preferred embodiment, the variant according to the invention is characterized in that it comprises deletions, substitutions and/or insertions wherein the deletions/insertions/substitutions are at positions 195, 73, 77, 132, and 364 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FG73SE77IG132AG364S.

In another preferred embodiment, the variant according to the invention is characterized in that it comprises deletions, substitutions and/or insertions wherein the deletions/insertions/substitutions are at positions 195, 20, 132, 170, 173, 181, 199, and 324 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FF20LG132VR170KA173RI181LD199NF324S.

In another preferred embodiment, the variant according to the invention is characterized in that it comprises deletions, substitutions and/or insertions wherein the deletions/insertions/substitutions are at positions 195, 367, and 382 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FL367FG382D.

In another preferred embodiment, the variant according to the invention is characterized in that it comprises deletions, substitutions and/or insertions wherein the deletions/insertions/substitutions are at positions 195, 10, 132, 170, 173, 181, 199, and 324 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FI10AG132VR170KA173RI181LD199NF324S.

In another preferred embodiment, the variant according to the invention is characterized in that it comprises deletions, substitutions and/or insertions wherein the deletions/insertions/substitutions are at positions 195, 73, 77, 84, and 132 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FG73SE77IT84IG132A.

In another preferred embodiment, the variant according to the invention is characterized in that it comprises deletions, substitutions and/or insertions wherein the deletions/insertions/substitutions are at positions 195, 20, 73, 132, 170, 181, and 324 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FF20LG73SG132GR170KI181LF324S.

In another preferred embodiment, the variant according to the invention is characterized in that it comprises deletions, substitutions and/or insertions wherein the deletions/insertions/substitutions are at positions 195, 132, 170, 173, 181, 199, and 324 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FG132VR170KA173RI181LD199NF324S.

In another preferred embodiment, the variant according to the invention is characterized in that it comprises deletions, substitutions and/or insertions wherein the deletions/insertions/substitutions are at positions 195, 73, 70, 77, and 132 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FG73SY70FE77IG132A.

In a preferred embodiment the alkenol dehydratase from which the variant is derived is an alkenol dehydratase which shows the amino acid sequence as shown in SEQ ID NO:1 or an amino acid sequence having at least 60% sequence identity to SEQ ID NO:1.

Accordingly, in one embodiment, the present invention relates to an alkenol dehydratase variant which has an amino acid sequence as shown in SEQ ID NO:1 or an amino acid sequence having at least 60% sequence identity to SEQ ID NO:1, wherein one or more amino acid residues at a position selected from the group consisting of positions 195, 116, 80, 106, 119, 357, 75, 132, 73, 199, 123, 68, 126, 159, 227, 367, 234, 192, 157, 169, 181, 156, 122, 84, 318, 389, 115, 76, 390, 255, 247, 50, 251, 158, 324, 281, 77, 285, 98, 95, 186, 248, 72, 175, 245, 173, 310, 140, 18, 20, 170, 269, 382, 39, 77, 144, 168, 386, 12, 151, 230, 194, 207, 114, 108, 210, 70, 364 and 10 in the amino acid sequence shown in SEQ ID NO:1 or at a position corresponding to any of these positions, are substituted with another amino acid residue or deleted or wherein an insertion has been effected at one or more of these positions and wherein said alkenol dehydratase has an improved activity in converting an alkenol as defined above, preferably crotyl alcohol into 1,3 butadiene.

The present inventors have found that the activity of an alkenol dehydratase to catalyze the conversion of an alkenol, e.g. of crotyl alcohol into 1,3 butadiene, can dramatically be improved by mutating the alkenol dehydratase enzyme at certain positions. They used as a model enzyme the enzyme "linalool dehydratase-isomerase" of *Castellaniella defragrans*, the sequence of which is shown in SEQ ID NO: 1. The mutations lead to an increase of activity of up to more than a factor of 24 when compared to the unmutated sequence of the *Castellaniella defragrans* enzyme (represented by SEQ ID NO: 1).

The variants of an alkenol dehydratase according to the second aspect of the present invention are preferably characterized in that they show an increased activity in converting crotyl alcohol into 1,3 butadiene when compared to the alkenol dehydratase from which they are derived. Thus, in the case where the variant is derived from the linalool dehydratase-isomerase of *Castellaniella defragrans* having the amino acid sequence shown in SEQ ID NO: 1, the variant shows an increased activity in converting crotyl alcohol into 1,3 butadiene when compared to the linalool dehydratase-isomerase having the amino acid sequence of SEQ ID NO:1. When the variant is derived from an alkenol dehydratase which is structurally related to the linalool dehydratase-isomerase as of *Castellaniella defragrans* as defined herein above, the variant shows an increased activity in converting crotyl alcohol into 1,3 butadiene when compared to the corresponding starting sequence into which the corresponding mutations have been introduced. In a particularly preferred embodiment such variants show also an increased activity in converting crotyl alcohol into 1,3 butadiene when compared to the linalool dehydratase-isomerase shown in SEQ ID NO: 1. The activity of converting crotyl alcohol into 1,3 butadiene may be determined by methods known to the person skilled in the art. In one embodiment, this activity is determined as described in the Examples appended hereto. In a particular embodiment this activity can be measured by incubating the enzyme, preferably a cell lysate containing the overexpressed recombinant protein, in vitro. Alternatively, a purified enzyme can be used. More specifically, the enzyme whose activity is to be assessed may be produced as outlined in the following: The sequence coding for the wild type version or variants of the alkenol dehydratase is subcloned in the pET25b+ expression vector (Novagen) or peT300/NT (Life technologies) using standard molecular biology techniques. The expression constructs are transformed into BL21(DE3) competent cells (Novagen). Isolated clones are used to inoculate 1 ml to 500 ml of auto-induction medium (Studier F. W, Protein Expr. Purif. 41 (2005), 207-234) and grown overnight at 30° C. for 20-22 hours in a shaking incubator set at 700 rpm (85% humidity for volume of 1 ml). The cells are pelleted and stored at −80° C. for at least overnight.

In one embodiment the enzymatic assay is set up using crude cell lysates: the frozen cell pellets are directly resuspended in a reaction mix containing 50 mM Tris-Cl pH7.5, 25 mM KCl, 25 mM MgCl2, 4 mM DTT, 10 mM glutathion and 0-100 mM crotyl alcohol (trans isomer from Alfa Aesar or cis-trans mixture from Sigma Aldrich). In another embodiment, the enzymatic assay is set up using clarified cell lysate: in this case the frozen cell pellets containing the overexpressed recombinant enzyme are resuspended in a lysis buffer (50 mM Tris-Cl pH7.5, 4 mM DTT, 25 mM MgCl2, 25 mM KCl) supplemented with Merck Novagen Lysonase (100 µl of Lysonase 15 ml of lysis buffer for a cell pellet produced from 1 litre culture). The cell suspension is incubated for 10 minutes at room temperature followed by 20 minutes on ice. Cell lysates are clarified by centrifugation and the supernatant is concentrated 2-3 fold using a centrifugal concentrator. The amount of the enzyme variant present in the concentrated soluble fraction is estimated on SDS-PAGE gel against a BSA calibration curve using gel densitometry. The assay is initiated by adding 0-100 mM crotyl alcohol (trans isomer from Alfa Aesar or cis-trans mixture from Sigma Aldrich) to the concentrated soluble fraction which has been supplemented with 4 mM glutathione.

Control reactions are set up using bacterial clones containing either the empty expression vector peT25b+ or the expression vector expressing the wild type enzyme. This reaction mix is incubated for a minimum of 1 hour up to 16 hours at 37° C. and the reaction is stopped by a 5-minute incubation at 80° C. 1,3 butadiene quantification: The amount of 1,3-butadiene produced is quantified by gas chromatography analysis. For the GC headspace analysis, 300 µl of the headspace gas is injected in a Bruker GC450 system equipped with a Restek RT-Alumina column (5 m×0.32 mm) and a Flame ionization detection system (FID). The GC analysis method used to detect 1,3 butadiene is characterised by a constant oven temperature at 140° C., injector port temperature at 200° C. with a split ratio of 1:4 and the FID detector temperature at 250° C. Nitrogen is used as a carrier gas (constant flow of 1.25 ml/min) and a mixture of air (air flow 300 ml/min), nitrogen (28 ml/min flow) and hydrogen (flow of 30 ml/min) is used to supply the FID detection system.

In the context of the present invention an "increased activity" means that the activity of the alkenol dehydratase variant in question is increased at least by a factor of 1.1, preferably at least by a factor of 2 and even more preferably at least by a factor of 24 or at least by a factor 100, 1000, 10000 or 10000 when compared to the enzyme from which it is derived, preferably when compared to the linalool dehydratase-isomerase having the amino acid sequence of SEQ ID NO:1.

According to one embodiment, the alkenol dehydratase variant of the second aspect of the present invention has an amino acid sequence as shown in SEQ ID NO:1 in which,
(1) an amino acid residue at position 195 in the amino acid sequence shown in SEQ ID NO:1 or at a position corresponding to this position, is deleted or substituted with phenylalanine or tyrosine; and/or
(2) an amino acid residue at position 116 in the amino acid sequence shown in SEQ ID NO:1 or at a position corresponding to this position, is deleted or substituted with lysine; and/or
(3) an amino acid residue at position 80 in the amino acid sequence shown in SEQ ID NO:1 or at a position corresponding to this position, is deleted or substituted with proline or tryptophan; and/or (4) an amino acid residue at position 106 in the amino acid sequence shown in SEQ ID NO:1 or at a position corresponding to this position, is deleted or substituted with asparagine; and/or (5) an amino acid residue at position 119 in the amino acid sequence shown in SEQ ID NO:1 or at a position corresponding to this position, is deleted or substituted with glycine or leucine; and/or (6) an amino acid residue at position 357 in the amino acid sequence shown in SEQ ID NO:1 or at a position corresponding to this position, is deleted or substituted with asparagine; and/or (7) an amino acid residue at position 75 in the amino acid sequence shown in SEQ ID NO:1 or at a position corresponding to this position, is deleted or substituted with methionine, alanine, glycine, asparagine, threonine, isoleucine, tyrosine or valine; and/or (8) an amino acid residue at position 367 in the amino acid sequence shown in SEQ ID NO:1 or at a position corresponding to this position, is deleted or substituted with phenylalanine or leucine; and/or (9) an amino acid residue at position 73 in the amino acid sequence shown in SEQ ID NO:1 at a position corresponding to this position, is deleted or substituted with tryptophan or serine; and/or

(10) an amino acid residue at position 199 in the amino acid sequence shown in SEQ ID NO:1 or at a position corresponding to this position, is deleted or substituted with asparagine; and/or

(11) an amino acid residue at position 255 in the amino acid sequence shown in SEQ ID NO:1 or at a position corresponding to this position, is deleted or substituted with threonine; and/or

(12) an amino acid residue at position 132 in the amino acid sequence shown in SEQ ID NO:1 or at a position corresponding to this position, is deleted or substituted with threonine, leucine, aspartic acid, tryptophan, serine, isoleucine, glutamine, valine, asparagine, arginine, methionine, histidine, phenylalanine, lysine, leucine, alanine, cysteine, glutamic acid or tyrosine; and/or

(13) an amino acid residue at position 123 in the amino acid sequence shown in SEQ ID NO:1 or at a position corresponding to this position, is deleted or substituted with histidine, tryptophan, arginine, glutamic acid, tyrosine, aspartic acid, isoleucine, lysine, phenylalanine, leucine, threonine, valine, glutamine, glycine or methionine; and/or

(14) an amino acid residue at position 68 in the amino acid sequence shown in SEQ ID NO:1 or at a position corresponding to this position, is deleted or substituted with leucine; and/or

(15) an amino acid residue at position 126 in the amino acid sequence shown in SEQ ID NO:1 at a position corresponding to this position, is deleted or substituted with tyrosine or alanine; and/or

(16) an amino acid residue at position 159 in the amino acid sequence shown in SEQ ID NO:1 or at a position corresponding to this position, is deleted or substituted with isoleucine, methionine or valine; and/or

(17) an amino acid residue at position 227 in the amino acid sequence shown in SEQ ID NO:1 or at a position corresponding to this position, is deleted or substituted with isoleucine or serine; and/or

(18) the amino acid residue at position 247 in the amino acid sequence shown in SEQ ID NO:1 or at a position corresponding to this position, is substituted with valine; and/or

(19) an amino acid residue at position 234 in the amino acid sequence shown in SEQ ID NO:1 or at a position corresponding to this position, is deleted or substituted with tryptophan; and/or

(20) an amino acid residue at position 76 in the amino acid sequence shown in SEQ ID NO:1 or at a position corresponding to this position, is deleted or substituted with leucine; and/or

(21) an amino acid residue at position 192 in the amino acid sequence shown in SEQ ID NO:1 or at a position corresponding to this position, is deleted or substituted with leucine, threonine or valine; and/or

(22) an amino acid residue at position 157 in the amino acid sequence shown in SEQ ID NO:1 or at a position corresponding to this position, is deleted or substituted with methionine; and/or

(23) an amino acid residue at position 169 in the amino acid sequence shown in SEQ ID NO:1 or at a position corresponding to this position, is deleted or substituted with threonine or asparagine; and/or

(24) an amino acid residue at position 181 in the amino acid sequence shown in SEQ ID NO:1 or at a position corresponding to this position, is deleted or substituted with alanine, serine, leucine or asparagine; and/or

(25) an amino acid residue at position 156 in the amino acid sequence shown in SEQ ID NO:1 or at a position corresponding to this position, is deleted or substituted with serine; and/or

(26) an amino acid residue at position 324 in the amino acid sequence shown in SEQ ID NO:1 or at a position corresponding to this position, is deleted or substituted with serine; and/or

(27) an amino acid residue at position 251 in the amino acid sequence shown in SEQ ID NO:1 or at a position corresponding to this position, is deleted or substituted with leucine or methionine; and/or

(28) an amino acid residue at position 122 in the amino acid sequence shown in SEQ ID NO:1 or at a position corresponding to this position, is deleted or substituted with leucine or isoleucine; and/or

(29) an amino acid residue at position 84 in the amino acid sequence shown in SEQ ID NO:1 or at a position corresponding to this position, is deleted or substituted with glutamine or isoleucine; and/or

(30) an amino acid residue at position 389 in the amino acid sequence shown in SEQ ID NO:1 or at a position corresponding to this position, is deleted or substituted with serine; and/or

(31) an amino acid residue at position 115 in the amino acid sequence shown in SEQ ID NO:1 or at a position corresponding to this position, is deleted or substituted with alanine; and/or

(32) an amino acid residue at position 50 in the amino acid sequence shown in SEQ ID NO:1 or at a position corresponding to this position, is deleted or substituted with arginine; and/or

(33) an amino acid residue at position 390 in the amino acid sequence shown in SEQ ID NO:1 or at a position corresponding to this position, is deleted or substituted with aspartic acid; and/or

(34) an amino acid residue at position 175 in the amino acid sequence shown in SEQ ID NO:1 or at a position corresponding to this position, is deleted or substituted with serine or asparagine; and/or
(35) an amino acid residue at position 158 in the amino acid sequence shown in SEQ ID NO:1 or at a position corresponding to this position, is deleted or substituted with isoleucine; and/or
(36) an amino acid residue at position 281 in the amino acid sequence shown in SEQ ID NO:1 or at a position corresponding to this position, is deleted or substituted with tyrosine; and/or
(37) an amino acid residue at position 98 in the amino acid sequence shown in SEQ ID NO:1 or at a position corresponding to this position, is deleted or substituted with methionine; and/or
(38) an amino acid residue at position 318 in the amino acid sequence shown in SEQ ID NO:1 or at a position corresponding to this position, is deleted or substituted with alanine; and/or
(39) an amino acid residue at position 77 in the amino acid sequence shown in SEQ ID NO:1 or at a position corresponding to this position, is deleted or substituted with leucine or isoleucine; and/or (40) an amino acid residue at position 285 in the amino acid sequence shown in SEQ ID NO:1 or at a position corresponding to this position, is deleted or substituted with leucine or methionine; and/or
(41) an amino acid residue at position 95 in the amino acid sequence shown in SEQ ID NO:1 or at a position corresponding to this position, is deleted or substituted with methionine; and/or
(42) an amino acid residue at position 186 in the amino acid sequence shown in SEQ ID NO:1 or at a position corresponding to this position, is deleted or substituted with valine or leucine; and/or
(43) an amino acid residue at position 248 in the amino acid sequence shown in SEQ ID NO:1 or at a position corresponding to this position, is deleted or substituted with lysine; and/or
(44) an amino acid residue at position 72 in the amino acid sequence shown in SEQ ID NO:1 or at a position corresponding to this position, is deleted or substituted with serine; and/or
(45) an amino acid residue at position 245 in the amino acid sequence shown in SEQ ID NO:1 or at a position corresponding to this position, is deleted or substituted with alanine; and/or
(46) an amino acid residue at position 310 in the amino acid sequence shown in SEQ ID NO:1 or at a position corresponding to this position, is deleted or substituted with isoleucine; and/or
(47) an amino acid residue at position 140 in the amino acid sequence shown in SEQ ID NO:1 or at a position corresponding to this position, is deleted or substituted with glycine or serine; and/or
(48) an amino acid residue at position 173 in the amino acid sequence shown in SEQ ID NO:1 or at a position corresponding to this position, is deleted or substituted with lysine, arginine, isoleucine or serine; and/or
(49) an amino acid residue at position 18 in the amino acid sequence shown in SEQ ID NO:1 or at a position corresponding to this position, is deleted or substituted with valine or isoleucine; and/or
(50) an amino acid residue at position 20 in the amino acid sequence shown in SEQ ID NO:1 or at a position corresponding to this position, is deleted or substituted with leucine; and/or
(51) an amino acid residue at position 170 in the amino acid sequence shown in SEQ ID NO:1 or at a position corresponding to this position, is deleted or substituted with lysine; and/or
(52) an amino acid residue at position 269 in the amino acid sequence shown in SEQ ID NO:1 or at a position corresponding to this position, is deleted or substituted with alanine; and/or
(53) an amino acid residue at position 382 in the amino acid sequence shown in SEQ ID NO:1 or at a position corresponding to this position, is deleted or substituted with aspartic acid; and/or
(54) an amino acid residue at position 39 in the amino acid sequence shown in SEQ ID NO:1 or at a position corresponding to this position, is deleted or substituted with alanine; and/or
(55) an amino acid residue at position 144 in the amino acid sequence shown in SEQ ID NO:1 or at a position corresponding to this position, is deleted or substituted with threonine; and/or
(56) an amino acid residue at position 168 in the amino acid sequence shown in SEQ ID NO:1 or at a position corresponding to this position, is deleted or substituted with asparagine; and/or
(57) an amino acid residue at position 386 in the amino acid sequence shown in SEQ ID NO:1 or at a position corresponding to this position, is deleted or substituted with serine; and/or
(58) an amino acid residue at position 367 in the amino acid sequence shown in SEQ ID NO:1 or at a position corresponding to this position, is deleted or substituted with phenylalanine; and/or
(59) an amino acid residue at position 12 in the amino acid sequence shown in SEQ ID NO:1 or at a position corresponding to this position, is deleted or substituted with leucine; and/or
(60) an amino acid residue at position 151 in the amino acid sequence shown in SEQ ID NO:1 or at a position corresponding to this position, is deleted or substituted with methionine; and/or
(61) an amino acid residue at position 230 in the amino acid sequence shown in SEQ ID NO:1 or at a position corresponding to this position, is deleted or substituted with glutamine; and/or
(62) an amino acid residue at position 194 in the amino acid sequence shown in SEQ ID NO:1 or at a position corresponding to this position, is deleted or substituted with arginine; and/or
(63) an amino acid residue at position 207 in the amino acid sequence shown in SEQ ID NO:1 or at a position corresponding to this position, is deleted or substituted with alanine or cysteine; and/or
(64) an amino acid residue at position 114 in the amino acid sequence shown in SEQ ID NO:1 or at a position corresponding to this position, is deleted or substituted with serine; and/or
(65) an amino acid residue at position 106 in the amino acid sequence shown in SEQ ID NO:1 or at a position corresponding to this position, is deleted or substituted with asparagine; and/or
(66) an amino acid residue at position 108 in the amino acid sequence shown in SEQ ID NO:1 or at a position corresponding to this position, is deleted or substituted with isoleucine; and/or

(67) an amino acid residue at position 210 in the amino acid sequence shown in SEQ ID NO:1 or at a position corresponding to this position, is deleted or substituted with leucine; and/or

(68) an amino acid residue at position 70 in the amino acid sequence shown in SEQ ID NO:1 or at a position corresponding to this position, is deleted or substituted with alanine or phenylalanine; and/or

(69) an amino acid residue at position 364 in the amino acid sequence shown in SEQ ID NO:1 or at a position corresponding to this position, is deleted or substituted with serine; and/or

(70) an amino acid residue at position 10 in the amino acid sequence shown in SEQ ID NO:1 or at a position corresponding to this position, is deleted or substituted with alanine.

The invention also relates to variants as defined in (1) to (70) hereinabove, wherein the amino acid residue indicated as substituting the amino acid residue at the position in SEQ ID NO: 1 is not that particular amino acid residue but an amino acid residue which is conservative in relation to the indicated substituting amino acid.

Whether an amino acid is conservative with respect to another amino acid can be judged according to means and methods known in the art. One possibility is the PAM 250 matrix; alternatively, the Blosum Family Matrices can be used.

In a preferred embodiment the enzymes according to the second aspect of the present invention are not only capable of converting crotyl alcohol or but-3-en-2-ol into 1,3 butadiene, but they are also able to act on structurally related substrates, in particular on compounds corresponding to the general formula $C_nH_{2n}O$ into $C_nH_{2n-2}+H_2O$, with $3<n<7$, i.e. they are preferably also able to act on but-3-en-1-ol so as to convert it into 1,3 butadiene, or on 3-methylbut-2-en-1-ol (prenol), 3-methylbut-3-en-1-ol (isoprenol), 2-methyl-but-3-en-1-ol, 2-methyl-but-2-en-1-ol, 3-methyl-but-3-en-2-ol or 2-methyl-but-3-en-2-ol so as to convert them into isoprene or on 2,3-dimethyl-but-2-en-1-ol, 2,3-dimethyl-but-3-en-2-ol or 2,3-dimethyl-but-3-en-1-ol so as to convert them into dimethylbutadiene.

In a particularly preferred embodiment the variants according to the second aspect of the present invention can catalyze any of these reactions with an increased activity when compared to the enzyme from which they are derived. The degree of increase is preferably as defined herein-above.

The present invention also relates to a method for providing a variant of an alkenol dehydratase wherein said variant shows an improved activity of converting an alkenol as defined above, preferably crotyl alcohol into 1,3 butadiene, said method comprising the step of effecting one or more changes in the sequence of the alkenol dehydratase wherein said change(s) is/are effected at one or more amino acid positions selected from the group consisting of the amino acid positions corresponding to positions 195, 116, 80, 106, 119, 357, 75, 132, 73, 199, 123, 68, 126, 159, 227, 367, 234, 192, 157, 169, 181, 156, 122, 84, 318, 389, 115, 76, 390, 255, 247, 50, 251, 158, 324, 281, 285, 98, 95, 186, 248, 72, 175, 245, 173, 310, 140, 18, 20, 170, 269, 382, 39, 77, 144, 168, 386, 12, 151, 230, 194, 207, 114, 108, 210, 70, 364 and 10 in the amino acid sequence shown in SEQ ID NO:1.

As regards the preferred embodiments of an alkenol dehydratase to be mutated according to such a method, the same applies as has been set forth herein-above. In one preferred embodiment the alkenol dehydratase from which the variant is derived is an alkenol dehydratase which shows the amino acid sequence as shown in SEQ ID NO: 1 or an amino acid sequence having at least 60% sequence identity to SEQ ID NO:1 or any of the preferred degrees of sequence identity as specified herein-above.

Moreover, as regards preferred embodiments of the degree of improvement in activity and the changes to be effected, the same applies as described herein-above.

In particular, the present invention more preferably relates to such a method wherein the changes which are effected in an alkenol dehydratase at one or more positions corresponding to positions corresponding to positions 195, 116, 80, 106, 119, 357, 75, 132, 73, 199, 123, 68, 126, 159, 227, 367, 234, 192, 157, 169, 181, 156, 122, 84, 318, 389, 115, 76, 390, 255, 247, 50, 251, 158, 324, 281, 285, 98, 95, 186, 248, 72, 175, 245, 173, 310 140, 18, 20, 170, 269, 382, 39, 77, 144, 168, 386, 12, 151, 230, 194, 207, 114, 108, 210, 70, 364 and 10 in the amino acid sequence shown in SEQ ID NO:1 are selected from the group consisting of those identified in items (1) to (70) as described in the context of the second aspect of the present invention under item (A).

The present invention also relates to the use of an alkenol dehydratase variant of the present invention as described above or of a host cell comprising such an alkenol dehydratase for the conversion of an alkenol as described above, preferably of crotyl alcohol into 1,3 butadiene.

B. Variants with an Improved Activity to Convert but-3-en-2-ol into 1,3 Butadiene In a third aspect, the present invention relates to a variant of an alkenol dehydratase showing an improved activity in converting an alkenol, preferably but-3-en-2-ol into 1,3 butadiene, compared to the corresponding alkenol dehydratase from which it is derived, wherein the alkenol dehydratase variant is characterized in that it shows one or more substitutions, deletions and/or insertions in comparison to the corresponding sequence from which it is derived and wherein these substitutions, deletions and/or insertions occur at one or more of the positions corresponding to positions 195, 106, 119, 357, 132, 123, 159, 227, 234, 157, 169, 324, 75, 126, 181, 156, 122, 84, 115, 76, 390, 255, 251, 247, 281, 77, 285, 95, 186, 248, 72, 175, 245, 199, 140, 310, 254, 373, 102, 166, 18, 20, 170, 269, 382, 39, 144, 173, 168, 39, 386, 12, 151, 230, 207, 114, 73, 181, 367, 389, 285, 318, 158, 70, 199, 364 and 10 in the amino acid sequence shown in SEQ ID NO:1.

In a preferred embodiment the alkenol dehydratase from which the variant is derived is an alkenol dehydratase which shows the amino acid sequence as shown in SEQ ID NO:1 or an amino acid sequence having at least 60% sequence identity to SEQ ID NO:1.

In a preferred embodiment, the variant according to the invention is characterized in that it contains at least two deletions, substitutions and/or insertions wherein the deletion/insertion/substitution is at position 310 in the amino acid sequence shown in SEQ ID NO:1 or at a position corresponding to this position and another deletion/insertion/substitution is at position 132 in the amino acid sequence shown in SEQ ID NO:1 or at a position corresponding to this position. Preferably, such a variant further has one or more substitutions, deletions and/or insertions in comparison to the corresponding sequence from which it is derived and wherein these substitutions, deletions and/or insertions occur at one or more of the positions corresponding to positions 195, 106, 119, 357, 123, 159, 227, 234, 157, 169, 324, 75, 126, 181, 156, 122, 84, 115, 76, 390, 255, 251, 247, 281, 77, 285, 95, 186, 248, 72, 175, 245, 199, 140, 254, 373, 102 166, 18, 20, 170, 269, 382, 39, 144, 173, 168, 39, 386, 12, 151, 230, 207, 114, 73, 181, 367, 389, 285, 318, 158, 70, 199, 364 and 10 in the amino acid sequence shown in SEQ ID NO:1.

In a preferred embodiment, the variant according to the invention is characterized in that it contains at least two deletions, substitutions and/or insertions wherein the deletion/insertion/substitution is at position 195 in the amino acid sequence shown in SEQ ID NO:1 or at a position corresponding to this position and another deletion/insertion/substitution is at position 132 in the amino acid sequence shown in SEQ ID NO:1 or at a position corresponding to this position. Preferably, such a variant further has one or more substitutions, deletions and/or insertions in comparison to the corresponding sequence from which it is derived and wherein these substitutions, deletions and/or insertions occur at one or more of the positions corresponding to positions 106, 119, 357, 123, 159, 227, 234, 157, 169, 324, 75, 126, 181, 156, 122, 84, 115, 76, 390, 255, 251, 247, 281, 77, 285, 95, 186, 248, 72, 175, 245, 199, 140, 310, 254, 373, 102 166, 18, 20, 170, 269, 382, 39, 144, 173, 168, 39, 386, 12, 151, 230, 207, 114, 73, 181, 367, 389, 285, 318, 158, 70, 199, 364 and 10 in the amino acid sequence shown in SEQ ID NO:1.

In a preferred embodiment, the variant according to the invention is characterized in that it contains at least two deletions, substitutions and/or insertions wherein the deletion/insertion/substitution is at position 195 in the amino acid sequence shown in SEQ ID NO:1 or at a position corresponding to this position and another deletion/insertion/substitution is at position 324 in the amino acid sequence shown in SEQ ID NO:1 or at a position corresponding to this position. Preferably, such a variant further has one or more substitutions, deletions and/or insertions in comparison to the corresponding sequence from which it is derived and wherein these substitutions, deletions and/or insertions occur at one or more of the positions corresponding to positions 106, 119, 357, 132, 123, 159, 227, 234, 157, 169, 75, 126, 181, 156, 122, 84, 115, 76, 390, 255, 251, 247, 281, 77, 285, 95, 186, 248, 72, 175, 245, 199, 140, 310, 254, 373, 102 166, 18, 20, 170, 269, 382, 39, 144, 173, 168, 39, 386, 12, 151, 230, 207, 114, 73, 181, 367, 389, 285, 318, 158, 70, 199, 364 and 10 in the amino acid sequence shown in SEQ ID NO:1.

In a preferred embodiment, the variant according to the invention is characterized in that it contains at least two deletions, substitutions and/or insertions wherein the deletion/insertion/substitution is at position 195 in the amino acid sequence shown in SEQ ID NO:1 or at a position corresponding to this position and another deletion/insertion/substitution is at position 199 in the amino acid sequence shown in SEQ ID NO:1 or at a position corresponding to this position. Preferably, such a variant further has one or more substitutions, deletions and/or insertions in comparison to the corresponding sequence from which it is derived and wherein these substitutions, deletions and/or insertions occur at one or more of the positions corresponding to positions 106, 119, 357, 132, 123, 159, 227, 234, 157, 169, 324, 75, 126, 181, 156, 122, 84, 115, 76, 390, 255, 251, 247, 281, 77, 285, 95, 186, 248, 72, 175, 245, 140, 310, 254, 373, 102 166, 18, 20, 170, 269, 382, 39, 144, 173, 168, 39, 386, 12, 151, 230, 207, 114, 73, 181, 367, 389, 285, 318, 158, 70, 199, 364 and 10 in the amino acid sequence shown in SEQ ID NO:1.

In a preferred embodiment, the variant according to the invention is characterized in that it contains at least two deletions, substitutions and/or insertions wherein the deletion/insertion/substitution is at position 132 in the amino acid sequence shown in SEQ ID NO:1 or at a position corresponding to this position and another deletion/insertion/substitution is at position 140 in the amino acid sequence shown in SEQ ID NO:1 or at a position corresponding to this position. Preferably, such a variant further has one or more substitutions, deletions and/or insertions in comparison to the corresponding sequence from which it is derived and wherein these substitutions, deletions and/or insertions occur at one or more of the positions corresponding to positions 195, 106, 119, 357, 123, 159, 227, 234, 157, 169, 324, 75, 126, 181, 156, 122, 84, 115, 76, 390, 255, 251, 247, 281, 77, 285, 95, 186, 248, 72, 175, 245, 199, 310, 254, 373, 102 166, 18, 20, 170, 269, 382, 39, 144, 173, 168, 39, 386, 12, 151, 230, 207, 114, 73, 181, 367, 389, 285, 318, 158, 70, 199, 364 and 10 in the amino acid sequence shown in SEQ ID NO:1.

In a preferred embodiment, the variant according to the invention is characterized in that it contains at least two deletions, substitutions and/or insertions wherein the deletion/insertion/substitution is at position 102 in the amino acid sequence shown in SEQ ID NO:1 or at a position corresponding to this position and another deletion/insertion/substitution is at position 166 in the amino acid sequence shown in SEQ ID NO:1 or at a position corresponding to this position. Preferably, such a variant further has one or more substitutions, deletions and/or insertions in comparison to the corresponding sequence from which it is derived and wherein these substitutions, deletions and/or insertions occur at one or more of the positions corresponding to positions 195, 106, 119, 357, 132, 123, 159, 227, 234, 157, 169, 324, 75, 126, 181, 156, 122, 84, 115, 76, 390, 255, 251, 247, 281, 77, 285, 95, 186, 248, 72, 175, 245, 199, 140, 310, 254, 373, 166, 18, 20, 170, 269, 382, 39, 144, 173, 168, 39, 386, 12, 151, 230, 207, 114, 73, 181, 367, 389, 285, 318, 158, 70, 199, 364 and 10 in the amino acid sequence shown in SEQ ID NO:1.

In a preferred embodiment, the variant according to the invention is characterized in that it contains at least two deletions, substitutions and/or insertions wherein the deletion/insertion/substitution is at position 195 in the amino acid sequence shown in SEQ ID NO:1 or at a position corresponding to this position and another deletion/insertion/substitution is at position 119 in the amino acid sequence shown in SEQ ID NO:1 or at a position corresponding to this position. Preferably, such a variant further has one or more substitutions, deletions and/or insertions in comparison to the corresponding sequence from which it is derived and wherein these substitutions, deletions and/or insertions occur at one or more of the positions corresponding to positions 106, 357, 132, 123, 159, 227, 234, 157, 169, 324, 75, 126, 181, 156, 122, 84, 115, 76, 390, 255, 251, 247, 281, 77, 285, 95, 186, 248, 72, 175, 245, 199, 140, 310, 254, 373, 102, 166, 18, 20, 170, 269, 382, 39, 144, 173, 168, 39, 386, 12, 151, 230, 207, 114, 73, 181, 367, 389, 285, 318, 158, 70, 199, 364 and 10 in the amino acid sequence shown in SEQ ID NO:1.

In even more preferred embodiments, the variant according to the invention showing an improved activity in converting but-3-en-2-ol into 1,3 butadiene is characterized in that it has multiple mutations. As it is exemplified in the examples further below, variants have been found bearing multiple mutations which exhibit an increase in the reaction rate of the conversion of but-3-en-2-ol into 1,3 butadiene. These variants bearing multiple mutations which exhibit an increase in the reaction rate of the conversion of but-3-en-2-ol into 1,3 butadiene correspond to those variants bearing multiple mutations which exhibit an increase in the reaction rate of the conversion of crotyl alcohol into 1,3 butadiene. Accordingly, as regards the preferred embodiments of variants bearing multiple mutations which exhibit an increase in the reaction rate of the conversion of but-3-en-2-ol into 1,3 butadiene, the same mutations apply as has been set forth herein-above for variants bearing multiple mutations which exhibit an increase in the reaction rate of the conversion of crotyl alcohol into 1,3 butadiene.

Moreover, in one embodiment, the present invention relates to an alkenol dehydratase variant which has an amino acid sequence as shown in SEQ ID NO:1 or an amino acid sequence having at least 60% sequence identity to SEQ ID NO:1, wherein one or more amino acid residues at a position selected from the group consisting of positions 195, 106, 119, 357, 132, 123, 159, 227, 234, 157, 169, 324, 75, 126, 181, 156, 122, 84, 115, 76, 390, 255, 251, 247, 281, 77, 285, 95, 186, 248, 72, 175, 245, 199, 140, 310, 254, 373, 102, 166, 18, 20, 170, 269, 382, 39, 144, 173, 168, 39, 386, 12, 151, 230, 207, 114, 73, 181, 367, 389, 285, 318, 158, 70, 199, 364 and 10 in the amino acid sequence shown in SEQ ID NO:1 or at a position corresponding to any of these positions, are substituted with another amino acid residue or deleted or wherein an insertion has been effected at one or more of these positions and wherein said alkenol dehydratase has an improved activity in converting but-3-en-2-ol into 1,3 butadiene.

The present inventors have found that the activity of an alkenol dehydratase to catalyze the conversion of an alkenol as defined above, preferably of but-3-en-2-ol into 1,3 butadiene, can dramatically be improved by mutating the alkenol dehydratase enzyme at certain positions. They used as a model enzyme the enzyme "linalool dehydratase-isomerase" of *Castellaniella defragrans*, the sequence of which is shown in SEQ ID NO: 1. The mutations lead to an increase of activity of up to more than a factor of 3.0 when compared to the unmutated sequence of the *Castellaniella defragrans* enzyme (represented by SEQ ID NO: 1).

The variants of an alkenol dehydratase according to the third aspect of the present invention are characterized in that they show an increased activity in converting an alkenol as defined above, preferably but-3-en-2-ol into 1,3 butadiene, when compared to the alkenol dehydratase from which they are derived. Thus, in the case where the variant is derived from the linalool dehydratase-isomerase of *Castellaniella defragrans* having the amino acid sequence shown in SEQ ID NO: 1, the variant shows an increased activity in converting but-3-en-2-ol into 1,3 butadiene when compared to the linalool dehydratase-isomerase having the amino acid sequence of SEQ ID NO:1. When the variant is derived from an alkenol dehydratase which is structurally related to the linalool dehydratase-isomerase as of *Castellaniella defragrans* as defined herein above, the variant shows an increased activity in converting but-3-en-2-ol into 1,3 butadiene when compared to the corresponding starting sequence into which the corresponding mutations have been introduced. In a particularly preferred embodiment such variants show also an increased activity in converting but-3-en-2-ol into 1,3 butadiene when compared to the linalool dehydratase-isomerase shown in SEQ ID NO: 1. The activity of converting but-3-en-2-ol into 1,3 butadiene may be determined by methods known to the person skilled in the art. In one embodiment, this activity is determined as described in the Examples appended hereto. In a particular embodiment this activity can be measured by incubating the enzyme, preferably a cell lysate containing the overexpressed recombinant protein, in vitro. Alternatively, a purified enzyme can be used. More specifically, the enzyme whose activity is to be assessed may be produced as outlined in the following: The sequence coding for the wild type version or variants of the alkenol dehydratase is subcloned in the pET25b+ expression vector (Novagen) or peT300/NT (Life technologies) using standard molecular biology techniques. The expression constructs are transformed into BL21(DE3) competent cells (Novagen). Isolated clones are used to inoculate 1 ml to 500 ml of auto-induction medium (Studier F. W, Protein Expr. Purif. 41 (2005), 207-234) and grown overnight at 30° C. for 20-22 hours in a shaking incubator set at 700 rpm (85% humidity for volume of 1 ml). The cells are pelleted and stored at −80° C. for at least overnight.

In one embodiment the enzymatic assay is set up using crude cell lysates: the frozen cell pellets are directly resuspended in a reaction mix containing 50 mM Tris-Cl pH7.5, 25 mM KCl, 25 mM MgCl2, 4 mM DTT, 10 mM glutathion and 0-100 mM but-3-en-2-ol (Sigma Aldrich).

In another embodiment, the enzymatic assay is set up using clarified cell lysate: in this case the frozen cell pellets containing the overexpressed recombinant enzyme are resuspended in a lysis buffer (50 mM Tris-Cl pH7.5, 4 mM DTT, 25 mM MgCl2, 25 mM KCl) supplemented with Merck Novagen Lysonase (100 µl Lysonase in 15 ml of lysis buffer for a cell pellet produced from 1 litre culture). The cell suspension is incubated for 10 minutes at room temperature followed by 20 minutes on ice. Cell lysates are clarified by centrifugation and the supernatant is concentrated 2-3 fold using a centrifugal concentrator. The amount of the enzyme variant present in the concentrated soluble fraction is estimated on SDS-PAGE gel against a BSA calibration curve using gel densitometry. The assay is initiated by adding 0-100 mM but-3-en-2-ol (Sigma Aldrich) to the concentrated soluble fraction which has been supplemented with 4 mM glutathione.

Control reactions are set up using bacterial clones containing either the empty expression vector peT25b+ or the expression vector expressing the wild type enzyme. This reaction mix is incubated for a minimum of 1 hour up to 16 hours at 37° C. and the reaction is stopped by a 5-minute incubation at 80° C. 1,3 butadiene quantification: The amount of 1,3-butadiene produced is then quantified by gas chromatography analysis. For the GC headspace analysis, 300 µl of the headspace gas is injected in a Bruker GC450 system equipped with a Restek RT-Alumina column (5 m×0.32 mm) and a Flame ionization detection system (FID). The GC analysis method used to detect 1,3 butadiene is characterised by a constant oven temperature at 140° C., injector port temperature at 200° C. with a split ratio of 1:4 and the FID detector temperature at 250° C. Nitrogen is used as a carrier gas (constant flow of 1.25 ml/min) and a mixture of air (air flow 300 ml/min), nitrogen (28 ml/min flow) and hydrogen (flow of 30 ml/min) is used to supply the FID detection system.

In the context of the present invention an "increased activity" means that activity of the alkenol dehydratase variant in question is increased at least by a factor of 1.1, preferably at least by a factor of 1.5 and even more preferably at least by a factor of 3.0 or at least by a factor 100, 1000, 10000 or 10000 when compared to the enzyme from which it is derived, preferably when compared to the linalool dehydratase-isomerase having the amino acid sequence of SEQ ID NO:1.

According to one embodiment, the alkenol dehydratase variant of the third aspect of the present invention has an amino acid sequence as shown in SEQ ID NO:1 in which (1) an amino acid residue at position 119 in the amino acid sequence shown in SEQ ID NO:1 or at a position corresponding to this position, is deleted or substituted with glycine or leucine; and/or
(2) an amino acid residue at position 357 in the amino acid sequence shown in SEQ ID NO:1 or at a position corresponding to this position, is deleted or substituted with asparagine; and/or
(3) an amino acid residue at position 132 in the amino acid sequence shown in SEQ ID NO:1 or at a position corresponding to this position, is deleted or substituted with threonine, lysine, leucine, isoleucine, glutamine, serine, tryptophan, valine, alanine, arginine, methionine, histidine, phenylalanine, asparagine, aspartic acid, glutamic acid, glycine or tyrosine; and/or
(4) an amino acid residue at position 254 in the amino acid sequence shown in SEQ ID NO:1 or at a position corresponding to this position, is deleted or substituted with glycine; and/or
(5) an amino acid residue at position 195 in the amino acid sequence shown in SEQ ID NO:1 or at a position corresponding to this position, is deleted or substituted with phenylalanine or tyrosine; and/or
(6) an amino acid residue at position 227 in the amino acid sequence shown in SEQ ID NO:1 or at a position corresponding to this position, is deleted or substituted with isoleucine or serine; and/or
(7) an amino acid residue at position 169 in the amino acid sequence shown in SEQ ID NO:1 or at a position corresponding to this position, is deleted or substituted with threonine or asparagine; and/or
(8) an amino acid residue at position 123 in the amino acid sequence shown in SEQ ID NO:1 or at a position corresponding to this position, is deleted or substituted with histidine, tryptophan, isoleucine, glutamic acid, lysine, glutamine, arginine, threonine, aspartic acid or leucine; and/or
(9) an amino acid residue at position 156 in the amino acid sequence shown in SEQ ID NO:1 at a position corresponding to this position, is deleted or substituted with serine; and/or
(10) an amino acid residue at position 159 in the amino acid sequence shown in SEQ ID NO:1 or at a position corresponding to this position, is deleted or substituted with valine, methionine or isoleucine; and/or
(11) an amino acid residue at position 324 in the amino acid sequence shown in SEQ ID NO:1 or at a position corresponding to this position, is deleted or substituted with serine; and/or
(12) an amino acid residue at position 186 in the amino acid sequence shown in SEQ ID NO:1 or at a position corresponding to this position, is deleted or substituted with leucine or valine; and/or
(13) an amino acid residue at position 75 in the amino acid sequence shown in SEQ ID NO:1 or at a position corresponding to this position, is deleted or substituted with glycine, asparagine or alanine; and/or
(14) an amino acid residue at position 106 in the amino acid sequence shown in SEQ ID NO:1 or at a position corresponding to this position, is deleted or substituted with asparagine; and/or
(15) an amino acid residue at position 157 in the amino acid sequence shown in SEQ ID NO:1 at a position corresponding to this position, is deleted or substituted with methionine; and/or
(16) an amino acid residue at position 251 in the amino acid sequence shown in SEQ ID NO:1 or at a position corresponding to this position, is deleted or substituted with methionine or leucine; and/or
(17) an amino acid residue at position 175 in the amino acid sequence shown in SEQ ID NO:1 or at a position corresponding to this position, is deleted or substituted with serine or asparagine; and/or
(18) the amino acid residue at position 76 in the amino acid sequence shown in SEQ ID NO:1 or at a position corresponding to this position, is substituted with leucine; and/or
(19) an amino acid residue at position 122 in the amino acid sequence shown in SEQ ID NO:1 or at a position corresponding to this position, is deleted or substituted with leucine or isoleucine; and/or
(20) an amino acid residue at position 84 in the amino acid sequence shown in SEQ ID NO:1 or at a position corresponding to this position, is deleted or substituted with glutamine or isoleucine; and/or
(21) an amino acid residue at position 77 in the amino acid sequence shown in SEQ ID NO:1 or at a position corresponding to this position, is deleted or substituted with leucine or isoleucine; and/or
(22) an amino acid residue at position 115 in the amino acid sequence shown in SEQ ID NO:1 or at a position corresponding to this position, is deleted or substituted with alanine; and/or
(23) an amino acid residue at position 234 in the amino acid sequence shown in SEQ ID NO:1 or at a position corresponding to this position, is deleted or substituted with tryptophan; and/or
(24) an amino acid residue at position 181 in the amino acid sequence shown in SEQ ID NO:1 or at a position corresponding to this position, is deleted or substituted with leucine, serine or asparagine; and/or
(25) an amino acid residue at position 126 in the amino acid sequence shown in SEQ ID NO:1 or at a position corresponding to this position, is deleted or substituted with alanine; and/or
(26) an amino acid residue at position 390 in the amino acid sequence shown in SEQ ID NO:1 or at a position corresponding to this position, is deleted or substituted with aspartic acid; and/or
(27) an amino acid residue at position 72 in the amino acid sequence shown in SEQ ID NO:1 or at a position corresponding to this position, is deleted or substituted with serine; and/or
(28) an amino acid residue at position 285 in the amino acid sequence shown in SEQ ID NO:1 or at a position corresponding to this position, is deleted or substituted with methionine; and/or
(29) an amino acid residue at position 255 in the amino acid sequence shown in SEQ ID NO:1 or at a position corresponding to this position, is deleted or substituted with threonine; and/or
(30) an amino acid residue at position 247 in the amino acid sequence shown in SEQ ID NO:1 or at a position corresponding to this position, is deleted or substituted with valine; and/or
(31) an amino acid residue at position 281 in the amino acid sequence shown in SEQ ID NO:1 or at a position corresponding to this position, is deleted or substituted with tyrosine; and/or
(32) an amino acid residue at position in the amino acid sequence shown in SEQ ID NO:1 or at a position corresponding to this position, is deleted or substituted with alanine; and/or

(33) an amino acid residue at position 248 in the amino acid sequence shown in SEQ ID NO:1 or at a position corresponding to this position, is deleted or substituted with lysine; and/or

(34) an amino acid residue at position 245 in the amino acid sequence shown in SEQ ID NO:1 or at a position corresponding to this position, is deleted or substituted with alanine; and/or

(35) an amino acid residue at position 199 in the amino acid sequence shown in SEQ ID NO:1 or at a position corresponding to this position, is deleted or substituted with asparagine; and/or

(36) an amino acid residue at position 140 in the amino acid sequence shown in SEQ ID NO:1 or at a position corresponding to this position, is deleted or substituted with serine; and/or

(37) an amino acid residue at position 310 in the amino acid sequence shown in SEQ ID NO:1 or at a position corresponding to this position, is deleted or substituted with isoleucine; and/or

(38) an amino acid residue at position 373 in the amino acid sequence shown in SEQ ID NO:1 or at a position corresponding to this position, is deleted or substituted with leucine; and/or

(39) an amino acid residue at position 102 in the amino acid sequence shown in SEQ ID NO:1 or at a position corresponding to this position, is deleted or substituted with methionine; and/or

(40) an amino acid residue at position 166 in the amino acid sequence shown in SEQ ID NO:1 or at a position corresponding to this position, is deleted or substituted with serine; and/or

(41) an amino acid residue at position 95 in the amino acid sequence shown in SEQ ID NO:1 or at a position corresponding to this position, is deleted or substituted with methionine; and/or

(42) an amino acid residue at position 18 in the amino acid sequence shown in SEQ ID NO:1 or at a position corresponding to this position, is deleted or substituted with isoleucine or valine; and/or

(43) an amino acid residue at position 20 in the amino acid sequence shown in SEQ ID NO:1 or at a position corresponding to this position, is deleted or substituted with leucine; and/or

(44) an amino acid residue at position 170 in the amino acid sequence shown in SEQ ID NO:1 or at a position corresponding to this position, is deleted or substituted with lysine; and/or

(45) an amino acid residue at position 269 in the amino acid sequence shown in SEQ ID NO:1 or at a position corresponding to this position, is deleted or substituted with alanine; and/or

(46) an amino acid residue at position 382 in the amino acid sequence shown in SEQ ID NO:1 or at a position corresponding to this position, is deleted or substituted with aspartic acid; and/or

(47) an amino acid residue at position 39 in the amino acid sequence shown in SEQ ID NO:1 or at a position corresponding to this position, is deleted or substituted with alanine; and/or

(48) an amino acid residue at position 144 in the amino acid sequence shown in SEQ ID NO:1 or at a position corresponding to this position, is deleted or substituted with threonine; and/or

(49) an amino acid residue at position 173 in the amino acid sequence shown in SEQ ID NO:1 or at a position corresponding to this position, is deleted or substituted with arginine; and/or

(50) an amino acid residue at position 168 in the amino acid sequence shown in SEQ ID NO:1 or at a position corresponding to this position, is deleted or substituted with asparagine; and/or

(51) an amino acid residue at position 39 in the amino acid sequence shown in SEQ ID NO:1 or at a position corresponding to this position, is deleted or substituted with alanine; and/or

(52) an amino acid residue at position 386 in the amino acid sequence shown in SEQ ID NO:1 or at a position corresponding to this position, is deleted or substituted with serine; and/or

(53) an amino acid residue at position 367 in the amino acid sequence shown in SEQ ID NO:1 or at a position corresponding to this position, is deleted or substituted with phenylalanine; and/or

(54) an amino acid residue at position 12 in the amino acid sequence shown in SEQ ID NO:1 or at a position corresponding to this position, is deleted or substituted with leucine; and/or

(55) an amino acid residue at position 151 in the amino acid sequence shown in SEQ ID NO:1 or at a position corresponding to this position, is deleted or substituted with methionine; and/or

(56) an amino acid residue at position 230 in the amino acid sequence shown in SEQ ID NO:1 or at a position corresponding to this position, is deleted or substituted with glutamine; and/or

(57) an amino acid residue at position 207 in the amino acid sequence shown in SEQ ID NO:1 or at a position corresponding to this position, is deleted or substituted with cysteine; and/or

(58) an amino acid residue at position 114 in the amino acid sequence shown in SEQ ID NO:1 or at a position corresponding to this position, is deleted or substituted with serine; and/or

(59) an amino acid residue at position 106 in the amino acid sequence shown in SEQ ID NO:1 or at a position corresponding to this position, is deleted or substituted with asparagine; and/or

(60) an amino acid residue at position 73 in the amino acid sequence shown in SEQ ID NO:1 or at a position corresponding to this position, is deleted or substituted with serine; and/or

(61) an amino acid residue at position 181 in the amino acid sequence shown in SEQ ID NO:1 or at a position corresponding to this position, is deleted or substituted with leucine or serine; and/or

(62) an amino acid residue at position 367 in the amino acid sequence shown in SEQ ID NO:1 or at a position corresponding to this position, is deleted or substituted with phenylalanine; and/or

(63) an amino acid residue at position 389 in the amino acid sequence shown in SEQ ID NO:1 or at a position corresponding to this position, is deleted or substituted with leucine or serine; and/or

(64) an amino acid residue at position 285 in the amino acid sequence shown in SEQ ID NO:1 or at a position corresponding to this position, is deleted or substituted with leucine; and/or

(65) an amino acid residue at position 318 in the amino acid sequence shown in SEQ ID NO:1 or at a position corresponding to this position, is deleted or substituted with alanine; and/or
(66) an amino acid residue at position 158 in the amino acid sequence shown in SEQ ID NO:1 or at a position corresponding to this position, is deleted or substituted with isoleucine; and/or
(67) an amino acid residue at position 70 in the amino acid sequence shown in SEQ ID NO:1 or at a position corresponding to this position, is deleted or substituted with phenylalanine; and/or
(68) an amino acid residue at position 199 in the amino acid sequence shown in SEQ ID NO:1 or at a position corresponding to this position, is deleted or substituted with asparagine; and/or
(69) an amino acid residue at position 364 in the amino acid sequence shown in SEQ ID NO:1 or at a position corresponding to this position, is deleted or substituted with serine; and/or
(70) an amino acid residue at position 10 in the amino acid sequence shown in SEQ ID NO:1 or at a position corresponding to this position, is deleted or substituted with alanine.

The invention also relates to variants as defined in (1) to (70) hereinabove, wherein the amino acid residue indicated as substituting the amino acid residue at the position in SEQ ID NO: 1 is not that particular amino acid residue but an amino acid residue which is conservative in relation to the indicated substituting amino acid. Whether an amino acid is conservative with respect to another amino acid can be judged according to means and methods known in the art. One possibility is the PAM 250 matrix; alternatively, the Blosum Family Matrices can be used.

In a preferred embodiment the enzymes according to the third aspect of the present invention are not only capable of converting crotyl alcohol or but-3-en-2-ol into 1,3 butadiene, but they are also able to act on structurally related substrates, in particular on compounds corresponding to the general formula $C_nH_{2n}O$ into $C_nH_{2n-2}+H_2O$, with $3<n<7$, i.e. they are preferably also able to act on but-3-en-1-ol so as to convert it into 1,3 butadiene, or on 3-methylbut-2-en-1-ol (prenol), 3-methylbut-3-en-1-ol (isoprenol), 2-methyl-but-3-en-1-ol, 2-methyl-but-2-en-1-ol, 3-methyl-but-3-en-2-ol or 2-methyl-but-3-en-2-ol so as to convert them into isoprene or on 2,3-dimethyl-but-2-en-1-ol, 2,3-dimethyl-but-3-en-2-ol or 2,3-dimethyl-but-3-en-1-ol so as to convert them into dimethylbutadiene. In a particularly preferred embodiment the variants according to the third aspect of the present invention can catalyze any of these reactions with an increased activity when compared to the enzyme from which they are derived. The degree of increase is preferably as defined herein-above.

The present invention also relates to a method for providing a variant of an alkenol dehydratase wherein said variant shows an improved activity of converting an alkenol as defined above, preferably but-3-en-2-ol into 1,3 butadiene, said method comprising the step of effecting one or more changes in the sequence of the alkenol dehydratase wherein said change(s) is/are effected at one or more amino acid positions selected from the group consisting of the amino acid positions corresponding to positions 195, 106, 119, 357, 132, 123, 159, 227, 234, 157, 169, 324, 75, 126, 181, 156, 122, 84, 115, 76, 390, 255, 251, 247, 281, 77, 285, 95, 186, 248, 72, 175, 245, 199, 140, 310, 254, 373, 102, 166, 18, 20, 170, 269, 382, 39, 144, 173, 168, 39, 386, 12, 151, 230, 207, 114, 73, 181, 367, 389, 285, 318, 158, 70, 199, 364 and 10 in the amino acid sequence shown in SEQ ID NO:1.

As regards the preferred embodiments of an alkenol dehydratase to be mutated according to such a method, the same applies as has been set forth herein-above. In one preferred embodiment the alkenol dehydratase from which the variant is derived is an alkenol dehydratase which shows the amino acid sequence as shown in SEQ ID NO: 1 or an amino acid sequence having at least 60% sequence identity to SEQ ID NO:1 or any of the preferred degrees of sequence identity as specified herein-above.

In particular, as regards preferred embodiments of the degree of improvement in activity and the changes to be effected, the same applies as described herein-above.

More preferably, the present invention relates to this method wherein the changes which are effected in an alkenol dehydratase at one or more positions corresponding to positions corresponding to positions 195, 106, 119, 357, 132, 123, 159, 227, 234, 157, 169, 324, 75, 126, 181, 156, 122, 84, 115, 76, 390, 255, 251, 247, 281, 77, 285, 95, 186, 248, 72, 175, 245, 199, 140, 310, 254, 373, 102, 166, 18, 20, 170, 269, 382, 39, 144, 173, 168, 39, 386, 12, 151, 230, 207, 114, 73, 181, 367, 389, 285, 318, 158, 70, 199, 364 and 10 in the amino acid sequence shown in SEQ ID NO:1 are selected from the group consisting of those identified in items (1) to (70) as described in the context of the third aspect of the present invention under item (B).

The present invention also relates to the use of an alkenol dehydratase variant of the present invention as described above or of a host cell comprising such an alkenol dehydratase for the conversion of an alkenol as defined above, preferably of but-3-en-2-ol into 1,3 butadiene.

The present invention also relates to a variant of an alkenol dehydratase showing an improved activity in converting isoprenol and/or prenol into isoprene over the corresponding alkenol dehydratase from which it is derived, wherein the alkenol dehydratase variant is characterized in that it shows one or more substitutions, deletions and/or insertions in comparison to the corresponding sequence from which it is derived and wherein these substitutions, deletions and/or insertions occur at one or more of the positions corresponding to positions 195, 132, 84, 18, 73, 77, 386, 119, 251, 141, 123, 364, 151, 312, 318, 168, 19, 8, 20, 39, 170, 181, 199, 269, 367, 324, 13, 122, 173, 389, 118, 144, 12, 382, 145, 71, 72, 75, 76, 78, 79, 115, 116, 120, 124, 126, 128, 130, 131, 135, 143, 148, 152, 155, 192, 193, 252, 253, 254, 255, 319, 361, 366, 383, 384, 387, 70, 77, 83, 129, 138, 239, 314, 247 and 390 in the amino acid sequence shown in SEQ ID NO:1.

In a preferred embodiment such an alkenol dehydratase variant has an amino acid sequence as shown in SEQ ID NO:1 or an amino acid sequence having at least 60% sequence identity to SEQ ID NO:1, in which one or more amino acid residues at a position selected from the group consisting of positions 195, 132, 84, 18, 73, 77, 386, 119, 251, 141, 123, 364, 151, 312, 318, 168, 19, 8, 20, 39, 170, 181, 199, 269, 367, 324, 13, 122, 173, 389, 118, 144, 12, 382, 145, 71, 72, 75, 76, 78, 79, 115, 116, 120, 124, 126, 128, 130, 131, 135, 143, 148, 152, 155, 192, 193, 252, 253, 254, 255, 319, 361, 366, 383, 384, 387, 70, 77, 83, 129, 138, 239, 314, 247 and 390 in the amino acid sequence shown in SEQ ID NO:1 or at a position corresponding to any of these positions, are substituted with another amino acid residue or deleted or wherein an insertion has been effected at one or more of these positions and said alkenol dehydratase has an improved activity in converting isoprenol and/or prenol into isoprene.

According to a preferred embodiment, the present invention also relates to a variant of an alkenol dehydratase showing an improved activity in converting isoprenol and/or prenol into isoprene over the corresponding alkenol dehydratase from which it is derived, wherein the alkenol dehydratase variant is characterized in that it shows one or more substitutions, deletions and/or insertions in comparison to the corresponding sequence from which it is derived and wherein these substitutions, deletions and/or insertions occur at one or more of the positions corresponding to positions 20, 71, 72, 73, 75, 76, 78, 79, 84, 115, 116, 119, 120, 122, 123, 124, 126, 128, 130, 131, 132, 135, 143, 145, 148, 151, 152, 155, 192, 193, 195, 199, 251, 252, 253, 254, 255, 318, 319, 361, 366, 367, 383, 384, 387 and 390 in the amino acid sequence shown in SEQ ID NO:1.

In a preferred embodiment such an alkenol dehydratase variant has an amino acid sequence as shown in SEQ ID NO:1 or an amino acid sequence having at least 60% sequence identity to SEQ ID NO:1, in which one or more amino acid residues at a position selected from the group consisting of positions 20, 71, 72, 73, 75, 76, 78, 79, 84, 115, 116, 119, 120, 122, 123, 124, 126, 128, 130, 131, 132, 135, 143, 145, 148, 151, 152, 155, 192, 193, 195, 199, 251, 252, 253, 254, 255, 318, 319, 361, 366, 367, 383, 384, 387 and 390 in the amino acid sequence shown in SEQ ID NO:1 or at a position corresponding to any of these positions, are substituted with another amino acid residue or deleted or wherein an insertion has been effected at one or more of these positions and said alkenol dehydratase has an improved activity in converting isoprenol and/or prenol into isoprene.

According to one embodiment, such an alkenol dehydratase variant has an amino acid sequence as shown in SEQ ID NO:1 in which (1) an amino acid residue at position 195 in the amino acid sequence shown in SEQ ID NO:1 or at a position corresponding to this position, is deleted or substituted with phenylalanine or tyrosine; and/or (2) an amino acid residue at position 132 in the amino acid sequence shown in SEQ ID NO:1 or at a position corresponding to this position, is deleted or substituted with alanine, lysine, arginine, glutamine, methionine, serine, valine, aspartic acid, asparagine, threonine, or glycine; and/or (3) an amino acid residue at position 84 in the amino acid sequence shown in SEQ ID NO:1 or at a position corresponding to this position, is deleted or substituted with isoleucine or histidine; and/or (4) an amino acid residue at position 18 in the amino acid sequence shown in SEQ ID NO:1 or at a position corresponding to this position, is deleted or substituted with valine, isoleucine or cysteine; and/or (5) an amino acid residue at position 73 in the amino acid sequence shown in SEQ ID NO:1 or at a position corresponding to this position, is deleted or substituted with serine or alanine; and/or (6) an amino acid residue at position 77 in the amino acid sequence shown in SEQ ID NO:1 or at a position corresponding to this position, is deleted or substituted with isoleucine or leucine; and/or (7) an amino acid residue at position 386 in the amino acid sequence shown in SEQ ID NO:1 or at a position corresponding to this position, is deleted or substituted with serine; and/or (8) an amino acid residue at position 119 in the amino acid sequence shown in SEQ ID NO:1 or at a position corresponding to this position, is deleted or substituted with glycine, histidine, glutamine or arginine; and/or (9) an amino acid residue at position 251 in the amino acid sequence shown in SEQ ID NO:1 or at a position corresponding to this position, is deleted or substituted with methionine; and/or

(10) an amino acid residue at position 141 in the amino acid sequence shown in SEQ ID NO:1 or at a position corresponding to this position, is deleted or substituted with serine; and/or

(11) an amino acid residue at position 123 in the amino acid sequence shown in SEQ ID NO:1 or at a position corresponding to this position, is deleted or substituted with glutamic acid, aspartic acid, tryptophan or arginine; and/or

(12) an amino acid residue at position 364 in the amino acid sequence shown in SEQ ID NO:1 or at a position corresponding to this position, is deleted or substituted with serine; and/or

(13) an amino acid residue at position 151 in the amino acid sequence shown in SEQ ID NO:1 or at a position corresponding to this position, is deleted or substituted with phenylalanine or methionine; and/or

(14) an amino acid residue at position 312 in the amino acid sequence shown in SEQ ID NO:1 or at a position corresponding to this position, is deleted or substituted with glutamic acid; and/or

(15) an amino acid residue at position 318 in the amino acid sequence shown in SEQ ID NO:1 or at a position corresponding to this position, is deleted or substituted with alanine or glycine; and/or

(16) an amino acid residue at position 168 in the amino acid sequence shown in SEQ ID NO:1 or at a position corresponding to this position, is deleted or substituted with aspartic acid; and/or

(17) an amino acid residue at position 19 in the amino acid sequence shown in SEQ ID NO:1 or at a position corresponding to this position, is deleted or substituted with threonine; and/or

(18) an amino acid residue at position 8 in the amino acid sequence shown in SEQ ID NO:1 or at a position corresponding to this position, is deleted or substituted with leucine; and/or

(19) an amino acid residue at position 195 in the amino acid sequence shown in SEQ ID NO:1 or at a position corresponding to this position, is deleted or substituted with leucine; and/or

(20) an amino acid residue at position 39 in the amino acid sequence shown in SEQ ID NO:1 or at a position corresponding to this position, is deleted or substituted with alanine; and/or

(21) an amino acid residue at position 170 in the amino acid sequence shown in SEQ ID NO:1 or at a position corresponding to this position, is deleted or substituted with lysine; and/or

(22) an amino acid residue at position 181 in the amino acid sequence shown in SEQ ID NO:1 or at a position corresponding to this position, is deleted or substituted with leucine or serine; and/or

(23) an amino acid residue at position 199 in the amino acid sequence shown in SEQ ID NO:1 or at a position corresponding to this position, is deleted or substituted with alanine, glutamic acid, leucine, methionine, glutamine, serine or asparagine; and/or

(24) an amino acid residue at position 269 in the amino acid sequence shown in SEQ ID NO:1 or at a position corresponding to this position, is deleted or substituted with alanine; and/or
(25) an amino acid residue at position 367 in the amino acid sequence shown in SEQ ID NO:1 or at a position corresponding to this position, is deleted or substituted with phenylalanine; and/or
(26) an amino acid residue at position 324 in the amino acid sequence shown in SEQ ID NO:1 or at a position corresponding to this position, is deleted or substituted with serine; and/or
(27) an amino acid residue at position 13 in the amino acid sequence shown in SEQ ID NO:1 or at a position corresponding to this position, is deleted or substituted with leucine or isoleucine; and/or
(28) an amino acid residue at position 173 in the amino acid sequence shown in SEQ ID NO:1 or at a position corresponding to this position, is deleted or substituted with arginine; and/or
(29) an amino acid residue at position 389 in the amino acid sequence shown in SEQ ID NO:1 or at a position corresponding to this position, is deleted or substituted with leucine; and/or
(30) an amino acid residue at position 118 in the amino acid sequence shown in SEQ ID NO:1 or at a position corresponding to this position, is deleted or substituted with leucine; and/or
(31) an amino acid residue at position 144 in the amino acid sequence shown in SEQ ID NO:1 or at a position corresponding to this position, is deleted or substituted with threonine; and/or
(32) an amino acid residue at position 12 in the amino acid sequence shown in SEQ ID NO:1 or at a position corresponding to this position, is deleted or substituted with alanine; and/or
(33) an amino acid residue at position 382 in the amino acid sequence shown in SEQ ID NO:1 or at a position corresponding to this position, is deleted or substituted with aspartic acid; and/or
(34) an amino acid residue at position 145 in the amino acid sequence shown in SEQ ID NO:1 or at a position corresponding to this position, is deleted or substituted with proline or glutamic acid; and/or
(35) an amino acid residue at position 20 in the amino acid sequence shown in SEQ ID NO:1 or at a position corresponding to this position, is deleted or substituted with threonine or leucine; and/or
(36) an amino acid residue at position 122 in the amino acid sequence shown in SEQ ID NO:1 or at a position corresponding to this position, is deleted or substituted with methionine or leucine; and/or
(37) an amino acid residue at position 71 in the amino acid sequence shown in SEQ ID NO:1 or at a position corresponding to this position, is deleted or substituted with alanine, aspartic acid, or threonine; and/or
(38) an amino acid residue at position 72 in the amino acid sequence shown in SEQ ID NO:1 or at a position corresponding to this position, is deleted or substituted with leucine, proline, or arginine; and/or
(39) an amino acid residue at position 75 in the amino acid sequence shown in SEQ ID NO:1 or at a position corresponding to this position, is deleted or substituted with alanine, aspartic acid, phenylalanine, isoleucine, leucine, methionine, threonine, valine, or asparagine; and/or
(40) an amino acid residue at position 76 in the amino acid sequence shown in SEQ ID NO:1 or at a position corresponding to this position, is deleted or substituted with isoleucine, leucine or valine; and/or
(41) an amino acid residue at position 78 in the amino acid sequence shown in SEQ ID NO:1 or at a position corresponding to this position, is deleted or substituted with glycine; and/or
(42) an amino acid residue at position 79 in the amino acid sequence shown in SEQ ID NO:1 or at a position corresponding to this position, is deleted or substituted with tyrosine; and/or
(43) an amino acid residue at position 70 in the amino acid sequence shown in SEQ ID NO:1 or at a position corresponding to this position, is deleted or substituted with phenylalanine; and/or
(44) an amino acid residue at position 83 in the amino acid sequence shown in SEQ ID NO:1 or at a position corresponding to this position, is deleted or substituted with methionine, tryptophan, threonine; and/or
(45) an amino acid residue at position 115 in the amino acid sequence shown in SEQ ID NO:1 or at a position corresponding to this position, is deleted or substituted with alanine or aspartic acid; and/or
(46) an amino acid residue at position 116 in the amino acid sequence shown in SEQ ID NO:1 or at a position corresponding to this position, is deleted or substituted with lysine or arginine; and/or
(47) an amino acid residue at position 120 in the amino acid sequence shown in SEQ ID NO:1 or at a position corresponding to this position, is deleted or substituted with arginine or valine; and/or
(48) an amino acid residue at position 124 in the amino acid sequence shown in SEQ ID NO:1 or at a position corresponding to this position, is deleted or substituted with leucine; and/or
(49) an amino acid residue at position 126 in the amino acid sequence shown in SEQ ID NO:1 or at a position corresponding to this position, is deleted or substituted with alanine, aspartic acid or phenylalanine; and/or
(50) an amino acid residue at position 128 in the amino acid sequence shown in SEQ ID NO:1 or at a position corresponding to this position, is deleted or substituted with aspartic acid or asparagine; and/or
(51) an amino acid residue at position 129 in the amino acid sequence shown in SEQ ID NO:1 or at a position corresponding to this position, is deleted or substituted with leucine; and/or
(52) an amino acid residue at position 130 in the amino acid sequence shown in SEQ ID NO:1 or at a position corresponding to this position, is deleted or substituted with isoleucine; and/or
(53) an amino acid residue at position 131 in the amino acid sequence shown in SEQ ID NO:1 or at a position corresponding to this position, is deleted or substituted with phenylalanine; and/or
(54) an amino acid residue at position 135 in the amino acid sequence shown in SEQ ID NO:1 or at a position corresponding to this position, is deleted or substituted with proline; and/or
(55) an amino acid residue at position 138 in the amino acid sequence shown in SEQ ID NO:1 or at a position corresponding to this position, is deleted or substituted with glutamine; and/or

(56) an amino acid residue at position 143 in the amino acid sequence shown in SEQ ID NO:1 or at a position corresponding to this position, is deleted or substituted with tyrosine; and/or
(57) an amino acid residue at position 148 in the amino acid sequence shown in SEQ ID NO:1 or at a position corresponding to this position, is deleted or substituted with aspartic acid; and/or
(58) an amino acid residue at position 152 in the amino acid sequence shown in SEQ ID NO:1 or at a position corresponding to this position, is deleted or substituted with arginine; and/or
(59) an amino acid residue at position 155 in the amino acid sequence shown in SEQ ID NO:1 or at a position corresponding to this position, is deleted or substituted with isoleucine; and/or
(60) an amino acid residue at position 192 in the amino acid sequence shown in SEQ ID NO:1 or at a position corresponding to this position, is deleted or substituted with leucine; and/or
(61) an amino acid residue at position 193 in the amino acid sequence shown in SEQ ID NO:1 or at a position corresponding to this position, is deleted or substituted with alanine; and/or
(62) an amino acid residue at position 239 in the amino acid sequence shown in SEQ ID NO:1 or at a position corresponding to this position, is deleted or substituted with methionine; and/or
(63) an amino acid residue at position 252 in the amino acid sequence shown in SEQ ID NO:1 or at a position corresponding to this position, is deleted or substituted with aspartic acid; and/or
(64) an amino acid residue at position 253 in the amino acid sequence shown in SEQ ID NO:1 or at a position corresponding to this position, is deleted or substituted with histidine; and/or
(65) an amino acid residue at position 254 in the amino acid sequence shown in SEQ ID NO:1 or at a position corresponding to this position, is deleted or substituted with glycine, histidine or proline; and/or
(66) an amino acid residue at position 255 in the amino acid sequence shown in SEQ ID NO:1 or at a position corresponding to this position, is deleted or substituted with glycine, histidine, leucine, glutamine or tyrosine; and/or
(67) an amino acid residue at position 314 in the amino acid sequence shown in SEQ ID NO:1 or at a position corresponding to this position, is deleted or substituted with threonine; and/or
(68) an amino acid residue at position 319 in the amino acid sequence shown in SEQ ID NO:1 or at a position corresponding to this position, is deleted or substituted with arginine; and/or
(69) an amino acid residue at position 361 in the amino acid sequence shown in SEQ ID NO:1 or at a position corresponding to this position, is deleted or substituted with threonine; and/or
(70) an amino acid residue at position 366 in the amino acid sequence shown in SEQ ID NO:1 or at a position corresponding to this position, is deleted or substituted with valine; and/or
(71) an amino acid residue at position 383 in the amino acid sequence shown in SEQ ID NO:1 or at a position corresponding to this position, is deleted or substituted with tyrosine; and/or
(72) an amino acid residue at position 384 in the amino acid sequence shown in SEQ ID NO:1 or at a position corresponding to this position, is deleted or substituted with methionine or tyrosine; and/or
(73) an amino acid residue at position 387 in the amino acid sequence shown in SEQ ID NO:1 or at a position corresponding to this position, is deleted or substituted with aspartic acid or asparagine; and/or
(74) an amino acid residue at position 390 in the amino acid sequence shown in SEQ ID NO:1 or at a position corresponding to this position, is deleted or substituted with aspartic acid; and/or
(75) an amino acid residue at position 247 in the amino acid sequence shown in SEQ ID NO:1 or at a position corresponding to this position, is deleted or substituted with valine.

In a preferred embodiment, the variant according to the invention showing an improved activity in converting prenol into isoprene is characterized in that it contains at least two deletions, substitutions and/or insertions wherein the deletion/insertion/substitution is at position 75 in the amino acid sequence shown in SEQ ID NO:1 or at a position corresponding to this position and another deletion/insertion/substitution is at position 83 in the amino acid sequence shown in SEQ ID NO:1 or at a position corresponding to this position. Preferably, such a variant further has one or more substitutions, deletions and/or insertions in comparison to the corresponding sequence from which it is derived and wherein these substitutions, deletions and/or insertions occur at one or more of the positions corresponding to positions 195, 132, 84, 18, 73, 77, 386, 119, 251, 141, 123, 364, 151, 312, 318, 168, 19, 8, 20, 39, 170, 181, 199, 269, 367, 324, 13, 122, 173, 389, 118, 144, 12, 382, 145, 71, 72, 76, 78, 79, 115, 116, 120, 124, 126, 128, 130, 131, 135, 143, 148, 152, 155, 192, 193, 252, 253, 254, 255, 319, 361, 366, 383, 384, 387, 70, 77, 129, 138, 239, 314, 247 and 390 in the amino acid sequence shown in SEQ ID NO:1.

In a preferred embodiment, the variant according to the invention showing an improved activity in converting prenol into isoprene is characterized in that it contains at least two deletions, substitutions and/or insertions wherein the deletion/insertion/substitution is at position 129 in the amino acid sequence shown in SEQ ID NO:1 or at a position corresponding to this position and another deletion/insertion/substitution is at position 367 in the amino acid sequence shown in SEQ ID NO:1 or at a position corresponding to this position. Preferably, such a variant further has one or more substitutions, deletions and/or insertions in comparison to the corresponding sequence from which it is derived and wherein these substitutions, deletions and/or insertions occur at one or more of the positions corresponding to positions 195, 132, 84, 18, 73, 77, 386, 119, 251, 141, 123, 364, 151, 312, 318, 168, 19, 8, 20, 39, 170, 181, 199, 269, 324, 13, 122, 173, 389, 118, 144, 12, 382, 145, 71, 72, 75, 76, 78, 79, 115, 116, 120, 124, 126, 128, 130, 131, 135, 143, 148, 152, 155, 192, 193, 252, 253, 254, 255, 319, 361, 366, 383, 384, 387, 70, 77, 83, 138, 239, 314, 247 and 390 in the amino acid sequence shown in SEQ ID NO:1.

In a preferred embodiment, the variant according to the invention showing an improved activity in converting prenol into isoprene is characterized in that it contains at least two deletions, substitutions and/or insertions wherein the deletion/insertion/substitution is at position 75 in the amino acid sequence shown in SEQ ID NO:1 or at a position corresponding to this position and another deletion/insertion/substitution is at position 83 in the amino acid sequence shown in SEQ ID NO:1 or at a position corresponding to this position. Preferably, such a variant further has one or more substitutions, deletions and/or insertions in comparison to the corresponding sequence from which it is derived and wherein these substitutions, deletions and/or insertions occur at one or more of the positions corresponding to positions 195, 132, 84, 18, 73, 77, 386, 119, 251, 141, 123, 364, 151, 312, 318, 168, 19, 8, 20, 39, 170, 181, 199, 269, 367, 324, 13, 122, 173, 389, 118, 144, 12, 382, 145, 71, 72, 76, 78, 79, 115, 116, 120, 124, 126, 128, 130, 131, 135, 143, 148, 152, 155, 192, 193, 252, 253, 254, 255, 319, 361, 366, 383, 384, 387, 70, 77, 129, 138, 239, 314, 247 and 390 in the amino acid sequence shown in SEQ ID NO:1.

In a preferred embodiment, the variant according to the invention showing an improved activity in converting prenol into isoprene is characterized in that it contains at least two deletions, substitutions and/or insertions wherein the deletion/insertion/substitution is at position 75 in the amino acid sequence shown in SEQ ID NO:1 or at a position corresponding to this position and another deletion/insertion/substitution is at position 138 in the amino acid sequence shown in SEQ ID NO:1 or at a position corresponding to this position. Preferably, such a variant further has one or more substitutions, deletions and/or insertions in comparison to the corresponding sequence from which it is derived and wherein these substitutions, deletions and/or insertions occur at one or more of the positions corresponding to positions 195, 132, 84, 18, 73, 77, 386, 119, 251, 141, 123, 364, 151, 312, 318, 168, 19, 8, 20, 39, 170, 181, 199, 269, 367, 324, 13, 122, 173, 389, 118, 144, 12, 382, 145, 71, 72, 76, 78, 79, 115, 116, 120, 124, 126, 128, 130, 131, 135, 143, 148, 152, 155, 192, 193, 252, 253, 254, 255, 319, 361, 366, 383, 384, 387, 70, 77, 83, 129, 239, 314, 247 and 390 in the amino acid sequence shown in SEQ ID NO:1.

In a preferred embodiment, the variant according to the invention showing an improved activity in converting prenol into isoprene is characterized in that it contains at least two deletions, substitutions and/or insertions wherein the deletion/insertion/substitution is at position 76 in the amino acid sequence shown in SEQ ID NO:1 or at a position corresponding to this position and another deletion/insertion/substitution is at position 77 in the amino acid sequence shown in SEQ ID NO:1 or at a position corresponding to this position. Preferably, such a variant further has one or more substitutions, deletions and/or insertions in comparison to the corresponding sequence from which it is derived and wherein these substitutions, deletions and/or insertions occur at one or more of the positions corresponding to positions 195, 132, 84, 18, 73, 386, 119, 251, 141, 123, 364, 151, 312, 318, 168, 19, 8, 20, 39, 170, 181, 199, 269, 367, 324, 13, 122, 173, 389, 118, 144, 12, 382, 145, 71, 72, 75, 78, 79, 115, 116, 120, 124, 126, 128, 130, 131, 135, 143, 148, 152, 155, 192, 193, 252, 253, 254, 255, 319, 361, 366, 383, 384, 387, 70, 77, 83, 129, 138, 239, 314, 247 and 390 in the amino acid sequence shown in SEQ ID NO:1.

In a preferred embodiment, the variant according to the invention showing an improved activity in converting prenol into isoprene is characterized in that it contains at least two deletions, substitutions and/or insertions wherein the deletion/insertion/substitution is at position 76 in the amino acid sequence shown in SEQ ID NO:1 or at a position corresponding to this position and another deletion/insertion/substitution is at position 84 in the amino acid sequence shown in SEQ ID NO:1 or at a position corresponding to this position. Preferably, such a variant further has one or more substitutions, deletions and/or insertions in comparison to the corresponding sequence from which it is derived and wherein these substitutions, deletions and/or insertions occur at one or more of the positions corresponding to positions 195, 132, 18, 73, 77, 386, 119, 251, 141, 123, 364, 151, 312, 318, 168, 19, 8, 20, 39, 170, 181, 199, 269, 367, 324, 13, 122, 173, 389, 118, 144, 12, 382, 145, 71, 72, 75, 78, 79, 115, 116, 120, 124, 126, 128, 130, 131, 135, 143, 148, 152, 155, 192, 193, 252, 253, 254, 255, 319, 361, 366, 383, 384, 387, 70, 77, 83, 129, 138, 239, 314, 247 and 390 in the amino acid sequence shown in SEQ ID NO:1.

In a preferred embodiment, the variant according to the invention showing an improved activity in converting prenol into isoprene is characterized in that it contains at least two deletions, substitutions and/or insertions wherein the deletion/insertion/substitution is at position 76 in the amino acid sequence shown in SEQ ID NO:1 or at a position corresponding to this position and another deletion/insertion/substitution is at position 314 in the amino acid sequence shown in SEQ ID NO:1 or at a position corresponding to this position. Preferably, such a variant further has one or more substitutions, deletions and/or insertions in comparison to the corresponding sequence from which it is derived and wherein these substitutions, deletions and/or insertions occur at one or more of the positions corresponding to positions 195, 132, 84, 18, 73, 77, 386, 119, 251, 141, 123, 364, 151, 312, 318, 168, 19, 8, 20, 39, 170, 181, 199, 269, 367, 324, 13, 122, 173, 389, 118, 144, 12, 382, 145, 71, 72, 75, 78, 79, 115, 116, 120, 124, 126, 128, 130, 131, 135, 143, 148, 152, 155, 192, 193, 252, 253, 254, 255, 319, 361, 366, 383, 384, 387, 70, 77, 83, 129, 138, 239, 247 and 390 in the amino acid sequence shown in SEQ ID NO:1.

In a preferred embodiment, the variant according to the invention showing an improved activity in converting prenol into isoprene is characterized in that it contains at least two deletions, substitutions and/or insertions wherein the deletion/insertion/substitution is at position 126 in the amino acid sequence shown in SEQ ID NO:1 or at a position corresponding to this position and another deletion/insertion/substitution is at position 364 in the amino acid sequence shown in SEQ ID NO:1 or at a position corresponding to this position. Preferably, such a variant further has one or more substitutions, deletions and/or insertions in comparison to the corresponding sequence from which it is derived and wherein these substitutions, deletions and/or insertions occur at one or more of the positions corresponding to positions 195, 132, 84, 18, 73, 77, 386, 119, 251, 141, 123, 151, 312, 318, 168, 19, 8, 20, 39, 170, 181, 199, 269, 367, 324, 13, 122, 173, 389, 118, 144, 12, 382, 145, 71, 72, 75, 76, 78, 79, 115, 116, 120, 124, 128, 130, 131, 135, 143, 148, 152, 155, 192, 193, 252, 253, 254, 255, 319, 361, 366, 383, 384, 387, 70, 77, 83, 129, 138, 239, 314, 247 and 390 in the amino acid sequence shown in SEQ ID NO:1.

In a preferred embodiment, the variant according to the invention showing an improved activity in converting prenol into isoprene is characterized in that it contains at least two deletions, substitutions and/or insertions wherein the deletion/insertion/substitution is at position 75 in the amino acid sequence shown in SEQ ID NO:1 or at a position corresponding to this position and another deletion/insertion/substitution is at position 83 in the amino acid sequence shown in SEQ ID NO:1 or at a position corresponding to this position. Preferably, such a variant further has one or more substitutions, deletions and/or insertions in comparison to the corresponding sequence from which it is derived and wherein these substitutions, deletions and/or insertions occur at one or more of the positions corresponding to positions 195, 132, 84, 18, 73, 77, 386, 119, 251, 141, 123, 364, 151, 312, 318, 168, 19, 8, 20, 39, 170, 181, 199, 269, 367, 324, 13, 122, 173, 389, 118, 144, 12, 382, 145, 71, 72, 76, 78, 79, 115, 116, 120, 124, 126, 128, 130, 131, 135, 143, 148, 152, 155, 192, 193, 252, 253, 254, 255, 319, 361, 366, 383, 384, 387, 70, 77, 129, 138, 239, 314, 247 and 390 in the amino acid sequence shown in SEQ ID NO:1.

In a preferred embodiment, the variant according to the invention showing an improved activity in converting prenol into isoprene is characterized in that it contains at least two deletions, substitutions and/or insertions wherein the deletion/insertion/substitution is at position 239 in the amino acid sequence shown in SEQ ID NO:1 or at a position corresponding to this position and another deletion/insertion/substitution is at position 247 in the amino acid sequence shown in SEQ ID NO:1 or at a position corresponding to this position. Preferably, such a variant further has one or more substitutions, deletions and/or insertions in comparison to the corresponding sequence from which it is derived and wherein these substitutions, deletions and/or insertions occur at one or more of the positions corresponding to positions 195, 132, 84, 18, 73, 77, 386, 119, 251, 141, 123, 364, 151, 312, 318, 168, 19, 8, 20, 39, 170, 181, 199, 269, 367, 324, 13, 122, 173, 389, 118, 144, 12, 382, 145, 71, 72, 75, 76, 78, 79, 115, 116, 120, 124, 126, 128, 130, 131, 135, 143, 148, 152, 155, 192, 193, 252, 253, 254, 255, 319, 361, 366, 383, 384, 387, 70, 77, 83, 129, 138, 314, and 390 in the amino acid sequence shown in SEQ ID NO:1.

In a preferred embodiment, the variant according to the invention showing an improved activity in converting prenol into isoprene is characterized in that it contains at least two deletions, substitutions and/or insertions wherein the deletion/insertion/substitution is at position 319 in the amino acid sequence shown in SEQ ID NO:1 or at a position corresponding to this position and another deletion/insertion/substitution is at position 382 in the amino acid sequence shown in SEQ ID NO:1 or at a position corresponding to this position. Preferably, such a variant further has one or more substitutions, deletions and/or insertions in comparison to the corresponding sequence from which it is derived and wherein these substitutions, deletions and/or insertions occur at one or more of the positions corresponding to positions 195, 132, 84, 18, 73, 77, 386, 119, 251, 141, 123, 364, 151, 312, 318, 168, 19, 8, 20, 39, 170, 181, 199, 269, 367, 324, 13, 122, 173, 389, 118, 144, 12, 145, 71, 72, 75, 76, 78, 79, 115, 116, 120, 124, 126, 128, 130, 131, 135, 143, 148, 152, 155, 192, 193, 252, 253, 254, 255, 361, 366, 383, 384, 387, 70, 77, 83, 129, 138, 239, 314, 247 and 390 in the amino acid sequence shown in SEQ ID NO:1.

In a preferred embodiment, the variant according to the invention showing an improved activity in converting prenol into isoprene is characterized in that it contains at least two deletions, substitutions and/or insertions wherein the deletion/insertion/substitution is at position 195 in the amino acid sequence shown in SEQ ID NO:1 or at a position corresponding to this position and another deletion/insertion/substitution is at position 132 in the amino acid sequence shown in SEQ ID NO:1 or at a position corresponding to this position. Preferably, such a variant further has one or more substitutions, deletions and/or insertions in comparison to the corresponding sequence from which it is derived and wherein these substitutions, deletions and/or insertions occur at one or more of the positions corresponding to positions 84, 18, 73, 77, 386, 119, 251, 141, 123, 364, 151, 312, 318, 168, 19, 8, 20, 39, 170, 181, 199, 269, 367, 324, 13, 122, 173, 389, 118, 144, 12, 382, 145, 71, 72, 75, 76, 78, 79, 115, 116, 120, 124, 126, 128, 130, 131, 135, 143, 148, 152, 155, 192, 193, 252, 253, 254, 255, 319, 361, 366, 383, 384, 387, 70, 77, 83, 129, 138, 239, 314, 247 and 390 in the amino acid sequence shown in SEQ ID NO:1.

In a preferred embodiment, the variant according to the invention showing an improved activity in converting prenol into isoprene is characterized in that it contains at least two deletions, substitutions and/or insertions wherein the deletion/insertion/substitution is at position 195 in the amino acid sequence shown in SEQ ID NO:1 or at a position corresponding to this position and another deletion/insertion/substitution is at position 324 in the amino acid sequence shown in SEQ ID NO:1 or at a position corresponding to this position. Preferably, such a variant further has one or more substitutions, deletions and/or insertions in comparison to the corresponding sequence from which it is derived and wherein these substitutions, deletions and/or insertions occur at one or more of the positions corresponding to positions 132, 84, 18, 73, 77, 386, 119, 251, 141, 123, 364, 151, 312, 318, 168, 19, 8, 20, 39, 170, 181, 199, 269, 367, 13, 122, 173, 389, 118, 144, 12, 382, 145, 71, 72, 75, 76, 78, 79, 115, 116, 120, 124, 126, 128, 130, 131, 135, 143, 148, 152, 155, 192, 193, 252, 253, 254, 255, 319, 361, 366, 383, 384, 387, 70, 77, 83, 129, 138, 239, 314, 247 and 390 in the amino acid sequence shown in SEQ ID NO:1.

In even more preferred embodiments, the variant according to the invention showing an improved activity in converting prenol into isoprene is characterized in that it has multiple mutations. As it is exemplified in the examples further below, variants have been found bearing multiple mutations which exhibit an increase in the reaction rate of the conversion of prenol into isoprene. These variants bearing multiple mutations are summarized in the following:

Accordingly, in a very preferred embodiment, the variant according to the invention is characterized in that it comprises deletions, substitutions and/or insertions wherein the deletions/insertions/substitutions are at positions 195, 84, and 132 in the amino acid sequence shown in SEQ ID NO:1 or at positions corresponding to these positions. Preferably, such a variant has the following substitutions in the amino acid sequence shown in SEQ ID NO:1 or at positions corresponding to these position: V195FT84IG132R.

In another preferred embodiment, the variant according to the invention is characterized in that it comprises deletions, substitutions and/or insertions wherein the deletions/insertions/substitutions are at positions 195, 18, 73, 77, and 386 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FA18VG73SE77IR386S.

In another preferred embodiment, the variant according to the invention is characterized in that it comprises deletions, substitutions and/or insertions wherein the deletions/insertions/substitutions are at positions 195, 119, 132, and 251 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FD119GG132KY251M.

In another preferred embodiment, the variant according to the invention is characterized in that it comprises deletions, substitutions and/or insertions wherein the deletions/insertions/substitutions are at positions 195, 132, 73, 77, and 84 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FG132AG73SE77IT84I.

In another preferred embodiment, the variant according to the invention is characterized in that it comprises deletions, substitutions and/or insertions wherein the deletions/insertions/substitutions are at positions 195, 132, 73, and 77 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FG132AG73SE77L.

In another preferred embodiment, the variant according to the invention is characterized in that it comprises deletions, substitutions and/or insertions wherein the deletions/insertions/substitutions are at positions 195, 132, 73, 77, and 141 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FG132AG73SE77IT141S.

In another preferred embodiment, the variant according to the invention is characterized in that it comprises deletions, substitutions and/or insertions wherein the deletions/insertions/substitutions are at positions 195, 132, 73, 77, and 141 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FG132AG73SE77IT141S.

In another preferred embodiment, the variant according to the invention is characterized in that it comprises deletions, substitutions and/or insertions wherein the deletions/insertions/substitutions are at positions 195, and 84 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FT84I.

In another preferred embodiment, the variant according to the invention is characterized in that it comprises deletions, substitutions and/or insertions wherein the deletions/insertions/substitutions are at positions 195, 119, and 123 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FD119GS123E.

In another preferred embodiment, the variant according to the invention is characterized in that it comprises deletions, substitutions and/or insertions wherein the deletions/insertions/substitutions are at positions 195, 132, 73, and 77 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FG132AG73SE77I.

In another preferred embodiment, the variant according to the invention is characterized in that it comprises deletions, substitutions and/or insertions wherein the deletions/insertions/substitutions are at positions 195, 132, 73, 77, and 364 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FG132AG73SE77IG364S.

In another preferred embodiment, the variant according to the invention is characterized in that it comprises deletions, substitutions and/or insertions wherein the deletions/insertions/substitutions are at positions 195, 132, 73, and 77 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FG132AG73SE77I.

In another preferred embodiment, the variant according to the invention is characterized in that it comprises deletions, substitutions and/or insertions wherein the deletions/insertions/substitutions are at positions 195, 132, 73, and 77 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FG132AG73AE77L.

In another preferred embodiment, the variant according to the invention is characterized in that it comprises deletions, substitutions and/or insertions wherein the deletions/insertions/substitutions are at positions 195, 119, and 151 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FD119GY151M.

In another preferred embodiment, the variant according to the invention is characterized in that it comprises deletions, substitutions and/or insertions wherein the deletions/insertions/substitutions are at positions 195, 132, 73, 77, and 312 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FG132AG73SE77ID312E.

In another preferred embodiment, the variant according to the invention is characterized in that it comprises deletions, substitutions and/or insertions wherein the deletions/insertions/substitutions are at positions 195, 119, and 251 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FD119GY251M.

In another preferred embodiment, the variant according to the invention is characterized in that it comprises deletions, substitutions and/or insertions wherein the deletions/insertions/substitutions are at positions 195, 132, and 318 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FG132QV318A.

In another preferred embodiment, the variant according to the invention is characterized in that it comprises deletions, substitutions and/or insertions wherein the deletions/insertions/substitutions are at positions 195 and 132 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FG132Q.

In another preferred embodiment, the variant according to the invention is characterized in that it comprises deletions, substitutions and/or insertions wherein the deletions/insertions/substitutions are at positions 195, 132, 73, 77, and 168 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FG132AG73SE77IS168D.

In another preferred embodiment, the variant according to the invention is characterized in that it comprises deletions, substitutions and/or insertions wherein the deletions/insertions/substitutions are at positions 195, 132, 73, 77, and 19 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FG132AG73SE77IG19T.

In another preferred embodiment, the variant according to the invention is characterized in that it comprises deletions, substitutions and/or insertions wherein the deletions/insertions/substitutions are at positions 195, 132, 73, 77, and 8 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FG132AG73SE77IT8L.

In another preferred embodiment, the variant according to the invention is characterized in that it comprises deletions, substitutions and/or insertions wherein the deletions/insertions/substitutions are at positions 75 and 83 in the amino acid sequence shown in SEQ ID NO:1 or at positions corresponding to these positions. Preferably, such a variant has the following substitutions in the amino acid sequence shown in SEQ ID NO:1 or at positions corresponding to these positions: S75VH83M.

In another preferred embodiment, the variant according to the invention is characterized in that it comprises deletions, substitutions and/or insertions wherein the deletions/insertions/substitutions are at positions 129 and 367 in the amino acid sequence shown in SEQ ID NO:1 or at positions corresponding to these positions. Preferably, such a variant has the following substitutions in the amino acid sequence shown in SEQ ID NO:1 or at positions corresponding to these positions: R129LL367F.

In another preferred embodiment, the variant according to the invention is characterized in that it comprises deletions, substitutions and/or insertions wherein the deletions/insertions/substitutions are at positions 75 and 83 in the amino acid sequence shown in SEQ ID NO:1 or at positions corresponding to these positions. Preferably, such a variant has the following substitutions in the amino acid sequence shown in SEQ ID NO:1 or at positions corresponding to these positions: S75AH83W.

In another preferred embodiment, the variant according to the invention is characterized in that it comprises deletions, substitutions and/or insertions wherein the deletions/insertions/substitutions are at positions 75 and 138 in the amino acid sequence shown in SEQ ID NO:1 or at positions corresponding to these positions. Preferably, such a variant has the following substitutions in the amino acid sequence shown in SEQ ID NO:1 or at positions corresponding to these positions: S75NG138Q.

In another preferred embodiment, the variant according to the invention is characterized in that it comprises deletions, substitutions and/or insertions wherein the deletions/insertions/substitutions are at positions 76 and 77 in the amino acid sequence shown in SEQ ID NO:1 or at positions corresponding to these positions. Preferably, such a variant has the following substitutions in the amino acid sequence shown in SEQ ID NO:1 or at positions corresponding to these positions: F76VE77L.

In another preferred embodiment, the variant according to the invention is characterized in that it comprises deletions, substitutions and/or insertions wherein the deletions/insertions/substitutions are at positions 76 and 84 in the amino acid sequence shown in SEQ ID NO:1 or at positions corresponding to these positions. Preferably, such a variant has the following substitutions in the amino acid sequence shown in SEQ ID NO:1 or at positions corresponding to these positions: F76LT84I.

In another preferred embodiment, the variant according to the invention is characterized in that it comprises deletions, substitutions and/or insertions wherein the deletions/insertions/substitutions are at positions 76 and 314 in the amino acid sequence shown in SEQ ID NO:1 or at positions corresponding to these positions. Preferably, such a variant has the following substitutions in the amino acid sequence shown in SEQ ID NO:1 or at positions corresponding to these positions: F76LA314T.

In another preferred embodiment, the variant according to the invention is characterized in that it comprises deletions, substitutions and/or insertions wherein the deletions/insertions/substitutions are at positions 126 and 364 in the amino acid sequence shown in SEQ ID NO:1 or at positions corresponding to these positions. Preferably, such a variant has the following substitutions in the amino acid sequence shown in SEQ ID NO:1 or at positions corresponding to these positions: K126FG364M.

In another preferred embodiment, the variant according to the invention is characterized in that it comprises deletions, substitutions and/or insertions wherein the deletions/insertions/substitutions are at positions 75 and 83 in the amino acid sequence shown in SEQ ID NO:1 or at positions corresponding to these positions. Preferably, such a variant has the following substitutions in the amino acid sequence shown in SEQ ID NO:1 or at positions corresponding to these positions: S75MH83T.

In another preferred embodiment, the variant according to the invention is characterized in that it comprises deletions, substitutions and/or insertions wherein the deletions/insertions/substitutions are at positions 239 and 247 in the amino acid sequence shown in SEQ ID NO:1 or at positions corresponding to these positions. Preferably, such a variant has the following substitutions in the amino acid sequence shown in SEQ ID NO:1 or at positions corresponding to these positions: L239MF247V.

In another preferred embodiment, the variant according to the invention is characterized in that it comprises deletions, substitutions and/or insertions wherein the deletions/insertions/substitutions are at positions 319 and 382 in the amino acid sequence shown in SEQ ID NO:1 or at positions corresponding to these positions. Preferably, such a variant has the following substitutions in the amino acid sequence shown in SEQ ID NO:1 or at positions corresponding to these positions: G319RG382Q.

In another preferred embodiment, the variant according to the invention is characterized in that it comprises deletions, substitutions and/or insertions wherein the deletions/insertions/substitutions are at positions 195 and 132 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FG132A.

In another preferred embodiment, the variant according to the invention is characterized in that it comprises deletions, substitutions and/or insertions wherein the deletions/insertions/substitutions are at positions 73, 77, 132, and 195 in the amino acid sequence shown in SEQ ID NO:1 or at positions corresponding to these positions. Preferably, such a variant has the following substitutions in the amino acid sequence shown in SEQ ID NO:1 or at positions corresponding to these positions: G73SE77IG132AV195F.

In another preferred embodiment, the variant according to the invention is characterized in that it comprises deletions, substitutions and/or insertions wherein the deletions/insertions/substitutions are at positions 73, 132, 170, 181, 195 and 324 in the amino acid sequence shown in SEQ ID NO:1 or at positions corresponding to these positions. Preferably, such a variant has the following substitutions in the amino acid sequence shown in SEQ ID NO:1 or at positions corresponding to these positions: G73SG132GR170KI181LV195FF324S.

In another preferred embodiment, the variant according to the invention is characterized in that it comprises deletions, substitutions and/or insertions wherein the deletions/insertions/substitutions are at positions 195 and 324 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FF324S.

In another preferred embodiment, the variant according to the invention is characterized in that it comprises deletions, substitutions and/or insertions wherein the deletions/insertions/substitutions are at positions 170, 132, 173, 181, 195, 199, and 324 in the amino acid sequence shown in SEQ ID NO:1 or at positions corresponding to these positions. Preferably, such a variant has the following substitutions in the amino acid sequence shown in SEQ ID NO:1 or at positions corresponding to these positions: R170KG132VA173RI181LV195FD199NF324S. In another preferred embodiment, the variant according to the invention is characterized in that it comprises deletions, substitutions and/or insertions wherein the deletions/insertions/substitutions are at positions 18, 20, 73, 132, 170, 181, 195, 199, 324, and 367 in the amino acid sequence shown in SEQ ID NO:1 or at positions corresponding to these positions. Preferably, such a variant has the following substitutions in the amino acid sequence shown in SEQ ID NO:1 or at positions corresponding to these positions: A18IF20LG73SG132MR170KI181LV195FD199NF324S L367F.

In another preferred embodiment, the variant according to the invention is characterized in that it comprises deletions, substitutions and/or insertions wherein the deletions/insertions/substitutions are at positions 18, 20, 70, 73, 132, 170, 181, 195, 199, 324, 364, and 367 in the amino acid sequence shown in SEQ ID NO:1 or at positions corresponding to these positions. Preferably, such a variant has the following substitutions in the amino acid sequence shown in SEQ ID NO:1 or at positions corresponding to these positions: A18IF20LY70FG73SG132MR170KI181LV195FD199NF 324SG364SL367F.

In other more preferred embodiments, the variant according to the invention showing an improved activity in converting isoprenol into isoprene is characterized in that it has multiple mutations. As it is exemplified in the examples further below, variants have been found bearing multiple mutations which exhibit an increase in the reaction rate of the conversion of isoprenol into isoprene. These variants bearing multiple mutations are summarized in the following:

Accordingly, in a very preferred embodiment, the variant according to the invention is characterized in that it comprises deletions, substitutions and/or insertions wherein the deletions/insertions/substitutions are at positions 195, 18, 20, 39, 73, 119, and 132 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FA18IF20LD39AG735D119GG132R.

In another preferred embodiment, the variant according to the invention is characterized in that it comprises deletions, substitutions and/or insertions wherein the deletions/insertions/substitutions are at positions 195, 18, 20, 73, 132, 170, 181, 199, 269, and 367 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FA18IF20LG73SG132MR170KI181LD199NW269 AL367F.

In another preferred embodiment, the variant according to the invention is characterized in that it comprises deletions, substitutions and/or insertions wherein the deletions/insertions/substitutions are at positions 195, 132, 73, 77, and 364 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FG132AG73SE77IG364S.

In another preferred embodiment, the variant according to the invention is characterized in that it comprises deletions, substitutions and/or insertions wherein the deletions/insertions/substitutions are at positions 195, 18, 39, 119, 170, and 324 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FA18VD39AD119GR170KF324S.

In another preferred embodiment, the variant according to the invention is characterized in that it comprises deletions, substitutions and/or insertions wherein the deletions/insertions/substitutions are at positions 195, 119, and 132 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FD119GG132S.

In another preferred embodiment, the variant according to the invention is characterized in that it comprises deletions, substitutions and/or insertions wherein the deletions/insertions/substitutions are at positions 195, 84, and 132 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FT84IG132R.

In another preferred embodiment, the variant according to the invention is characterized in that it comprises deletions, substitutions and/or insertions wherein the deletions/insertions/substitutions are at positions 195, 132, and 324 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FG132VF324S.

In another preferred embodiment, the variant according to the invention is characterized in that it comprises deletions, substitutions and/or insertions wherein the deletions/insertions/substitutions are at positions 195 and 367 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FL367F.

In another preferred embodiment, the variant according to the invention is characterized in that it comprises deletions, substitutions and/or insertions wherein the deletions/insertions/substitutions are at positions 195, 132, 73, 77, and 13 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FG132AG73SE77IA13I.

In another preferred embodiment, the variant according to the invention is characterized in that it comprises deletions, substitutions and/or insertions wherein the deletions/insertions/substitutions are at positions 195, 122, and 132 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FV122LG132V.

In another preferred embodiment, the variant according to the invention is characterized in that it comprises deletions, substitutions and/or insertions wherein the deletions/insertions/substitutions are at positions 195, 132, 73, 77, and 18 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FG132AG73SE77IA18C.

In another preferred embodiment, the variant according to the invention is characterized in that it comprises deletions, substitutions and/or insertions wherein the deletions/insertions/substitutions are at positions 195, 18, 39, 170, 181, 199, 324, and 367 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FA18VD39AR170KI181LD199NF324SL367F.

In another preferred embodiment, the variant according to the invention is characterized in that it comprises deletions, substitutions and/or insertions wherein the deletions/insertions/substitutions are at positions 195, 18, 73, 170, 173, and 389 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FA18VG73SR170KA173RP389L.

In another preferred embodiment, the variant according to the invention is characterized in that it comprises deletions, substitutions and/or insertions wherein the deletions/insertions/substitutions are at positions 195, 181, and 324 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FI181LF324S.

In another preferred embodiment, the variant according to the invention is characterized in that it comprises deletions, substitutions and/or insertions wherein the deletions/insertions/substitutions are at positions 195, 18, 39, 77, 170, 173, 199, 269, and 324 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FA18VD39AE77IR170KA173RD199NW269AF324S.

In another preferred embodiment, the variant according to the invention is characterized in that it comprises deletions, substitutions and/or insertions wherein the deletions/insertions/substitutions are at positions 195, 170, 173, and 324 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FR170KA173RF324S.

In another preferred embodiment, the variant according to the invention is characterized in that it comprises deletions, substitutions and/or insertions wherein the deletions/insertions/substitutions are at positions 195, 18, 39, 73, and 269 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FA18ID39AG73SW269A.

In another preferred embodiment, the variant according to the invention is characterized in that it comprises deletions, substitutions and/or insertions wherein the deletions/insertions/substitutions are at positions 195, 18, 73, 119, 123, 181, and 199 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FA18VG73SD119GS123EI181LD199N.

In another preferred embodiment, the variant according to the invention is characterized in that it comprises deletions, substitutions and/or insertions wherein the deletions/insertions/substitutions are at positions 195, 18, 73, 170, 199, 324, and 367 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FA18IG73SR170KD199NF324SL367F.

In another preferred embodiment, the variant according to the invention is characterized in that it comprises deletions, substitutions and/or insertions wherein the deletions/insertions/substitutions are at positions 195, 18, 20, 39, 73, 118, 144, 170, 181, 199, 324, and 367 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FA18VF20LD39AG73SL118LI144TR170KI181L D199NF324SL367F.

In another preferred embodiment, the variant according to the invention is characterized in that it comprises deletions, substitutions and/or insertions wherein the deletions/insertions/substitutions are at positions 195, 119, 132, and 251 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FD119GG132KY251M.

In another preferred embodiment, the variant according to the invention is characterized in that it comprises deletions, substitutions and/or insertions wherein the deletions/insertions/substitutions are at positions 195, 122, and 132 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FV122LG132Q.

In another preferred embodiment, the variant according to the invention is characterized in that it comprises deletions, substitutions and/or insertions wherein the deletions/insertions/substitutions are at positions 195, 132, 73, 77, and 12 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FG132AG73SE77IS12A.

In another preferred embodiment, the variant according to the invention is characterized in that it comprises deletions, substitutions and/or insertions wherein the deletions/insertions/substitutions are at positions 195, 132, 73, 77, and 8 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FG132AG73SE77IT8L.

In another preferred embodiment, the variant according to the invention is characterized in that it comprises deletions, substitutions and/or insertions wherein the deletions/insertions/substitutions are at positions 195, 18, 39, 119, and 181 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FA18VD39AD119GI181L.

In another preferred embodiment, the variant according to the invention is characterized in that it comprises deletions, substitutions and/or insertions wherein the deletions/insertions/substitutions are at positions 195, 119, and 251 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FD119GY251M.

In another preferred embodiment, the variant according to the invention is characterized in that it comprises deletions, substitutions and/or insertions wherein the deletions/insertions/substitutions are at positions 195, 18, 39, 170, 181, and 269 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FA18ID39AR170KI181SW269A.

In another preferred embodiment, the variant according to the invention is characterized in that it comprises deletions, substitutions and/or insertions wherein the deletions/insertions/substitutions are at positions 195, 39, 73, 77, 132, 170, 199, 367, and 382 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FD39AG73SE77IG132QR170KD199NL367FG382D.

In another preferred embodiment, the variant according to the invention is characterized in that it comprises deletions, substitutions and/or insertions wherein the deletions/insertions/substitutions are at positions 195, 132, 199, and 324 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FG132RD199NF324S.

In another preferred embodiment, the variant according to the invention is characterized in that it comprises deletions, substitutions and/or insertions wherein the deletions/insertions/substitutions are at positions 195, 132, 73, 77, and 19 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FG132AG73SE77IG19T.

In another preferred embodiment, the variant according to the invention is characterized in that it comprises deletions, substitutions and/or insertions wherein the deletions/insertions/substitutions are at positions 195, and 132 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FG132Q.

In another preferred embodiment, the variant according to the invention is characterized in that it comprises deletions, substitutions and/or insertions wherein the deletions/insertions/substitutions are at positions 195, 18, 20, 39, 132, 170, 181, 324, and 367 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FA18IF20LD39AG132VR170KI181LF324SL367F.

In another preferred embodiment, the variant according to the invention is characterized in that it comprises deletions, substitutions and/or insertions wherein the deletions/insertions/substitutions are at positions 195, 367, and 382 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FL367FG382D.

In another preferred embodiment, the variant according to the invention is characterized in that it comprises deletions, substitutions and/or insertions wherein the deletions/insertions/substitutions are at positions 195, 39, 73, 170, 181, 199, and 324 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FD39AG73SR170KI181LD199NF324S.

In another preferred embodiment, the variant according to the invention is characterized in that it comprises deletions, substitutions and/or insertions wherein the deletions/insertions/substitutions are at positions 195, 18, 39, 73, 77, 119, and 170 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FA18VD39AG73SE77ID119GR170K.

In another preferred embodiment, the variant according to the invention is characterized in that it comprises deletions, substitutions and/or insertions wherein the deletions/insertions/substitutions are at positions 195, 18, 119, 132, 170, 173, 181, 199, and 269 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FA18VD119GG132SR170KA173RI181LD199NW269A.

In another preferred embodiment, the variant according to the invention is characterized in that it comprises deletions, substitutions and/or insertions wherein the deletions/insertions/substitutions are at positions 195, 132, and 318 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FG132QV318A.

In another preferred embodiment, the variant according to the invention is characterized in that it comprises deletions, substitutions and/or insertions wherein the deletions/insertions/substitutions are at positions 195, 132, 73, 77, and 145 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FG132AG73SE77IE145E.

In another preferred embodiment, the variant according to the invention is characterized in that it comprises deletions, substitutions and/or insertions wherein the deletions/insertions/substitutions are at positions 195 and 324 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FF324S.

In another preferred embodiment, the variant according to the invention is characterized in that it comprises deletions, substitutions and/or insertions wherein the deletions/insertions/substitutions are at positions 195, 73, 132, 170, 181, and 324 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FG73SG132GR170KI181LF324S.

In another preferred embodiment, the variant according to the invention is characterized in that it comprises deletions, substitutions and/or insertions wherein the deletions/insertions/substitutions are at positions 195, 39, 132, 170, 199, and 269 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FD39AG132AR170KD199NW269A.

In another preferred embodiment, the variant according to the invention is characterized in that it comprises deletions, substitutions and/or insertions wherein the deletions/insertions/substitutions are at positions 195, 39, 73, 170, 181, and 199 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FD39AG73SR170KI181LD199N.

In another preferred embodiment, the variant according to the invention is characterized in that it comprises deletions, substitutions and/or insertions wherein the deletions/insertions/substitutions are at positions 195, 119, and 123 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FD119GS123R.

In another preferred embodiment, the variant according to the invention is characterized in that it comprises deletions, substitutions and/or insertions wherein the deletions/insertions/substitutions are at positions 195, 73, 132, 170, and 181 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FG73SG132GR170KI181L.

In another preferred embodiment, the variant according to the invention is characterized in that it comprises deletions, substitutions and/or insertions wherein the deletions/insertions/substitutions are at positions 195, and 84 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FT84I.

In another preferred embodiment, the variant according to the invention is characterized in that it comprises deletions, substitutions and/or insertions wherein the deletions/insertions/substitutions are at positions 195, 18, 73, 77, and 386 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FA18VG73SE77IR386S.

In another preferred embodiment, the variant according to the invention is characterized in that it comprises deletions, substitutions and/or insertions wherein the deletions/insertions/substitutions are at positions 195, 73, 122, 123, 132, 199, and 269 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FG73SV122IS123EG132AD199NW269A.

In another preferred embodiment, the variant according to the invention is characterized in that it comprises deletions, substitutions and/or insertions wherein the deletions/insertions/substitutions are at positions 195, 18, 73, 170, 181, and 367 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FA18IG73SR170KI181SL367F.

In another preferred embodiment, the variant according to the invention is characterized in that it comprises deletions, substitutions and/or insertions wherein the deletions/insertions/substitutions are at positions 195, 132, 73, 77, and 141 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FG132AG73SE77IT141S.

In another preferred embodiment, the variant according to the invention is characterized in that it comprises deletions, substitutions and/or insertions wherein the deletions/insertions/substitutions are at positions 195, 39, 73, 170, 181, 199, and 367 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FD39AG73SR170KI181LD199NL367F.

In another preferred embodiment, the variant according to the invention is characterized in that it comprises deletions, substitutions and/or insertions wherein the deletions/insertions/substitutions are at positions 195, 18, 20, 39, 132, 170, 181, and 269 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FA18VF20LD39AG132KR170KI181LW269A.

In another preferred embodiment, the variant according to the invention is characterized in that it comprises deletions, substitutions and/or insertions wherein the deletions/insertions/substitutions are at positions 195, 18, 132, 170, 269 and 324 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FA18IG132KR170KW269AF324S.

In another preferred embodiment, the variant according to the invention is characterized in that it comprises deletions, substitutions and/or insertions wherein the deletions/insertions/substitutions are at positions 195, 132, 73, and 77 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FG132AG73SE77I.

In another preferred embodiment, the variant according to the invention is characterized in that it comprises deletions, substitutions and/or insertions wherein the deletions/insertions/substitutions are at positions 195, and 324 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FF324S.

In another preferred embodiment, the variant according to the invention is characterized in that it comprises deletions, substitutions and/or insertions wherein the deletions/insertions/substitutions are at positions 195, 132, and 269 in the amino acid sequence shown in SEQ ID NO:1 or at positions corresponding to these positions. Preferably, such a variant has the following substitutions in the amino acid sequence shown in SEQ ID NO:1 or at positions corresponding to these positions: V195FG132AW269A.

An alkenol dehydratase of the present invention can be fused to a homologous or heterologous polypeptide or protein, an enzyme, a substrate or a tag to form a fusion protein. Fusion proteins in accordance with the present invention will have the same improved activity as the alkenol dehydratase of the present invention. Polypeptides, enzymes, substrates or tags that can be added to another protein are known in the art. They may useful for purifying or detecting the proteins of the invention. For instance, tags that can be used for detection and/or purification are e.g. FLAG-tag, His6-tag or a Strep-tag. Alternatively, the protein of the invention can be fused to an enzyme e.g. luciferase, for the detection or localisation of said protein. Other fusion partners include, but are not limited to, bacterial β-galactosidase, trpE, Protein A, β-lactamase, alpha amylase, alcohol dehydrogenase or yeast alpha mating factor. It is also conceivable that the polypeptide, enzyme, substrate or tag is removed from the protein of the invention after e.g. purification. Fusion proteins can typically be made by either recombinant nucleic acid methods or by synthetic polypeptide methods known in art.

The present invention further relates to a nucleic acid molecule encoding an alkenol dehydratase of the present invention and to a vector comprising said nucleic acid molecules. Vectors that can be used in accordance with the present invention are known in the art. The vectors can further comprise expression control sequences operably linked to the nucleic acid molecules of the present invention contained in the vectors. These expression control sequences may be suited to ensure transcription and synthesis of a translatable RNA in bacteria or fungi. Expression control sequences can for instance be promoters. Promoters for use in connection with the nucleic acid molecules of the present invention may be homologous or heterologous with regard to its origin and/or with regard to the gene to be expressed. Suitable promoters are for instance promoters which lend themselves to constitutive expression. However, promoters which are only activated at a point in time determined by external influences can also be used. Artificial and/or chemically inducible promoters may be used in this context.

Preferably, the vector of the present invention is an expression vector. Expression vectors have been widely described in the literature. As a rule, they contain not only a selection marker gene and a replication-origin ensuring replication in the host selected, but also a bacterial or viral promoter, and in most cases a termination signal for transcription. Between the promoter and the termination signal there is in general at least one restriction site or a polylinker which enables the insertion of a coding DNA sequence. The DNA sequence naturally controlling the transcription of the corresponding gene can be used as the promoter sequence, if it is active in the selected host organism. However, this sequence can also be exchanged for other promoter sequences. It is possible to use promoters ensuring constitutive expression of the gene and inducible promoters which permit a deliberate control of the expression of the gene. Bacterial and viral promoter sequences possessing these properties are described in detail in the literature. Regulatory sequences for the expression in microorganisms (for instance E. coli, S. cerevisiae) are sufficiently described in the literature. Promoters permitting a particularly high expression of a downstream sequence are for instance the T7 promoter (Studier et al., Methods in Enzymology 185 (1990), 60-89), lacUV5, trp, trp-lacUV5 (DeBoer et al., in Rodriguez and Chamberlin (Eds), Promoters, Structure and Function; Praeger, N.Y., (1982), 462-481; DeBoer et al., Proc. Natl. Acad. Sci. USA (1983), 21-25), lp1, rac (Boros et al., Gene 42 (1986), 97-100). Inducible promoters are preferably used for the synthesis of polypeptides. These promoters often lead to higher polypeptide yields than do constitutive promoters. In order to obtain an optimum amount of polypeptide, a two-stage process is often used. First, the host cells are cultured under optimum conditions up to a relatively high cell density. In the second step, transcription is induced depending on the type of promoter used. In this regard, a tac promoter is particularly suitable which can be induced by lactose or IPTG (=isopropyl-β-D-thiogalactopyranoside) (deBoer et al., Proc. Natl. Acad. Sci. USA 80 (1983), 21-25). Termination signals for transcription are also described in the literature.

In addition, the present invention relates to a host cell comprising the vector of the present invention.

In a preferred embodiment, the host cell according to the presenting invention is a microorganism, in particular a bacterium or a fungus. In a more preferred embodiment, the host cell of the present invention is E. coli, a bacterium of the genus Clostridium or a yeast cell, such as S. cerevisiae. In another preferred embodiment the host cell is a plant cell or a non-human animal cell.

The transformation of the host cell with a vector according to the invention can be carried out by standard methods, as for instance described in Sambrook and Russell (2001), Molecular Cloning: A Laboratory Manual, CSH Press, Cold Spring Harbor, N.Y., USA; Methods in Yeast Genetics, A Laboratory Course Manual, Cold Spring Harbor Laboratory Press, 1990. The host cell is cultured in nutrient media meeting the requirements of the particular host cell used, in particular in respect of the pH value, temperature, salt concentration, aeration, antibiotics, vitamins, trace elements etc.

As described above, an alkenol dehydratase variant of the present invention is not only capable of converting crotyl alcohol into 1,3 butadiene, but is preferably also capable of converting at least one other compound responding to the general formula $C_nH_{2n}O$ into $C_nH_{2n-2}+H_2O$, with $3<n<7$.

Accordingly, the present invention also relates to a method for producing a compound of the formula $C_nH_{2n-2}$ from a compound of the formula $C_nH_{2n}O$ with $3<n<7$ comprising the step of incubating an alkenol dehydratase of the invention with said starting compound under conditions allowing said conversion or comprising the step of culturing a host cell of the present invention in a suitable medium and recovering the desired compound. Preferably, in such a method
(i) the compound corresponding to the general formula $C_nH_{2n}O$ is crotyl alcohol, but-3-en-2-ol or but-3-en-1-ol and the compound corresponding to the general formula $C_nH_{2n-2}$ is 1,3 butadiene; or
(ii) the compound corresponding to the general formula $C_nH_{2n}O$ is prenol, isoprenol, 2-methyl-but-3-en-1-ol, 2-methyl-but-2-en-1-ol, 3-methyl-but-3-en-2-ol or 2-methyl-but-3-en-2-ol and the compound corresponding to the general formula $C_nH_{2n-2}$ is isoprene; or
(iii) the compound corresponding to the general formula $C_nH_{2n}O$ is 2,3-dimethyl-but-2-en-1-ol, 2,3-dimethyl-but-3-en-2-ol or 2,3-dimethyl-but-3-en-1-ol and the compound corresponding to the general formula $C_nH_{2n-2}$ is dimethylbutadiene.

Thus, the present invention also relates to a method for producing 1,3 butadiene from crotyl alcohol comprising the steps of incubating an alkenol dehydratase according to the present invention with crotyl alcohol under conditions allowing the conversion of crotyl alcohol into 1,3 butadiene and recovering said 1,3 butadiene. The present invention also relates to a method for producing 1,3 butadiene from crotyl alcohol comprising the steps of culturing the host cell of the present invention in a suitable medium and recovering said 1,3 butadiene. In a preferred embodiment the alkenol dehydratase employed in such a method or expressed by the host cell is an alkenol dehydratase according to the first or second aspect of the present invention.

It is also conceivable in this context that in such methods not only one enzyme according to the present invention is employed but a combination of two or more enzymes.

The present invention also relates to a method for producing 1,3 butadiene from but-3-en-2-ol comprising the steps of incubating an alkenol dehydratase according to the present invention with but-3-en-2-ol under conditions allowing the conversion of but-3-en-2-ol into 1,3 butadiene and recovering said 1,3 butadiene.

The present invention also relates to a method for producing 1,3 butadiene from but-3-en-2-ol comprising the steps of culturing the host cell of the present invention in a suitable medium and recovering said 1,3 butadiene. In a preferred embodiment the alkenol dehydratase employed in such a method or expressed by the host cell is an alkenol dehydratase according to the first, second or third aspect of the present invention.

As mentioned above, in a preferred embodiment an alkenol dehydratase of the present invention is not only capable of converting crotyl alcohol and/or but-3-en-2-ol into 1,3 butadiene but is in general capable of converting a compound responding to the general formula $C_nH_{2n}O$ into $C_nH_{2n-2}+H_2O$, with $3<n<7$. Preferably, such an enzyme is also capable of converting 3-methylbut-2-en-1-ol (prenol) or isoprenol into isoprene or is also capable of converting 2,3-dimethyl-but-2-en-1-ol into dimethyl-butadiene.

Therefore, the present invention also relates in a further embodiment to the use of an alkenol dehydratase variant or a host cell of the present invention as described above for the conversion of a compound of the general formula $C_nH_{2n}O$ into $C_nH_{2n-2}+H_2O$, with $3<n<7$. Preferably in such a use
(i) the compound corresponding to the general formula $C_nH_{2n}O$ is crotyl alcohol, but-3-en-2-ol or but-3-en-1-ol and the compound corresponding to the general formula $C_nH_{2n-2}$ is 1,3 butadiene; or
(ii) the compound corresponding to the general formula $C_nH_{2n}O$ is prenol, isoprenol, 2-methyl-but-3-en-1-ol, 2-methyl-but-2-en-1-ol, 3-methyl-but-3-en-2-ol or 2-methyl-but-3-en-2-ol and the compound corresponding to the general formula $C_nH_{2n-2}$ is isoprene; or
(iii) the compound corresponding to the general formula $C_nH_{2n}O$ is 2,3-dimethyl-but-2-en-1-ol, 2,3-dimethyl-but-3-en-2-ol or 2,3-dimethyl-but-3-en-1-ol and the compound corresponding to the general formula $C_nH_{2n-2}$ is dimethylbutadiene.

Preferably, the present invention relates to the use of an alkenol dehydratase variant or a host cell of the present invention as described above for the conversion of 3-methylbut-2-en-1-ol (prenol) or isoprenol into isoprene. Moreover, in a further embodiment, the present invention relates to a method for producing isoprene from 3-methylbut-2-en-1-ol (prenol) or from isoprenol comprising the steps of: (i) culturing the above-described host cell of the invention in a suitable medium; and (ii) recovering the produced isoprene.

Finally, in yet a further embodiment, the present invention also relates to the use of the alkenol dehydratase variants or the host cells of the invention as defined above for the conversion of 2,3-dimethyl-but-2-en-1-ol into dimethylbutadiene. Moreover, in a further embodiment, the present invention also relates to a method for producing dimethylbutadiene from 2,3-dimethyl-but-2-en-1-ol comprising the steps of: (i) culturing the host cell of the invention in a suitable medium; and (ii) recovering the produced dimethylbutadiene.

Thus, in a preferred embodiment, the present invention relates to methods and uses utilizing a host cell of the present invention wherein such a host cell is a recombinant organism in the sense that it is genetically modified due to the introduction of at least one nucleic acid molecule encoding an alkenol dehydratase variant as described above. Preferably, such a nucleic acid molecule is heterologous with regard to the organism which means that it does not naturally occur in said host cell.

In another preferred embodiment, such a host cell is an organism which is capable of producing a compound corresponding to the general formula $C_nH_{2n}O$, with $3<n<7$, such as crotyl alcohol, but-3-en-2-ol, but-3-en-1-ol, 3-methylbut-2-en-1-ol (prenol), 3-methylbut-3-en-1-ol (isoprenol), 2-methyl-but-3-en-1-ol, 2-methyl-but-2-en-1-ol, 3-methyl-but-3-en-2-ol, 2-methyl-but-3-en-2-ol, 2,3-dimethyl-but-2-en-1-ol, 2,3-dimethyl-but-3-en-2-ol or 2,3-dimethyl-but-3-en-1-ol.

Thus, in another preferred embodiment the method according to the invention is carried out in culture, in the presence of an organism, preferably a microorganism, producing an enzyme variant of the present invention. Thus, in such an embodiment of the invention, an organism, preferably a microorganism, that produces an enzyme of the present invention is used. In a preferred embodiment, the (micro)organism is recombinant in that the enzyme produced by the host is heterologous relative to the production host. The method can thus be carried out directly in the culture medium, without the need to separate or purify the enzymes. In an especially advantageous manner, a (micro) organism is used having the natural or artificial property of endogenously producing a compound corresponding to the general formula $C_nH_{2n}O$, with $3<n<7$, so as to produce the product directly from the substrate already present in the culture in solution.

In connection with the above described methods and uses, the microorganisms are cultivated under suitable culture conditions allowing the occurrence of the enzymatic reaction of the alkenol dehydratase variants of the present invention. The specific culture conditions depend on the specific microorganism employed but are well known to the person skilled in the art. The culture conditions are generally chosen in such a manner that they allow the expression of the genes encoding the alkenol dehydratases of the present invention. Various methods are known to the person skilled in the art in order to improve and fine-tune the expression of certain genes at certain stages of the culture such as induction of gene expression by chemical inducers or by a temperature shift.

The method according to the invention furthermore comprises the step of collecting gaseous products, e.g. 1,3 butadiene or isoprene, degassing out of the reaction, i.e. recovering the products which degas, e.g., out of the culture. Thus in a preferred embodiment, the method is carried out in the presence of a system for collecting 1,3 butadiene or isoprene under gaseous form during the reaction.

As a matter of fact, short alkenes such as 1,3 butadiene adopt the gaseous state at room temperature and atmospheric pressure. Moreover, isoprene also adopts the gaseous state under culture conditions at 37° C. The method according to the invention therefore does not require extraction of the product from the liquid culture medium, a step which is always very costly when performed at industrial scale. The evacuation and storage of the gaseous hydrocarbons and their possible subsequent physical separation and chemical conversion can be performed according to any method known to one of skill in the art.

In yet a further embodiment, the method according to the invention can be carried out in vitro, e.g. in the presence of isolated enzyme or of cell lysates comprising the enzyme or partially purified enzyme preparations comprising the alkenol dehydratase variant of the present invention. In vitro preferably means in a cell-free system.

In one embodiment, the enzyme employed in the method is used in purified form. However, such a method may be costly, since enzyme and substrate production and purification costs are high.

Thus, in another preferred embodiment, the enzymes employed in the method are present in the reaction as a non-purified extract, or else in the form of non-lysed bacteria, so as to economize on protein purification costs. However, the costs associated with such a method may still be quite high due to the costs of producing and purifying the substrates.

In an in vitro reaction the enzymes, native or recombinant, purified or not, are incubated in the presence of the substrate in physicochemical conditions allowing the enzymes to be active, and the incubation is allowed to proceed for a sufficient period of time allowing production of the desired product as described above. At the end of the incubation, one optionally measures the presence of the desired compound by using any detection system known to one of skill in the art such as gas chromatography or colorimetric tests for measuring the formation such compounds.

In a particularly preferred embodiment of the invention the method is carried out in vitro and the enzyme is immobilized. Means and methods for immobilizing enzymes on different supports are well-known to the person skilled in the art.

Figure 1B:
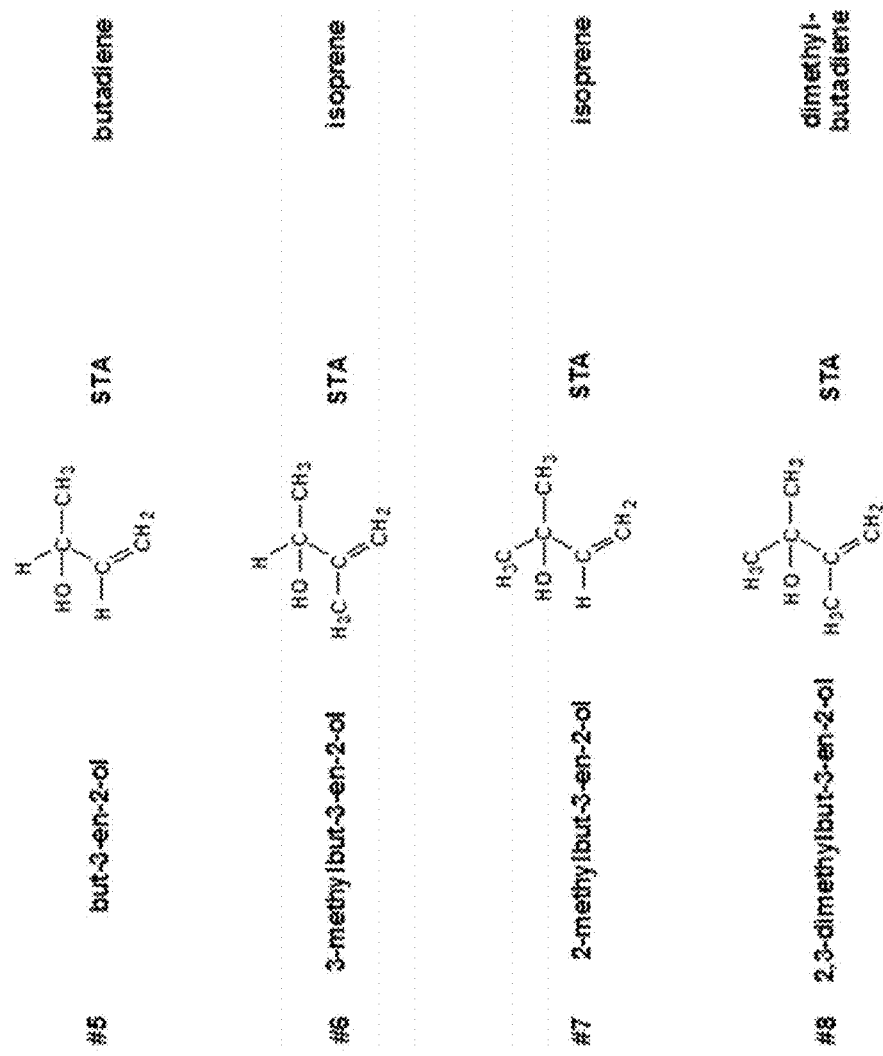
Figure 1C:
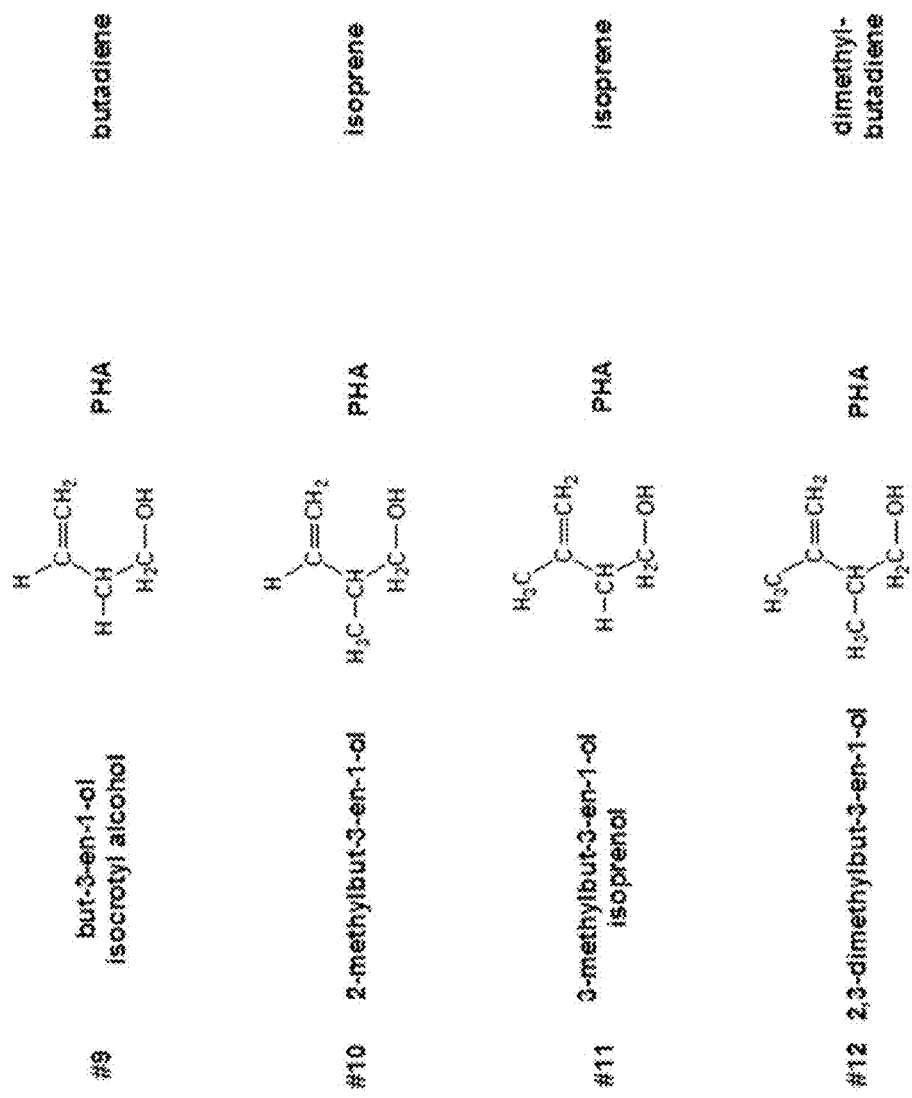

FIG. 1: Examples of alkenol substrates corresponding to the general formula $C_nH_{2n}O$, with $3<n<7$ whose conversion into a conjugated diene (butadiene, isoprene, dimethylbutadiene) is catalyzed by the wild type alkenol dehydratase and the alkenol dehydratase variants. FIG. 1(a) shows schematically the primary allyl alcohols (PRA) corresponding to the general formula $C_nH_{2n}O$, with $3<n<7$. The substrate name, the systematic name, the formula, the category and the product are indicated. FIG. 1(b) shows schematically the secondary and tertiary allyl alchohols (STA) corresponding to the general formula $C_nH_{2n}O$, with $3<n<7$. The substrate name, the systematic name, the formula, the category and the product are indicated. FIG. 1(c) shows schematically the primary homoallyl alcohols (PHA) corresponding to the general formula $C_nH_{2n}O$, with $3<n<7$. The substrate name, the systematic name, the formula, the category and the product are indicated.

Figure 2:
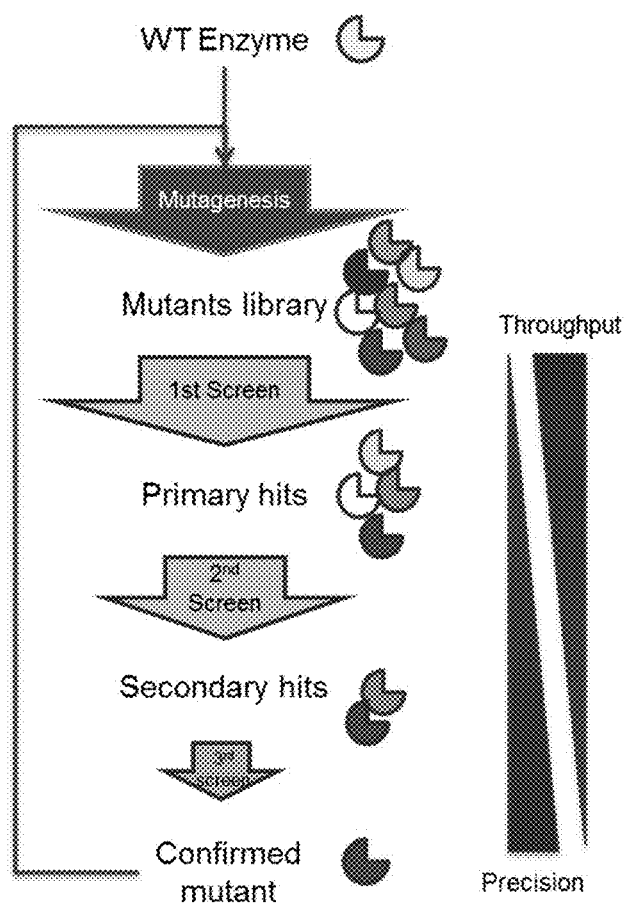

FIG. 2: Schematic representation of a directed evolution approach.

Figure 3:
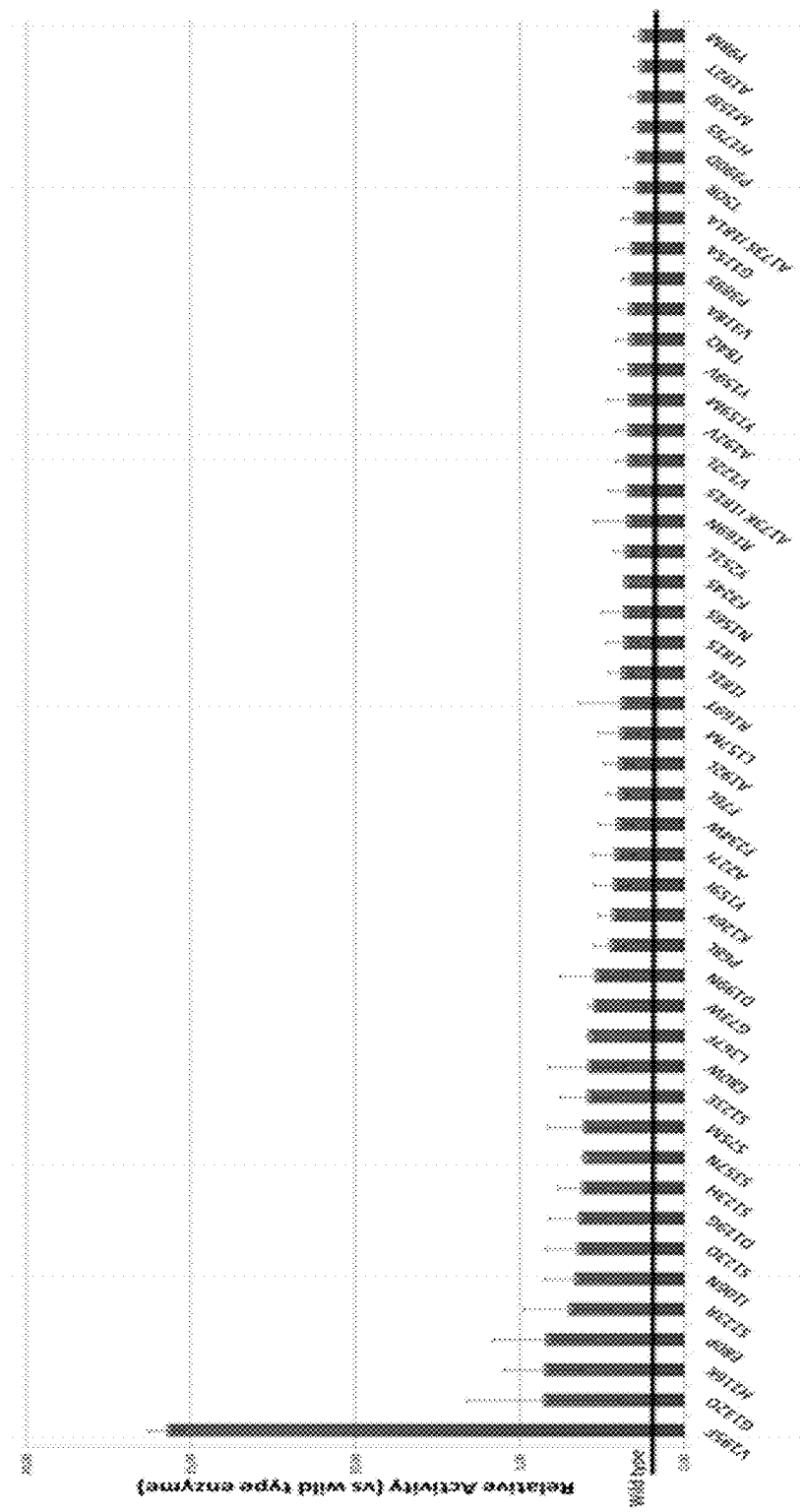

FIG. 3: The complete collection of mutants identified in a screen for enhanced activity in converting crotyl alcohol into 1,3 butadiene ordered according to their relative activity compared to the wild type enzyme.

Figure 4:
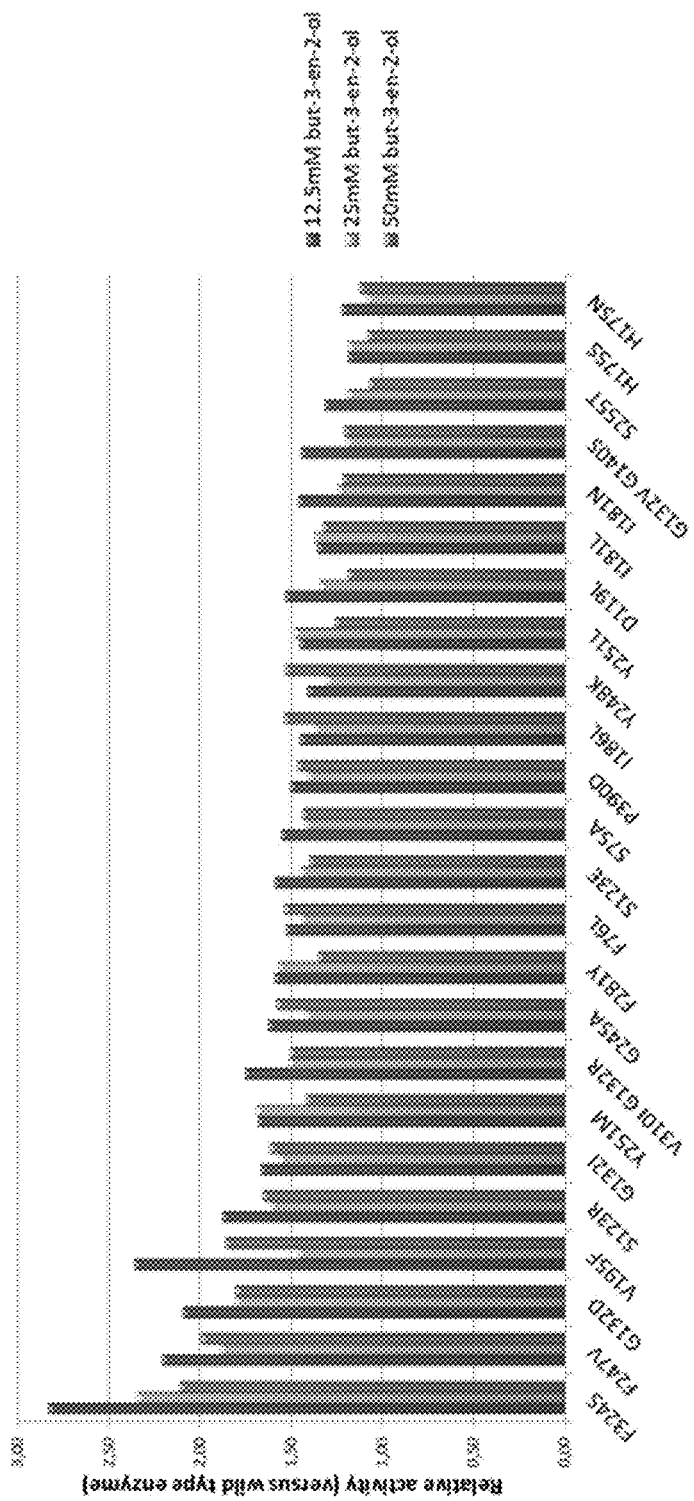

FIG. 4: Mutations identified in a screen for enhanced activity in converting but-3-en-2-ol into 1,3 butadiene ordered according to their relative activity compared to the wild type enzyme.

Figure 5:
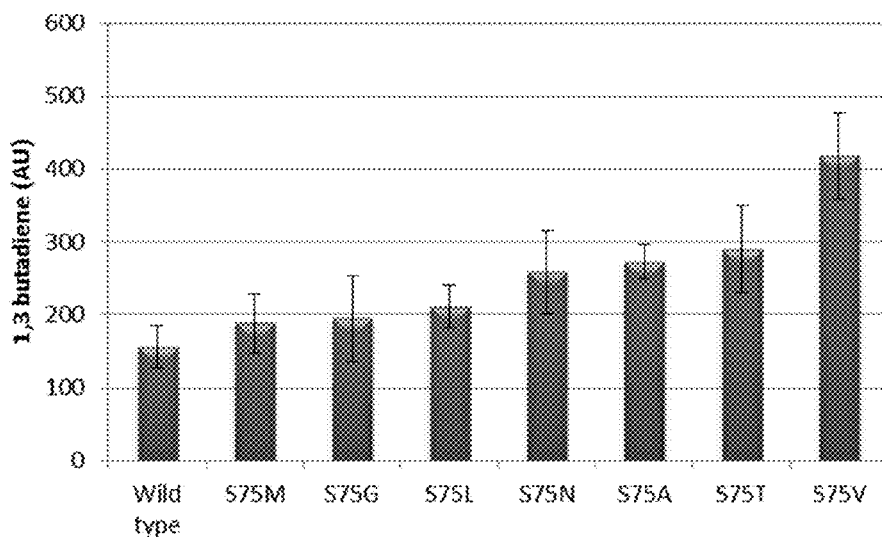

FIG. 5: Effect of mutations at position S75 on the production of 1,3 butadiene.

Figure 6:
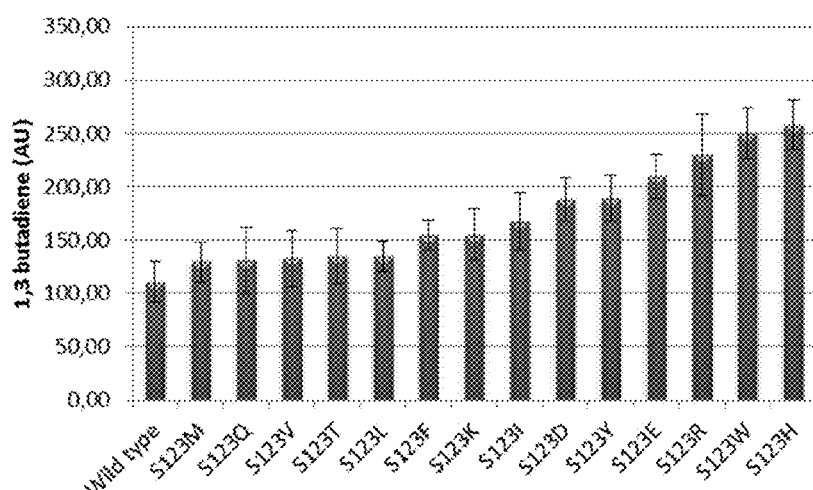

FIG. 6: Effect of mutations at position S123 on the production of 1,3 butadiene.

Figure 7:
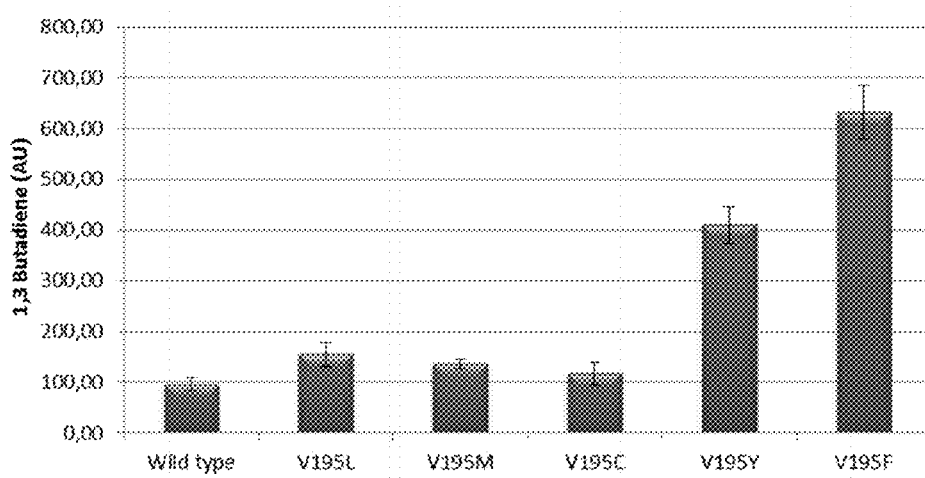

FIG. 7: Effect of mutations at position V195 on the production of 1,3 butadiene.

Figure 8:
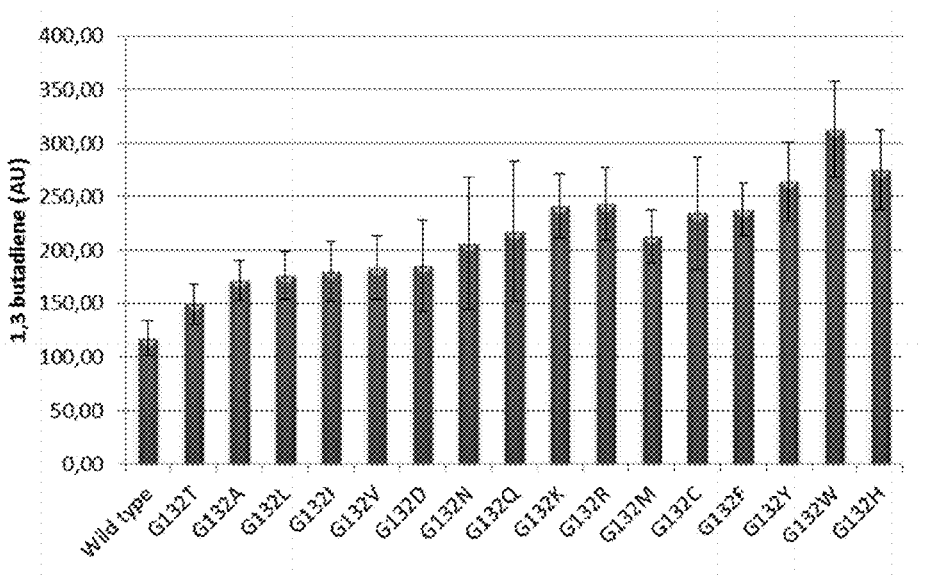

FIG. 8: Effect of mutations at position G132 on the production of 1,3 butadiene.

Figure 9:
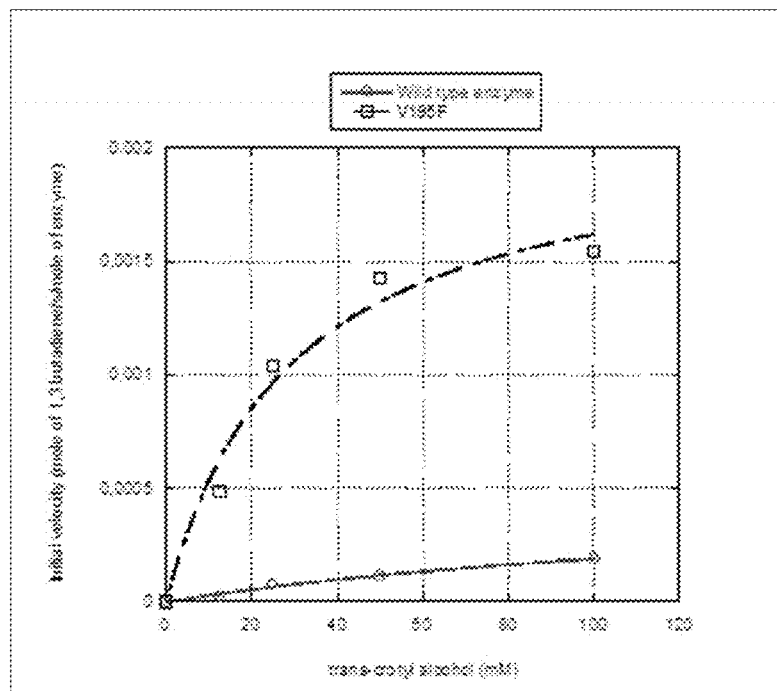

FIG. 9: Specific activity of wild type enzyme versus V195F for the conversion of t-crotyl alcohol into 1,3 butadiene.

Figure 10:
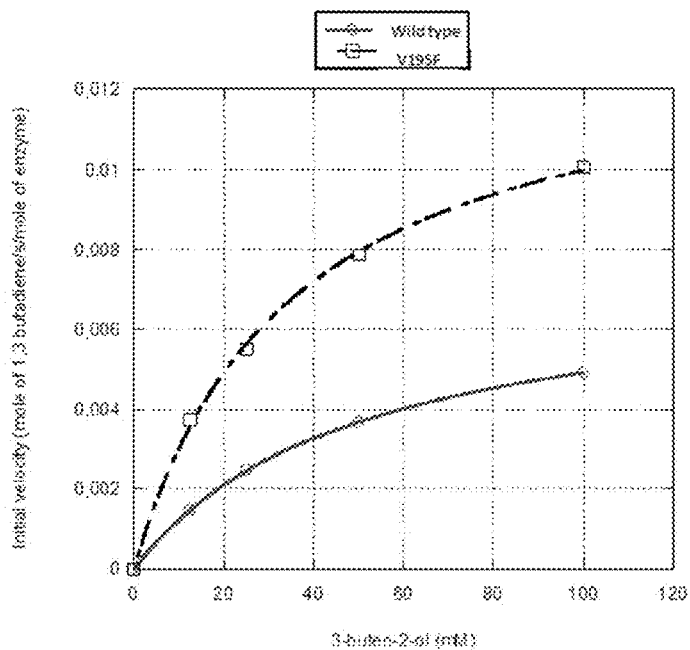

FIG. 10: Specific activity of wild type enzyme versus V195F for the conversion of but-3-en-2-ol into 1,3 butadiene.

Figure 11:
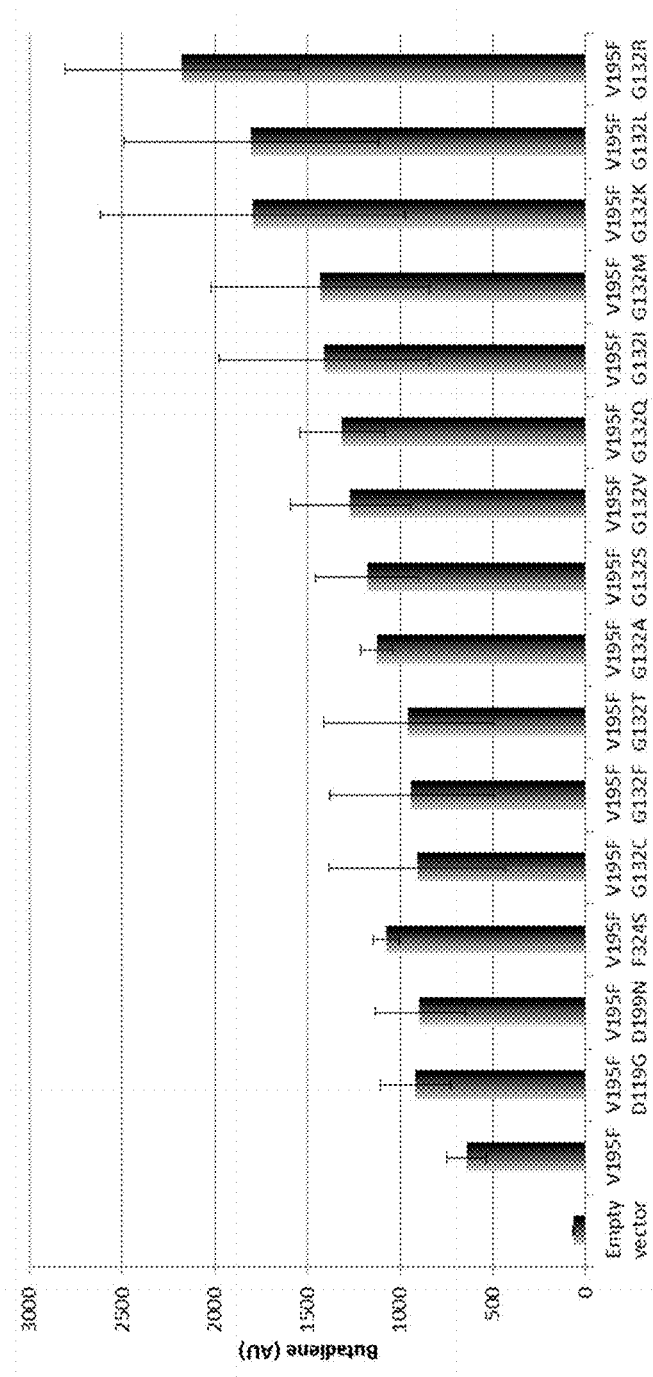

FIG. 11: Enzyme variants bearing double-residue mutations with an increased activity in converting crotyl alcohol into 1,3 butadiene.

Figure 12:
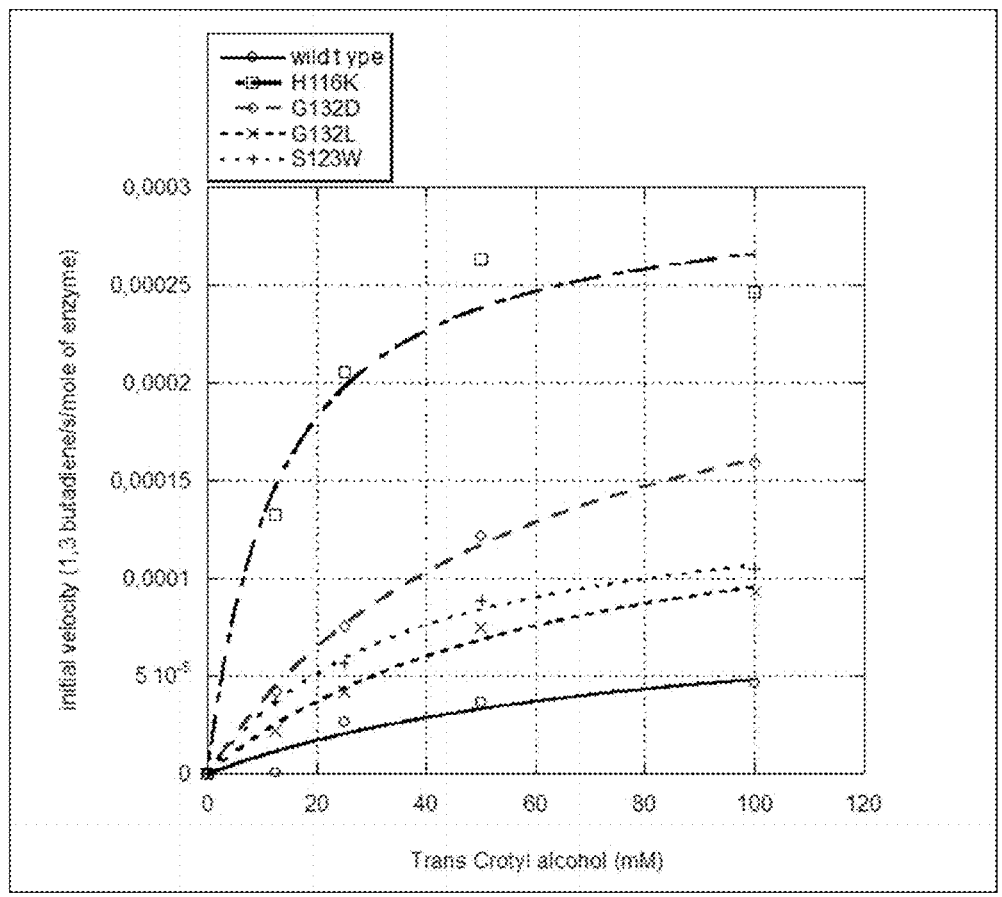

FIG. 12: Specific activity of wild type enzyme versus a panel of enzyme variants for the conversion of trans-crotyl alcohol into 1,3 butadiene.

Figure 13:
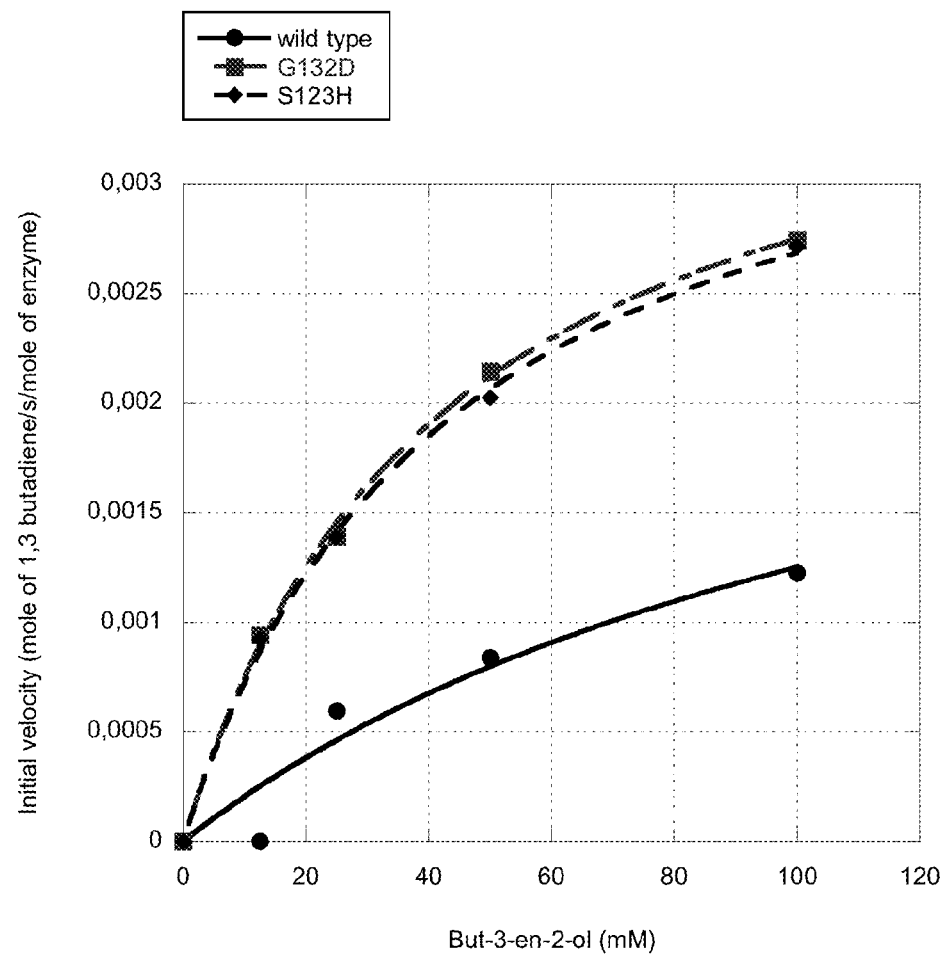

FIG. 13: Specific activity of wild type enzyme versus a panel of variants for the conversion of 3-buten-2-ol alcohol into 1,3 butadiene.

Figure 14:
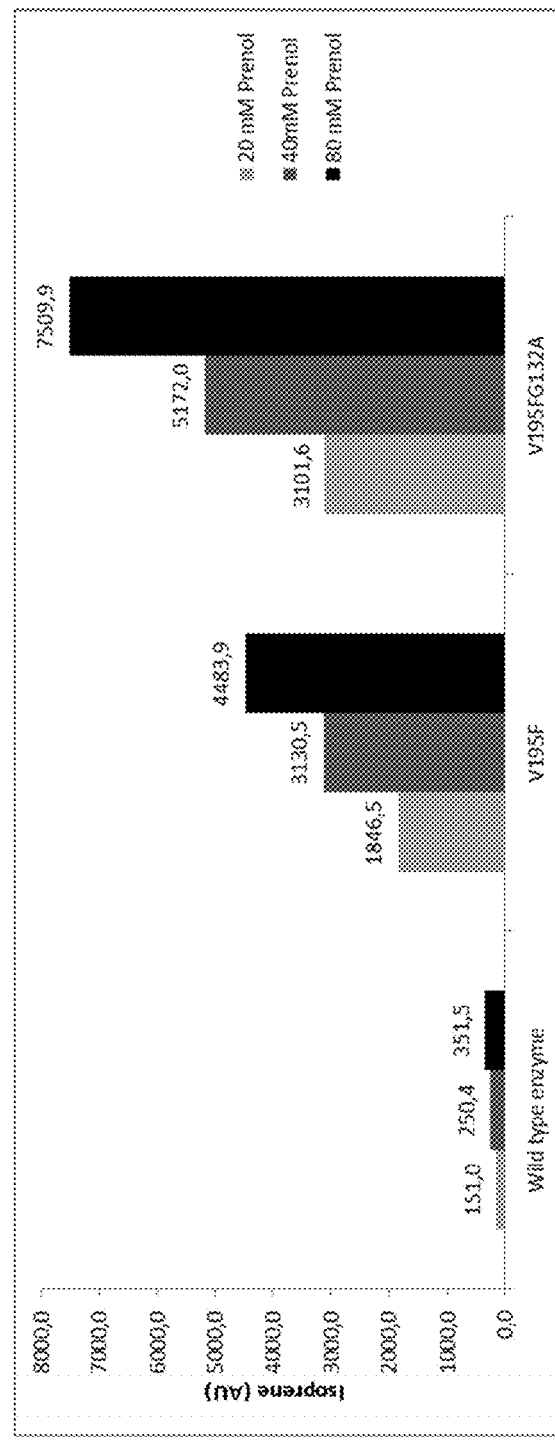

FIG. 14: V195F and V195FG132A variants lead to a 12 and 20 fold increase respectively in the ability of the alkenol dehydratase enzyme to convert prenol into isoprene.

Figure 15:
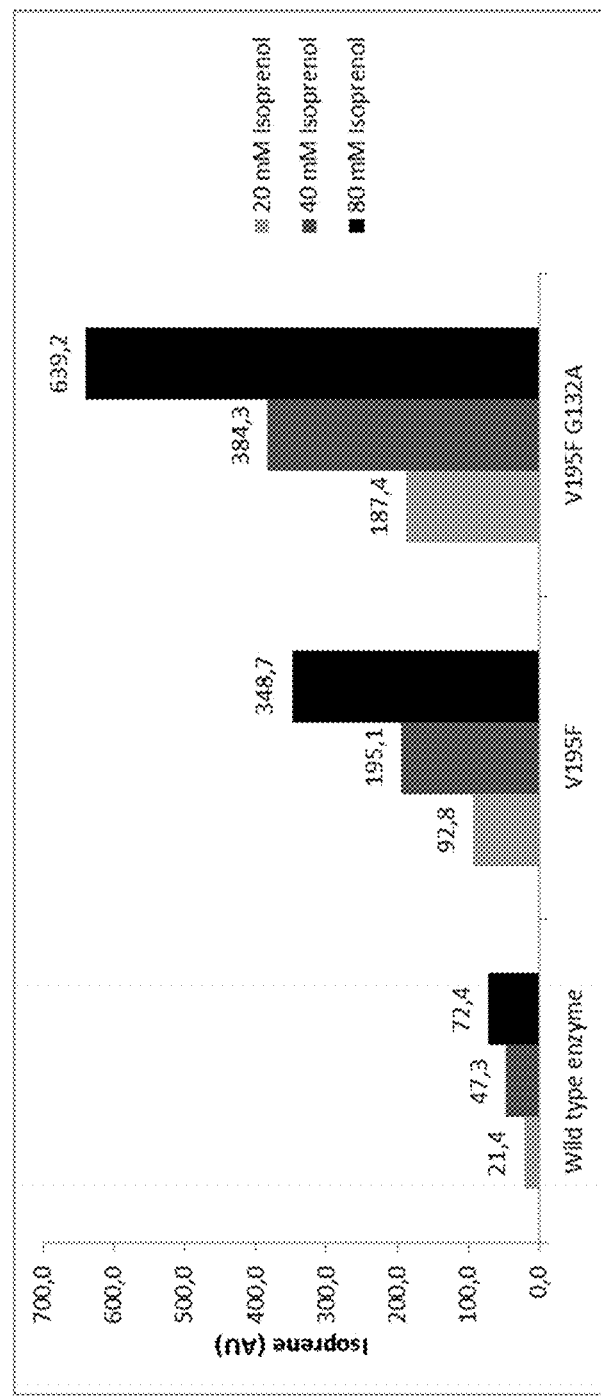

FIG. 15: V195F and V195FG132A variants lead to a 4-5 and 8-9 fold increase respectively in the ability of the alkenol dehydratase enzyme to convert isoprenol into isoprene.

FIG. 16: Illustration of sequence features of SEQ ID NOs: 2 and 3:
Underlined sequences represent the His6tag and bold italics show the amino acid residue M1 of the native sequence.

Figure 17:
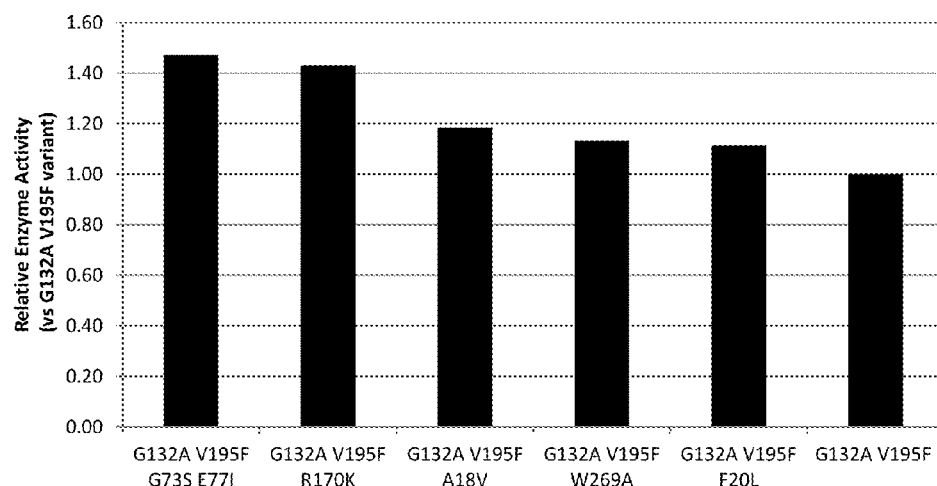

FIG. 17: Mutations identified in a screen for enhanced activity in converting crotyl alcohol into 1,3 butadiene ordered according to their relative activity compared to the G132A V195F alkenol dehydratase enzyme variant.

Figure 18:
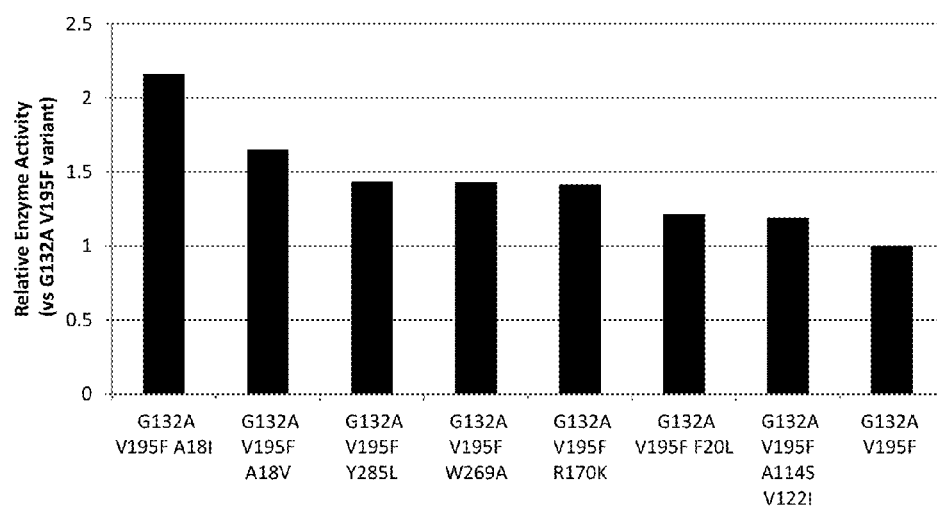

FIG. 18: Mutations identified in a screen for enhanced activity in converting but-3-en-2-ol into 1,3 butadiene ordered according to their relative activity compared to the G132A V195F alkenol dehydratase enzyme variant.

Figure 19:
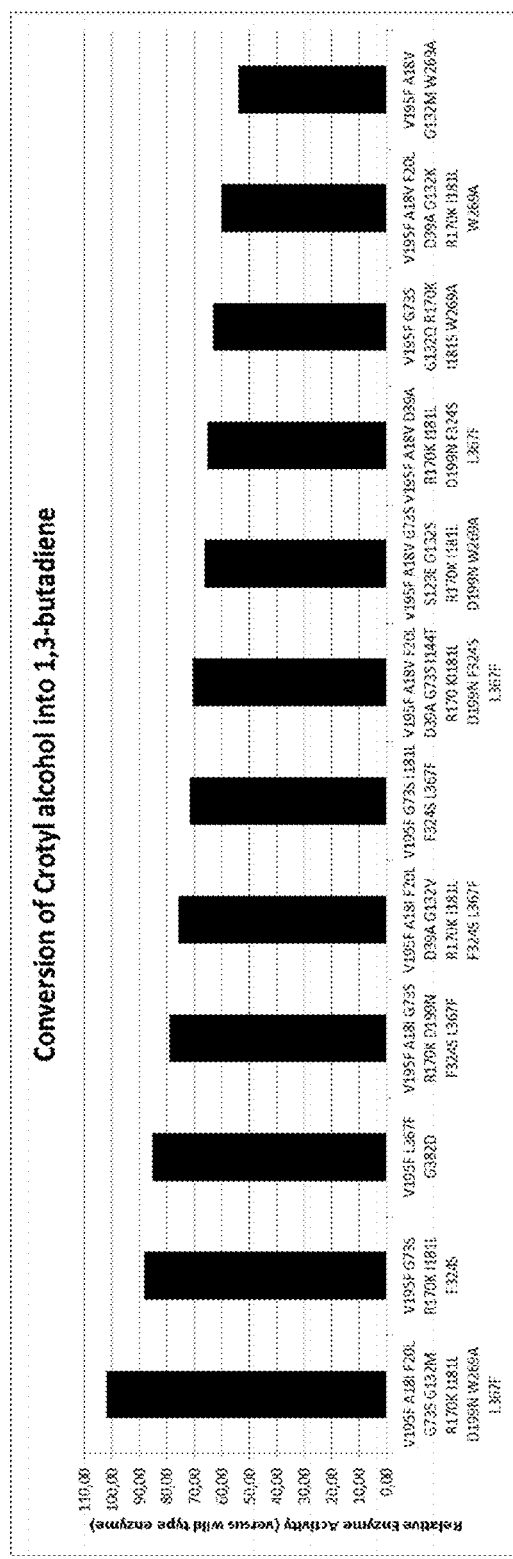

FIG. 19: Mutations identified in a screen for enhanced activity in converting crotyl alcohol into 1,3 butadiene ordered according to their relative activity compared to the wild type enzyme.

Figure 20:
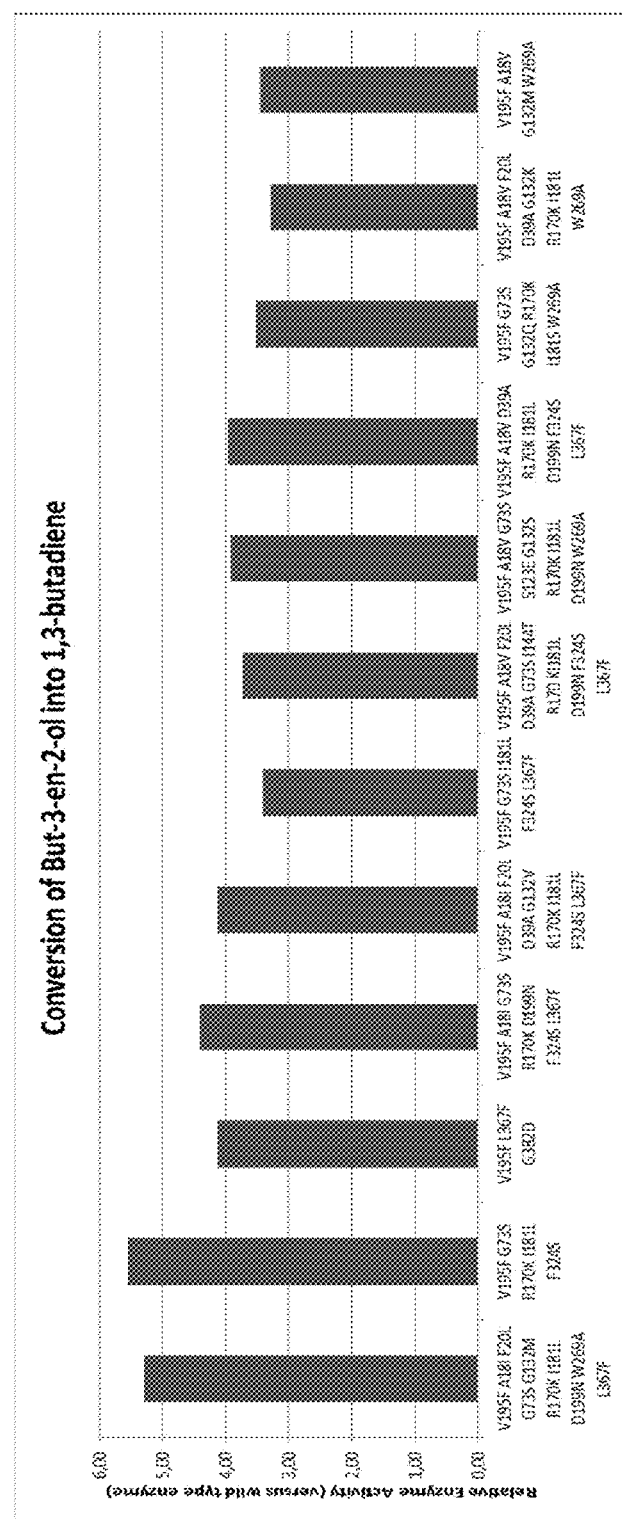

FIG. 20: Mutations identified in a screen for enhanced activity in converting but-3-en-2-ol into 1,3 butadiene ordered according to their relative activity compared to the wild type enzyme.

Figure 21:
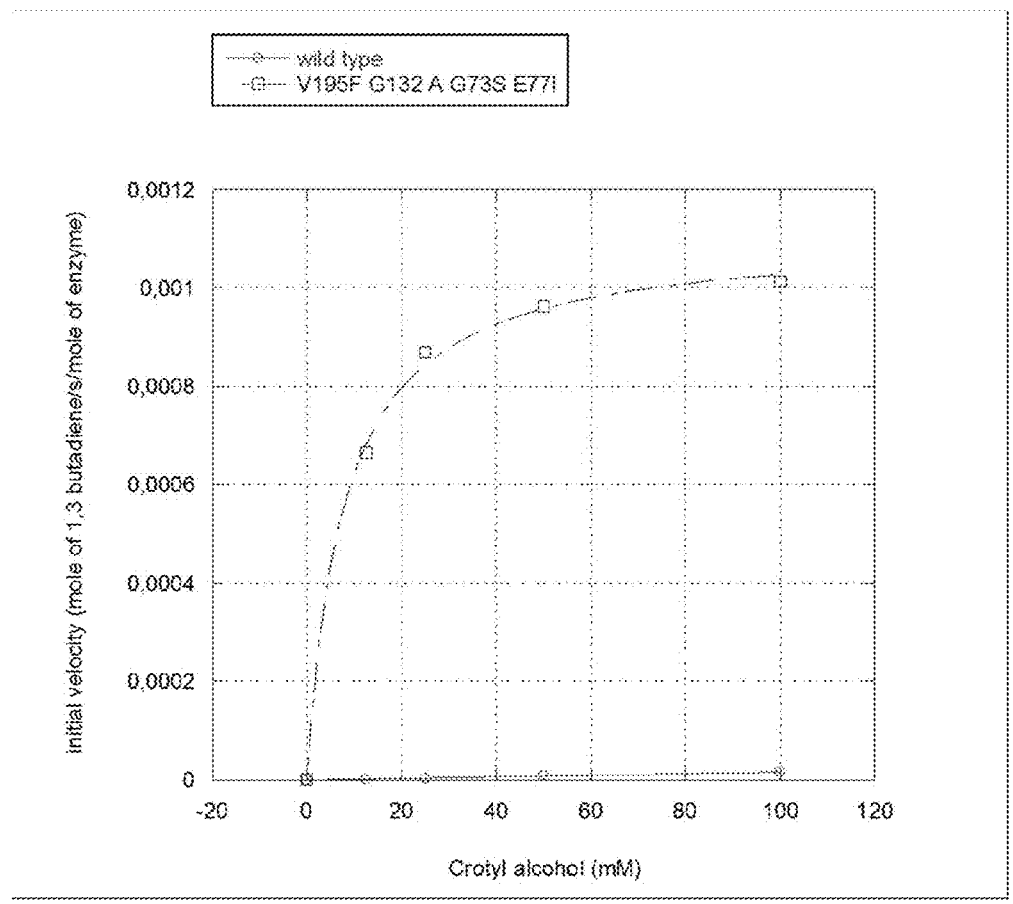

FIG. 21: Conversion of crotyl alcohol into butadiene by the alkenol dehydratase V195F G132A G73S E77I variant. Butadiene production is plotted as a function of substrate concentration.

Figure 22:
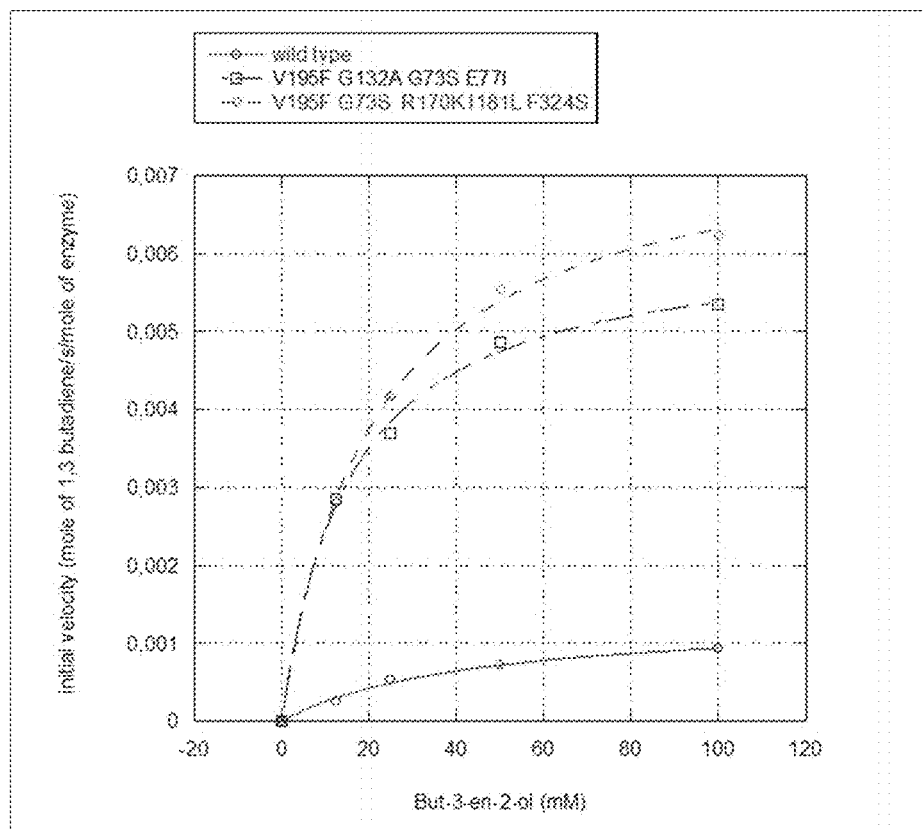

FIG. 22: Conversion of but-3-en-2-ol into butadiene by the alkenol dehydratase V195F G132A G73S E77I and V195F G73S R170K I181L F324S variants. Butadiene production is plotted as a function of substrate concentration.

FIG. 23: Illustration of sequence features of SEQ ID NOs: 4 and 5 of the V195F-G132A variant used in Example 15:
Underlined sequences represent the His6tag and bold italics show the amino acid residue F3 of the native sequence. The modifications V195F-G132A are highlighted in bold. The sequence "ITSLYKKAGC" in italics is encoded by the peT300:NT-DEST vector.

FIG. 24: Illustration of sequence features of SEQ ID NOs: 6 and 7 of the V195F variant used in Example 16:
Underlined sequences represent the His6tag and bold italics show the amino acid residue F3 of the native sequence. The modification V195F is highlighted in bold. The sequence "ITSLYKKAGC" in italics is encoded by the peT300:NT-DEST vector.

FIG. 25: Illustration of sequence features of SEQ ID NOs:8 and 9 wild type sequence used in Example 6:
Underlined sequences represent the His6tag and bold italics show the amino acid residue F3 of the native sequence. The sequence "ITSLYKKAGC" in italics is encoded by the peT300/:NT-DEST vector.

Figure 26:
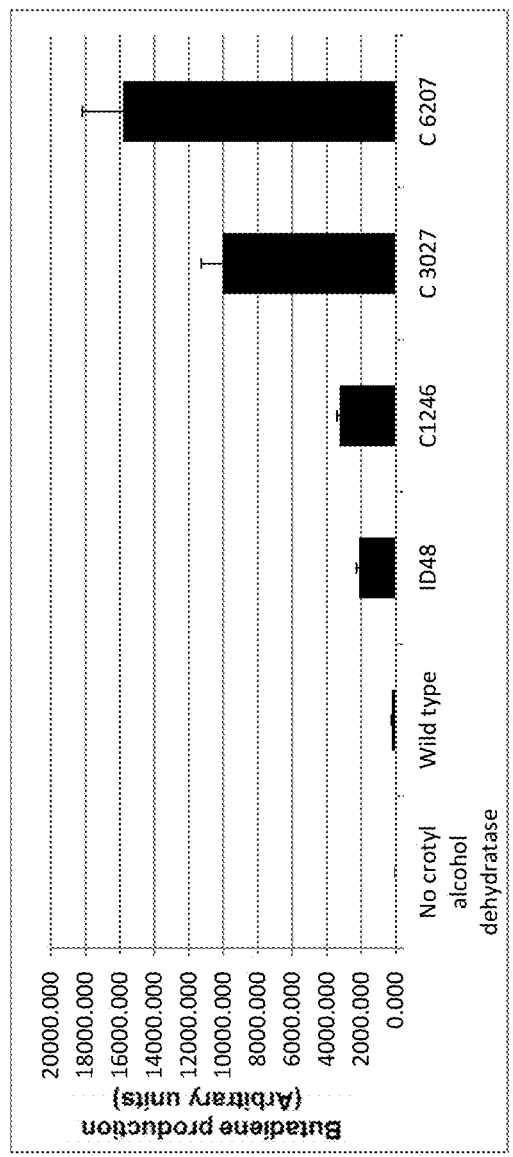

FIG. 26: Characterisation of a set of mutants using an in vitro assay. Empty vector, wild type LDI, and clones ID48, C1246, C3027 and C6207, described in Table 16, were tested using the in vitro assay described in example 1. Measurements were made 16 hours after adding 50 mM crotyl alcohol.

Figure 27:
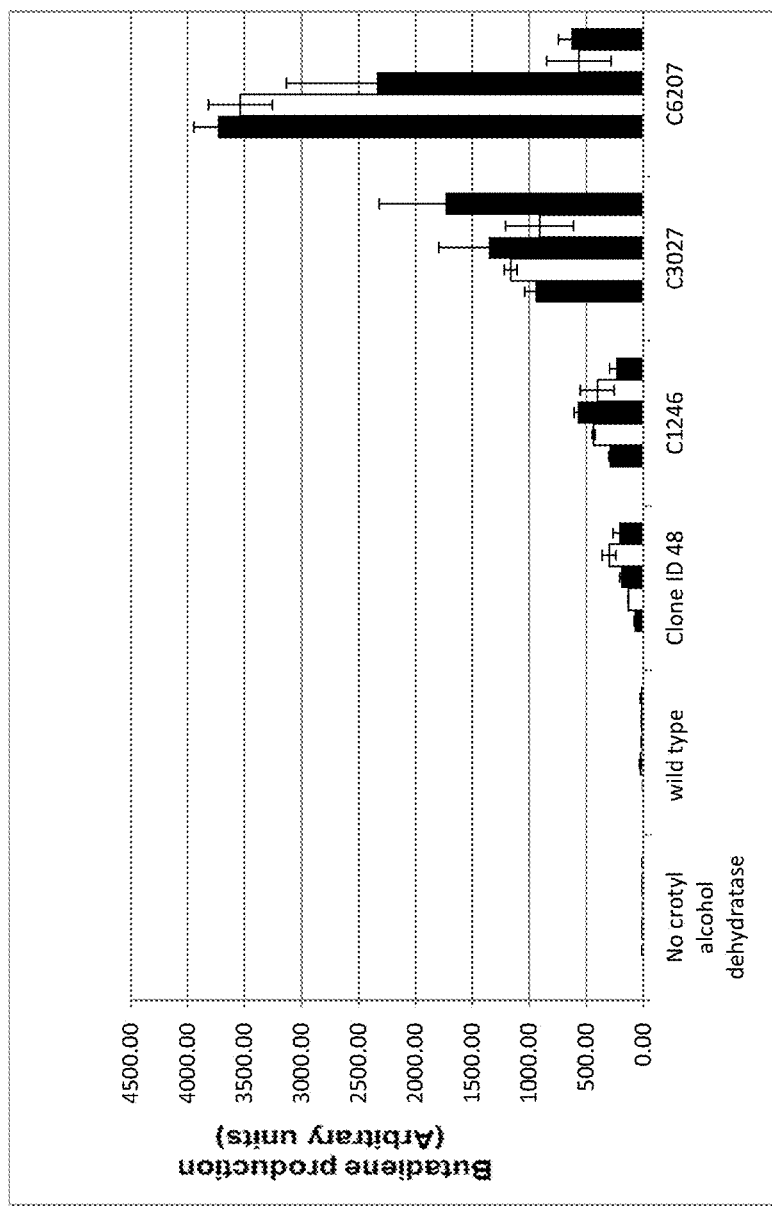

FIG. 27: Characterisation of a set of mutants using an in vivo assay. Empty vector, wild type LDI, and clones ID48, C1246, C3027 and C6207, described in Table 16, were tested using the in vivo assay described in example 21. Measurements were made 4 hours after adding 0, 5, 10, 25, 50 or 100 mM crotyl alcohol. Results with 0 mM crotyl alcohol are not visible on the graph.

Figure 28:
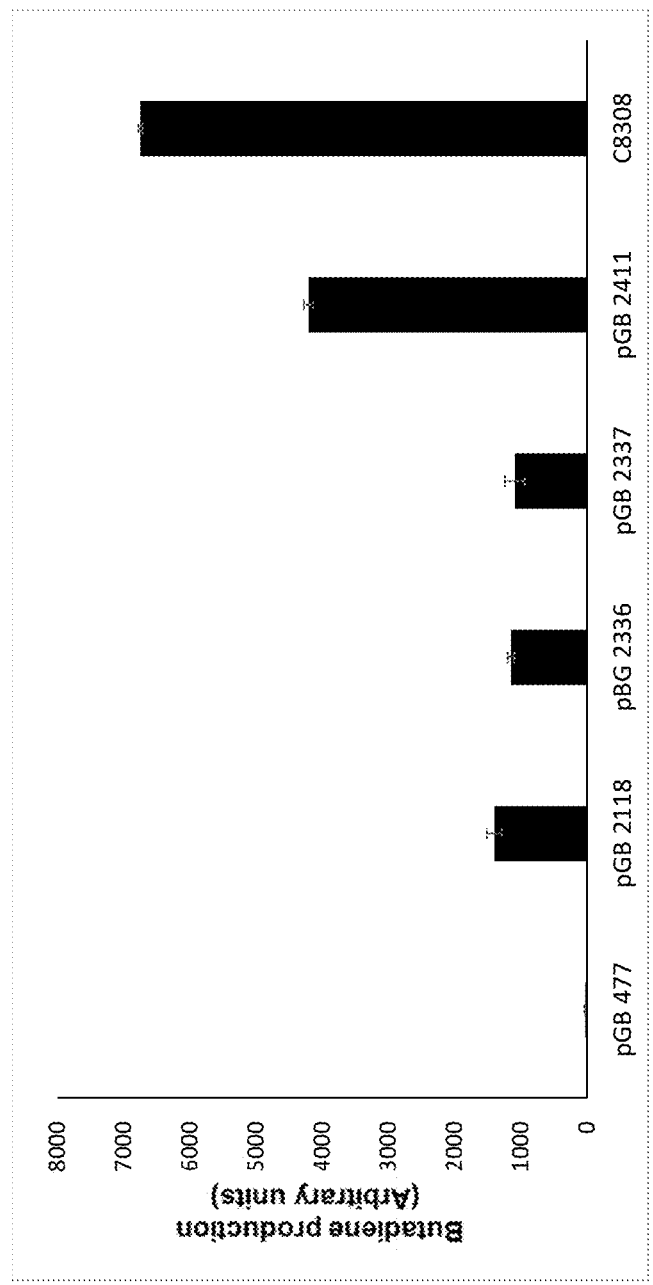

FIG. 28: Characterisation of a set of mutants using an in vitro assay. Mutants were tested as described in Example 1.

Other aspects and advantages of the invention will be described in the following examples, which are given for purposes of illustration and not by way of limitation.

EXAMPLES

I. General Outline of the Screening for Alkenol Dehydratase Variants Showing Improved Activity in Converting Crotyl Alcohol into 1,3 Butadiene and/or Showing an Improved Activity in Converting Crotyl Alcohol into but-3-en-2-ol and/or Showing an Improved Activity in Converting but-3-en-2-ol into 1,3 Butadiene The screening was based on a directed evolution approach which consisted in (1) the generation of a DNA library coding for single point mutants of the alkenol dehydratase enzyme, (2) the design and validation of an assay to test the activity of these enzyme variants, (3) the use of the activity assay to screen the collection of mutants in order to identify mutants with improved activity compared to the wild type alkenol dehydratase. A schematic diagram of this approach is presented in FIG. 2. The screening method consists generally of several steps (up to 4) in order to eliminate false negatives or assay artefacts amongst the initial positive hits and thus allows to only retain true leads.

The screening aimed at identifying enzyme variants with higher rates of conversion of crotyl alcohol into 1,3 butadiene and/or higher rates of conversion of but-3-en-2-ol into 1,3 butadiene. To do so, the screening assay was carried out using similar protocols except that either crotyl alcohol (trans-cis isomer mixture) or but-3-en-2-ol (R, S enantiomer mixture) were used as substrates. The variants obtained from both screens were subjected to further tests to assess their relative activity on a range of substrates: (1) the variants obtained from the screen on the crotyl alcohol (trans-cis isomer mixture) were tested on but-3-en-2-ol (2) the variants obtained from the screen on but-3-en-2-ol (R, S enantiomer mixture) were tested on crotyl alcohol (trans-cis isomer mixture and pure trans isomer) (3) all the variants obtained from either screen were also tested on the pure trans isomer (>96%).

The variants obtained from this series of screening experiments are described in Tables 1 to 4 where they have been organized according to their range of activities. In addition, mutations resulting in improved activity were combined on a regular basis, using classical methods in molecular biology, and the resulting multiple mutants were tested with the same assays as the simple mutants. Table 5 lists multiple mutants.

Table 1 shows a list of mutations conferring an increased activity in converting crotyl alcohol into 1,3 butadiene.

The fold increase is the ratio of gas chromatograph signal obtained for the alkenol dehydratase variant over the gas chromatograph signal obtained for the wild type enzyme at 50 mM crotyl alcohol (trans+cis isomer mixture or pure trans isomer) following a 16 hour-incubation at 37° C. The full protocol is detailed in the material and method section of Example 1. Table 1 lists all the enzyme variants bearing single residue mutations. These mutations increase the catalysis of the reaction of the conversion of crotyl alcohol into 1,3 butadiene.

TABLE 1

| Mutation | Fold increase |
| --- | --- |
| V195F | 8.0 |
| H116K | 4.3 |
| E80P | 4.3 |
| V195Y | 3.5 |
| I106N | 3.4 |
| D119G | 3.3 |
| S357N | 3.1 |
| S75M | 3.1 |
| E80W | 3.0 |
| G73W | 2.8 |
| D199N | 2.7 |
| G132T | 2.6 |
| G132L | 2.6 |
| S123H | 2.6 |
| S75V | 2.6 |
| G132I | 2.58 |
| G132D | 2.5 |
| P68L | 2.3 |
| G132W | 2.3 |
| G132S | 2.3 |
| K126Y | 2.2 |
| Y159I | 2.2 |
| A227I | 2.2 |
| L367F | 2.1 |
| F234W | 2.1 |
| S123W | 2.1 |
| G132Q | 2.0 |
| A192L | 2.0 |
| G132V | 2.0 |
| G132N | 2.0 |
| L157M | 2.0 |
| R169T | 2.0 |
| S75A | 2.0 |
| K126A | 1.9 |
| I181N | 1.9 |
| I181L | 1.9 |
| I181S | 1.9 |
| N156S | 1.9 |
| G132A | 1.8 |
| S75T | 1.8 |
| R169N | 1.8 |
| G132R | 1.8 |
| G132M | 1.8 |
| V122L | 1.8 |
| A192V | 1.8 |
| Y159M | 1.7 |
| G132H | 1.7 |
| Y159V | 1.7 |
| S123Y | 1.7 |
| T84Q | 1.7 |
| V318A | 1.7 |
| S123D | 1.7 |
| G132F | 1.7 |
| P389S | 1.7 |
| G115A | 1.7 |
| F76L | 1.7 |
| S75G | 1.7 |
| S123R | 1.6 |
| P390D | 1.6 |
| S75N | 1.6 |
| S75I | 1.6 |
| S255T | 1.6 |
| Y251M | 1.6 |
| S123I | 1.5 |
| F247V | 1.5 |
| S123E | 1.5 |
| T50R | 1.5 |
| G132K | 1.5 |
| Y251L | 1.5 |
| M158I | 1.4 |
| S75Y | 1.4 |
| F324S | 1.4 |
| F281Y | 1.4 |
| S123K | 1.4 |
| E77L | 1.4 |
| Y285M | 1.4 |
| A192T | 1.4 |
| Y98M | 1.4 |

TABLE 1-continued

| Mutation | Fold increase |
| --- | --- |
| I186V | 1.3 |
| F95M | 1.3 |
| S123F | 1.3 |
| G132C | 1.2 |
| S123L | 1.2 |
| Y248K | 1.2 |
| R72S | 1.2 |
| S123T | 1.2 |
| H175S | 1.2 |
| S123V | 1.2 |
| G132Y | 1.2 |
| S123Q | 1.2 |
| S123M | 1.2 |
| H175N | 1.1 |
| I186L | 1.1 |

Table 2 shows a list of mutations conferring an increased activity in converting crotyl alcohol into 1,3 butadiene.

The fold increase is the ratio of gas chromatograph signal obtained for a mutant/gas chromatograph signal obtained for the wild type enzyme at 50 mM crotyl alcohol (trans+cis isomer mixture or pure trans isomer) following 16 hours incubation at 37° C. The full protocol is detailed in the material and method section of Example 1. Table 2 lists all the alkenol dehydratase variants bearing two mutations. These variants show an increase of catalysis for the reaction of conversion of crotyl alcohol into 1,3 butadiene.

TABLE 2

| Mutation | Fold increase |
| --- | --- |
| G132R V195F | 24.0 |
| G132L V195F | 20.0 |
| G132Q V195F | 20.0 |
| G132K V195F | 20.0 |
| G132V V195F | 16.0 |
| G132M V195F | 16.0 |
| G132I V195F | 16.0 |
| F324S V195F | 16.0 |
| G132A V195F | 15.2 |
| D119G V195F | 14.4 |
| G132S V195F | 13.6 |
| V195F D199N | 12.8 |
| G132T V195F | 12.0 |
| G132N V195F | 11.2 |
| G132F V195F | 10.4 |
| G132C V195F | 10.4 |
| A173K I181S | 1.8 |
| A173S I181A | 1.6 |
| G132R V310I | 1.4 |
| G132V G140S | 1.2 |

Table 3 shows a list of mutations conferring an increased activity in converting but-3-en-2-ol into 1,3 butadiene.

The fold increase is the ratio of gas chromatograph signal obtained for a mutant/gas chromatograph signal obtained for the wild type enzyme at 50 mM but-3-en-2-ol following a 16 hour-incubation at 37° C. Table 3 lists all the enzyme variants bearing a single mutation. These mutations increase the reaction rate of the conversion of but-3-en-2-ol into 1,3 butadiene. They were obtained by either screening the enzyme library on but-3-en-2-ol or on crotyl alcohol. For the variants obtained from the screen on crotyl alcohol, their ability to convert but-3-en-2-ol into 1,3 butadiene was assessed in a separate assay.

TABLE 3

| Mutation | Fold increase |
|---|---|
| F324S | 2.4 |
| V195F | 2.0 |
| F247V | 2.0 |
| G132A | 2.0 |
| G132D | 1.9 |
| I106N | 1.9 |
| G132T | 1.8 |
| R169T | 1.8 |
| S123R | 1.7 |
| G132H | 1.7 |
| N156S | 1.7 |
| S123K | 1.7 |
| Y159M | 1.6 |
| G132I | 1.6 |
| E254G | 1.6 |
| G132W | 1.6 |
| Y251M | 1.6 |
| G245A | 1.5 |
| I186L | 1.5 |
| F281Y | 1.5 |
| F76L | 1.5 |
| L157M | 1.5 |
| S123E | 1.5 |
| S75A | 1.5 |
| G132S | 1.5 |
| P390D | 1.5 |
| S75G | 1.4 |
| Y248K | 1.4 |
| F95M | 1.4 |
| Y251L | 1.4 |
| G132F | 1.4 |
| S123I | 1.4 |
| I181L | 1.4 |
| E77L | 1.4 |
| G115A | 1.3 |
| R169N | 1.3 |
| F234W | 1.3 |
| F373L | 1.3 |
| K126A | 1.3 |
| I181N | 1.3 |
| G132L | 1.3 |
| G132Y | 1.3 |
| S123Q | 1.3 |
| G132N | 1.3 |
| G132R | 1.3 |
| R72S | 1.2 |
| V195Y | 1.2 |
| Y285M | 1.2 |
| A227I | 1.2 |
| Y159I | 1.2 |
| G132V | 1.2 |
| S123L | 1.2 |
| S255T | 1.2 |
| S123H | 1.2 |
| S123W | 1.2 |
| V122L | 1.2 |
| T84Q | 1.2 |
| I181S | 1.2 |
| Y159V | 1.2 |
| S357N | 1.2 |
| I186V | 1.2 |
| H175S | 1.2 |
| D119G | 1.1 |

TABLE 3-continued

| Mutation | Fold increase |
|---|---|
| H175N | 1.1 |
| G132M | 1.1 |

Table 4 shows a list of mutations conferring an increased activity in converting but-3-en-2-ol into 1,3 butadiene (double mutants).

The fold increase is the ratio of gas chromatograph signal obtained for a mutant/gas chromatograph signal obtained for the wild type enzyme at 50 mM but-3-en-2-ol following a 16 hour-incubation at 37° C. Table 4 lists all the enzyme variants bearing double mutations. These mutations increase the reaction rate of the conversion of but-3-en-2-ol into 1,3 butadiene. They were obtained by either screening the enzyme library on but-3-en-2-ol or on crotyl alcohol. For the variants obtained from the screen on crotyl alcohol, their ability to convert but-3-en-2-ol into 1,3 butadiene was assessed in a separate assay.

TABLE 4

| Mutation | Fold increase |
|---|---|
| G132Q V195F | 3.0 |
| F324S V195F | 2.8 |
| D199N V195F | 2.7 |
| G132T V195F | 2.5 |
| G132A V195F | 2.4 |
| G132N V195F | 2.4 |
| G132L V195F | 2.3 |
| D119G V195F | 2.2 |
| G132R V195F | 2.0 |
| G132K V195F | 2.0 |
| G132V V195F | 2.0 |
| G132M V195F | 2.0 |
| G132I V195F | 2.0 |
| G132S V195F | 2.0 |
| V310I G132R | 1.6 |
| V195F G132F | 1.5 |
| G132V G140S | 1.3 |
| S102M T166S | 1.3 |

Table 5 shows a list of mutants displaying an increased activity in converting crotyl-alcohol and/or but-3-en-2-ol into 1,3 butadiene (multiple mutations). The fold increase is the ratio of gas chromatograph signal obtained for a mutant/ gas chromatograph signal obtained for the wild type enzyme at 50 mM crotyl alcohol (trans+cis isomer mixture or pure trans isomer) following 16 hours incubation at 37° C. or 50 mM but-3-en-2-ol following a 16 hour-incubation at 37° C. The full protocol is detailed in the material and method section of Example 15. Table 5 lists all the enzyme variants bearing multiple mutations. These mutations increase the reaction rate of the conversion of but-3-en-2-ol into 1,3 butadiene. They were obtained by either screening the enzyme library on but-3-en-2-ol or on crotyl alcohol. For the variants obtained from the screen on crotyl alcohol, their ability to convert but-3-en-2-ol into 1,3 butadiene was assessed in a separate assay.

TABLE 5

| Mutations | Relative activity vs wild type | |
|---|---|---|
| | Conversion of crotyl alcohol into 1,3 Butadiene | Conversion of but-3-en-2-ol into 1,3 Butadiene |
| V195FA18IF20LY70FG73SG132MR170KI181LD199NF324SG364SL367F | 345.6 | |
| V195FA18IF20LG73SG132MR170KI181LD199NF324SL367F | 216 | |
| V195FG73SE77IG132AG364S | 138.00 | 7.60 |
| V195FF20LG132VR170KA173RI181LD199NF324S | 108.00 | 10.00 |
| V195FA18IF20LG73SG132MR170KI181LD199NW269AL367F | 102.08 | 5.29 |
| V195FL367FG382D | 100.00 | 4.56 |
| V195FI10AG132VR170KA173RI181LD199NF324S | 100.00 | 8.00 |
| V195FG73SR170KI181LF324S | 88.07 | 5.55 |
| V195FG73SG132GR170KI181LF324S | 86.00 | 6.00 |
| V195FG73SE77IT84IG132A | 86.00 | 7.70 |
| V195FF20LG73SG132GR170KI181LF324S | 86.00 | 7.60 |
| V195FL367FG382D | 85.18 | 4.14 |
| V195FA18IG73SR170KD199NF324SL367F | 78.90 | 4.41 |
| V195FA18IF20LD39AG132VR170KI181LF324SL367F | 75.79 | 4.14 |
| V195FG132AG73SE77I | 72.00 | 4.00 |
| V195FG73SI181LF324SL367F | 71.82 | 3.40 |
| V195FA18VF20LD39AG73SI144TR170KI181LD199NF324SL367F | 70.34 | 3.73 |
| V195FA18VG73SS123EG132SR170KI181LD199NW269A | 66.31 | 3.92 |
| V195FA18VD39AR170KI181LD199NF324SL367F | 65.33 | 3.97 |
| V195FG73SG132QR170KI181SW269A | 63.17 | 3.52 |
| V195FA18VF20LD39AG132KR170KI181LW269A | 60.17 | 3.29 |
| V195FG132VR170KA173RI181LD199NF324S | 57.6 | |
| V195FA18VG132MW269A | 53.90 | 3.46 |
| V195FG132VR170KA173RI181LF324S | 47.72 | 3.63 |
| V195FG132AG73SE77L | 47.51 | 0.00 |
| V195FA18VG73SR170KA173RP389L | 46.98 | 3.51 |
| V195FS168NR170KF324SL367F | 46.85 | 3.43 |
| V195FD39AG73SE77IG132QR170KD199NL367FG382D | 46.68 | 3.13 |
| V195FA18VG73SE77IR386S | 46.54 | 3.20 |
| V195FG73SY70FE77IG132A | 42.00 | 3.00 |
| V195FD39AG73SR170KI181LD199NF324S | 36.89 | 2.92 |
| V195FF324SL367L | 36.82 | 2.93 |
| G132AV195FG73S-E77L | 32.20 | 5.7 |
| V195FG132VF324S | 31.79 | 5.39 |
| V195FD199NF324S | 31.30 | 5.49 |
| V195FR170KA173RF324S | 30.82 | 2.77 |
| V195FG132MI181LF324S | 29.00 | 2.90 |
| V195FG132QF324S | 27.00 | 3.78 |
| V195FG132MF324S | 26.92 | 3.67 |
| V195FG132LF324S | 25.70 | 3.59 |
| V195FD119GS123EL365F | 25.63 | 2.11 |
| V195FS12L | 25.44 | 3.38 |
| V195FG132AD199N | 24.69 | 4.20 |
| V195FD119GS123E | 24.38 | 4.22 |
| V195FD119GG132A | 22.96 | 3.03 |
| G132AV195FR170K | 22.8 | 3.38 |
| V195FG132RF324S | 22.80 | 3.94 |
| V195FG132TD199N | 22.47 | 3.93 |
| V195FG132AD199NF324S | 22.02 | 4.85 |
| V195FG132AA173R | 22.00 | 2.97 |
| V195FG132AR170K | 21.99 | 3.49 |
| V195FG132ED199NF324S | 21.49 | 4.87 |
| G132AV195FF20L | 21.4 | 2.9 |
| V195FG132AW269A | 21 | 1.78 |
| V195FG132SD199N | 20.95 | 4.08 |
| V195FG132ND199N | 20.30 | 3.27 |
| V195FG132QD199NF324S | 20.23 | 5.68 |
| G132AV195FW269A | 20.1 | 3.4 |
| V195FG132KD199N | 20.03 | 3.40 |
| G132AV195FD39A | 20.0 | 1.64 |
| G132AV195FA18I | 19.9 | 5.2 |
| G132AV195FD119G | 19.8 | 1.42 |
| G132AV195FA173R | 19.8 | 2.4 |
| V195FG132QI181SD199N | 19.71 | 7.82 |
| V195FG132RD199NF324S | 19.67 | 5.03 |
| V195FG132KI181LD199N | 19.22 | 3.53 |
| G132RF324S | 19.22 | 3.32 |
| V195FD119GG132K | 19.19 | 2.62 |
| V195FG132AF20L | 19.18 | 2.89 |
| V195FD119GV122L | 19.2 | 7.3 |
| V195FG132TD199NF324S | 18.68 | 4.70 |
| V195FD119GS123EF324S | 18.64 | 3.58 |
| V195FD119GY151M | 18.29 | 3.12 |

TABLE 5-continued

| Mutations | Relative activity vs wild type | |
|---|---|---|
| | Conversion of crotyl alcohol into 1,3 Butadiene | Conversion of but-3-en-2-ol into 1,3 Butadiene |
| V195FA230Q | 18.24 | 2.3 |
| G132AV195FA18V | 18.2 | 3.96 |
| V195FG132AA18I | 17.98 | 2.27 |
| V195FV122LG132Q | 17.7 | 3.5 |
| V195FG132KF324S | 17.54 | 3.00 |
| V195FD119GY251M | 17.22 | 3.16 |
| V195FG132AA18V | 17.03 | 2.70 |
| V195FG132VD199NF324S | 17 | 1.74 |
| V195FG132LD199N | 16.87 | 5.57 |
| V195FG132MD199NF324S | 16.70 | 4.06 |
| V195FK126AG132AD199N | 16.7 | 2.6 |
| V195FD119GG132T | 16.66 | 2.61 |
| V195FG132AD39A | 16.65 | 2.14 |
| V195FG132AD119G | 16.56 | 2.26 |
| G132AI194RS207A | 16.25 | |
| V195FG132AY285L | 16.20 | 3.43 |
| V195FG132RD199N | 16.02 | 2.70 |
| V195FG132KP389S | 16.0 | 2.6 |
| V195FG132QV318A | 16.0 | 2.7 |
| V195FG132QY159M | 15.9 | 3.2 |
| V195FG132ND199NQ204Q | 15.8 | 2.5 |
| V195FD119GS123Q | 15.72 | 3.31 |
| V195FG132QD199NA314A | 15.5 | 3.1 |
| V195FG132AA114SV122I | 15.39 | 2.8 |
| V195FD199NL367F | 15.38 | 2.33 |
| V195FD119GG132S | 15.00 | 2.50 |
| V195FG132KL367F | 15.00 | 2.35 |
| V195FD119GS123H | 14.9 | 3.0 |
| V195FG132KR169ND199N | 14.80 | 3.05 |
| V195FG132DD199N | 14.79 | 3.76 |
| V195FG132TD199N/D119G | 14.7 | 2.8 |
| V195FV122IG132L | 14.7 | 3.9 |
| V195FD199NV318A | 14.7 | 2.8 |
| V195FD119GG132N | 14.7 | 2.5 |
| V195FD119GS123EL367F | 14.57 | 2.16 |
| V195FG132KD119G | 14.5 | 2.3 |
| V195FL100LD119GGF324S | 14.30 | 2.92 |
| V195FI107ND119GS123EG132M | 14.22 | 2.08 |
| V195FG132HD199N | 14.2 | 2.9 |
| V195FG132QI181L | 14.2 | 2.6 |
| V195FM158IF324S | 14.0 | 2.7 |
| V195FS123TF324S | 13.82 | 2.75 |
| V195FV122LG132V | 13.6 | 3.4 |
| V195FD199N/Y251L | 13.21 | 3.37 |
| V195FD119GS123R | 13.12 | 2.70 |
| V195FD119GS123D | 13.10 | 2.62 |
| V195FG132TF195Y | 13.1 | 2.1 |
| V195FG132VA227I | 13.1 | 2.8 |
| V195FD119GG132KY251M | 13.00 | 3.33 |
| V195FG132KM158ID199N | 12.9 | 2.6 |
| V195FS123ED199N | 12.9 | 3.1 |
| V195FG132KR169TD199N | 12.7 | 3.0 |
| V195FD119GG132EY251M | 12.69 | 2.96 |
| V195FD119GG132AY251M | 12.61 | 3.38 |
| V195FG115AD119G | 12.5 | 2.0 |
| V195FS123RG132K | 12.4 | 3.1 |
| V195FD119GS123K | 12.4 | 3.0 |
| V195FD119GL367F | 12.32 | 1.53 |
| V195FI106ND119GS123E | 12.27 | 1.90 |
| V195FI107ND119GS123EG132Q | 12.15 | 2.73 |
| V195FG132TR169T | 12.1 | 2.2 |
| V195FG132K/G132TD199N | 12.0 | 2.2 |
| V195FG132AD119L | 11.82 | 1.2 |
| V195FG132TG140G | 11.8 | 2.5 |
| V195FG132TS357N | 11.7 | 2.2 |
| V195FD119GG132SY251M | 11.68 | 2.63 |
| V195FS123QG132S | 11.6 | 2.6 |
| V195FF76LD199N | 11.51 | 3.89 |
| V195FI107ND119GS123E | 11.20 | 3.40 |
| V195FH175N | 11.20 | 1.94 |
| V195FT84IG132R | 11.01 | 2.24 |
| V195FR169TD199N | 10.9 | 2.5 |
| V195FG132AS207C | 10.76 | 1.2 |

TABLE 5-continued

| | Relative activity vs wild type | |
|---|---|---|
| Mutations | Conversion of crotyl alcohol into 1,3 Butadiene | Conversion of but-3-en-2-ol into 1,3 Butadiene |
| V195FT84I | 10.54 | 2.10 |
| V195FA227S | 10.30 | 2.04 |
| V195FS75N | 10.13 | 3.56 |
| V195FE77L | 10.10 | 2.46 |
| V195FF76L | 9.25 | 2.07 |
| V195FG132AP108I | 8.51 | 1 |
| V195FG132AY210L | 8.28 | ND |
| V195FG132AY70A | 8.24 | ND |
| S102MT166S | 0.90 | 1.30 |

II. Example 1

Identification of Alkenol Dehydratase Enzyme Variants with Enhanced Activity in Converting Crotyl Alcohol into 1,3 Butadiene a) Library Construction A DNA library coding for single residue mutants of the alkenol dehydratase was constructed using standard mutagenesis techniques. The DNA library was developed based on the full-length coding sequence of the alkenol dehydratase enzyme, in particular the enzyme having the amino acid sequence shown in SEQ ID NO: 1, with an N-term His6 tag (as shown in SEQ ID NO: 3). The corresponding encoding nucleotide sequence is shown in SEQ ID NO: 2. The sequence was subcloned into the commercial peT-25b+ expression vector and used as the template for the mutagenic PCR. The quality control for the library construction consisted of two steps: (1) the amplified DNA fragments obtained were analyzed and quantified against a range of control reactions (2) DNA sequencing was carried out on 200 randomly-selected clones. The profiles of the DNA fragments were as expected. In term of the DNA sequence analysis of the gene coding for the alkenol dehydratase, 73% of the clones presented a single residue mutation while the rest were found wildtype.

b) Screening Assay

A screening assay was specifically developed in order to identify enzyme variants of interest. This assay was set up as follows: The alkenol dehydratase single point mutation DNA library in the pET25b+ expression vector was transformed into BL21(DE3) competent cells. Isolated clones were used to inoculate 1 ml of autoinduction medium (Studier F. W, Protein Expr. Purif. 41 (2005), 207-234) and grown overnight at 30° C. for 20-22 hours in a shaking incubator set at 700 rpm and 85% humidity. The cells were pelleted and stored at −80° C. overnight. These cell pellets that contain the expressed recombinant alkenol dehydratase variants were resuspended in a reaction mix containing 50 mM Tris-Cl pH7.5, 25 mM KCl, 25 mM MgCl2, 4 mM DTT, 10 mM glutathion and 50 mM crotyl alcohol (trans-cis mixture obtained from Sigma Aldrich). Control reactions were set up using either bacterial clones containing either the empty expression vector peT25b+ or the expression vector expressing the wild type enzyme. This reaction mix was incubated for 16 hours at 37° C. and the reaction was stopped by a 5-minute incubation at 80° C. The amount of 1,3 butadiene produced was then quantified by gas chromatography analysis. For the GC headspace analysis, 300 µl of the headspace gas was injected in a Bruker GC450 system equipped with a Restek RT-Alumina column (5 m×0.32 mm) and a Flame ionization detection system (FID). The GC analysis method used to detect 1,3 butadiene is characterised by a constant oven temperature at 140° C., injector port temperature at 200° C. with a split ratio of 1:4 and the FID detector temperature at 250° C. Nitrogen was used as a carrier gas (constant flow of 1.25 ml/min) and a mixture of air (air flow 300 ml/min), nitrogen (28 ml/min flow) and hydrogen (flow of 30 ml/min) was used to supply the FID detection system.

c) Identification of Enzyme Variants with Increased Activity

The library of single residue variants of alkenol dehydratase was screened using the screening assay described above. A total number of 16,318 variants were assayed. Alongside the alkenol dehydratase variants, control reactions were set up including reference controls using wild type alkenol dehydratase enzyme and negative controls (no alkenol dehydratase enzyme). Altogether 19,900 clones were screened. Out of the 16,318 alkenol dehydratase enzyme variants analysed, 353 positive hits were identified, they represent 2.18% of the population screened. Out of the 353 variants isolated in the primary screen, 52 variants remained after the two additional rounds of screening. These variants were tested in multiple replicates and in a range of conditions to ensure that the increase of activity is reproducible and not due to an artefact of the assay. Finally, each clone was subjected to DNA sequencing in order to identify the mutation responsible for the change in enzyme activity. FIG. 3 shows the complete collection of mutants identified and ordered according to their relative activity compared to the wild type enzyme.

III. Example 2

Identification of Alkenol Dehydratase Enzyme Variants with Enhanced Activity in Converting but-3-en-2-ol into 1,3 Butadiene The library of single residue mutants described in Example 1 was screened following the protocol also described in Example 1 except that the assay reaction mix was modified as follows: The cell pellets containing the expressed recombinant alkenol dehydratase variants were resuspended in a reaction mix containing 50 mM Tris-Cl pH7.5, 25 mM KCl, 25 mM MgCl2, 4 mM DTT, 10 mM glutathion and 50 mM but-3-en-2-ol (Sigma Aldrich). The variants showing an increased activity at 50 mM but-3-en-2-ol were further assayed using 12.5 and 25 mM but-3-en-2-ol. FIG. 4 shows the complete collection of mutations identified through this screen ordered according to their relative activity compared to the wild type enzyme.

IV. Example 3

Identification of Mutations on Residue S75 of the Alkenol Dehydratase that Lead to an Increase in the Activity of Conversion of Trans Crotyl Alcohol into 1, 3 Butadiene The screening allowed the identification of the mutation S75M as able to increase the conversion of crotyl alcohol into 1,3 butadiene. The effect of a range of other substitutions at position S75 was tested in order to assess whether other substitutions could, similarly to S75M, enhance the activity of the wild type enzyme. The plasmid DNA for the expression vectors encoding the S75 variants were transformed in BL21(DE3) and single transformants were used to inoculate 1 ml of autoinduction medium in order to produce recombinant enzyme in bacteria. Frozen cell pellets containing the expressed recombinant alkenol dehydratase variants were resuspended in a reaction mix containing 50 mM Tris-Cl pH7.5, 25 mM KCl, 25 mM MgCl2, 4 mM DTT, 10 mM glutathion and 25 mM trans crotyl alcohol (Alfa Aesar). Following a 16-hour incubation at 37° C., the amount of 1,3 butadiene produced was quantified by gas chromatography according to the GC method described in Example 1. Control reactions were set up using bacterial clones containing either the empty expression vector peT25b+ or the expression vector expressing the wild type enzyme. All variants were tested in 8 replicates. The raw GC data are presented in FIG. 5. Substitutions of S75 with T, A, N, V lead to an approx. 2-fold increase in the amount of 1,3 butadiene produced compared to the wild type enzyme. Substitution of S75 with M, G, L lead to a 1.3-1.5-fold increase in the amount of 1,3 butadiene produced.

V. Example 4

Identification of Mutations on Residue S123 of the Alkenol Dehydratase that Lead to an Increase in the Activity of Conversion of Trans Crotyl Alcohol into 1, 3 Butadiene The screening described in Example 1 allowed the identification of four substitutions at position S123 of the alkenol dehydratase that lead to a approx. 3-fold increase in the conversion of crotyl alcohol into 1,3 butadiene (S123R, S123H, S123E, S123D). The effect of a range of other substitutions at position S123 was tested in order to assess whether other substitutions could, similarly to S123R, S123H, S123E, S123D, enhance the activity of the wild type enzyme. The plasmid DNA for the expression vectors encoding S123 variants were transformed in BL21(DE3) and single transformants were used to inoculate 1 ml of autoinduction medium in order to produce recombinant enzyme in bacteria. Frozen cell pellets containing the expressed recombinant alkenol dehydratase variants were resuspended in a reaction mix containing 50 mM Tris-Cl pH7.5, 25 mM KCl, 25 mM MgCl2, 4 mM DTT, 10 mM glutathion and 50 mM trans crotyl alcohol (Alfa Aesar). Following a 16-hour incubation at 37° C., the amount of 1,3 butadiene produced was quantified by gas chromatography according to the GC method described in Example 1. Control reactions were set up using bacterial clones containing either the empty expression vector peT25b+ or the expression vector expressing the wild type enzyme. All variants were tested in 8 replicates. The raw GC data are presented in FIG. 6. In addition to S123R, S123H, S123E, S123D, this assay identified S123W, S123Y, as mutations conferring a 1.7-2-fold increase in activity, mutations S123K and S123I conferring an approx. 1.5-fold increase in activity and mutations S123M/Q/V/T/L/F that lead to an increase of 1.2-1.3-fold.

VI. Example 5

Identification of Mutations on Residue V195 of the Alkenol Dehydratase that Lead to an Increase in the Activity of Conversion of Trans Crotyl Alcohol into 1,3 Butadiene The screening described in Example 1 allowed the identification of V195F variant which has an activity approx. 8-fold higher than the wild type enzyme in catalysing the conversion of crotyl alcohol into 1,3 butadiene. V195F was identified as the best performing variant. The effect of a range of other substitutions at position V195 was tested in order to assess whether other substitutions could, similarly to V195F enhance the activity of the wild type enzyme. The plasmid DNA for the expression vectors encoding V195 variants were transformed in BL21(DE3) and single transformants were used to inoculate 1 ml of autoinduction medium in order to produce recombinant enzyme in bacteria. Frozen cell pellets containing the expressed recombinant alkenol dehydratase variants were resuspended in a reaction mix containing 50 mM Tris-Cl pH7.5, 25 mM KCl, 25 mM MgCl2, 4 mM DTT, 10 mM glutathion and 50 mM trans crotyl alcohol (Alfa Aesar). Following a 16-hour incubation at 37° C., the amount of 1,3 butadiene produced was quantified by gas chromatography according to the GC method described in Example 1. Control reactions were set up using bacterial clones containing either the empty expression vector peT25b+ or the expression vector expressing the wild type enzyme. All variants were tested in 8 replicates. The raw GC data are presented in FIG. 7. In addition to V195F, V195Y was found to have an activity increase by a factor 3.5 compared to the wild type enzyme. V195L, V195M, V195C also show an increase in activity of 1.2-1.3-fold.

VII. Example 6

Identification of Mutations on Residue G132 of the Alkenol Dehydratase that Lead to an Increase in the Activity of Conversion of Trans Crotyl Alcohol into 1,3 Butadiene The screening described in Example 1 allowed the identification of G132D alkenol dehydratase variant that lead to a 4-fold increase in the conversion of crotyl alcohol into 1,3 butadiene. The effect of a range of substitution at position G132 was tested in order to assess whether other substitutions could, similarly to G132D enhance the activity of the wild type enzyme. The plasmid DNA for the expression vectors encoding the G132 variants were transformed in BL21(DE3) and single transformants were used to inoculate 1 ml of autoinduction medium in order to produce recombinant enzyme in bacteria. Frozen cell pellets containing the expressed recombinant alkenol dehydratase variants were resuspended in a reaction mix containing 50 mM Tris-Cl pH7.5, 25 mM KCl, 25 mM MgCl2, 4 mM DTT, 10 mM glutathion and 50 mM trans crotyl alcohol (Alfa Aesar). Following a 16-hour incubation at 37° C., the amount of 1,3 butadiene produced was quantified by gas chromatography according to the GC method described in Example 1. Control reactions were set up using bacterial clones containing either the empty expression vector peT25b+ or the expression vector expressing the wild type enzyme. All variants were tested in 8 replicates. The raw GC data are presented in FIG. 8. These results indicate that G132 is a position critical to the enzyme activity since, in addition to G132D variant, 9 other substitutions increase the activity of the enzyme by a factor 2 fold an above (H, W, Y, F, C, M, R, K, Q, N) while substitutions to V, I, L, A, T lead to an increase of 1.2-1.8-fold.

VIII. Example 7

Determination of the Kinetic Constants for the Alkenol Dehydratase V195F Variant—Conversion of Crotyl Alcohol into Butadiene Michaelis-Menten $k_{cat}$ and $K_m$ steady state kinetics constants for the reaction of conversion of crotyl alcohol into 1,3 butadiene were determined using the following protocol: The wild type alkenol dehydratase and the V195F variant sub-cloned into the commercial Novagen peT-25b+ bacterial expression vector were transformed into BL21(DE3) competent cells and plated out on LB agar plates supplemented with the appropriate antibiotic. Isolated transformants were used to inoculate auto-induction medium (Studier F. W, Protein Expr. Purif. 41 (2005), 207-234) and the culture were incubated overnight at 30° C. in a shaker incubator. Cell pellets containing the overexpressed recombinant enzyme were stored overnight at −80° C. before being resuspended in a lysis buffer (50 mM Tris-Cl pH7.5, 4 mM DTT, 25 mM $MgCl_2$, 25 mM KCl) supplemented with Merck Novagen Lysonase (100 µl Lysonase in 15 ml of lysis buffer for a cell pellet produced from 1 litre culture). The cell suspension was incubated for 10 minutes at room temperature followed by 20 minutes on ice. Cell lysates were clarified by centrifugation and the supernatant was concentrated 2-fold using a filtration concentrator. The amount of the enzyme variant present in the concentrated soluble fraction was estimated on SDS-PAGE gel against a BSA calibration curve using gel densitometry. Enzymatic reactions were set up in 2 ml glass vials with 450 µl of the cell lysate supernatant, a range of 0 to 100 mM trans-crotyl alcohol, 4 mM DTT, 25 mM MgCl2, 25 mM KCl, 4 mM glutathion and 50 mM Tris-Cl pH7.5. The vials were sealed and incubated for 1 to 6 hours at 37° C. The enzymatic reactions were stopped by incubating for 5 minutes at 80° C. and the 1,3 butadiene produced was quantified by gas chromatography as previously described. In order to quantify the absolute amount of 1,3 butadiene produced by the reaction, the gas chromatograph was calibrated using a range of concentration of pure butadiene (1 to 10,000 ppm). The calibration table was found to be linear in this range of butadiene concentration. The production rates of butadiene (mole of butadiene/mole enzyme/sec) were plotted as a function of the concentration of trans crotyl alcohol (FIG. 9) and the curve was fitted using the Michaelis Menten equation (V=(Vmax*(substrate))/(Km+(substrate))) to extract the $k_{cat}$ (s$^{-1}$) and the $K_m$ values (mM) that are presented in Table 5.

TABLE 5

Kinetic constants of the conversion of t-crotyl alcohol into 1,3 butadiene

|  | $K_{cat}$ (s$^{-1}$) | $K_m$ (mM) | $K_{cat}/K_m$ (10$^{-3}$ s$^{-1}$ · mM$^{-1}$) | $K_{cat}/K_m$ Fold increase |
|---|---|---|---|---|
| Wild type enzyme | 0.2 10$^{-3}$ | ~50 | 0.004 | — |
| V195F variant | 2 10$^{-3}$ | 29 | 0.0689 | 17.2 |

IX. Example 8

Determination of the Kinetic Constants for the Alkenol Dehydratase V195F Variant-Conversion of but-3-en-2-ol into Butadiene Michaelis-Menten $k_{cat}$ (s$^{-1}$) and $K_m$ values (mM) steady state kinetic constants for the reaction of the conversion of but-3-en-2-ol into 1,3 butadiene were determined using the following protocol: The wild type alkenol dehydratase and the V195F variant sub-cloned into the commercial Novagen peT-25b+ bacterial expression vector were transformed into BL21(DE3) competent cells and plated out on LB agar plates supplemented with the appropriate antibiotic. Isolated transformants were used to inoculate autoinduction medium (Studier F. W, Protein Expr. Purif. 41 (2005), 207-234) and the cultures were incubated overnight at 30° C. in a shaker incubator. Cell pellets containing the overexpressed recombinant enzyme were stored overnight at −80° C. before being resuspended in a lysis buffer (50 mM Tris-Cl pH7.5, 4 mM DTT, 25 mM $MgCl_2$, 25 mM KCl) supplemented with Merck Novagen Lysonase (15 ml of lysis buffer for a cell pellet produced from 1 litre culture). The cell suspension was incubated for 10 minutes at room temperature followed by 20 minutes on ice. Cell lysates were clarified by centrifugation and the supernatant was concentrated 2-fold using a centrifugal concentrator. The amount of the enzyme variant present in the concentrated soluble fraction was estimated on SDS-PAGE gel against a BSA calibration curve using gel densitometry. Enzymatic reactions were set up in 2 ml glass vials with 450 µl of the cell lysate supernatant, a range of 0 to 100 mM but-3-en-2-ol, 4 mM DTT, 25 mM MgCl2, 25 mM KCl, 4 mM glutathion and 50 mM Tris-Cl pH7.5. The vials were sealed and incubated for 1 to 6 hours at 37° C. The enzymatic reactions were stopped by incubating for 5 minutes at 80° C. and the 1,3 butadiene produced was quantified by gas chromatography as previously described. In order to quantify the absolute amount of 1,3 butadiene produced by the reaction, the gas chromatograph was calibrated using a range of concentration of pure butadiene (1 to 10,000 ppm). The calibration table was found to be linear in this range of butadiene concentration. The production rates of butadiene (mole of butadiene/mole enzyme/sec) were plotted as a function of the concentration of but-3-en-2-ol (FIG. 10) and the curve was fitted using the Michaelis Menten equation (V=(Vmax*(substrate))/(Km+ (substrate))) to extract the kcat (s−1) and the Km values (mM) that are summarized in Table 6.

TABLE 6

Kinetic constants or the conversion of but-3-en-2-ol into 1,3 butadiene

|  | $K_{cat}$ (s−1) | $K_m$ (mM) | $K_{cat}/Km$ (10$^{-3}$ s$^{-1}$ · mM$^{-1}$) | $K_{cat}/K_m$ Fold increase |
|---|---|---|---|---|
| Wild type enzyme | 7.3 10$^{-3}$ | 50 mM | 0.146 | — |

TABLE 6-continued

Kinetic constants or the conversion of but-3-en-2-ol into 1,3 butadiene

| | $K_{cat}$ (s-1) | $K_m$ (mM) | $K_{cat}$/Km ($10^{-3}$ $s^{-1}\cdot mM^{-1}$) | $K_{cat}/K_m$ Fold increase |
|---|---|---|---|---|
| V195F variant | 13 $10^{-3}$ | 34 mM | 0.38 | 2.6 |

X. Example 9

Identification of Enzyme Variants Bearing Double-Residue Mutations with an Increased Activity in Converting Crotyl Alcohol into 1,3 Butadiene A collection of double mutants was constructed using the V195F alkenol dehydratase variant (SEQ ID N° 2) as a template. To assess the activity of the variants, this collection was sub-cloned in the pET300/NT-DEST expression vector (Life technologies) and transformed into BL21(DE3) competent cells. Isolated clones were used to inoculate 1 ml of auto-induction medium (Studier F. W, Protein Expr. Purif. 41 (2005), 207-234) and grown overnight at 30° C. for 20-22 hours in a shaking incubator set at 700 rpm and 85% humidity. The cells were pelleted and stored at −80° C. overnight. These cell pellets that contain the expressed recombinant alkenol dehydratase variants were resuspended in a reaction mix containing 50 mM Tris-Cl pH7.5, 25 mM KCl, 25 mM MgCl2, 4 mM DTT, 10 mM glutathion and 50 mM crotyl alcohol (trans isomer obtained from Alfa Aesar). Control reactions were set up using either bacterial clones containing either the empty expression vector peT25b+ or the expression vector expressing the V195F variant. This reaction mix was incubated for 16 hours at 37° C. and the reaction was stopped by a 5-minute incubation at 80° C. The amount of 1,3 butadiene produced was then quantified by gas chromatography analysis according to the method described in Example 1. The data are presented in FIG. 11. These data indicate that 15 substitutions including 12 on position G132 further increase the activity of the V195F variant by a factor approx. 1.4 to 3.4. The variants carrying double mutations V195F-G132R and V195F-G132L, respectively, are among the best performing variants.

XI. Example 10

Determination of the Kinetic Constants for a Collection of Alkenol Dehydratase Variants—Conversion of Trans-Crotyl Alcohol into 1,3 Butadiene Michaelis-Menten $k_{cat}$ and $K_m$ steady state kinetic constants for the reaction of conversion of trans-crotyl alcohol into 1,3 butadiene were determined using the protocols described in Example 7. The production rates of butadiene (mole of butadiene/mole enzyme/sec) were plotted as a function of the concentration of trans crotyl alcohol (FIG. 12) and the curve was fitted using the Michaelis Menten equation (V=(Vmax*(substrate))/(Km+(substrate))) to extract the $k_{cat}$ (s$^{-1}$) and the $K_m$ values (mM) that are summarized in Table 7.

TABLE 7

Kinetic constants for the conversion of trans-crotyl alcohol into 1,3 butadiene

| | $K_{cat}$ (s-1) | $K_m$ (mM) | $K_{cat}/K_m$ ($10^{-3}$ $s^{-1}\cdot mM^{-1}$) | $K_{cat}/K_m$ Fold increase |
|---|---|---|---|---|
| Wild type enzyme | 0.08 $10^{-3}$ | ~50 | 0.0016 | — |
| H116K | 0.3 $10^{-3}$ | 12.9 | 0.023 | 14.37 |
| G132D | 0.25 $10^{-3}$ | 58 | 0.0043 | 2.68 |
| G132L | 0.15 $10^{-3}$ | 65 | 0.0023 | 1.43 |
| S123W | 0.14 $10^{-3}$ | 37 | 0.0037 | 2.3 |

XII. Example 11

Determination of the Kinetic Constants for a Collection of Alkenol Dehydratase Variants—Conversion of but-3-en-2-ol into 1,3 Butadiene Michaelis-Menten $k_{cat}$ and $K_m$ steady state kinetic constants for the reaction of conversion of but-3-en-2-ol into 1,3 butadiene were determined using the protocols described in Example 10. The recombinant protein present in the concentrated soluble fraction was estimated on SDS-PAGE by gel densitometry against a BSA standard curve. The production rates of butadiene (mole of butadiene/mole enzyme/sec) were plotted as a function of the concentration of 3-but-en-2-ol and the curve was fitted using the Michaelis Menten equation (V=(Vmax*(substrate))/(Km+(substrate))) to extract the kcat (s−1) and the Km values (mM) that are summarized in Table 8 (see also FIG. 13).

TABLE 8

Kinetic constants for the conversion of 3-but-en-2-ol into 1,3 butadiene

| | $K_{cat}$ (s-1) | $K_m$ (mM) | $K_{cat}$/Km ($10^{-3}$ $s^{-1}\cdot mM^{-1}$) | $K_{cat}/K_m$ Fold increase |
|---|---|---|---|---|
| Wild type enzyme | 1.5 $10^{-3}$ | 40 | 0.037 | — |
| G132D | 3.9 $10^{-3}$ | 42 | 0.092 | 2.48 |
| S123H | 3.8 $10^{-3}$ | 40 | 0.095 | 2.56 |

XIII. Example 12

Alkenol Dehydratase Variants V195F and V195F G132A have an Increased Activity in Converting Prenol into Isoprene Compared to the Wild Type Enzyme The alkenol dehydratase catalyses the conversion of prenol into isoprene. The effect of the V195F and V197FG132A mutations (high performing variants for the production of 1,3 butadiene) on the ability of the alkenol dehydratase to catalyse the conversion of prenol into isoprene was evaluated. The assay was set up as follows: the wild type alkenol dehydratase and the V195F and V197FG132A variant were sub-cloned into the commercial pET300/NT-DEST expression vector (Life technologies), transformed into BL21 (DE3) competent cells and plated out on LB agar plates supplemented with the appropriate antibiotic. Isolated transformants were used to inoculate auto-induction medium (Studier F. W, Protein Expr. Purif. 41 (2005), 207-234) and the cultures were incubated overnight at 30° C. in a shaker incubator. Cell pellets obtained from a 200 ml culture and containing the overexpressed recombinant enzyme were stored overnight at −80° C. before being resuspended in 3 ml of lysis buffer (50 mM Tris-Cl pH7.5, 4 mM DTT, 25 mM MgCl$_2$, 25 mM KCl, 20 mM glutathion) supplemented with 10 µl Merck Novagen Lysonase. The cell suspension was incubated for 10 minutes at room temperature followed by 20 minutes on ice. Cell lysates were clarified by centrifugation (10 000 rpm for 20 minutes) and the supernatant was concentration 3-fold using a filtration concentrator (Millipore Amicon). Enzymatic reactions were set up in 2 ml glass vials with 200 µl of the concentrated cell lysate supernatant (variant), with 200 µl of the concentrated cell lysate supernatant (cell transformed with empty vector) and a range of 20, 40, 80 mM prenol (Sigma Aldrich). The vials were sealed and incubated for 1 hour at 37° C. The amount of enzyme variants was quantified on SDS-PAGE gel against a BSA calibration curve. The enzymatic reactions were stopped by incubating for 5 minutes at 80° C. and the isoprene produced was quantified by gas chromatography. For the GC headspace analysis, 100 µl of the headspace gas was injected in a Bruker GC450 system equipped with a Restek RT-Alumina column (30 m×0.32 mm) and a Flame ionization detection system (FID). The GC analysis method used to detect isoprene is characterised by a constant oven temperature at 180° C., injector port temperature at 200° C. with a split ratio of 1:10 and the FID detector temperature at 250° C. Nitrogen was used as a carrier gas (constant flow of 1.5 ml/min) and a mixture of air (air flow 300 ml/min), nitrogen (30 ml/min flow) and hydrogen (flow of 30 ml/min) was used to supply the FID detection system. Using these parameters, isoprene has a retention time of 5.75 min. GC data were normalised against equal amounts of protein. Data presented in FIG. 14 indicate that V195F and V195FG132A variants lead to a 12 and 20 fold increase respectively in the ability of the alkenol dehydratase enzyme to convert prenol into isoprene.

XIV. Example 13

Alkenol Dehydratase Variants V195F and V195F G132A have an Increased Activity in Converting Isoprenol into Isoprene Compared to the Wild Type Enzyme The alkenol dehydratase catalyses the conversion of isoprenol into isoprene. The ability of the best performing variants V195F and V197FG132A to catalyse the conversion of isoprenol into isoprene was evaluated and compared to the wild type enzyme. The assay was set up as follows: the wild type alkenol dehydratase and the V195F and V197FG132A variant were sub-cloned into the commercial pET300/NT-DEST expression vector (Life technologies), transformed into BL21(DE3) competent cells and plated out on LB agar plates supplemented with the appropriate antibiotic. Isolated transformants were used to inoculate auto-induction medium (Studier F. W, Protein Expr. Purif. 41 (2005), 207-234) and the cultures were incubated overnight at 30° C. in a shaker incubator. Cell pellets obtained from a 200 ml culture and containing the overexpressed recombinant enzyme were stored overnight at −80° C. before being resuspended in 3 ml of lysis buffer (50 mM Tris-Cl pH7.5, 4 mM DTT, 25 mM MgCl$_2$, 20 mM KCl, 20 mM glutathion) supplemented with 10 µl Merck Novagen Lysonase. The cell suspension was incubated for 10 minutes at room temperature followed by 20 minutes on ice. Cell lysates were clarified by centrifugation (10 000 rpm for 20 minutes) and the supernatant was concentrated 3-fold using a filtration concentrator (Millipore Amicon). Enzymatic reactions were set up in 2 ml glass vials with 200 µl of the concentrated cell lysate supernatant (variant), with 200 µl of the concentrated cell lysate supernatant (cell transformed with empty vector) and a range of 20, 40, 80 mM isoprenol (Sigma Aldrich). The vials were sealed and incubated for 1 hour at 37° C. The amount of enzyme variants was quantified on SDS-PAGE gel against a BSA calibration curve. The enzymatic reactions were stopped by incubating for 5 minutes at 80° C. and the isoprene was quantified by gas chromatography. For the GC headspace analysis, 100 µl of the headspace gas was injected in a Bruker GC450 system equipped with a Restek RT-Alumina column (30 m×0.32 mm) and a Flame ionization detection system (FID). The GC analysis method used to detect isoprene is characterised by a constant oven temperature at 180° C., injector port temperature at 200° C. with a split ratio of 1:4 and the FID detector temperature at 250° C. Nitrogen was used as a carrier gas (constant flow of 1.25 ml/min) and a mixture of air (air flow 300 ml/min), nitrogen (25 ml/min flow) and hydrogen (flow of 30 ml/min) was used to supply the FID detection system. Using these parameters, isoprene has a retention time of 5.75 min. GC data were normalised against equal amount of protein. Data presented in FIG. 15 indicate that V195F and V195FG132A variants lead to a 4-5 and 8-9 fold increase respectively in the ability of the alkenol enzyme to convert isoprenol into isoprene.

XV. Example 14

Determination of the Kinetic Constants for the Alkenol Dehydratase V195F and V195G132A Variants—Conversion of Prenol into Isoprene Michaelis-Menten $k_{cat}$ and $K_m$ steady state kinetic constants for the reaction of the conversion of prenol into isoprene were determined using the following protocol: The wild type alkenol dehydratase, the V195F and V197FG132A variants were sub-cloned into the commercial pET300/NT-DEST expression vector (Life technologies), transformed into BL21(DE3) competent cells and plated out on LB agar plates supplemented with the appropriate antibiotic. Isolated transformants were used to inoculate auto-induction medium (Studier F. W, Protein Expr. Purif. 41 (2005), 207-234) and the cultures were incubated overnight at 30° C. in a shaker incubator. Cell pellets obtained from a 200 ml culture and containing the overexpressed recombinant enzyme were stored overnight at −80° C. before being resuspended in 3 ml of lysis buffer (50 mM Tris-Cl pH7.5, 4 mM DTT, 25 mM MgCl$_2$, 25 mM KCl, 20 mM glutathion) supplemented with 10 µl Merck Novagen Lysonase. The cell suspension was incubated for 10 minutes at room temperature followed by 20 minutes on ice. Cell lysates were clarified by centrifugation (10 000 rpm for 20 minutes) and the supernatant was concentrated 3-fold using a filtration concentrator (Millipore Amicon) to a final volume of 1 ml. 500 µl enzymatic reactions were set up in 2 ml glass vials with 200 µl of the concentrated cell lysate supernatant (variant), with 200 µl of the concentrated cell lysate supernatant (cell transformed with empty vector) and a range of 20, 40, 80, 120 mM prenol (Sigma Aldrich). The vials were sealed and incubated for 20, 40, 60, 90, 120 and 180 min at 37° C. The amount of enzyme variant was quantified on SDS-PAGE gel against a BSA calibration curve. The enzymatic reactions were stopped by incubating for 5 minutes at 80° C. and the isoprene produced was quantified by gas chromatography. For the GC headspace analysis, 100 µl of the headspace gas was injected in a Bruker GC450 system equipped with a Restek RT-Alumina column (30 m×0.32 mm) and a Flame ionization detection system (FID). The GC analysis method used to detect isoprene is characterised by a constant oven temperature at 180° C., injector port temperature at 200° C. with a split ratio of 1:10 and the FID detector temperature at 250° C. Nitrogen was used as a carrier gas (constant flow of 1.5 ml/min) and a mixture of air (air flow 300 ml/min), nitrogen (25 ml/min flow) and hydrogen (flow of 30 ml/min) was used to supply the FID detection system. Using these parameters, isoprene has a retention time of 5.75 min. The production rates of isoprene (mole of isoprene/mole enzyme/sec) were plotted as a function of the concentration of prenol and the curve was fitted using Michaelis Menten equation (V=(Vmax*(substrate))/(Km+(substrate))) to extract the $k_{cat}$ ($s^{-1}$) and the $K_m$ values (mM) that are presented in Table 9.

TABLE 9

|  | $K_{cat}$ (s−1) | $K_m$ (mM) | $K_{cat}/K_m$ ($10^{-1}$ $s^{-1}$ · $mM^{-1}$) | $K_{cat}/K_m$ Fold increase |
|---|---|---|---|---|
| Wild type enzyme | 0.77 $10^{-1}$ | 61 | 0.012 | — |
| V195F | 6.51 $10^{-1}$ | 55 | 0.118 | 9.8 |
| V195F G132A | 9.91 $10^{-1}$ | 72 | 0.13 | 10.8 |

XVI. Example 15

Identification of Alkenol Dehydratase Enzyme Variants with Enhanced Activity in Converting Crotyl Alcohol and but-3-en-2-ol into 1,3 Butadiene a) Library Construction A DNA library coding for single residue mutants of the alkenol dehydratase was constructed using standard mutagenesis techniques. The DNA library was based on the full-length coding sequence of the alkenol dehydratase enzyme variant V195F-G132A, encoded by the amino acid sequence shown in SEQ ID NO: 5 (see FIG. 23), with an N-term His6 tag. The sequence was subcloned into the commercial peT300:NT-DEST (Life technologies) expression vector and used as the template for the mutagenic PCR.

b) Screening Assay

This assay was set up as follows: The alkenol dehydratase point mutation DNA library in the pET25b+ expression vector was transformed into BL21(DE3) competent cells. Isolated clones were used to inoculate 0.3 ml of autoinduction medium (Studier F. W, Protein Expr. Purif. 41 (2005), 207-234) and grown overnight at 30° C. for 20-22 hours in a shaking incubator set at 700 rpm and 85% humidity. The cells were pelleted and stored at −80° C. overnight. These cell pellets that contain the expressed recombinant alkenol dehydratase variants were resuspended in a reaction mix containing 50 mM Tris-Cl pH7.5, 25 mM KCl, 25 mM $MgCl_2$, 4 mM DTT, 10 mM glutathion and 50 mM crotyl alcohol (trans isomer obtained from Alfa aesar). Control reactions were set up using either bacterial clones containing either the empty expression vector peT25b+ or the expression vector expressing the V195F-G132A enzyme variant. This reaction mix was incubated for 16 hours at 37° C. and the reaction was stopped by a 5-minute incubation at 80° C. The amount of 1,3 butadiene produced was then quantified by gas chromatography analysis. For the GC headspace analysis, 100 µl of the headspace gas was injected in a Bruker GC450 system equipped with a Restek RT-Alumina column (5 m×0.32 mm) and a Flame ionization detection system (FID). The GC analysis method used to detect 1,3 butadiene is characterised by a constant oven temperature at 140° C., injector port temperature at 200° C. with a split ratio of 1:4 and the FID detector temperature at 250° C. Nitrogen was used as a carrier gas (constant flow of 1.25 ml/min) and a mixture of air (air flow 300 ml/min), nitrogen (28 ml/min flow) and hydrogen (flow of 30 ml/min) was used to supply the FID detection system.

c) Identification of Enzyme Variants with Increased Activity

The library of single residue variants of alkenol dehydratase was screened using the screening assay described above. A total number of 16,318 variants were assayed. Alongside the alkenol dehydratase variants, control reactions were set up including reference controls using V195F-G132A enzyme variant and negative controls (no alkenol dehydratase enzyme). These variants were subjected in total to three rounds of screening. During this screening process, the variants were tested in multiple replicates and in a range of conditions to ensure that the increase of activity is reproducible and not due to an artefact of the assay. In the latter stage of screening, the remaining hits were assayed to assess their ability to convert also but-3-en-2-ol into 1,3 butadiene. Finally, each clone was subjected to DNA sequencing in order to identify the mutation responsible for the change in enzyme activity. FIG. 17 shows the collection of 5 alkenol dehydratase variants with increased activity in converting crotyl alcohol into 1,3 butadiene. FIG. 18 shows the collection of 7 alkenol dehydratase variants with increased activity in converting but-3-en-2-ol into 1,3 butadiene.

XVII. Example 16

Identification of Alkenol Dehydratase Enzyme Variants with Enhanced Activity in Converting Crotyl Alcohol and but-3-en-2-ol into 1,3 Butadiene a) Library Construction A combinatorial library was constructed in order to recombine a collection of amino acids mutations that had been identified in previous screens. The combinatorial library was constructed using the alkenol dehydratase V195F variant sequence as a template (SEQ ID NO: 7, i.e., the sequence for variant V195F; see FIG. 24). This sequence was randomized at 15 positions in order to introduce 25 distinct mutations as detailed in Table 10. The construction of the combinatorial library used standard techniques of gene synthesis based on the assembly of overlapping sense and antisense oligonucleotides designed to match the targeted gene sequence (Czar et al, 2009 Trends in Biotechnology 27:63-72; Kodumal et al, 2004 Proc. Natl. Acad. Sci. USA 101:15573-15578; Smith et al. 2003 Proc. Natl. Acad. Sci. USA 101:15440-15445; Xiong et al, 2008 FEMS Microbiol Rev 32:522-540). Briefly, a mixture of 69 34-35-mer oligonucleotides representing the V195F alkenol dehydratase variant backbone was prepared at a final concentration of 50 µM and spiked with oligonucleotides mutated at the targeted amino acid positions (0.05 to 0.6 µM). PCR like reactions, without DNA template, were set up using 3 µl of the oligonucleotide mixtures and 0.5 µl of Pfx polymerase (LifeTechnologies) in order to assemble the gene from the oligonucleotides. The rate of mutations per clone was controlled by the ratio of backbone oligonucleotides to mutated oligonucleotides. A further cycle of PCR amplification of the reassembled gene was performed using primers situated at the 5' and 3' end of the gene was carried out. Finally, the amplified fragment was sub-cloned into the commercial peT-300/NT-DEST (LifeTechnologies).

b) Screening Assay and Identification of Enzyme Variants with Increased Activity The combinatorial library of multiple residue variants of alkenol dehydratase was screened using the screening assay described in example 15. Approximately 13,500 variants were assayed in parallel to assess their ability to convert crotyl alcohol as well as but-3-en-2-ol into 1,3 butadiene. Alongside the alkenol dehydratase variants, control reactions were set up including reference controls using wild type enzyme (see SEQ ID NO:9 as illustrated in FIG. 25), V195F enzyme variant and negative controls (no alkenol dehydratase enzyme). These variants were subjected in total to three rounds of screening. During this screening process, the variants were tested in multiple replicates and in a range of conditions to ensure that the increase of activity is reproducible and not due to an artefact of the assay. Finally, each clone was subjected to DNA sequencing in order to identify the mutation responsible for the change in enzyme activity. FIGS. 19 and 20 show the collection of 5 alkenol dehydratase variants with increased activity in converting crotyl alcohol or but-3-en-2-ol into 1,3 butadiene (relative activity compared to the wild type enzyme).

Expr. Purif. 41 (2005), 207-234) and the culture were incubated overnight at 30° C. in a shaker incubator. Cell pellets containing the overexpressed recombinant enzyme were stored overnight at −80° C. before being resuspended in a lysis buffer (50 mM Tris-Cl pH7.5, 4 mM DTT, 25 mM MgCl$_2$, 25 mM KCl) supplemented with Merck Novagen Lysonase (100 μl Lysonase in 15 ml of lysis buffer for a cell pellet produced from 1 litre culture). The cell suspension was incubated for 10 minutes at room temperature followed by 20 minutes on ice. Cell lysates were clarified by centrifugation (15 min at 10,000 rpm) and the supernatant was concentrated 2-fold using a filtration concentrator. The amount of the enzyme variant present in the concentrated soluble fraction was estimated on SDS-PAGE gel against a BSA calibration curve using gel densitometry. Enzymatic reactions were set up in 2 ml glass vials with 250 μl of the cell lysate supernatant, a range of 0 to 100 mM trans-crotyl alcohol, 4 mM DTT, 25 mM MgCl2, 25 mM KCl, 4 mM glutathion and 50 mM Tris-Cl pH7.5. The vials were sealed and incubated for 1 to 4 hours at 37° C. The enzymatic reactions were stopped by incubating for 5 minutes at 80° C. and the 1,3 butadiene produced was quantified by gas chromatography as previously described. In order to quantify the absolute amount of 1,3 butadiene produced by the reaction, the gas chromatograph was calibrated using a range of concentration of pure butadiene (1 to 10,000 ppm). The calibration table was found to be linear in this range of butadiene concentration. The production rates of butadiene (mole of butadiene/mole enzyme/sec) were plotted as a function of the concentration of trans crotyl alcohol (FIG.

TABLE 10

| Position [aa] | wild type aa | Substitution 1 aa | Substitution 2 aa | Substitution 3 aa | Substitution 4 aa | Substitution 5 aa | Substitution 6 aa | Substitution 7 aa | Substitution 8 aa | Substitution 9 aa |
|---|---|---|---|---|---|---|---|---|---|---|
| 18 | A | I | V | | | | | | | |
| 20 | F | L | | | | | | | | |
| 39 | D | A | | | | | | | | |
| 73 | G | S | | | | | | | | |
| 77 | E | I | | | | | | | | |
| 119 | D | G | | | | | | | | |
| 123 | S | E | | | | | | | | |
| 132 | G | K | L | M | N | Q | R | S | T | V |
| 170 | R | K | | | | | | | | |
| 173 | A | R | | | | | | | | |
| 181 | I | L | S | | | | | | | | |
| 199 | D | N | | | | | | | | |
| 269 | W | A | | | | | | | | |
| 324 | F | S | | | | | | | | |
| 365 | L | F | | | | | | | | |

XVIII. Example 17

Determination of the Kinetic Constants for the Alkenol Dehydratase V195F G132A G73S E77I Variant—Conversion of Crotyl Alcohol into Butadiene Michaelis-Menten $k_{cat}$ and $K_m$ steady state kinetics constants for the reaction of conversion of crotyl alcohol into 1,3 butadiene were determined using the following protocol: The wild type alkenol dehydratase and the V195FG132AG73SE77I variant sub-cloned into the commercial Novagen peT-300/NT-DEST bacterial expression vector were transformed into BL21(DE3) competent cells and plated out on LB agar plates supplemented with the appropriate antibiotic. Isolated transformants were used to inoculate auto-induction medium (Studier F. W, Protein 21) and the curve was fitted using the Michaelis Menten equation (V=(Vmax*(substrate))/(Km+(substrate))) to extract the $k_{cat}$ (s$^{-1}$) and the $K_m$ values (mM) that are presented in Table 11.

TABLE 11

Kinetic constants of the conversion of t-crotyl alcohol into 1,3 butadiene

| | $K_{cat}$ (s$^{-1}$) | $K_m$ (mM) | $K_{cat}/K_m$ (10$^{-3}$ s$^{-1}$ · mM$^{-1}$) | $K_{cat}/K_m$ Fold increase |
|---|---|---|---|---|
| Wild type enzyme* | ~1.5 10$^{-5}$ | ~50 | 0.0003 | — |
| V195F G132A G73S E77I variant | 1.1 10$^{-3}$ | 7.8 | 0.141 | 470 |

*SEQ ID NO: 9

XIX. Example 18

Determination of the Kinetic Constants for the Alkenol Dehydratase V195F G132A G73S E77I and V195F G73S R170K I181L F324S Variants-Conversion of but-3-en-2-ol into Butadiene Michaelis-Menten $k_{cat}$ and $K_m$ steady state kinetics constants for the reaction of conversion of but-3-en-2-ol into 1,3 butadiene were determined using the following protocol: The wild type alkenol dehydratase, the V195FG132AG73SE77I variant and the V195FG73SR170K I181LF324S variants variant sub-cloned into the commercial Novagen peT-300/NT-DEST bacterial expression vector were transformed into BL21 (DE3) competent cells and plated out on LB agar plates supplemented with the appropriate antibiotic. Isolated transformants were used to inoculate autoinduction medium (Studier F. W, Protein Expr. Purif. 41 (2005), 207-234) and the cultures were incubated overnight at 30° C. in a shaker incubator. Cell pellets containing the overexpressed recombinant enzyme were stored overnight at −80° C. before being resuspended in a lysis buffer (50 mM Tris-Cl pH7.5, 4 mM DTT, 25 mM MgCl2, 25 mM KCl) supplemented with Merck Novagen Lysonase (15 ml of lysis buffer for a cell pellet produced from 1 litre culture). The cell suspension was incubated for 10 minutes at room temperature followed by 20 minutes on ice. Cell lysates were clarified by centrifugation and the supernatant was concentrated 2-fold using a centrifugal concentrator. The amount of the enzyme variant present in the concentrated soluble fraction was estimated on SDS-PAGE gel against a BSA calibration curve using gel densitometry. Enzymatic reactions were set up in 2 ml glass vials with 250 µl of the cell lysate supernatant, a range of 0 to 100 mM but-3-en-2-ol, 4 mM DTT, 25 mM MgCl2, 25 mM KCl, 4 mM glutathion and 50 mM Tris-Cl pH7.5. The vials were sealed and incubated for 1 to 4 hours at 37° C. The enzymatic reactions were stopped by incubating for 5 minutes at 80° C. and the 1,3 butadiene produced was quantified by gas chromatography as previously described. In order to quantify the absolute amount of 1,3 butadiene produced by the reaction, the gas chromatograph was calibrated using a range of concentration of pure butadiene (1 to 10,000 ppm). The calibration table was found to be linear in this range of butadiene concentration. The production rates of butadiene (mole of butadiene/mole enzyme/sec) were plotted as a function of the concentration of but-3-en-2-ol (FIG. 22) and the curve was fitted using the Michaelis Menten equation (V=(Vmax*(substrate))/(Km+(substrate))) to extract the kcat (s−1) and the Km values (mM) that are summarized in Table 12.

XX. Example 19

Identification of Alkenol Dehydratase Variants with Increased Activity in Converting Prenol and Isoprenol into Isoprene Compared to the Wild Type Enzyme A screen was set up to assay the ability of the high-performing alkenol dehydratase variants for the production of 1,3 butadiene to catalyse the conversion of prenol and isoprenol into isoprene. The assay was set up as follows: the alkenol dehydratase variants and the wild type enzyme were sub-cloned into the commercial pET300/NT-DEST expression vector (Life technologies), transformed into BL21 (DE3) competent cells and plated out on LB agar plates supplemented with the appropriate antibiotic. Isolated transformants were used to inoculate auto-induction medium (Studier F. W, Protein Expr. Purif. 41 (2005), 207-234) and the cultures were incubated overnight at 30° C. in a shaker incubator. These cell pellets that contain the expressed recombinant alkenol dehydratase variants were resuspended in a reaction mix containing 50 mM Tris-Cl pH7.5, 25 mM KCl, 25 mM MgCl2, 4 mM DTT, 10 mM glutathion and 50 mM prenol or isoprenol (Sigma Aldrich). Control reactions were set up using either bacterial clones containing either the empty expression vector peT25b+ or the expression vector expressing the V195F enzyme variant. For the prenol screening assay, this reaction mix was incubated for 4 hours at 37° C. and 16 hours at 20° C. For the isoprenol screening assay, this reaction mix was incubated for 16 hours at 37° C. and 4 hours at 20° C. The amount of isoprene produced was immediately quantified by gas chromatography analysis. For the GC headspace analysis, 100 µl of the headspace gas was injected in a Bruker GC450 system equipped with a Restek RT-Alumina column (5 m×0.32 mm) and a Flame ionization detection system (FID). The GC analysis method used to detect isoprene is characterised by a constant oven temperature at 105° C., injector port temperature at 200° C. with a split ratio of 1:10 and the FID detector temperature at 250° C. Nitrogen was used as a carrier gas (constant flow of 1.20 ml/min) and a mixture of air (air flow 300 ml/min), nitrogen (28 ml/min flow) and hydrogen (flow of 30 ml/min) was used to supply the FID detection system. The results of the assay for prenol and isoprenol substrates are presented in Table 13 and 14 respectively.

TABLE 12

Kinetic constants or the conversion of but-3-en-2-ol into 1.3 butadiene

| | $K_{cat}$ (s−1) | $K_m$ (mM) | $K_{cat}$/Km ($10^{-3}$ s$^{-1}$ · mM$^{-1}$) | $K_{cat}/K_m$ Fold increase |
|---|---|---|---|---|
| Wild type enzyme | 1.3 $10^{-3}$ | 42 mM | 0.031 | — |
| V195FG132AG73SE77I | 6 $10^{-3}$ | 15.37 mM | 0.39 | 12.5 |
| V195FG73SR170KI181LF324S | 7.6 $10^{-3}$ | 20.6 | 0.37 | 12 |

TABLE 13

Mutants with increased activity for conversion of prenol into isoprene

| Mutations | Relative activity compared to V195F variant |
|---|---|
| V195FT84IG132R | 1.21 |
| V195FA18VG73SE77IR386S | 1.16 |
| V195FD119GG132KY251M | 1.14 |
| V195FG132AG73SE77IT84I | 1.12 |
| V195FG132AG73SE77L | 1.11 |
| V195FG132AG73SE77IT141S | 1.10 |
| V195FG132AG73SE77IT141S | 1.10 |
| V195FT84I | 1.10 |
| V195FD119GS123E | 1.10 |
| V195FG132AG73SE77I | 1.09 |
| V195FG132AG73SE77IG364S | 1.09 |
| V195FG132AG73SE77I | 1.07 |

TABLE 13-continued

Mutants with increased activity for conversion of prenol into isoprene

| Mutations | Relative activity compared to V195F variant |
|---|---|
| V195FG132AG73AE77L | 1.04 |
| V195FD119GY151M | 1.04 |
| V195FG132AG73SE77ID312E | 1.04 |
| V195FD119GY251M | 1.03 |
| V195FG132QV318A | 1.03 |
| V195FG132Q | 1.02 |
| V195FG132AG73SE77IS168D | 1.00 |
| V195FG132AG73SE77IG19T | 1.00 |
| V195FG132AG73SE77IT8L | 1.00 |
| V195F | 1.00 |

TABLE 14

Mutants with increased activity for conversion of isoprenol into isoprene

| Mutations | Relative activity compared to V195F variant |
|---|---|
| V195FA18IF20LD39AG73SD119GG132R | 2.54 |
| V195FA18IF20LG73SG132MR170KI181LD199NW269AL367F | 2.18 |
| V195FG132AG73SE77IG364S | 2.16 |
| V195FA18VD39AD119GR170KF324S | 2.15 |
| V195FD119GG132S | 2.15 |
| V195FT84IG132R | 2.10 |
| V195FG132VF324S | 2.08 |
| V195FL367F | 1.98 |
| V195FG132AG73SE77IA13I | 1.98 |
| V195FV122LG132V | 1.97 |
| V195FG132AG73SE77IA18C | 1.91 |
| V195FA18VD39AR170KI181LD199NF324SL367F | 1.85 |
| V195FA18VG73SR170KA173RP389L | 1.83 |
| V195FI181LF324S | 1.76 |
| V195FA18VD39AE77IR170KA173RD199NW269AF324S | 1.75 |
| V195FR170KA173RF324S | 1.71 |
| V195FA18ID39AG73SW269A | 1.63 |
| V195FA18VG73SD119GS123EI181LD199N | 1.57 |
| V195FA18IG73SR170KD199NF324SL367F | 1.56 |
| V195FA18VF20LD39AG73SL118LI144TR170KI181LD199NF324SL367F | 1.55 |
| V195FD119GG132KY251M | 1.52 |
| V195FV122LG132Q | 1.52 |
| V195FG132AG73SE77IS12A | 1.51 |
| V195FG132AG73SE77IT8L | 1.48 |
| V195FA18VD39AD119GI181L | 1.47 |
| V195FD119GY251M | 1.47 |
| V195FA18ID39AR170KI181SW269A | 1.46 |
| V195FD39AG73SE77IG132QR170KD199NL367FG382D | 1.46 |
| V195FG132RD199NF324S | 1.44 |
| V195FG132AG73SE77IG19T | 1.44 |
| V195FG132Q | 1.44 |
| V195FA18IF20LD39AG132VR170KI181LF324SL367F | 1.43 |
| V195FL367FG382D | 1.41 |
| V195FD39AG73SR170KI181LD199NF324S | 1.37 |
| V195FA18VD39AG73SE77ID119GR170K | 1.37 |
| V195FA18VD119GG132SR170KA173RI181LD199NW269A | 1.36 |
| V195FG132QV318A | 1.32 |
| V195FG132AG73SE77IE145E | 1.29 |
| V195FF324S | 1.27 |
| V195FG73SG132GR170KI181LF324S | 1.20 |
| V195FD39AG132AR170KD199NW269A | 1.20 |
| V195FD39AG73SR170KI181LD199N | 1.19 |
| V195FD119GS123R | 1.19 |
| V195FG735G132GR170KI181L | 1.17 |
| V195FT84I | 1.17 |
| V195FA18VG73SE77IR386S | 1.17 |
| V195FG735V122IS123EG132AD199NW269A | 1.14 |
| V195FA18IG73SR170KI181SL367F | 1.08 |
| V195FG132AG73SE77IT141S | 1.07 |
| V195FD39AG73SR170KI181LD199NL367F | 1.05 |

TABLE 14-continued

Mutants with increased activity for conversion of isoprenol into isoprene

| Mutations | Relative activity compared to V195F variant |
|---|---|
| V195FA18VF20LD39AG132KR170KI181LW269A | 1.03 |
| V195FA18IG132KR170KW269AF3245 | 1.03 |
| V195FG132AG73SE77I | 1.03 |
| V195FF324S | 1.02 |
| V195FG132AW269A | 1.02 |
| V195F | 1.00 |

XXI. Example 20

Determination of the Kinetic Constants for the Alkenol Dehydratase Best Performing Variants—Conversion of Isoprenol into Isoprene Michaelis-Menten $k_{cat}$ and $K_m$ steady state kinetic constants for the reaction of the conversion of isoprenol into isoprene were determined using the following protocol: The wild type alkenol dehydratase, the alkenol dehydratase variants were sub-cloned into the commercial pET300/NT-DEST expression vector (Life technologies), transformed into BL21(DE3) competent cells and plated out on LB agar plates supplemented with the appropriate antibiotic. Isolated transformants were used to inoculate auto-induction medium (Studier F. W, Protein Expr. Purif. 41 (2005), 207-234) and the cultures were incubated overnight at 30° C. in a shaker incubator. Cell pellets obtained from a 200 ml culture and containing the overexpressed recombinant enzyme were stored overnight at −80° C. before being resuspended in 3 ml of lysis buffer (50 mM Tris-Cl pH7.5, 4 mM DTT, 25 mM MgCl$_2$, 25 mM KCl, 20 mM glutathion) supplemented with 10 µl Merck Novagen Lysonase. The cell suspension was incubated for 10 minutes at room temperature followed by 20 minutes on ice. Cell lysates were clarified by centrifugation (10 000 rpm for 20 minutes) and the supernatant was concentrated 3-fold using a filtration concentrator (Millipore Amicon) to a final volume of 1 ml. 500 µl enzymatic reactions were set up in 2 ml glass vials with 200 µl of the concentrated cell lysate supernatant (variant), with 200 µl of the concentrated cell lysate supernatant (cell transformed with empty vector) and a range of 20, 40, 80, 120 mM isoprenol (Sigma Aldrich). The vials were sealed and incubated for 20, 40, 60, 90, 120 and 180 min at 37° C. The amount of enzyme variant was quantified on SDS-PAGE gel against a BSA calibration curve. The enzymatic reactions were stopped by incubating for 5 minutes at 80° C. and the isoprene produced was quantified by gas chromatography. For the GC headspace analysis, 100 µl of the headspace gas was injected in a Bruker GC450 system equipped with a Restek RT-Alumina column (30 m×0.32 mm) and a Flame ionization detection system (FID). The GC analysis method used to detect isoprene is characterised by a constant oven temperature at 180° C., injector port temperature at 200° C. with a split ratio of 1:10 and the FID detector temperature at 250° C. Nitrogen was used as a carrier gas (constant flow of 1.5 ml/min) and a mixture of air (air flow 300 ml/min), nitrogen (25 ml/min flow) and hydrogen (flow of 30 ml/min) was used to supply the FID detection system. Using these parameters, isoprene has a retention time of 5.75 min. The production rates of isoprene (mole of isoprene/mole enzyme/sec) were plotted as a function of the concentration of prenol and the curve was fitted using Michaelis Menten equation (V=(Vmax*(substrate))/(Km+(substrate))) to extract the $k_{cat}$ (s$^{-1}$) and the $K_m$ values (mM) that are presented in Table 15.

TABLE 15

| Enzyme variant | $K_{cat}$ (s−1) | $K_m$ (mM) | $K_{cat}/K_m$ (s$^{-1}$ · mM$^{-1}$) | $K_{cat}/K_m$ Fold increase |
|---|---|---|---|---|
| Wild type enzyme | 7.00E−05 | 11.9 | 5.88E−06 | — |
| V195F D119G G132W Y251M | 8.60E−05 | 25.5 | 3.37E−06 | 0.6 |
| V195F D119G S123E | 6.90E−04 | 24.3 | 2.84E−05 | 4.8 |
| V195F G132Q V318A | 1.33E−03 | 110 | 1.21E−05 | 2.1 |
| V195F G123V F324S | 1.20E−04 | 6.7 | 1.79E−05 | 3.0 |
| V195F | 1.18E−03 | 47.1 | 2.51E−05 | 4.3 |
| V195F G132A | 3.70E−03 | 13.6 | 2.72E−04 | 46.3 |

XXII. Example 21

Characterization of Variants Using an In Vivo Screening Assay

An assay has been developed to identify crotyl alcohol dehydratase variants with higher activity compared to the wild type enzyme in vivo in 96 well plates, and therefore, compatible with high throughput screening approaches. This in vivo assay is based on the use of a bacterial strain transformed with an expression vector that contains the coding sequence for the crotyl alcohol dehydratase. This bacterial strain is thus able to produce the crotyl alcohol dehydratase recombinant enzyme and to convert the crotyl alcohol that has been supplemented into the culture medium into butadiene.

The alkenol dehydratase variants cloned into the pET25b+ expression vector were transformed into BL21 (DE3) competent cells. Isolated clones were used to inoculate 1 ml of autoinduction medium (Studier F. W, Protein Expr. Purif. 41 (2005), 207-234) in 96 well microplates, with Ampicillin at 0.1 mg/ml and grown overnight at 30° C. for 20-22 hours in a shaking incubator set at 700 rpm and 85% humidity. The day after, the microplates were replicated, and grown 20 hours at 30° C. Cells were then centrifuged 10 minutes at 4000 rpm in an eppendorf centrifuge, and pellets were resuspended in 0.5 ml of MS medium (Richaud C., Mengin-Leucreulx D., Pochet S., Johnson E J., Cohen G N. and Marliere P; The Journal of Biological Chemistry; 1993; Vol. 268; No. 36; pp. 26827-26835) with glucose as the source of carbon (45 g/L), 1 mM MgSO4, at pH=8.5, and with crotyl alcohol (trans-cis mixture obtained from Sigma Aldrich) at various concentrations (5 to 100 mM). Control reactions were set up using either bacterial clones containing either the empty expression vector peT25b+ or the expression vector expressing the wild type enzyme. This reaction mix was incubated for 4 hours at 37° C., using a Titramax microplate agitator, and the reaction was stopped by a 5-minute incubation at 80° C. The amount of 1,3 butadiene produced was then quantified by gas chromatography analysis. For the GC headspace analysis, 300 µl of the headspace gas was injected in a Bruker GC450 system equipped with a Restek RT-Alumina column (5 m×0.32 mm) and a Flame ionization detection system (FID). The GC analysis method used to detect 1,3 butadiene is characterised by a constant oven temperature at 140° C., injector port temperature at 200° C. with a split ratio of 1:4 and the FID detector temperature at 250° C. Nitrogen was used as a carrier gas (constant flow of 1.25 ml/min) and a mixture of air (air flow 300 ml/min), nitrogen (28 ml/min flow) and hydrogen (flow of 30 ml/min) was used to supply the FID detection system.

This in vivo assay was used to characterize a set of mutants described in Table 16. We have in particular identified one variant, named C6207, which shows an approximately 260 fold increase in butadiene production compared to the wild type enzyme using our in vivo assay. Data for the in vitro and in vivo assays are presented in FIG. 26 and FIG. 27, respectively.

TABLE 16

Description of mutants

| ID | Mutations |
| --- | --- |
| Wild type enzyme | No mutations |
| Clone ID48 | V195F |
| C1246 | V195F G132A |
| C3027 | V195F G73S E77I G132A |
| C6207 | V195F A18I F20L G73S G132M R170K I181L D199N W269A L367F |

XXIII. Example 22

Comparison of Some of the Best Variants

A set of variants, among the best ones listed on Table 5, were compared using the in vitro assay described in Example 1. Variants are described in Table 17. Results are described in FIG. 28.

TABLE 17

| Plasmide | Mutations |
| --- | --- |
| pGB 477 | Empty vector |
| pGB 2118 (=C3027) | V195F G132A G73S E77I |
| pBG 2336 | G73S G132G R170K I181L V195F F324S |
| pGB 2337 | G132V R170K A173R I181L V195F D199N F324S |
| pGB 2411 (=C6207) | A18I F20L G73S G132M R170K I181L V195F D199N F324S L367F |
| C8308 | A18I F20L Y70F G73S G132M R170K I181L V195F D199N F324S G364S L367F |

XIX. Example 23

Identification of Alkenol Dehydratase Enzyme Variants with Enhanced Activity in Converting Prenol into 1,3 Isoprene a) Rationale In order to identify residues improving the activity of the alkenol dehydratase (as depicted in SEQ ID NO 1) for the conversion of prenol into isoprene, a new library of mutants was designed, constructed and screened. 132 residues out of 397 were individually mutated. These residues belong to 9 different protein segments, listed in Table 18.

TABLE 18

Positions mutated in Example 23. The positions mutated in Example 23 belong to 9 different protein segments, described in this table. The first and last residue, respectively, referred to in the following table corresponds to the position in SEQ ID NO: 1.

| protein segment | first residue | last residue |
| --- | --- | --- |
| 1 | 13 | 24 |
| 2 | 68 | 69 |
| 3 | 71 | 90 |
| 4 | 114 | 156 |
| 5 | 190 | 200 |
| 6 | 246 | 256 |
| 7 | 313 | 323 |
| 8 | 359 | 369 |
| 9 | 381 | 391 | b) Library Construction

A DNA library coding for single residue mutants of the alkenol dehydratase was constructed using standard mutagenesis techniques. The DNA library was based on the full-length coding sequence of the alkenol dehydratase enzyme, encoded by the amino acid sequence shown in SEQ ID NO: 1, with an N-term His6 tag. The sequence was subcloned into the commercial peT300:NT-DEST (Life technologies) expression vector and used as the template for the mutagenic PCR.

c) Screening Assay

This assay was set up as follows: The alkenol dehydratase point mutation DNA library in the pET25b+ expression vector was transformed into BL21(DE3) competent cells. Isolated clones were used to inoculate 0.3 ml of autoinduction medium (Studier F. W, Protein Expr. Purif. 41 (2005), 207-234) in deep well 96 well microplates, and grown overnight at 30° C. for 20-22 hours in a shaking incubator set at 700 rpm and 85% humidity. The cells were pelleted and stored at −80° C. overnight. These cell pellets that contain the expressed recombinant alkenol dehydratase variants were resuspended in a reaction mix containing 50 mM Tris-Cl pH7.5, 25 mM KCl, 25 mM MgCl2, 4 mM DTT, 10 mM glutathione, supplemented with 0.25% Merck Novagen Lysonase, and 50 mM prenol (Sigma Aldrich). The reaction was incubated for 4 hours at 37° C., then for 16 hours at 20° C., and finally, stopped by a 5-minute incubation at 80° C.

The amount of isoprene produced was then quantified by gas chromatography analysis. For the GC headspace analysis, 100 µl of the headspace gas was injected in a Bruker GC450 system equipped with a Restek RT-Alumina column (5 m×0.32 mm) and a Flame ionization detection system (FID). The GC analysis method used to detect isoprene is characterised by a constant oven temperature at 180° C., injector port temperature at 200° C. with a split ratio of 1:4 and the FID detector temperature at 250° C. Nitrogen was used as a carrier gas (constant flow of 1.25 ml/min) and a mixture of air (air flow 300 ml/min), nitrogen (25 ml/min flow) and hydrogen (flow of 30 ml/min) was used to supply the FID detection system. Using these parameters, isoprene has a retention time of 5.75 min.

d) Identification of Enzyme Variants with Increased Activity

The library of single residue variants of alkenol dehydratase was screened using the screening assay described above. About 72 clones were tested for each of the 132 randomized position. A total number of 9,504 variants were assayed. Alongside the alkenol dehydratase variants, control reactions were set up using either bacterial clones containing either the empty expression vector peT25b+(negative control) or the expression vector expressing the wild type enzyme (positive control). In addition, a series of 8 mutants, previously identified as having a better activity than the wild type enzyme for the conversion of trans crotyl alcohol into 1,3 butadiene, were tested in the same experiment.

These variants were subjected to three consecutive rounds of screening. After primary screening, 433 variants displaying higher activity than the wt protein, were selected, and tested, in 12 replicates, in a second screening round. Following secondary screening, 176 variants were selected, including the 105 strongest variants (displaying at least a 2.5-fold increase in activity but covering, only 23 different positions) and 71 additional variants displaying lesser improvement factors, but covering as many different positions as possible (e.g. a total of 59 positions out of the 132 targeted by mutagenesis, and for which candidates were identified by this step).

These 176 variants were subjected a third round of screening, also in 12 replicates, and in parallel, subjected to DNA sequencing in order to identify the mutation responsible for the change in enzyme activity. Most candidates were confirmed by tertiary screening, but sequencing showed that a significant fraction of them were identical, and that unexpected mutations were sometimes observed. Finally, a total of 100 different mutants with improved activity were identified.

Among these 100 mutants, 89 were simple mutants covering 46 different positions. These mutants are listed in Table 19, and the corresponding mutated positions in Table 20. In addition, 11 variants displaying two mutations, and having improved activity, were identified. These double mutants are listed in Table 21. Finally, a series of mutants identified as having an improved activity for the conversion of crotyl alcohol into 1,3 butadiene were also tested in the same assay. The activity of these variants, for the conversion of prenol into isoprene (monitored in this experiment), and crotyl alcohol into 1,3 butadiene (monitored in former experiments) is shown on Table 22.

TABLE 19

Single mutants of SEQ ID NO 1 displaying improved activity of conversion of prenol into isoprene. The relative activity values correspond to the mean value of 12 replicates normalized by the activity of the wt. In addition, when a same single mutation was found in different clones, the relative activity value corresponds to the mean value of all replicates for all clones carrying the same mutation normalized by the activity of the wt.

| Mutated position | Mutation(s) | Relative activity vs. wt |
|---|---|---|
| 20 | F20T | 1.55 |
| 71 | S71A | 5.27 |
| 71 | S71D | 4.16 |
| 71 | S71T | 2.02 |
| 72 | R72L | 3.11 |
| 72 | R72P | 4.47 |
| 72 | R72R | 2.60 |
| 73 | G73A | 3.49 |
| 73 | G73S | 3.42 |
| 75 | S75A | 4.53 |
| 75 | S75D | 2.86 |
| 75 | S75F | 2.33 |
| 75 | S75I | 3.68 |
| 75 | S75L | 2.62 |
| 75 | S75M | 3.03 |
| 75 | S75T | 4.29 |
| 75 | S75V | 3.88 |
| 76 | F76I | 1.46 |
| 76 | F76L | 2.65 |
| 78 | A78G | 1.35 |
| 79 | W79Y | 1.18 |
| 84 | T84H | 1.68 |
| 115 | G115A | 2.28 |
| 115 | G115D | 2.03 |
| 116 | H116K | 3.60 |
| 116 | H116R | 2.49 |
| 119 | D119H | 2.44 |
| 119 | D119Q | 3.08 |
| 119 | D119R | 3.42 |
| 120 | I120R | 3.22 |
| 120 | I120V | 1.98 |
| 122 | V122M | 2.56 |
| 123 | S123D | 2.50 |
| 123 | S123E | 3.01 |
| 123 | S123R | 2.96 |
| 123 | S123W | 3.59 |
| 124 | K124L | 1.29 |
| 126 | K126A | 2.70 |
| 126 | K126D | 2.39 |
| 128 | K128D | 1.45 |
| 128 | K128N | 1.41 |
| 130 | V130I | 1.64 |
| 131 | W131F | 2.02 |
| 132 | G132D | 2.50 |
| 132 | G132N | 2.14 |
| 132 | G132Q | 1.88 |
| 132 | G132S | 2.10 |
| 132 | G132T | 2.36 |
| 135 | E135P | 2.29 |
| 143 | P143Y | 1.39 |
| 145 | E145P | 1.52 |
| 148 | N148D | 3.95 |
| 151 | Y151F | 2.16 |
| 152 | K152R | 3.30 |
| 155 | L155I | 1.23 |
| 192 | A192L | 2.15 |
| 193 | G193A | 5.00 |
| 195 | V195F | 6.40 |
| 195 | V195Y | 3.22 |
| 199 | D199A | 3.91 |
| 199 | D199E | 6.25 |
| 199 | D199L | 3.19 |
| 199 | D199M | 3.42 |
| 199 | D199N | 4.41 |
| 199 | D199Q | 4.78 |
| 199 | D199S | 4.46 |
| 251 | Y251M | 3.81 |
| 252 | H252D | 1.70 |
| 253 | P253H | 3.41 |
| 254 | E254G | 2.65 |
| 254 | E254H | 3.51 |
| 254 | E254P | 3.48 |
| 255 | S255G | 3.70 |
| 255 | S255H | 2.58 |
| 255 | S255L | 3.32 |
| 255 | S255Q | 2.52 |
| 255 | S255Y | 2.56 |
| 318 | V318A | 2.04 |
| 318 | V318G | 1.53 |
| 319 | G319R | 1.80 |

TABLE 19-continued

Single mutants of SEQ ID NO 1 displaying improved activity of conversion of prenol into isoprene. The relative activity values correspond to the mean value of 12 replicates normalized by the activity of the wt. In addition, when a same single mutation was found in different clones, the relative activity value corresponds to the mean value of all replicates for all clones carrying the same mutation normalized by the activity of the wt.

| Mutated position | Mutation(s) | Relative activity vs. wt |
|---|---|---|
| 361 | E361T | 1.72 |
| 366 | L366V | 2.45 |
| 367 | L367F | 3.10 |
| 383 | A383Y | 1.52 |
| 384 | L384M | 1.49 |
| 384 | L384Y | 1.49 |
| 387 | M387D | 1.80 |
| 387 | M387N | 1.78 |
| 390 | P390D | 1.67 |

TABLE 20

Positions of SEQ ID NO 1 for which mutations improving activity of conversion of prenol into isoprene have been identified.

| Positions |
|---|
| 20 |
| 71 |
| 72 |
| 73 |
| 75 |
| 76 |
| 78 |
| 79 |
| 84 |
| 115 |
| 116 |
| 119 |
| 120 |
| 122 |
| 123 |
| 124 |
| 126 |
| 128 |
| 130 |
| 131 |
| 132 |
| 135 |
| 143 |
| 145 |
| 148 |
| 151 |
| 152 |
| 155 |
| 192 |
| 193 |
| 195 |
| 199 |
| 251 |
| 252 |
| 253 |
| 254 |
| 255 |
| 318 |
| 319 |
| 361 |
| 366 |
| 367 |
| 383 |
| 384 |
| 387 |
| 390 |

TABLE 21

Double mutants of SEQ ID NO 1 displaying improved activity of conversion of prenol into isoprene. The relative activity values correspond to the mean value of 12 replicates normalized by the activity of the wt.

| Mutations | Relative activity vs. wt |
|---|---|
| S75V H83M | 4.30 |
| R129L L367F | 2.91 |
| S75A H83W | 2.81 |
| S75N G138Q | 2.71 |
| F76V E77L | 2.67 |
| F76L T84I | 2.59 |
| F76L A314T | 2.30 |
| K126F G364M | 2.20 |
| S75M H83T | 2.15 |
| L239M F247V | 2.01 |
| G319R G382Q | 1.51 |

TABLE 22

Compared activities for the conversion of prenol into isoprene and of crotyl alcohol into 1,3 butadiene, for a series of variants of SEQ ID NO 1. The relative activity values correspond to the mean value of 12 replicates normalized by the activity of the wt on the same substrate.

| Mutation(s) | Relative activity on prenol vs. wt | Relative activity on crotyl alcohol vs. wt |
|---|---|---|
| V195F G132A | 7.10 | 15.2 |
| V195F | 6.40 | 8 |
| G73S E77I G132A V195F | 6.30 | 72 |
| G73S G132G R170K I181L V195F F324S | 5.50 | 86 |
| V195F F324S | 5.03 | 16 |
| R170K G132V A173R I181L V195F D199N F324S | 4.12 | 57.6 |
| A18I F20L G73S G132M R170K I181L V195F D199N F324S L367F | 3.83 | 216 |
| A18I F20L Y70F G73S G132M R170K I181L V195F D199N F324S G364S L367F | 3.70 | 345.6 |

The invention claimed is:

1. Linalool dehydratase-isomerase variant having an amino acid sequence at least 80% sequence identity to SEQ ID NO:1, wherein said variant is capable of converting at least one alkenol compound corresponding to the general formula $C_nH_{2n}O$ into a conjugated diene $C_nH_{2n-2}$ with an improved activity over the activity of the amino acid sequence from which the variant is derived, wherein 3<n<7, and wherein said variant (a) is characterized in that it is capable of converting crotyl alcohol into 1,3 butadiene with a turnover rate of at least $0.033 \times 10^{-3}$ s$^{-1}$ of crotyl alcohol into 1,3 butadiene; or (b) is characterized in that it is capable of converting but-3-en-2-ol into 1,3 butadiene with a turnover rate of at least $1.1 \times 10^{-4}$ s$^{-1}$ of but-3-en-2-ol into 1,3 butadiene; or (c) is characterized in that it is capable of converting-prenol into isoprene with a turnover rate of at least $3.3 \times 10^{-4}$ s$^{-1}$ of prenol into isoprene; or (d) is characterized in that it is capable of converting isoprenol into isoprene with a turnover rate of at least $3.3 \times 10^{-5}$ s$^{-1}$ of isoprenol into isoprene.

2. The variant of claim 1 wherein, (i) the compound corresponding to the general formula $C_nH_{2n}O$ is crotyl alcohol, but-3-en-2-ol or but-3-en-1-ol and the compound corresponding to the general formula $C_nH_{2n-2}$ is 1,3 butadiene; or (ii) the compound corresponding to the general formula $C_nH_{2n}O$ is prenol, isoprenol, 2-methyl-but-3-en-1-ol, 2-methyl-but-2-en-1-ol, 3-methyl-but-3-en-2-ol or 2-methyl-but-3-en-2-ol and the compound corresponding to the general formula $C_nH_{2n-2}$ is isoprene; or (iii) the compound corresponding to the general formula $C_nH_{2n}O$ is 2,3-dimethyl-but-2-en-1-ol, 2,3-dimethyl-but-3-en-2-ol or 2,3-dimethyl-but-3-en-1-ol and the compound corresponding to the general formula $C_nH_{2n-2}$ is dimethylbutadiene.

3. The variant of claim 1, wherein said variant comprises an amino acid sequence having at least 85% sequence identity to the amino acid sequence of SEQ ID NO:1.

4. The variant of claim 1 comprising one or more substitutions, deletions and/or insertions in the corresponding sequence from which the variant is derived and wherein the substitutions, deletions and/or insertions occur at one or more of the positions corresponding to amino acid residue positions Thr8, Ile10, Ser12, Ala13, Ala18, Gly19, Phe20, Asp39, Thr50, Pro68, Tyr70, Ser71, Arg72, Gly73, Ser75, Phe76, Glu77, Ala78, Trp79, Glu80, His83, Thr84, Phe95, Tyr98, Ser102, Ile106, Pro108, Ala114, Gly115, His116, Leu118, Asp119, Ile120, Val122, Ser123, Lys124, Lys126, Lys128, Arg129, Val130, Trp131, Gly132, Glu135, Gly138, Gly140, Thr141, Pro143, Ile144, Glu145, Asn148, Tyr151, Lys152, Leu155, Asn156, Leu157, Met158, Tyr159, Thr166, Ser168, Arg169, Arg170, Ala173, His175, Ile181, Ile186, Ala192, Gly193, Ile194, Val195, Asp199, Ser207, Tyr210, Ala227, Ala230, Phe234, Leu239, Gly245, Phe247, Tyr248, Tyr251, His252, Pro253, Glu254, Ser255, Trp269, Phe281, Tyr285, Gly310, Asp312, Ala314, Val318, Gly319, Phe324, Ser357, Glu361, Gly364, Leu366, Leu367, Phe373, Gly382, Ala383, Leu384, Arg386, Met387, Pro389 and Pro390 in the amino acid sequence shown in SEQ ID NO:1.

5. The variant of claim 4, wherein said variant has improved activity in converting crotyl alcohol into 1,3 butadiene as compared to the amino acid sequence from which the variant is derived.

6. The variant of claim 5 wherein the variant comprises an amino acid sequence at least 85% identical to the amino acid sequence of SEQ ID NO:1.

7. The variant of claim 6 comprising one or more substitutions, deletions and/or insertions in the sequence from which the variant is derived and wherein the substitutions, deletions and/or insertions occur at one or more of the positions corresponding to amino acid residue positions Ile10, Ser12, Ala18, Phe20, Asp39, Thr50, Pro68, Tyr70, Arg72, Gly73, Ser75, Phe76, Glu77, Glu80, Thr84, Phe95, Tyr98, Ile106, Pro108, Ala114, Gly115, His116, Asp119, Val122, Ser123, Lys126, Gly132, Gly140, Ile144, Tyr151, Asn156, Leu157, Met158, Tyr159, Ser168, Arg169, Arg170, Ala173, His175, Ile181, Ile186, Ala192, Ile194, Val195, Asp199, Ser207, Tyr210, Ala227, Ala230, Phe234, Gly245, Phe247, Tyr248, Tyr251, Ser255, Trp269, Phe281, Tyr285, Gly310, Val318, Phe324, Ser357, Gly364, Leu367, Gly382, Arg386, Pro389 and Pro390 in the amino acid sequence shown in SEQ ID NO:1.

8. The variant of claim 7, wherein:
(1) an amino acid residue at position Ile10 in the amino acid sequence shown in SEQ ID NO:1 or at a position corresponding to this position, is deleted or substituted with alanine; and/or
(2) an amino acid residue at position Ser12 in the amino acid sequence shown in SEQ ID NO:1 or at a position corresponding to this position, is deleted or substituted with leucine; and/or
(3) an amino acid residue at position Ala18 in the amino acid sequence shown in SEQ ID NO:1 or at a position corresponding to this position, is deleted or substituted with valine or isoleucine; and/or
(4) an amino acid residue at position Phe20 in the amino acid sequence shown in SEQ ID NO:1 or at a position corresponding to this position, is deleted or substituted with leucine; and/or
(5) an amino acid residue at position Asp39 in the amino acid sequence shown in SEQ ID NO:1 or at a position corresponding to this position, is deleted or substituted with alanine; and/or (6) an amino acid residue at position Thr50 in the amino acid sequence shown in SEQ ID NO:1 or at a position corresponding to this position, is deleted or substituted with arginine; and/or
(7) an amino acid residue at position Pro68 in the amino acid sequence shown in SEQ ID NO:1 or at a position corresponding to this position, is deleted or substituted with leucine; and/or
(8) an amino acid residue at position Tyr70 in the amino acid sequence shown in SEQ ID NO:1 or at a position corresponding to this position, is deleted or substituted with alanine or phenylalanine; and/or
(9) an amino acid residue at position Arg72 in the amino acid sequence shown in SEQ ID NO:1 or at a position corresponding to this position, is deleted or substituted with serine; and/or
(10) an amino acid residue at position Gly73 in the amino acid sequence shown in SEQ ID NO:1 at a position corresponding to this position, is deleted or substituted with tryptophan or serine; and/or
(11) an amino acid residue at position Ser75 in the amino acid sequence shown in SEQ ID NO:1 or at a position corresponding to this position, is deleted or substituted with methionine, alanine, glycine, asparagine, threonine, isoleucine, tyrosine or valine; and/or
(12) an amino acid residue at position Phe76 in the amino acid sequence shown in SEQ ID NO:1 or at a position corresponding to this position, is deleted or substituted with leucine; and/or
(13) an amino acid residue at position Glu77 in the amino acid sequence shown in SEQ ID NO:1 or at a position corresponding to this position, is deleted or substituted with leucine or isoleucine; and/or
(14) an amino acid residue at position Glu80 in the amino acid sequence shown in SEQ ID NO:1 or at a position corresponding to this position, is deleted or substituted with proline or tryptophan; and/or
(15) an amino acid residue at position Thr84 in the amino acid sequence shown in SEQ ID NO:1 or at a position corresponding to this position, is deleted or substituted with glutamine or isoleucine; and/or
(16) an amino acid residue at position Phe95 in the amino acid sequence shown in SEQ ID NO:1 or at a position corresponding to this position, is deleted or substituted with methionine; and/or
(17) an amino acid residue at position Tyr98 in the amino acid sequence shown in SEQ ID NO:1 or at a position corresponding to this position, is deleted or substituted with methionine; and/or
(18) an amino acid residue at position Ile106 in the amino acid sequence shown in SEQ ID NO:1 or at a position corresponding to this position, is deleted or substituted with asparagine; and/or
(19) an amino acid residue at position Pro108 in the amino acid sequence shown in SEQ ID NO:1 or at a position corresponding to this position, is deleted or substituted with isoleucine; and/or
(20) an amino acid residue at position Ala114 in the amino acid sequence shown in SEQ ID NO:1 or at a position corresponding to this position, is deleted or substituted with serine; and/or
(21) an amino acid residue at position Gly115 in the amino acid sequence shown in SEQ ID NO:1 or at a position corresponding to this position, is deleted or substituted with alanine; and/or

(22) an amino acid residue at position His116 in the amino acid sequence shown in SEQ ID NO:1 or at a position corresponding to this position, is deleted or substituted with lysine; and/or
(23) an amino acid residue at position Asp119 in the amino acid sequence shown in SEQ ID NO:1 or at a position corresponding to this position, is deleted or substituted with glycine or leucine; and/or
(24) an amino acid residue at position Val122 in the amino acid sequence shown in SEQ ID NO:1 or at a position corresponding to this position, is deleted or substituted with leucine or isoleucine; and/or
(25) an amino acid residue at position Ser123 in the amino acid sequence shown in SEQ ID NO:1 or at a position corresponding to this position, is deleted or substituted with histidine, tryptophan, arginine, glutamic acid, tyrosine, aspartic acid, isoleucine, lysine, phenylalanine, leucine, threonine, valine, glutamine or methionine; and/or
(26) an amino acid residue at position Lys126 in the amino acid sequence shown in SEQ ID NO:1 at a position corresponding to this position, is deleted or substituted with tyrosine or alanine; and/or
(27) an amino acid residue at position Gly132 in the amino acid sequence shown in SEQ ID NO:1 or at a position corresponding to this position, is deleted or substituted with threonine, leucine, aspartic acid, tryptophan, serine, isoleucine, glutamine, valine, asparagine, arginine, methionine, histidine, phenylalanine, lysine, leucine, alanine, cysteine, glutamic acid, glycine or tyrosine; and/or
(28) an amino acid residue at position Gly140 in the amino acid sequence shown in SEQ ID NO:1 or at a position corresponding to this position, is deleted or substituted with glycine or serine; and/or
(29) an amino acid residue at position Ile144 in the amino acid sequence shown in SEQ ID NO:1 or at a position corresponding to this position, is deleted or substituted with threonine; and/or
(30) an amino acid residue at position Tyr151 in the amino acid sequence shown in SEQ ID NO:1 or at a position corresponding to this position, is deleted or substituted with methionine; and/or
(31) an amino acid residue at position Asn156 in the amino acid sequence shown in SEQ ID NO:1 or at a position corresponding to this position, is deleted or substituted with serine; and/or
(32) an amino acid residue at position Leu157 in the amino acid sequence shown in SEQ ID NO:1 or at a position corresponding to this position, is deleted or substituted with methionine; and/or
(33) an amino acid residue at position Met158 in the amino acid sequence shown in SEQ ID NO:1 or at a position corresponding to this position, is deleted or substituted with isoleucine; and/or
(34) an amino acid residue at position Tyr159 in the amino acid sequence shown in SEQ ID NO:1 or at a position corresponding to this position, is deleted or substituted with isoleucine, methionine or valine; and/or
(35) an amino acid residue at position Ser168 in the amino acid sequence shown in SEQ ID NO:1 or at a position corresponding to this position, is deleted or substituted with asparagine; and/or
(36) an amino acid residue at position Arg169 in the amino acid sequence shown in SEQ ID NO:1 or at a position corresponding to this position, is deleted or substituted with threonine or asparagine; and/or
(37) an amino acid residue at position Arg170 in the amino acid sequence shown in SEQ ID NO:1 or at a position corresponding to this position, is deleted or substituted with lysine; and/or
(38) an amino acid residue at position Ala173 in the amino acid sequence shown in SEQ ID NO:1 or at a position corresponding to this position, is deleted or substituted with lysine, arginine or isoleucine; and/or
(39) an amino acid residue at position His175 in the amino acid sequence shown in SEQ ID NO:1 or at a position corresponding to this position, is deleted or substituted with serine or asparagine; and/or
(40) an amino acid residue at position Ile181 in the amino acid sequence shown in SEQ ID NO:1 or at a position corresponding to this position, is deleted or substituted with alanine, serine, leucine or asparagine; and/or
(41) an amino acid residue at position Ile186 in the amino acid sequence shown in SEQ ID NO:1 or at a position corresponding to this position, is deleted or substituted with valine or leucine; and/or
(42) an amino acid residue at position Ala192 in the amino acid sequence shown in SEQ ID NO:1 or at a position corresponding to this position, is deleted or substituted with leucine, threonine or valine; and/or
(43) an amino acid residue at position Ile194 in the amino acid sequence shown in SEQ ID NO:1 or at a position corresponding to this position, is deleted or substituted with arginine; and/or
(44) an amino acid residue at position Val195 in the amino acid sequence shown in SEQ ID NO:1 or at a position corresponding to this position, is deleted or substituted with phenylalanine or tyrosine; and/or
(45) an amino acid residue at position Asp199 in the amino acid sequence shown in SEQ ID NO:1 or at a position corresponding to this position, is deleted or substituted with asparagine; and/or
(46) an amino acid residue at position Ser207 in the amino acid sequence shown in SEQ ID NO:1 or at a position corresponding to this position, is deleted or substituted with alanine or cysteine; and/or
(47) an amino acid residue at position Tyr210 in the amino acid sequence shown in SEQ ID NO:1 or at a position corresponding to this position, is deleted or substituted with leucine; and/or
(48) an amino acid residue at position Ala227 in the amino acid sequence shown in SEQ ID NO:1 or at a position corresponding to this position, is deleted or substituted with isoleucine or serine; and/or
(49) an amino acid residue at position Ala230 in the amino acid sequence shown in SEQ ID NO:1 or at a position corresponding to this position, is deleted or substituted with glutamine; and/or
(50) an amino acid residue at position Phe234 in the amino acid sequence shown in SEQ ID NO:1 or at a position corresponding to this position, is deleted or substituted with tryptophan; and/or
(51) an amino acid residue at position Gly245 in the amino acid sequence shown in SEQ ID NO:1 or at a position corresponding to this position, is deleted or substituted with alanine; and/or
(52) the amino acid residue at position Phe247 in the amino acid sequence shown in SEQ ID NO:1 or at a position corresponding to this position, is substituted with valine; and/or

(53) an amino acid residue at position Tyr248 in the amino acid sequence shown in SEQ ID NO:1 or at a position corresponding to this position, is deleted or substituted with lysine; and/or
(54) an amino acid residue at position Tyr251 in the amino acid sequence shown in SEQ ID NO:1 or at a position corresponding to this position, is deleted or substituted with leucine or methionine; and/or
(55) an amino acid residue at position Ser255 in the amino acid sequence shown in SEQ ID NO:1 or at a position corresponding to this position, is deleted or substituted with threonine; and/or
(56) an amino acid residue at position Trp269 in the amino acid sequence shown in SEQ ID NO:1 or at a position corresponding to this position, is deleted or substituted with alanine; and/or
(57) an amino acid residue at position Phe281 in the amino acid sequence shown in SEQ ID NO:1 or at a position corresponding to this position, is deleted or substituted with tyrosine; and/or
(58) an amino acid residue at position Tyr285 in the amino acid sequence shown in SEQ ID NO:1 or at a position corresponding to this position, is deleted or substituted with leucine or methionine; and/or
(59) an amino acid residue at position Gly310 in the amino acid sequence shown in SEQ ID NO:1 or at a position corresponding to this position, is deleted or substituted with isoleucine; and/or
(60) an amino acid residue at position Val318 in the amino acid sequence shown in SEQ ID NO:1 or at a position corresponding to this position, is deleted or substituted with alanine; and/or
(61) an amino acid residue at position Phe324 in the amino acid sequence shown in SEQ ID NO:1 or at a position corresponding to this position, is deleted or substituted with serine; and/or
(62) an amino acid residue at position Ser357 in the amino acid sequence shown in SEQ ID NO:1 or at a position corresponding to this position, is deleted or substituted with asparagine; and/or
(63) an amino acid residue at position Gly364 in the amino acid sequence shown in SEQ ID NO:1 or at a position corresponding to this position, is deleted or substituted with serine; and/or
(64) an amino acid residue at position Leu367 in the amino acid sequence shown in SEQ ID NO:1 or at a position corresponding to this position, is deleted or substituted with phenylalanine; and/or
(65) an amino acid residue at position Gly382 in the amino acid sequence shown in SEQ ID NO:1 or at a position corresponding to this position, is deleted or substituted with aspartic acid; and/or
(66) an amino acid residue at position Arg386 in the amino acid sequence shown in SEQ ID NO:1 or at a position corresponding to this position, is deleted or substituted with serine; and/or
(67) an amino acid residue at position Pro389 in the amino acid sequence shown in SEQ ID NO:1 or at a position corresponding to this position, is deleted or substituted with leucine or serine; and/or
(68) an amino acid residue at position Pro390 in the amino acid sequence shown in SEQ ID NO:1 or at a position corresponding to this position, is deleted or substituted with aspartic acid.

9. The variant of claim 4, wherein said variant has an improved activity in converting but-3-en-2-ol into 1,3 butadiene as compared to the corresponding sequence from which the variant is derived.

10. The variant of claim 9 wherein the variant comprises an amino acid sequence having at least 85% sequence identity to the amino acid sequence of SEQ ID NO:1.

11. The variant of claim 10 wherein the substitutions, deletions and/or insertions occur at one or more of the positions corresponding to amino acid residue positions Ile10, Ser12, Ala18, Phe20, Asp39, Tyr70, Arg72, Gly73, Ser75, Phe76, Glu77, Thr84, Phe95, Ser102, Ile106, Ala114, Gly115, Asp119, Val122, Ser123, Lys126, Gly132, Gly140, Ile144, Tyr151, Asn156, Leu157, Met158, Tyr159, Thr166, Ser168, Arg169, Arg170, Ala173, His175, Ile181, Ile186, Val195, Asp199, Ser207, Ala227, Ala230, Phe234, Gly245, Phe247, Tyr248, Tyr251, Glu254, Ser255, Trp269, Phe281, Tyr285, Gly310, Val318, Phe324, Ser357, Gly364, Leu367, Phe373, Gly382, Arg386, Pro389 and Pro390 of SEQ ID NO: 1.

12. The variant of claim 11, wherein:
(1) an amino acid residue at position Ile10 in the amino acid sequence shown in SEQ ID NO:1 or at a position corresponding to this position, is deleted or substituted with alanine; and/or
(2) an amino acid residue at position Ser12 in the amino acid sequence shown in SEQ ID NO:1 or at a position corresponding to this position, is deleted or substituted with leucine; and/or
(3) an amino acid residue at position Ala18 in the amino acid sequence shown in SEQ ID NO:1 or at a position corresponding to this position, is deleted or substituted with isoleucine or valine; and/or
(4) an amino acid residue at position Phe20 in the amino acid sequence shown in SEQ ID NO:1 or at a position corresponding to this position, is deleted or substituted with leucine; and/or
(5) an amino acid residue at position Asp39 in the amino acid sequence shown in SEQ ID NO:1 or at a position corresponding to this position, is deleted or substituted with alanine; and/or
(6) an amino acid residue at position Tyr70 in the amino acid sequence shown in SEQ ID NO:1 or at a position corresponding to this position, is deleted or substituted with phenylalanine; and/or
(7) an amino acid residue at position Arg72 in the amino acid sequence shown in SEQ ID NO:1 or at a position corresponding to this position, is deleted or substituted with serine; and/or
(8) an amino acid residue at position Gly73 in the amino acid sequence shown in SEQ ID NO:1 or at a position corresponding to this position, is deleted or substituted with serine; and/or
(9) an amino acid residue at position Ser75 in the amino acid sequence shown in SEQ ID NO:1 or at a position corresponding to this position, is deleted or substituted with glycine, asparagine or alanine; and/or
(10) the amino acid residue at position Phe76 in the amino acid sequence shown in SEQ ID NO:1 or at a position corresponding to this position, is substituted with leucine; and/or
(11) an amino acid residue at position Glu77 in the amino acid sequence shown in SEQ ID NO:1 or at a position corresponding to this position, is deleted or substituted with leucine or isoleucine; and/or
(12) an amino acid residue at position Thr84 in the amino acid sequence shown in SEQ ID NO:1 or at a position corresponding to this position, is deleted or substituted with glutamine or isoleucine; and/or
(13) an amino acid residue at position Phe95 in the amino acid sequence shown in SEQ ID NO:1 or at a position corresponding to this position, is deleted or substituted with methionine; and/or
(14) an amino acid residue at position Ser102 in the amino acid sequence shown in SEQ ID NO:1 or at a position corresponding to this position, is deleted or substituted with methionine; and/or
(15) an amino acid residue at position Ile106 in the amino acid sequence shown in SEQ ID NO:1 or at a position corresponding to this position, is deleted or substituted with asparagine; and/or
(16) an amino acid residue at position Ala114 in the amino acid sequence shown in SEQ ID NO:1 or at a position corresponding to this position, is deleted or substituted with serine; and/or
(17) an amino acid residue at position Gly115 in the amino acid sequence shown in SEQ ID NO:1 or at a position corresponding to this position, is deleted or substituted with alanine; and/or
(18) an amino acid residue at position Asp119 in the amino acid sequence shown in SEQ ID NO:1 or at a position corresponding to this position, is deleted or substituted with glycine or leucine; and/or
(19) an amino acid residue at position Val122 in the amino acid sequence shown in SEQ ID NO:1 or at a position corresponding to this position, is deleted or substituted with leucine or isoleucine; and/or
(20) an amino acid residue at position Ser123 in the amino acid sequence shown in SEQ ID NO:1 or at a position corresponding to this position, is deleted or substituted with histidine, tryptophan, isoleucine, glutamic acid, lysine, glutamine, arginine, threonine, aspartic acid or leucine; and/or
(21) an amino acid residue at position Lys126 in the amino acid sequence shown in SEQ ID NO:1 or at a position corresponding to this position, is deleted or substituted with alanine; and/or
(22) an amino acid residue at position Gly132 in the amino acid sequence shown in SEQ ID NO:1 or at a position corresponding to this position, is deleted or substituted with threonine, leucine, isoleucine, glutamine, serine, tryptophan, valine, alanine, arginine, methionine, histidine, phenylalanine, asparagine, aspartic acid, glutamic acid, lysine, glycine or tyrosine; and/or
(23) an amino acid residue at position Gly140 in the amino acid sequence shown in SEQ ID NO:1 or at a position corresponding to this position, is deleted or substituted with serine; and/or
(24) an amino acid residue at position Ile144 in the amino acid sequence shown in SEQ ID NO:1 or at a position corresponding to this position, is deleted or substituted with threonine; and/or
(25) an amino acid residue at position Tyr151 in the amino acid sequence shown in SEQ ID NO:1 or at a position corresponding to this position, is deleted or substituted with methionine; and/or
(26) an amino acid residue at position Asn156 in the amino acid sequence shown in SEQ ID NO:1 at a position corresponding to this position, is deleted or substituted with serine; and/or
(27) an amino acid residue at position Leu157 in the amino acid sequence shown in SEQ ID NO:1 at a position corresponding to this position, is deleted or substituted with methionine; and/or
(28) an amino acid residue at position Met158 in the amino acid sequence shown in SEQ ID NO:1 or at a position corresponding to this position, is deleted or substituted with isoleucine; and/or
(29) an amino acid residue at position Tyr159 in the amino acid sequence shown in SEQ ID NO:1 or at a position corresponding to this position, is deleted or substituted with valine, methionine or isoleucine; and/or
(30) an amino acid residue at position Thr166 in the amino acid sequence shown in SEQ ID NO:1 or at a position corresponding to this position, is deleted or substituted with serine; and/or
(31) an amino acid residue at position Ser168 in the amino acid sequence shown in SEQ ID NO:1 or at a position corresponding to this position, is deleted or substituted with asparagine; and/or
(32) an amino acid residue at position Arg169 in the amino acid sequence shown in SEQ ID NO:1 or at a position corresponding to this position, is deleted or substituted with threonine or asparagine; and/or
(33) an amino acid residue at position Arg170 in the amino acid sequence shown in SEQ ID NO:1 or at a position corresponding to this position, is deleted or substituted with lysine; and/or
(34) an amino acid residue at position Ala173 in the amino acid sequence shown in SEQ ID NO:1 or at a position corresponding to this position, is deleted or substituted with arginine; and/or
(35) an amino acid residue at position His175 in the amino acid sequence shown in SEQ ID NO:1 or at a position corresponding to this position, is deleted or substituted with serine or asparagine; and/or
(36) an amino acid residue at position Ile181 in the amino acid sequence shown in SEQ ID NO:1 or at a position corresponding to this position, is deleted or substituted with leucine, serine or asparagine; and/or
(37) an amino acid residue at position Ile186 in the amino acid sequence shown in SEQ ID NO:1 or at a position corresponding to this position, is deleted or substituted with leucine or valine; and/or
(38) an amino acid residue at position Val195 in the amino acid sequence shown in SEQ ID NO:1 or at a position corresponding to this position, is deleted or substituted with phenylalanine or tyrosine; and/or
(39) an amino acid residue at position Asp199 in the amino acid sequence shown in SEQ ID NO:1 or at a position corresponding to this position, is deleted or substituted with asparagine; and/or
(40) an amino acid residue at position Ser207 in the amino acid sequence shown in SEQ ID NO:1 or at a position corresponding to this position, is deleted or substituted with cysteine; and/or
(41) an amino acid residue at position Ala227 in the amino acid sequence shown in SEQ ID NO:1 or at a position corresponding to this position, is deleted or substituted with isoleucine or serine; and/or
(42) an amino acid residue at position Ala230 in the amino acid sequence shown in SEQ ID NO:1 or at a position corresponding to this position, is deleted or substituted with glutamine; and/or
(43) an amino acid residue at position Phe234 in the amino acid sequence shown in SEQ ID NO:1 or at a position corresponding to this position, is deleted or substituted with tryptophan; and/or

(44) an amino acid residue at position Gly245 in the amino acid sequence shown in SEQ ID NO:1 or at a position corresponding to this position, is deleted or substituted with alanine; and/or
(45) an amino acid residue at position Phe247 in the amino acid sequence shown in SEQ ID NO:1 or at a position corresponding to this position, is deleted or substituted with valine; and/or
(46) an amino acid residue at position Tyr248 in the amino acid sequence shown in SEQ ID NO:1 or at a position corresponding to this position, is deleted or substituted with lysine; and/or
(47) an amino acid residue at position Tyr251 in the amino acid sequence shown in SEQ ID NO:1 or at a position corresponding to this position, is deleted or substituted with methionine or leucine; and/or
(48) an amino acid residue at position Glu254 in the amino acid sequence shown in SEQ ID NO:1 or at a position corresponding to this position, is deleted or substituted with lysine or glycine or alanine; and/or
(49) an amino acid residue at position Ser255 in the amino acid sequence shown in SEQ ID NO:1 or at a position corresponding to this position, is deleted or substituted with threonine; and/or
(50) an amino acid residue at position Trp269 in the amino acid sequence shown in SEQ ID NO:1 or at a position corresponding to this position, is deleted or substituted with alanine; and/or
(51) an amino acid residue at position Phe281 in the amino acid sequence shown in SEQ ID NO:1 or at a position corresponding to this position, is deleted or substituted with tyrosine; and/or
(52) an amino acid residue at position Tyr285 in the amino acid sequence shown in SEQ ID NO:1 or at a position corresponding to this position, is deleted or substituted with methionine or leucine; and/or
(53) an amino acid residue at position Gly310 in the amino acid sequence shown in SEQ ID NO:1 or at a position corresponding to this position, is deleted or substituted with isoleucine; and/or
(54) an amino acid residue at position Val318 in the amino acid sequence shown in SEQ ID NO:1 or at a position corresponding to this position, is deleted or substituted with alanine; and/or
(55) an amino acid residue at position Phe324 in the amino acid sequence shown in SEQ ID NO:1 or at a position corresponding to this position, is deleted or substituted with serine; and/or
(56) an amino acid residue at position Ser357 in the amino acid sequence shown in SEQ ID NO:1 or at a position corresponding to this position, is deleted or substituted with asparagine or serine; and/or
(57) an amino acid residue at position Gly364 in the amino acid sequence shown in SEQ ID NO:1 or at a position corresponding to this position, is deleted or substituted with serine; and/or
(58) an amino acid residue at position Leu367 in the amino acid sequence shown in SEQ ID NO:1 or at a position corresponding to this position, is deleted or substituted with phenylalanine; and/or
(59) an amino acid residue at position Phe373 in the amino acid sequence shown in SEQ ID NO:1 or at a position corresponding to this position, is deleted or substituted with leucine; and/or
(60) an amino acid residue at position Gly382 in the amino acid sequence shown in SEQ ID NO:1 or at a position corresponding to this position, is deleted or substituted with aspartic acid; and/or
(61) an amino acid residue at position Arg386 in the amino acid sequence shown in SEQ ID NO:1 or at a position corresponding to this position, is deleted or substituted with serine; and/or
(62) an amino acid residue at position Pro389 in the amino acid sequence shown in SEQ ID NO:1 or at a position corresponding to this position, is deleted or substituted with leucine or serine; and/or
(63) an amino acid residue at position Pro390 in the amino acid sequence shown in SEQ ID NO:1 or at a position corresponding to this position, is deleted or substituted with aspartic acid.

13. The variant of claim 4 wherein said variant has an improved activity in converting isoprenol and/or prenol into isoprene as compared to the corresponding amino acid sequence from which the variant is derived.

14. The variant of claim 13 wherein the variant comprises an amino acid sequence having at least 85% sequence identity to the amino acid sequence of SEQ ID NO:1.

15. The variant of claim 14 wherein the substitutions, deletions and/or insertions occur at one or more of the positions corresponding to amino acid residue positions Thr8, Ser12, Ala13, Ala18, Gly19, Phe20, Asp39, Tyr70, Ser71, Arg72, Gly73, Ser75, Phe76, Glu77, Ala78, Trp79, His83, Thr84, Gly115, His116, Leu118, Asp119, Ile120, Val122, Ser123, Lys124, Lys126, Lys128, Arg129, Val130, Trp131, Gly132, Glu135, Gly138, Thr141, Pro143, Ile144, Glu145, Asn148, Tyr151, Lys152, Leu155, Ser168, Arg170, Ala173, Ile181, Ala192, Gly193, Val195, Asp199, Leu239, Phe247, Tyr251, His252, Pro253, Glu254, Ser255, Trp269, Asp312, Ala314, Val318, Gly319, Phe324, Glu361, Gly364, Leu366, Leu367, Gly382, Ala383, Leu384, Arg386, Met387, Pro389 and Pro390 of SEQ ID NO:1.

16. The variant of claim 15, wherein:
(1) an amino acid residue at position Thr8 in the amino acid sequence shown in SEQ ID NO:1 or at a position corresponding to this position, is deleted or substituted with leucine; and/or
(2) an amino acid residue at position Ser12 in the amino acid sequence shown in SEQ ID NO:1 or at a position corresponding to this position, is deleted or substituted with alanine; and/or
(3) an amino acid residue at position Ala13 in the amino acid sequence shown in SEQ ID NO:1 or at a position corresponding to this position, is deleted or substituted with leucine or isoleucine; and/or
(4) an amino acid residue at position Ala18 in the amino acid sequence shown in SEQ ID NO:1 or at a position corresponding to this position, is deleted or substituted with valine, isoleucine or cysteine; and/or
(5) an amino acid residue at position Gly19 in the amino acid sequence shown in SEQ ID NO:1 or at a position corresponding to this position, is deleted or substituted with threonine; and/or
(6) an amino acid residue at position Phe20 in the amino acid sequence shown in SEQ ID NO:1 or at a position corresponding to this position, is deleted or substituted with threonine or leucine; and/or
(7) an amino acid residue at position Asp39 in the amino acid sequence shown in SEQ ID NO:1 or at a position corresponding to this position, is deleted or substituted with alanine; and/or (8) an amino acid residue at position Tyr70 in the amino acid sequence shown in SEQ ID NO:1 or at a position corresponding to this position, is deleted or substituted with phenylalanine; and/or
(9) an amino acid residue at position Ser71 in the amino acid sequence shown in SEQ ID NO:1 or at a position corresponding to this position, is deleted or substituted with alanine, aspartic acid, or threonine; and/or
(10) an amino acid residue at position Arg72 in the amino acid sequence shown in SEQ ID NO:1 or at a position corresponding to this position, is deleted or substituted with leucine, proline, or arginine; and/or
(11) an amino acid residue at position Gly73 in the amino acid sequence shown in SEQ ID NO:1 or at a position corresponding to this position, is deleted or substituted with serine or alanine; and/or
(12) an amino acid residue at position Ser75 in the amino acid sequence shown in SEQ ID NO:1 or at a position corresponding to this position, is deleted or substituted with alanine, aspartic acid, phenylalanine, isoleucine, leucine, methionine, threonine, valine, or asparagine; and/or
(13) an amino acid residue at position Phe76 in the amino acid sequence shown in SEQ ID NO:1 or at a position corresponding to this position, is deleted or substituted with isoleucine, leucine or valine; and/or
(14) an amino acid residue at position Glu77 in the amino acid sequence shown in SEQ ID NO:1 or at a position corresponding to this position, is deleted or substituted with isoleucine or leucine; and/or
(15) an amino acid residue at position Ala78 in the amino acid sequence shown in SEQ ID NO:1 or at a position corresponding to this position, is deleted or substituted with glycine; and/or
(16) an amino acid residue at position Trp79 in the amino acid sequence shown in SEQ ID NO:1 or at a position corresponding to this position, is deleted or substituted with tyrosine; and/or
(17) an amino acid residue at position His83 in the amino acid sequence shown in SEQ ID NO:1 or at a position corresponding to this position, is deleted or substituted with methionine, tryptophan, threonine; and/or
(18) an amino acid residue at position Thr84 in the amino acid sequence shown in SEQ ID NO:1 or at a position corresponding to this position, is deleted or substituted with histidine or isoleucine; and/or
(19) an amino acid residue at position Gly115 in the amino acid sequence shown in SEQ ID NO:1 or at a position corresponding to this position, is deleted or substituted with alanine or aspartic acid; and/or
(20) an amino acid residue at position His116 in the amino acid sequence shown in SEQ ID NO:1 or at a position corresponding to this position, is deleted or substituted with lysine or arginine; and/or
(21) an amino acid residue at position Leu118 in the amino acid sequence shown in SEQ ID NO:1 or at a position corresponding to this position, is deleted or substituted with leucine; and/or
(22) an amino acid residue at position Asp119 in the amino acid sequence shown in SEQ ID NO:1 or at a position corresponding to this position, is deleted or substituted with histidine, glutamine, arginine or glycine; and/or
(23) an amino acid residue at position Ile120 in the amino acid sequence shown in SEQ ID NO:1 or at a position corresponding to this position, is deleted or substituted with arginine or valine; and/or
(24) an amino acid residue at position Val122 in the amino acid sequence shown in SEQ ID NO:1 or at a position corresponding to this position, is deleted or substituted with methionine or leucine; and/or
(25) an amino acid residue at position Ser123 in the amino acid sequence shown in SEQ ID NO:1 or at a position corresponding to this position, is deleted or substituted with glutamic acid, aspartic acid, tryptophan or arginine; and/or
(26) an amino acid residue at position Lys124 in the amino acid sequence shown in SEQ ID NO:1 or at a position corresponding to this position, is deleted or substituted with leucine; and/or
(27) an amino acid residue at position Lys126 in the amino acid sequence shown in SEQ ID NO:1 or at a position corresponding to this position, is deleted or substituted with alanine, aspartic acid or phenylalanine; and/or
(28) an amino acid residue at position Lys128 in the amino acid sequence shown in SEQ ID NO:1 or at a position corresponding to this position, is deleted or substituted with aspartic acid or asparagine; and/or
(29) an amino acid residue at position Arg129 in the amino acid sequence shown in SEQ ID NO:1 or at a position corresponding to this position, is deleted or substituted with leucine; and/or
(30) an amino acid residue at position Val130 in the amino acid sequence shown in SEQ ID NO:1 or at a position corresponding to this position, is deleted or substituted with isoleucine; and/or
(31) an amino acid residue at position Trp131 in the amino acid sequence shown in SEQ ID NO:1 or at a position corresponding to this position, is deleted or substituted with phenylalanine; and/or
(32) an amino acid residue at position Gly132 in the amino acid sequence shown in SEQ ID NO:1 or at a position corresponding to this position, is deleted or substituted with alanine, lysine, arginine, glutamine, methionine, serine, valine, aspartic acid, asparagine, threonine, or glycine; and/or
(33) an amino acid residue at position Glu135 in the amino acid sequence shown in SEQ ID NO:1 or at a position corresponding to this position, is deleted or substituted with proline; and/or
(34) an amino acid residue at position Gly138 in the amino acid sequence shown in SEQ ID NO:1 or at a position corresponding to this position, is deleted or substituted with glutamine; and/or
(35) an amino acid residue at position Thr141 in the amino acid sequence shown in SEQ ID NO:1 or at a position corresponding to this position, is deleted or substituted with serine; and/or
(36) an amino acid residue at position Pro143 in the amino acid sequence shown in SEQ ID NO:1 or at a position corresponding to this position, is deleted or substituted with tyrosine; and/or
(37) an amino acid residue at position Ile144 in the amino acid sequence shown in SEQ ID NO:1 or at a position corresponding to this position, is deleted or substituted with threonine; and/or
(38) an amino acid residue at position Glu145 in the amino acid sequence shown in SEQ ID NO:1 or at a position corresponding to this position, is deleted or substituted with proline or glutamic acid; and/or
(39) an amino acid residue at position Asn148 in the amino acid sequence shown in SEQ ID NO:1 or at a position corresponding to this position, is deleted or substituted with aspartic acid; and/or
(40) an amino acid residue at position Tyr151 in the amino acid sequence shown in SEQ ID NO:1 or at a position corresponding to this position, is deleted or substituted with phenylalanine or methionine; and/or
(41) an amino acid residue at position Lys152 in the amino acid sequence shown in SEQ ID NO:1 or at a position corresponding to this position, is deleted or substituted with arginine; and/or
(42) an amino acid residue at position Leu155 in the amino acid sequence shown in SEQ ID NO:1 or at a position corresponding to this position, is deleted or substituted with isoleucine; and/or
(43) an amino acid residue at position Ser168 in the amino acid sequence shown in SEQ ID NO:1 or at a position corresponding to this position, is deleted or substituted with aspartic acid; and/or
(44) an amino acid residue at position Arg170 in the amino acid sequence shown in SEQ ID NO:1 or at a position corresponding to this position, is deleted or substituted with lysine; and/or
(45) an amino acid residue at position Ala173 in the amino acid sequence shown in SEQ ID NO:1 or at a position corresponding to this position, is deleted or substituted with arginine; and/or
(46) an amino acid residue at position Ile181 in the amino acid sequence shown in SEQ ID NO:1 or at a position corresponding to this position, is deleted or substituted with leucine or serine; and/or
(47) an amino acid residue at position Ala192 in the amino acid sequence shown in SEQ ID NO:1 or at a position corresponding to this position, is deleted or substituted with leucine; and/or
(48) an amino acid residue at position Gly193 in the amino acid sequence shown in SEQ ID NO:1 or at a position corresponding to this position, is deleted or substituted with alanine; and/or
(49) an amino acid residue at position Val195 in the amino acid sequence shown in SEQ ID NO:1 or at a position corresponding to this position, is deleted or substituted with phenylalanine or tyrosine; and/or
(50) an amino acid residue at position Val195 in the amino acid sequence shown in SEQ ID NO:1 or at a position corresponding to this position, is deleted or substituted with leucine; and/or
(51) an amino acid residue at position Asp199 in the amino acid sequence shown in SEQ ID NO:1 or at a position corresponding to this position, is deleted or substituted with asparagine, alanine, glutamic acid, leucine, methionine, glutamine or serine; and/or
(52) an amino acid residue at position Leu239 in the amino acid sequence shown in SEQ ID NO:1 or at a position corresponding to this position, is deleted or substituted with methionine; and/or
(53) an amino acid residue at position Phe247 in the amino acid sequence shown in SEQ ID NO:1 or at a position corresponding to this position, is deleted or substituted with valine; and/or
(54) an amino acid residue at position Tyr251 in the amino acid sequence shown in SEQ ID NO:1 or at a position corresponding to this position, is deleted or substituted with methionine; and/or
(55) an amino acid residue at position His252 in the amino acid sequence shown in SEQ ID NO:1 or at a position corresponding to this position, is deleted or substituted with aspartic acid; and/or
(56) an amino acid residue at position Pro253 in the amino acid sequence shown in SEQ ID NO:1 or at a position corresponding to this position, is deleted or substituted with histidine; and/or
(57) an amino acid residue at position Glu254 in the amino acid sequence shown in SEQ ID NO:1 or at a position corresponding to this position, is deleted or substituted with glycine, histidine or proline; and/or
(58) an amino acid residue at position Ser255 in the amino acid sequence shown in SEQ ID NO:1 or at a position corresponding to this position, is deleted or substituted with glycine, histidine, leucine, glutamine or tyrosine; and/or
(59) an amino acid residue at position Trp269 in the amino acid sequence shown in SEQ ID NO:1 or at a position corresponding to this position, is deleted or substituted with alanine; and/or
(60) an amino acid residue at position Asp312 in the amino acid sequence shown in SEQ ID NO:1 or at a position corresponding to this position, is deleted or substituted with glutamic acid; and/or
(61) an amino acid residue at position Ala314 in the amino acid sequence shown in SEQ ID NO:1 or at a position corresponding to this position, is deleted or substituted with threonine; and/or
(62) an amino acid residue at position Val318 in the amino acid sequence shown in SEQ ID NO:1 or at a position corresponding to this position, is deleted or substituted with alanine or glycine; and/or
(63) an amino acid residue at position Gly319 in the amino acid sequence shown in SEQ ID NO:1 or at a position corresponding to this position, is deleted or substituted with arginine; and/or
(64) an amino acid residue at position Phe324 in the amino acid sequence shown in SEQ ID NO:1 or at a position corresponding to this position, is deleted or substituted with serine; and/or
(65) an amino acid residue at position Glu361 in the amino acid sequence shown in SEQ ID NO:1 or at a position corresponding to this position, is deleted or substituted with threonine; and/or
(66) an amino acid residue at position Gly364 in the amino acid sequence shown in SEQ ID NO:1 or at a position corresponding to this position, is deleted or substituted with serine; and/or
(67) an amino acid residue at position Leu366 in the amino acid sequence shown in SEQ ID NO:1 or at a position corresponding to this position, is deleted or substituted with valine; and/or
(68) an amino acid residue at position Leu367 in the amino acid sequence shown in SEQ ID NO:1 or at a position corresponding to this position, is deleted or substituted with phenylalanine; and/or
(69) an amino acid residue at position Gly382 in the amino acid sequence shown in SEQ ID NO:1 or at a position corresponding to this position, is deleted or substituted with glutamine or aspartic acid; and/or
(70) an amino acid residue at position Ala383 in the amino acid sequence shown in SEQ ID NO:1 or at a position corresponding to this position, is deleted or substituted with tyrosine; and/or
(71) an amino acid residue at position Leu384 in the amino acid sequence shown in SEQ ID NO:1 or at a position corresponding to this position, is deleted or substituted with methionine or tyrosine; and/or
(72) an amino acid residue at position Arg386 in the amino acid sequence shown in SEQ ID NO:1 or at a position corresponding to this position, is deleted or substituted with serine; and/or

(73) an amino acid residue at position Met387 in the amino acid sequence shown in SEQ ID NO:1 or at a position corresponding to this position, is deleted or substituted with aspartic acid or asparagine; and/or

(74) an amino acid residue at position Pro389 in the amino acid sequence shown in SEQ ID NO:1 or at a position corresponding to this position, is deleted or substituted with leucine; and/or

(75) an amino acid residue at position Pro390 in the amino acid sequence shown in SEQ ID NO:1 or at a position corresponding to this position, is deleted or substituted with aspartic acid.

17. A nucleic acid molecule encoding the variant of claim 1.

18. A vector comprising the nucleic acid molecule of claim 17.

19. A host cell comprising the vector of claim 18.

20. An in vitro method of producing $C_nH_{2n-2}$ comprising: converting a compound corresponding to the general formula $C_nH_{2n}O$ into $C_nH_{2n-2}+H_2O$, with 3<n<7 by the variant of claim 1.

21. The method of claim 20 wherein:
(i) the compound corresponding to the general formula $C_nH_{2n}O$ is crotyl alcohol, but-3-en-2-ol or but-3-en-1-ol and the compound corresponding to the general formula $C_nH_{2n-2}$ is 1,3 butadiene; or
(ii) the compound corresponding to the general formula $C_nH_{2n}O$ is prenol, isoprenol, 2-methyl-but-3-en-1-ol, 2-methyl-but-2-en-1-ol, 3-methyl-but-3-en-2-ol or 2-methyl-but-3-en-2-ol and the compound corresponding to the general formula $C_nH_{2n-2}$ is isoprene; or
(iii) the compound corresponding to the general formula $C_nH_{2n}O$ is 2,3-dimethyl-but-2-en-1-ol, 2,3-dimethyl-but-3-en-2-ol or 2,3-dimethyl-but-3-en-1-ol and the compound corresponding to the general formula $C_nH_{2n-2}$ is dimethylbutadiene.

22. The method of claim 20, wherein said method further comprises
recovering the produced compound corresponding to the general formula $C_nH_{2n-2}$.

23. A method of producing $C_nH_{2n-2}$ comprising culturing a host cell comprising the variant of claim 1 in a suitable medium to convert a compound corresponding to the general formula $C_nH_{2n}O$ into $C_nH_{2n-2}+H_2O$, with 3<n<7.

24. The method of claim 23, wherein said method further comprises recovering the produced compound corresponding to the general formula $C_nH_{2n-2}$.

25. The method of claim 23 wherein:
(i) the compound corresponding to the general formula $C_nH_{2n}O$ is crotyl alcohol, but-3-en-2-ol or but-3-en-1-ol and the compound corresponding to the general formula $C_nH_{2n-2}$ is 1,3 butadiene; or
(ii) the compound corresponding to the general formula $C_nH_{2n}$ is prenol, isoprenol, 2-methyl-but-3-en-1-ol, 2-methyl-but-2-en-1-ol, 3-methyl-but-3-en-2-ol or 2-methyl-but-3-en-2-ol and the compound corresponding to the general formula $C_nH_{2n-2}$ is isoprene; or
(iii) the compound corresponding to the general formula $C_nH_{2n}O$ is 2,3-dimethyl-but-2-en-1-ol, 2,3-dimethyl-but-3-en-2-ol or 2,3-dimethyl-but-3-en-1-ol and the compound corresponding to the general formula $C_nH_{2n-2}$ is dimethylbutadiene.

26. The method of claim 23 wherein the host cell is a cell which is capable of producing said compound corresponding to the general formula $C_nH_{2n}O$.

* * * * *

UNITED STATES PATENT AND TRADEMARK OFFICE
CERTIFICATE OF CORRECTION

PATENT NO. : 10,036,003 B2
APPLICATION NO. : 14/891665
DATED : July 31, 2018
INVENTOR(S) : Philippe Marlière, Marc Delcourt and Sabine Mazaleyrat Page 1 of 1

It is certified that error appears in the above-identified patent and that said Letters Patent is hereby corrected as shown below:

In the Claims

Column 141, Claim 6 should read:
-- The variant of claim 5 wherein the variant comprises an amino acid sequence having at least 85% sequence identity to the amino acid sequence of SEQ ID NO:1. --

Column 156, Claim 22 should read:
-- The method of claim 20, wherein said method further comprises recovering the produced compound corresponding to the general formula $C_nH_{2n-2}$. --

Column 156, Claim 25 (ii) should read:
-- the compound corresponding to the general formula $C_nH_{2n}O$ is prenol, isoprenol, 2-methyl-but-3-en-1-ol, 2-methyl-but-2-en-1-ol, 3-methyl-but-3-en-2-ol or 2-methyl-but-3-en-2-ol and the compound corresponding to the general formula $C_nH_{2n-2}$ is isoprene; or --

Signed and Sealed this
Fourth Day of June, 2019

Andrei Iancu
*Director of the United States Patent and Trademark Office*

SEQUENCE LISTING

<160> NUMBER OF SEQ ID NOS: 9

<210> SEQ ID NO 1
<211> LENGTH: 397
<212> TYPE: PRT
<213> ORGANISM: Castellaniella defragrans

<400> SEQUENCE: 1

```
Met Arg Phe Thr Leu Lys Thr Thr Ala Ile Val Ser Ala Ala Ala Leu
1               5                   10                  15

Leu Ala Gly Phe Gly Pro Pro Arg Ala Ala Glu Leu Pro Pro Gly
            20                  25                  30

Arg Leu Ala Thr Thr Glu Asp Tyr Phe Ala Gln Gln Ala Lys Gln Ala
            35                  40                  45

Val Thr Pro Asp Val Met Ala Gln Leu Ala Tyr Met Asn Tyr Ile Asp
50                  55                  60

Phe Ile Ser Pro Phe Tyr Ser Arg Gly Cys Ser Phe Glu Ala Trp Glu
65                  70                  75                  80

Leu Lys His Thr Pro Gln Arg Val Ile Lys Tyr Ser Ile Ala Phe Tyr
            85                  90                  95

Ala Tyr Gly Leu Ala Ser Val Ala Leu Ile Asp Pro Lys Leu Arg Ala
            100                 105                 110

Leu Ala Gly His Asp Leu Asp Ile Ala Val Ser Lys Met Lys Cys Lys
            115                 120                 125

Arg Val Trp Gly Asp Trp Glu Glu Asp Gly Phe Gly Thr Asp Pro Ile
130                 135                 140

Glu Lys Glu Asn Ile Met Tyr Lys Gly His Leu Asn Leu Met Tyr Gly
145                 150                 155                 160

Leu Tyr Gln Leu Val Thr Gly Ser Arg Arg Tyr Glu Ala Glu His Ala
            165                 170                 175

His Leu Thr Arg Ile Ile His Asp Glu Ile Ala Ala Asn Pro Phe Ala
            180                 185                 190

Gly Ile Val Cys Glu Pro Asp Asn Tyr Phe Val Gln Cys Asn Ser Val
            195                 200                 205

Ala Tyr Leu Ser Leu Trp Val Tyr Asp Arg Leu His Gly Thr Asp Tyr
210                 215                 220

Arg Ala Ala Thr Arg Ala Trp Leu Asp Phe Ile Gln Lys Asp Leu Ile
225                 230                 235                 240

Asp Pro Glu Arg Gly Ala Phe Tyr Leu Ser Tyr His Pro Glu Ser Gly
            245                 250                 255

Ala Val Lys Pro Trp Ile Ser Ala Tyr Thr Thr Ala Trp Thr Leu Ala
            260                 265                 270

Met Val His Gly Met Asp Pro Ala Phe Ser Glu Arg Tyr Tyr Pro Arg
            275                 280                 285

Phe Lys Gln Thr Phe Val Glu Val Tyr Asp Glu Gly Arg Lys Ala Arg
            290                 295                 300

Val Arg Glu Thr Ala Gly Thr Asp Ala Asp Gly Val Gly Leu
305                 310                 315                 320

Ala Ser Ala Phe Thr Leu Leu Leu Ala Arg Glu Met Gly Asp Gln Gln
            325                 330                 335

Leu Phe Asp Gln Leu Leu Asn His Leu Glu Pro Pro Lys Pro Ser
            340                 345                 350

Ile Val Ser Ala Ser Leu Arg Tyr Glu His Pro Gly Ser Leu Leu Phe
            355                 360                 365

Asp Glu Leu Leu Phe Leu Ala Lys Val His Ala Gly Phe Gly Ala Leu
370                 375                 380

Leu Arg Met Pro Pro Pro Ala Ala Lys Leu Ala Gly Lys
385                 390                 395
```

<210> SEQ ID NO 2

<211> LENGTH: 1218
<212> TYPE: DNA
<213> ORGANISM: Artificial Sequence
<220> FEATURE:
<221> NAME/KEY: source
<222> LOCATION: 1..1218
<223> OTHER INFORMATION: /mol_type="unassigned DNA"
      /note="E. coli codon optimized sequence coding for linalool
      dehydratase-isomerase from Castellaniella defragrans"
      /organism="Artificial Sequence"
<220> FEATURE:
<221> NAME/KEY: CDS
<222> LOCATION: 1..1215
<223> OTHER INFORMATION: /transl_table=1

<400> SEQUENCE: 2

```
atg cac cat cat cat cat cac atg cgt ttt acc ctg aaa acc acc gca      48
Met His His His His His His Met Arg Phe Thr Leu Lys Thr Thr Ala
1               5                   10                  15 att gtg agc gca gca gca ctg ctg gca ggt ttt ggt cct ccg cct cgt      96
Ile Val Ser Ala Ala Ala Leu Leu Ala Gly Phe Gly Pro Pro Pro Arg
                20                  25                  30 gca gca gaa ctg cct ccg ggt cgt ctg gca acc acc gaa gat tat ttt     144
Ala Ala Glu Leu Pro Pro Gly Arg Leu Ala Thr Thr Glu Asp Tyr Phe
            35                  40                  45 gca cag cag gca aaa cag gca gtt aca ccg gat gtt atg gca cag ctg     192
Ala Gln Gln Ala Lys Gln Ala Val Thr Pro Asp Val Met Ala Gln Leu
        50                  55                  60 gca tat atg aac tat att gat ttt atc agc ccg ttt tat agc cgt ggc     240
Ala Tyr Met Asn Tyr Ile Asp Phe Ile Ser Pro Phe Tyr Ser Arg Gly
65                  70                  75                  80 tgt agc ttt gaa gca tgg gaa ctg aaa cat aca ccg cag cgt gtt atc     288
Cys Ser Phe Glu Ala Trp Glu Leu Lys His Thr Pro Gln Arg Val Ile
                85                  90                  95 aaa tat agc att gcc ttt tat gcc tat ggt ctg gca agc gtt gca ctg     336
Lys Tyr Ser Ile Ala Phe Tyr Ala Tyr Gly Leu Ala Ser Val Ala Leu
                100                 105                 110 att gat ccg aaa ctg cgt gca ctg gca ggt cat gat ctg gat att gca     384
Ile Asp Pro Lys Leu Arg Ala Leu Ala Gly His Asp Leu Asp Ile Ala
            115                 120                 125 gtt agc aaa atg aaa tgc aaa cgt gtt tgg ggt gat tgg gaa gaa gat     432
Val Ser Lys Met Lys Cys Lys Arg Val Trp Gly Asp Trp Glu Glu Asp
        130                 135                 140 ggt ttt ggc acc gat ccg att gaa aaa gaa aac att atg tat aaa ggc     480
Gly Phe Gly Thr Asp Pro Ile Glu Lys Glu Asn Ile Met Tyr Lys Gly
145                 150                 155                 160 cat ctg aat ctg atg tat ggt ctg tat cag ctg gtt acc ggt agc cgt     528
His Leu Asn Leu Met Tyr Gly Leu Tyr Gln Leu Val Thr Gly Ser Arg
                165                 170                 175 cgt tat gaa gca gaa cat gca cat ctg acc cgt att att cat gat gaa     576
Arg Tyr Glu Ala Glu His Ala His Leu Thr Arg Ile Ile His Asp Glu
                180                 185                 190 att gca gca aat ccg ttt gcc ggt att gtt tgt gaa ccg gat aac tat     624
Ile Ala Ala Asn Pro Phe Ala Gly Ile Val Cys Glu Pro Asp Asn Tyr
            195                 200                 205 ttt gtg cag tgt aat agc gtt gcc tat ctg agc ctg tgg gtt tat gat     672
Phe Val Gln Cys Asn Ser Val Ala Tyr Leu Ser Leu Trp Val Tyr Asp
        210                 215                 220 cgt ctg cat ggc acc gat tat cgt gca gca acc cgt gca tgg ctg gat     720
Arg Leu His Gly Thr Asp Tyr Arg Ala Ala Thr Arg Ala Trp Leu Asp
225                 230                 235                 240 ttt att cag aaa gat ctg att gat cct gaa cgc ggt gcc ttt tat ctg     768
Phe Ile Gln Lys Asp Leu Ile Asp Pro Glu Arg Gly Ala Phe Tyr Leu
```

-continued

```
                245                 250                 255
agc tat cat ccg gaa agt ggt gca gtt aaa ccg tgg att agc gca tat       816
Ser Tyr His Pro Glu Ser Gly Ala Val Lys Pro Trp Ile Ser Ala Tyr
            260                 265                 270 acc acc gca tgg acc ctg gca atg gtt cat ggt atg gac cct gca ttt       864
Thr Thr Ala Trp Thr Leu Ala Met Val His Gly Met Asp Pro Ala Phe
        275                 280                 285 agc gaa cgt tat tat ccg cgt ttt aaa cag acc ttt gtg gaa gtg tat       912
Ser Glu Arg Tyr Tyr Pro Arg Phe Lys Gln Thr Phe Val Glu Val Tyr
    290                 295                 300 gat gaa ggt cgt aaa gca cgt gtt cgt gaa acc gca ggc acc gat gat       960
Asp Glu Gly Arg Lys Ala Arg Val Arg Glu Thr Ala Gly Thr Asp Asp
305                 310                 315                 320 gca gat ggt ggt gtt ggt ctg gcc agc gca ttt acc ctg ctg ctg gca      1008
Ala Asp Gly Gly Val Gly Leu Ala Ser Ala Phe Thr Leu Leu Leu Ala
                325                 330                 335 cgt gaa atg ggt gat cag caa ctg ttc gat cag ctg ctg aat cat ctg      1056
Arg Glu Met Gly Asp Gln Gln Leu Phe Asp Gln Leu Leu Asn His Leu
            340                 345                 350 gaa cct ccg gca aaa ccg agc att gtt agc gcc agc ctg cgt tat gaa      1104
Glu Pro Pro Ala Lys Pro Ser Ile Val Ser Ala Ser Leu Arg Tyr Glu
        355                 360                 365 cat ccg ggt agc ctg ctg ttt gat gaa ctg ctg ttt ctg gca aaa gtt      1152
His Pro Gly Ser Leu Leu Phe Asp Glu Leu Leu Phe Leu Ala Lys Val
    370                 375                 380 cat gcc ggt ttt ggt gcc ctg ctg cgt atg cct cct ccg gca gca aaa      1200
His Ala Gly Phe Gly Ala Leu Leu Arg Met Pro Pro Pro Ala Ala Lys
385                 390                 395                 400 ctg gca ggt aag taa taa                                              1218
Leu Ala Gly Lys
```

<210> SEQ ID NO 3
<211> LENGTH: 404
<212> TYPE: PRT
<213> ORGANISM: Artificial Sequence
<220> FEATURE:
<223> OTHER INFORMATION: [CDS]:1..1215 from SEQ ID NO 2

<400> SEQUENCE: 3

```
Met His His His His His Met Arg Phe Thr Leu Lys Thr Thr Ala
1               5                  10                  15

Ile Val Ser Ala Ala Leu Leu Ala Gly Phe Gly Pro Pro Arg
                20                  25                  30

Ala Ala Glu Leu Pro Pro Gly Arg Leu Ala Thr Thr Glu Asp Tyr Phe
            35                  40                  45

Ala Gln Gln Ala Lys Gln Ala Val Thr Pro Asp Val Met Ala Gln Leu
        50                  55                  60

Ala Tyr Met Asn Tyr Ile Asp Phe Ile Ser Pro Phe Tyr Ser Arg Gly
    65                  70                  75                  80

Cys Ser Phe Glu Ala Trp Glu Leu Lys His Thr Pro Gln Arg Val Ile
                85                  90                  95

Lys Tyr Ser Ile Ala Phe Tyr Ala Tyr Gly Leu Ala Ser Val Ala Leu
                100                 105                 110

Ile Asp Pro Lys Leu Arg Ala Leu Ala Gly His Asp Leu Asp Ile Ala
            115                 120                 125

Val Ser Lys Met Lys Cys Lys Arg Val Trp Gly Asp Trp Glu Glu Asp
        130                 135                 140

Gly Phe Gly Thr Asp Pro Ile Glu Lys Glu Asn Ile Met Tyr Lys Gly
```

```
                145                 150                 155                 160
His Leu Asn Leu Met Tyr Gly Leu Tyr Gln Leu Val Thr Gly Ser Arg
                    165                 170                 175

Arg Tyr Glu Ala Glu His Ala His Leu Thr Arg Ile Ile His Asp Glu
                180                 185                 190

Ile Ala Ala Asn Pro Phe Ala Gly Ile Val Cys Glu Pro Asp Asn Tyr
            195                 200                 205

Phe Val Gln Cys Asn Ser Val Ala Tyr Leu Ser Leu Trp Val Tyr Asp
        210                 215                 220

Arg Leu His Gly Thr Asp Tyr Arg Ala Ala Thr Arg Ala Trp Leu Asp
225                 230                 235                 240

Phe Ile Gln Lys Asp Leu Ile Asp Pro Glu Arg Gly Ala Phe Tyr Leu
                245                 250                 255

Ser Tyr His Pro Glu Ser Gly Ala Val Lys Pro Trp Ile Ser Ala Tyr
                260                 265                 270

Thr Thr Ala Trp Thr Leu Ala Met Val His Gly Met Asp Pro Ala Phe
                275                 280                 285

Ser Glu Arg Tyr Tyr Pro Arg Phe Lys Gln Thr Phe Val Glu Val Tyr
            290                 295                 300

Asp Glu Gly Arg Lys Ala Arg Val Arg Glu Thr Ala Gly Thr Asp Asp
305                 310                 315                 320

Ala Asp Gly Gly Val Gly Leu Ala Ser Ala Phe Thr Leu Leu Leu Ala
                325                 330                 335

Arg Glu Met Gly Asp Gln Gln Leu Phe Asp Gln Leu Leu Asn His Leu
                340                 345                 350

Glu Pro Pro Ala Lys Pro Ser Ile Val Ser Ala Ser Leu Arg Tyr Glu
            355                 360                 365

His Pro Gly Ser Leu Leu Phe Asp Glu Leu Leu Phe Leu Ala Lys Val
        370                 375                 380

His Ala Gly Phe Gly Ala Leu Leu Arg Met Pro Pro Ala Ala Lys
385                 390                 395                 400

Leu Ala Gly Lys

<210> SEQ ID NO 4
<211> LENGTH: 1242
<212> TYPE: DNA
<213> ORGANISM: Artificial Sequence
<220> FEATURE:
<221> NAME/KEY: source
<222> LOCATION: 1..1242
<223> OTHER INFORMATION: /mol_type="unassigned DNA"
      /note="E. coli codon optimized sequence coding for linalool
      dehydratase-isomerase from Castellaniella defragrans variant
      V195F-G132A"
      /organism="Artificial Sequence"
<220> FEATURE:
<221> NAME/KEY: CDS
<222> LOCATION: 1..1236
<223> OTHER INFORMATION: /transl_table=1

<400> SEQUENCE: 4 atg cat cat cat cat cat cac atc aca agt ttg tac aaa aaa gca ggc    48
Met His His His His His His Ile Thr Ser Leu Tyr Lys Lys Ala Gly
1               5                   10                  15 tgt ttt acc ctg aaa acc acc gca att gtg agc gca gca gca ctg ctg    96
Cys Phe Thr Leu Lys Thr Thr Ala Ile Val Ser Ala Ala Ala Leu Leu
                20                  25                  30 gca ggt ttt ggt cct ccg cct cgt gca gca gaa ctg cct ccg ggt cgt    144
Ala Gly Phe Gly Pro Pro Pro Arg Ala Ala Glu Leu Pro Pro Gly Arg
```

|  |  |  |  |  |  |  |  |  |  |  |  |  |  |  |  |
|---|---|---|---|---|---|---|---|---|---|---|---|---|---|---|---|
| | | 35 | | | | 40 | | | | | 45 | | | | |
| ctg | gca | acc | acc | gaa | gat | tat | ttt | gca | cag | cag | gca | aaa | cag | gca | gtt | 192 |
| Leu | Ala | Thr | Thr | Glu | Asp | Tyr | Phe | Ala | Gln | Gln | Ala | Lys | Gln | Ala | Val | |
| | | 50 | | | | 55 | | | | 60 | | | | | |

| aca | ccg | gat | gtt | atg | gca | cag | ctg | gca | tat | atg | aac | tat | att | gat | ttt | 240 |
| Thr | Pro | Asp | Val | Met | Ala | Gln | Leu | Ala | Tyr | Met | Asn | Tyr | Ile | Asp | Phe | |
| 65 | | | | 70 | | | | 75 | | | | 80 | | | | |

| atc | agc | ccg | ttt | tat | agc | cgt | ggc | tgt | agc | ttt | gaa | gca | tgg | gaa | ctg | 288 |
| Ile | Ser | Pro | Phe | Tyr | Ser | Arg | Gly | Cys | Ser | Phe | Glu | Ala | Trp | Glu | Leu | |
| | | | | 85 | | | | | 90 | | | | 95 | | | |

| aaa | cat | aca | ccg | cag | cgt | gtt | atc | aaa | tat | agc | att | gcc | ttt | tat | gcc | 336 |
| Lys | His | Thr | Pro | Gln | Arg | Val | Ile | Lys | Tyr | Ser | Ile | Ala | Phe | Tyr | Ala | |
| | | | 100 | | | | | 105 | | | | 110 | | | | |

| tat | ggt | ctg | gca | agc | gtt | gca | ctg | att | gat | ccg | aaa | ctg | cgt | gca | ctg | 384 |
| Tyr | Gly | Leu | Ala | Ser | Val | Ala | Leu | Ile | Asp | Pro | Lys | Leu | Arg | Ala | Leu | |
| | | | 115 | | | | | 120 | | | | | 125 | | | |

| gca | ggt | cat | gat | ctg | gat | att | gca | gtt | agc | aaa | atg | aaa | tgc | aaa | cgt | 432 |
| Ala | Gly | His | Asp | Leu | Asp | Ile | Ala | Val | Ser | Lys | Met | Lys | Cys | Lys | Arg | |
| | 130 | | | | | 135 | | | | | 140 | | | | | |

| gtt | tgg | gcg | gat | tgg | gaa | gaa | gat | ggt | ttt | ggc | acc | gat | ccg | att | gaa | 480 |
| Val | Trp | Ala | Asp | Trp | Glu | Glu | Asp | Gly | Phe | Gly | Thr | Asp | Pro | Ile | Glu | |
| 145 | | | | | 150 | | | | | 155 | | | | | 160 | |

| aaa | gaa | aac | att | atg | tat | aaa | ggc | cat | ctg | aat | ctg | atg | tat | ggt | ctg | 528 |
| Lys | Glu | Asn | Ile | Met | Tyr | Lys | Gly | His | Leu | Asn | Leu | Met | Tyr | Gly | Leu | |
| | | | | 165 | | | | | 170 | | | | | 175 | | |

| tat | cag | ctg | gtt | acc | ggt | agc | cgt | cgt | tat | gaa | gca | gaa | cat | gca | cat | 576 |
| Tyr | Gln | Leu | Val | Thr | Gly | Ser | Arg | Arg | Tyr | Glu | Ala | Glu | His | Ala | His | |
| | | | 180 | | | | | 185 | | | | 190 | | | | |

| ctg | acc | cgt | att | att | cat | gat | gaa | att | gca | gca | aat | ccg | ttt | gcc | ggt | 624 |
| Leu | Thr | Arg | Ile | Ile | His | Asp | Glu | Ile | Ala | Ala | Asn | Pro | Phe | Ala | Gly | |
| | | 195 | | | | | 200 | | | | | 205 | | | | |

| att | ttt | tgt | gaa | ccg | gat | aac | tat | ttt | gtg | cag | tgt | aat | agc | gtt | gcc | 672 |
| Ile | Phe | Cys | Glu | Pro | Asp | Asn | Tyr | Phe | Val | Gln | Cys | Asn | Ser | Val | Ala | |
| | 210 | | | | | 215 | | | | | 220 | | | | | |

| tat | ctg | agc | ctg | tgg | gtt | tat | gat | cgt | ctg | cat | ggc | acc | gat | tat | cgt | 720 |
| Tyr | Leu | Ser | Leu | Trp | Val | Tyr | Asp | Arg | Leu | His | Gly | Thr | Asp | Tyr | Arg | |
| 225 | | | | | 230 | | | | | 235 | | | | | 240 | |

| gca | gca | acc | cgt | gca | tgg | ctg | gat | ttt | att | cag | aaa | gat | ctg | att | gat | 768 |
| Ala | Ala | Thr | Arg | Ala | Trp | Leu | Asp | Phe | Ile | Gln | Lys | Asp | Leu | Ile | Asp | |
| | | | 245 | | | | | 250 | | | | | 255 | | | |

| cct | gaa | cgc | ggt | gcc | ttt | tat | ctg | agc | tat | cat | ccg | gaa | agt | ggt | gca | 816 |
| Pro | Glu | Arg | Gly | Ala | Phe | Tyr | Leu | Ser | Tyr | His | Pro | Glu | Ser | Gly | Ala | |
| | | 260 | | | | | 265 | | | | | 270 | | | | |

| gtt | aaa | ccg | tgg | att | agc | gca | tat | acc | acc | gca | tgg | acc | ctg | gca | atg | 864 |
| Val | Lys | Pro | Trp | Ile | Ser | Ala | Tyr | Thr | Thr | Ala | Trp | Thr | Leu | Ala | Met | |
| | | 275 | | | | | 280 | | | | | 285 | | | | |

| gtt | cat | ggt | atg | gac | cct | gca | ttt | agc | gaa | cgt | tat | tat | ccg | cgt | ttt | 912 |
| Val | His | Gly | Met | Asp | Pro | Ala | Phe | Ser | Glu | Arg | Tyr | Tyr | Pro | Arg | Phe | |
| | 290 | | | | | 295 | | | | | 300 | | | | | |

| aaa | cag | acc | ttt | gtg | gaa | gtg | tat | gat | gaa | ggt | cgt | aaa | gca | cgt | gtt | 960 |
| Lys | Gln | Thr | Phe | Val | Glu | Val | Tyr | Asp | Glu | Gly | Arg | Lys | Ala | Arg | Val | |
| 305 | | | | | 310 | | | | | 315 | | | | | 320 | |

| cgt | gaa | acc | gca | ggc | acc | gat | gat | gca | gat | ggt | ggt | gtt | ggt | ctg | gcc | 1008 |
| Arg | Glu | Thr | Ala | Gly | Thr | Asp | Asp | Ala | Asp | Gly | Gly | Val | Gly | Leu | Ala | |
| | | | | 325 | | | | | 330 | | | | | 335 | | |

| agc | gca | ttt | acc | ctg | ctg | ctg | gca | cgt | gaa | atg | ggt | gat | cag | caa | ctg | 1056 |
| Ser | Ala | Phe | Thr | Leu | Leu | Leu | Ala | Arg | Glu | Met | Gly | Asp | Gln | Gln | Leu | |
| | | | 340 | | | | | 345 | | | | | 350 | | | |

| ttc | gat | cag | ctg | ctg | aat | cat | ctg | gaa | cct | ccg | gca | aaa | ccg | agc | att | 1104 |

```
                Phe Asp Gln Leu Leu Asn His Leu Glu Pro Pro Ala Lys Pro Ser Ile
                            355                 360                 365 gtt agc gcc agc ctg cgt tat gaa cat ccg ggt agc ctg ctg ttt gat              1152
Val Ser Ala Ser Leu Arg Tyr Glu His Pro Gly Ser Leu Leu Phe Asp
370                 375                 380 gaa ctg ctg ttt ctg gca aaa gtt cat gcc ggt ttt ggt gcc ctg ctg              1200
Glu Leu Leu Phe Leu Ala Lys Val His Ala Gly Phe Gly Ala Leu Leu
385                 390                 395                 400 cgt atg cct cct ccg gca gca aaa ctg gca ggt aag taataa                       1242
Arg Met Pro Pro Pro Ala Ala Lys Leu Ala Gly Lys
                405                 410

<210> SEQ ID NO 5
<211> LENGTH: 412
<212> TYPE: PRT
<213> ORGANISM: Artificial Sequence
<220> FEATURE:
<223> OTHER INFORMATION: [CDS]:1..1236 from SEQ ID NO 4

<400> SEQUENCE: 5

Met His His His His His Ile Thr Ser Leu Tyr Lys Lys Ala Gly
1               5                   10                  15

Cys Phe Thr Leu Lys Thr Thr Ala Ile Val Ser Ala Ala Ala Leu Leu
                20                  25                  30

Ala Gly Phe Gly Pro Pro Pro Arg Ala Ala Glu Leu Pro Pro Gly Arg
            35                  40                  45

Leu Ala Thr Thr Glu Asp Tyr Phe Ala Gln Gln Ala Lys Gln Ala Val
        50                  55                  60

Thr Pro Asp Val Met Ala Gln Leu Ala Tyr Met Asn Tyr Ile Asp Phe
65                  70                  75                  80

Ile Ser Pro Phe Tyr Ser Arg Gly Cys Ser Phe Glu Ala Trp Glu Leu
                85                  90                  95

Lys His Thr Pro Gln Arg Val Ile Lys Tyr Ser Ile Ala Phe Tyr Ala
            100                 105                 110

Tyr Gly Leu Ala Ser Val Ala Leu Ile Asp Pro Lys Leu Arg Ala Leu
        115                 120                 125

Ala Gly His Asp Leu Asp Ile Ala Val Ser Lys Met Lys Cys Lys Arg
    130                 135                 140

Val Trp Ala Asp Trp Glu Glu Asp Gly Phe Gly Thr Asp Pro Ile Glu
145                 150                 155                 160

Lys Glu Asn Ile Met Tyr Lys Gly His Leu Asn Leu Met Tyr Gly Leu
                165                 170                 175

Tyr Gln Leu Val Thr Gly Ser Arg Arg Tyr Glu Ala Glu His Ala His
            180                 185                 190

Leu Thr Arg Ile Ile His Asp Glu Ile Ala Ala Asn Pro Phe Ala Gly
        195                 200                 205

Ile Phe Cys Glu Pro Asp Asn Tyr Phe Val Gln Cys Asn Ser Val Ala
    210                 215                 220

Tyr Leu Ser Leu Trp Val Tyr Asp Arg Leu His Gly Thr Asp Tyr Arg
225                 230                 235                 240

Ala Ala Thr Arg Ala Trp Leu Asp Phe Ile Gln Lys Asp Leu Ile Asp
                245                 250                 255

Pro Glu Arg Gly Ala Phe Tyr Leu Ser Tyr His Pro Glu Ser Gly Ala
            260                 265                 270

Val Lys Pro Trp Ile Ser Ala Tyr Thr Thr Ala Trp Thr Leu Ala Met
        275                 280                 285
```

```
Val His Gly Met Asp Pro Ala Phe Ser Glu Arg Tyr Pro Arg Phe
    290                 295                 300

Lys Gln Thr Phe Val Glu Val Tyr Asp Glu Gly Arg Lys Ala Arg Val
305                 310                 315                 320

Arg Glu Thr Ala Gly Thr Asp Asp Ala Asp Gly Gly Val Gly Leu Ala
                325                 330                 335

Ser Ala Phe Thr Leu Leu Ala Arg Glu Met Gly Asp Gln Gln Leu
            340                 345                 350

Phe Asp Gln Leu Leu Asn His Leu Glu Pro Pro Ala Lys Pro Ser Ile
            355                 360                 365

Val Ser Ala Ser Leu Arg Tyr Glu His Pro Gly Ser Leu Leu Phe Asp
370                 375                 380

Glu Leu Leu Phe Leu Ala Lys Val His Ala Gly Phe Gly Ala Leu Leu
385                 390                 395                 400

Arg Met Pro Pro Pro Ala Ala Lys Leu Ala Gly Lys
                405                 410

<210> SEQ ID NO 6
<211> LENGTH: 1242
<212> TYPE: DNA
<213> ORGANISM: Artificial Sequence
<220> FEATURE:
<221> NAME/KEY: source
<222> LOCATION: 1..1242
<223> OTHER INFORMATION: /mol_type="unassigned DNA"
    /note="E. coli codon optimized sequence coding for linalool
    dehydratase-isomerase from Castellaniella defragrans variant
    V195F"
    /organism="Artificial Sequence"
<220> FEATURE:
<221> NAME/KEY: CDS
<222> LOCATION: 1..1236
<223> OTHER INFORMATION: /transl_table=1

<400> SEQUENCE: 6 atg cat cat cat cat cat cac atc aca agt ttg tac aaa aaa gca ggc    48
Met His His His His His His Ile Thr Ser Leu Tyr Lys Lys Ala Gly
1               5                   10                  15 tgt ttt acc ctg aaa acc acc gca att gtg agc gca gca gca ctg ctg    96
Cys Phe Thr Leu Lys Thr Thr Ala Ile Val Ser Ala Ala Ala Leu Leu
            20                  25                  30 gca ggt ttt ggt cct ccg cct cgt gca gca gaa ctg cct ccg ggt cgt   144
Ala Gly Phe Gly Pro Pro Pro Arg Ala Ala Glu Leu Pro Pro Gly Arg
        35                  40                  45 ctg gca acc acc gaa gat tat ttt gca cag cag gca aaa cag gca gtt   192
Leu Ala Thr Thr Glu Asp Tyr Phe Ala Gln Gln Ala Lys Gln Ala Val
    50                  55                  60 aca ccg gat gtt atg gca cag ctg gca tat atg aac tat att gat ttt   240
Thr Pro Asp Val Met Ala Gln Leu Ala Tyr Met Asn Tyr Ile Asp Phe
65                  70                  75                  80 atc agc ccg ttt tat agc cgt ggc tgt agc ttt gaa gca tgg gaa ctg   288
Ile Ser Pro Phe Tyr Ser Arg Gly Cys Ser Phe Glu Ala Trp Glu Leu
                85                  90                  95 aaa cat aca ccg cag cgt gtt atc aaa tat agc att gcc ttt tat gcc   336
Lys His Thr Pro Gln Arg Val Ile Lys Tyr Ser Ile Ala Phe Tyr Ala
            100                 105                 110 tat ggt ctg gca agc gtt gca ctg att gat ccg aaa ctg cgt gca ctg   384
Tyr Gly Leu Ala Ser Val Ala Leu Ile Asp Pro Lys Leu Arg Ala Leu
        115                 120                 125 gca ggt cat gat ctg gat att gca gtt agc aaa atg aaa tgc aaa cgt   432
Ala Gly His Asp Leu Asp Ile Ala Val Ser Lys Met Lys Cys Lys Arg
    130                 135                 140
```

```
gtt tgg ggt gat tgg gaa gaa gat ggt ttt ggc acc gat ccg att gaa      480
Val Trp Gly Asp Trp Glu Glu Asp Gly Phe Gly Thr Asp Pro Ile Glu
145                 150                 155                 160 aaa gaa aac att atg tat aaa ggc cat ctg aat ctg atg tat ggt ctg      528
Lys Glu Asn Ile Met Tyr Lys Gly His Leu Asn Leu Met Tyr Gly Leu
            165                 170                 175 tat cag ctg gtt acc ggt agc cgt cgt tat gaa gca gaa cat gca cat      576
Tyr Gln Leu Val Thr Gly Ser Arg Arg Tyr Glu Ala Glu His Ala His
        180                 185                 190 ctg acc cgt att att cat gat gaa att gca gca aat ccg ttt gcc ggt      624
Leu Thr Arg Ile Ile His Asp Glu Ile Ala Ala Asn Pro Phe Ala Gly
    195                 200                 205 att ttt tgt gaa ccg gat aac tat ttt gtg cag tgt aat agc gtt gcc      672
Ile Phe Cys Glu Pro Asp Asn Tyr Phe Val Gln Cys Asn Ser Val Ala
210                 215                 220 tat ctg agc ctg tgg gtt tat gat cgt ctg cat ggc acc gat tat cgt      720
Tyr Leu Ser Leu Trp Val Tyr Asp Arg Leu His Gly Thr Asp Tyr Arg
225                 230                 235                 240 gca gca acc cgt gca tgg ctg gat ttt att cag aaa gat ctg att gat      768
Ala Ala Thr Arg Ala Trp Leu Asp Phe Ile Gln Lys Asp Leu Ile Asp
                245                 250                 255 cct gaa cgc ggt gcc ttt tat ctg agc tat cat ccg gaa agt ggt gca      816
Pro Glu Arg Gly Ala Phe Tyr Leu Ser Tyr His Pro Glu Ser Gly Ala
            260                 265                 270 gtt aaa ccg tgg att agc gca tat acc acc gca tgg acc ctg gca atg      864
Val Lys Pro Trp Ile Ser Ala Tyr Thr Thr Ala Trp Thr Leu Ala Met
        275                 280                 285 gtt cat ggt atg gac cct gca ttt agc gaa cgt tat tat ccg cgt ttt      912
Val His Gly Met Asp Pro Ala Phe Ser Glu Arg Tyr Tyr Pro Arg Phe
    290                 295                 300 aaa cag acc ttt gtg gaa gtg tat gat gaa ggt cgt aaa gca cgt gtt      960
Lys Gln Thr Phe Val Glu Val Tyr Asp Glu Gly Arg Lys Ala Arg Val
305                 310                 315                 320 cgt gaa acc gca ggc acc gat gat gca gat ggt ggt gtt ggt ctg gcc     1008
Arg Glu Thr Ala Gly Thr Asp Asp Ala Asp Gly Gly Val Gly Leu Ala
                325                 330                 335 agc gca ttt acc ctg ctg ctg gca cgt gaa atg ggt gat cag caa ctg     1056
Ser Ala Phe Thr Leu Leu Leu Ala Arg Glu Met Gly Asp Gln Gln Leu
            340                 345                 350 ttc gat cag ctg ctg aat cat ctg gaa cct ccg gca aaa ccg agc att     1104
Phe Asp Gln Leu Leu Asn His Leu Glu Pro Pro Ala Lys Pro Ser Ile
        355                 360                 365 gtt agc gcc agc ctg cgt tat gaa cat ccg ggt agc ctg ctg ttt gat     1152
Val Ser Ala Ser Leu Arg Tyr Glu His Pro Gly Ser Leu Leu Phe Asp
    370                 375                 380 gaa ctg ctg ttt ctg gca aaa gtt cat gcc ggt ttt ggt gcc ctg ctg     1200
Glu Leu Leu Phe Leu Ala Lys Val His Ala Gly Phe Gly Ala Leu Leu
385                 390                 395                 400 cgt atg cct cct ccg gca gca aaa ctg gca ggt aag taataa              1242
Arg Met Pro Pro Pro Ala Ala Lys Leu Ala Gly Lys
                405                 410

<210> SEQ ID NO 7
<211> LENGTH: 412
<212> TYPE: PRT
<213> ORGANISM: Artificial Sequence
<220> FEATURE:
<223> OTHER INFORMATION: [CDS]:1..1236 from SEQ ID NO 6

<400> SEQUENCE: 7
```

```
Met His His His His His Ile Thr Ser Leu Tyr Lys Lys Ala Gly
1               5                   10                  15

Cys Phe Thr Leu Lys Thr Thr Ala Ile Val Ser Ala Ala Ala Leu Leu
            20                  25                  30

Ala Gly Phe Gly Pro Pro Arg Ala Ala Glu Leu Pro Pro Gly Arg
        35                  40                  45

Leu Ala Thr Thr Glu Asp Tyr Phe Ala Gln Gln Ala Lys Gln Ala Val
    50                  55                  60

Thr Pro Asp Val Met Ala Gln Leu Ala Tyr Met Asn Tyr Ile Asp Phe
65                  70                  75                  80

Ile Ser Pro Phe Tyr Ser Arg Gly Cys Ser Phe Glu Ala Trp Glu Leu
                85                  90                  95

Lys His Thr Pro Gln Arg Val Ile Lys Tyr Ser Ile Ala Phe Tyr Ala
                100                 105                 110

Tyr Gly Leu Ala Ser Val Ala Leu Ile Asp Pro Lys Leu Arg Ala Leu
            115                 120                 125

Ala Gly His Asp Leu Asp Ile Ala Val Ser Lys Met Lys Cys Lys Arg
        130                 135                 140

Val Trp Gly Asp Trp Glu Glu Asp Gly Phe Gly Thr Asp Pro Ile Glu
145                 150                 155                 160

Lys Glu Asn Ile Met Tyr Lys Gly His Leu Asn Leu Met Tyr Gly Leu
                165                 170                 175

Tyr Gln Leu Val Thr Gly Ser Arg Arg Tyr Glu Ala Glu His Ala His
            180                 185                 190

Leu Thr Arg Ile Ile His Asp Glu Ile Ala Ala Asn Pro Phe Ala Gly
        195                 200                 205

Ile Phe Cys Glu Pro Asp Asn Tyr Phe Val Gln Cys Asn Ser Val Ala
        210                 215                 220

Tyr Leu Ser Leu Trp Val Tyr Asp Arg Leu His Gly Thr Asp Tyr Arg
225                 230                 235                 240

Ala Ala Thr Arg Ala Trp Leu Asp Phe Ile Gln Lys Asp Leu Ile Asp
                245                 250                 255

Pro Glu Arg Gly Ala Phe Tyr Leu Ser Tyr His Pro Glu Ser Gly Ala
            260                 265                 270

Val Lys Pro Trp Ile Ser Ala Tyr Thr Thr Ala Trp Thr Leu Ala Met
        275                 280                 285

Val His Gly Met Asp Pro Ala Phe Ser Glu Arg Tyr Tyr Pro Arg Phe
        290                 295                 300

Lys Gln Thr Phe Val Glu Val Tyr Asp Glu Gly Arg Lys Ala Arg Val
305                 310                 315                 320

Arg Glu Thr Ala Gly Thr Asp Asp Ala Asp Gly Gly Val Gly Leu Ala
                325                 330                 335

Ser Ala Phe Thr Leu Leu Leu Ala Arg Glu Met Gly Asp Gln Gln Leu
            340                 345                 350

Phe Asp Gln Leu Leu Asn His Leu Glu Pro Pro Ala Lys Pro Ser Ile
        355                 360                 365

Val Ser Ala Ser Leu Arg Tyr Glu His Pro Gly Ser Leu Leu Phe Asp
        370                 375                 380

Glu Leu Leu Phe Leu Ala Lys Val His Ala Gly Phe Gly Ala Leu Leu
385                 390                 395                 400

Arg Met Pro Pro Ala Ala Lys Leu Ala Gly Lys
                405                 410
```

<210> SEQ ID NO 8
<211> LENGTH: 1242
<212> TYPE: DNA
<213> ORGANISM: Artificial Sequence
<220> FEATURE:
<221> NAME/KEY: source
<222> LOCATION: 1..1242
<223> OTHER INFORMATION: /mol_type="unassigned DNA"
    /note="E. coli codon optimized sequence coding for linalool
    dehydratase-isomerase from Castellaniella defragrans wild type
    sequence encoded by pET300NT/DEST"
    /organism="Artificial Sequence"
<220> FEATURE:
<221> NAME/KEY: CDS
<222> LOCATION: 1..1236
<223> OTHER INFORMATION: /transl_table=1

<400> SEQUENCE: 8

```
atg cat cat cat cat cat cac atc aca agt ttg tac aaa aaa gca ggc      48
Met His His His His His His Ile Thr Ser Leu Tyr Lys Lys Ala Gly
1               5                   10                  15 tgt ttt acc ctg aaa acc acc gca att gtg agc gca gca gca ctg ctg      96
Cys Phe Thr Leu Lys Thr Thr Ala Ile Val Ser Ala Ala Ala Leu Leu
            20                  25                  30 gca ggt ttt ggt cct ccg cct cgt gca gca gaa ctg cct ccg ggt cgt     144
Ala Gly Phe Gly Pro Pro Pro Arg Ala Ala Glu Leu Pro Pro Gly Arg
        35                  40                  45 ctg gca acc acc gaa gat tat ttt gca cag cag gca aaa cag gca gtt     192
Leu Ala Thr Thr Glu Asp Tyr Phe Ala Gln Gln Ala Lys Gln Ala Val
    50                  55                  60 aca ccg gat gtt atg gca cag ctg gca tat atg aac tat att gat ttt     240
Thr Pro Asp Val Met Ala Gln Leu Ala Tyr Met Asn Tyr Ile Asp Phe
65                  70                  75                  80 atc agc ccg ttt tat agc cgt ggc tgt agc ttt gaa gca tgg gaa ctg     288
Ile Ser Pro Phe Tyr Ser Arg Gly Cys Ser Phe Glu Ala Trp Glu Leu
                85                  90                  95 aaa cat aca ccg cag cgt gtt atc aaa tat agc att gcc ttt tat gcc     336
Lys His Thr Pro Gln Arg Val Ile Lys Tyr Ser Ile Ala Phe Tyr Ala
            100                 105                 110 tat ggt ctg gca agc gtt gca ctg att gat ccg aaa ctg cgt gca ctg     384
Tyr Gly Leu Ala Ser Val Ala Leu Ile Asp Pro Lys Leu Arg Ala Leu
        115                 120                 125 gca ggt cat gat ctg gat att gca gtt agc aaa atg aaa tgc aaa cgt     432
Ala Gly His Asp Leu Asp Ile Ala Val Ser Lys Met Lys Cys Lys Arg
    130                 135                 140 gtt tgg ggt gat tgg gaa gaa gat ggt ttt ggc acc gat ccg att gaa     480
Val Trp Gly Asp Trp Glu Glu Asp Gly Phe Gly Thr Asp Pro Ile Glu
145                 150                 155                 160 aaa gaa aac att atg tat aaa ggc cat ctg aat ctg atg tat ggt ctg     528
Lys Glu Asn Ile Met Tyr Lys Gly His Leu Asn Leu Met Tyr Gly Leu
                165                 170                 175 tat cag ctg gtt acc ggt agc cgt cgt tat gaa gca gaa cat gca cat     576
Tyr Gln Leu Val Thr Gly Ser Arg Arg Tyr Glu Ala Glu His Ala His
            180                 185                 190 ctg acc cgt att att cat gat gaa att gca gca aat ccg ttt gcc ggt     624
Leu Thr Arg Ile Ile His Asp Glu Ile Ala Ala Asn Pro Phe Ala Gly
        195                 200                 205 att gtt tgt gaa ccg gat aac tat ttt gtg cag tgt aat agc gtt gcc     672
Ile Val Cys Glu Pro Asp Asn Tyr Phe Val Gln Cys Asn Ser Val Ala
    210                 215                 220 tat ctg agc ctg tgg gtt tat gat cgt ctg cat ggc acc gat tat cgt     720
Tyr Leu Ser Leu Trp Val Tyr Asp Arg Leu His Gly Thr Asp Tyr Arg
225                 230                 235                 240
```

| | | |
|---|---|---|
| gca gca acc cgt gca tgg ctg gat ttt att cag aaa gat ctg att gat<br>Ala Ala Thr Arg Ala Trp Leu Asp Phe Ile Gln Lys Asp Leu Ile Asp<br>                               245                        250                  255 | 768 |
| cct gaa cgc ggt gcc ttt tat ctg agc tat cat ccg gaa agt ggt gca<br>Pro Glu Arg Gly Ala Phe Tyr Leu Ser Tyr His Pro Glu Ser Gly Ala<br>260                      265                      270 | 816 |
| gtt aaa ccg tgg att agc gca tat acc acc gca tgg acc ctg gca atg<br>Val Lys Pro Trp Ile Ser Ala Tyr Thr Thr Ala Trp Thr Leu Ala Met<br>      275                    280                      285 | 864 |
| gtt cat ggt atg gac cct gca ttt agc gaa cgt tat tat ccg cgt ttt<br>Val His Gly Met Asp Pro Ala Phe Ser Glu Arg Tyr Tyr Pro Arg Phe<br>290                      295                      300 | 912 |
| aaa cag acc ttt gtg gaa gtg tat gat gaa ggt cgt aaa gca cgt gtt<br>Lys Gln Thr Phe Val Glu Val Tyr Asp Glu Gly Arg Lys Ala Arg Val<br>305                             310                      315                      320 | 960 |
| cgt gaa acc gca ggc acc gat gat gca gat ggt ggt gtt ggt ctg gcc<br>Arg Glu Thr Ala Gly Thr Asp Asp Ala Asp Gly Gly Val Gly Leu Ala<br>                               325                      330                      335 | 1008 |
| agc gca ttt acc ctg ctg ctg gca cgt gaa atg ggt gat cag caa ctg<br>Ser Ala Phe Thr Leu Leu Leu Ala Arg Glu Met Gly Asp Gln Gln Leu<br>                340                      345                      350 | 1056 |
| ttc gat cag ctg ctg aat cat ctg gaa cct ccg gca aaa ccg agc att<br>Phe Asp Gln Leu Leu Asn His Leu Glu Pro Pro Ala Lys Pro Ser Ile<br>355                             360                      365 | 1104 |
| gtt agc gcc agc ctg cgt tat gaa cat ccg ggt agc ctg ctg ttt gat<br>Val Ser Ala Ser Leu Arg Tyr Glu His Pro Gly Ser Leu Leu Phe Asp<br>      370                    375                      380 | 1152 |
| gaa ctg ctg ttt ctg gca aaa gtt cat gcc ggt ttt ggt gcc ctg ctg<br>Glu Leu Leu Phe Leu Ala Lys Val His Ala Gly Phe Gly Ala Leu Leu<br>385                             390                      395                      400 | 1200 |
| cgt atg cct cct ccg gca gca aaa ctg gca ggt aag taataa<br>Arg Met Pro Pro Pro Ala Ala Lys Leu Ala Gly Lys<br>              405                      410 | 1242 |

<210> SEQ ID NO 9
<211> LENGTH: 412
<212> TYPE: PRT
<213> ORGANISM: Artificial Sequence
<220> FEATURE:
<223> OTHER INFORMATION: [CDS]:1..1236 from SEQ ID NO 8

<400> SEQUENCE: 9

Met His His His His His Ile Thr Ser Leu Tyr Lys Lys Ala Gly
1               5                   10                  15

Cys Phe Thr Leu Lys Thr Thr Ala Ile Val Ser Ala Ala Leu Leu
            20                  25                  30

Ala Gly Phe Gly Pro Pro Pro Arg Ala Ala Glu Leu Pro Pro Gly Arg
        35                  40                  45

Leu Ala Thr Thr Glu Asp Tyr Phe Ala Gln Gln Ala Lys Gln Ala Val
    50                  55                  60

Thr Pro Asp Val Met Ala Gln Leu Ala Tyr Met Asn Tyr Ile Asp Phe
65                  70                  75                  80

Ile Ser Pro Phe Tyr Ser Arg Gly Cys Ser Phe Glu Ala Trp Glu Leu
                85                  90                  95

Lys His Thr Pro Gln Arg Val Ile Lys Tyr Ser Ile Ala Phe Tyr Ala
            100                 105                 110

Tyr Gly Leu Ala Ser Val Ala Leu Ile Asp Pro Lys Leu Arg Ala Leu
        115                 120                 125

Ala Gly His Asp Leu Asp Ile Ala Val Ser Lys Met Lys Cys Lys Arg

-continued

```
                    130                 135                 140
Val Trp Gly Asp Trp Glu Glu Asp Gly Phe Gly Thr Asp Pro Ile Glu
145                 150                 155                 160

Lys Glu Asn Ile Met Tyr Lys Gly His Leu Asn Leu Met Tyr Gly Leu
                    165                 170                 175

Tyr Gln Leu Val Thr Gly Ser Arg Arg Tyr Glu Ala Glu His Ala His
                    180                 185                 190

Leu Thr Arg Ile Ile His Asp Glu Ile Ala Ala Asn Pro Phe Ala Gly
                195                 200                 205

Ile Val Cys Glu Pro Asp Asn Tyr Phe Val Gln Cys Asn Ser Val Ala
            210                 215                 220

Tyr Leu Ser Leu Trp Val Tyr Asp Arg Leu His Gly Thr Asp Tyr Arg
225                 230                 235                 240

Ala Ala Thr Arg Ala Trp Leu Asp Phe Ile Gln Lys Asp Leu Ile Asp
                245                 250                 255

Pro Glu Arg Gly Ala Phe Tyr Leu Ser Tyr His Pro Glu Ser Gly Ala
                260                 265                 270

Val Lys Pro Trp Ile Ser Ala Tyr Thr Thr Ala Trp Thr Leu Ala Met
                275                 280                 285

Val His Gly Met Asp Pro Ala Phe Ser Glu Arg Tyr Tyr Pro Arg Phe
            290                 295                 300

Lys Gln Thr Phe Val Glu Val Tyr Asp Glu Gly Arg Lys Ala Arg Val
305                 310                 315                 320

Arg Glu Thr Ala Gly Thr Asp Asp Ala Asp Gly Gly Val Gly Leu Ala
                325                 330                 335

Ser Ala Phe Thr Leu Leu Leu Ala Arg Glu Met Gly Asp Gln Gln Leu
                340                 345                 350

Phe Asp Gln Leu Leu Asn His Leu Glu Pro Pro Ala Lys Pro Ser Ile
            355                 360                 365

Val Ser Ala Ser Leu Arg Tyr Glu His Pro Gly Ser Leu Leu Phe Asp
370                 375                 380

Glu Leu Leu Phe Leu Ala Lys Val His Ala Gly Phe Gly Ala Leu Leu
385                 390                 395                 400

Arg Met Pro Pro Pro Ala Ala Lys Leu Ala Gly Lys
                405                 410
```